US008093356B2

(12) United States Patent
Hays et al.

(10) Patent No.: US 8,093,356 B2
(45) Date of Patent: Jan. 10, 2012

(54) PEGYLATED HUMAN INTERFERON POLYPEPTIDES

(75) Inventors: Anna-Maria A. Hays, San Diego, CA (US); Bruce E. Kimmel, San Diego, CA (US); Ho Sung Cho, San Diego, CA (US); Bee-Cheng Sim, San Diego, CA (US); David C. Litzinger, Poway, CA (US); Roberto Mariani, San Diego, CA (US); Vadim Kraynov, San Diego, CA (US); Nick Knudsen, San Diego, CA (US); Thomas O. Daniel, La Jolla, CA (US); Alan Koder, San Diego, CA (US); Stuart Bussell, Carlsbad, CA (US); Junjie Liu, San Diego, CA (US); Zhenwei Miao, San Diego, CA (US); Theresa Morrow, San Diego, CA (US)

(73) Assignee: Ambrx, Inc., La Jolla, CA (US)

( * ) Notice: Subject to any disclaimer, the term of this patent is extended or adjusted under 35 U.S.C. 154(b) by 0 days.

(21) Appl. No.: 11/925,337

(22) Filed: Oct. 26, 2007

(65) Prior Publication Data
US 2008/0132681 A1 Jun. 5, 2008

Related U.S. Application Data

(63) Continuation of application No. PCT/US2006/021738, filed on Jun. 2, 2006.

(60) Provisional application No. 60/687,173, filed on Jun. 3, 2005, provisional application No. 60/753,375, filed on Dec. 21, 2005.

(51) Int. Cl.
C07K 14/52 (2006.01)
C07K 14/00 (2006.01)
C12N 15/00 (2006.01)

(52) U.S. Cl. ......... 530/351; 530/350; 530/402; 435/440

(58) Field of Classification Search ............................ None
See application file for complete search history.

(56) References Cited

U.S. PATENT DOCUMENTS

| 3,773,919 | A | 11/1973 | Boswell et al. |
|---|---|---|---|
| 4,289,872 | A | 9/1981 | Denkewalter et al. |
| 4,412,989 | A | 11/1983 | Iwashita et al. |
| 4,414,148 | A | 11/1983 | Jansen et al. |
| 4,485,045 | A | 11/1984 | Regen |
| 4,511,502 | A | 4/1985 | Builder et al. |
| 4,511,503 | A | 4/1985 | Olson et al. |
| 4,512,922 | A | 4/1985 | Jones et al. |
| 4,544,545 | A | 10/1985 | Ryan et al. |
| 4,551,433 | A | 11/1985 | Deboer |
| 4,569,789 | A | 2/1986 | Blattler et al. |
| 4,619,794 | A | 10/1986 | Hauser |
| 4,659,839 | A | 4/1987 | Nicolotti et al. |
| 4,670,417 | A | 6/1987 | Iwasaki et al. |
| 4,671,958 | A | 6/1987 | Rodwell et al. |
| 4,680,338 | A | 7/1987 | Sundoro |
| 4,689,406 | A | 8/1987 | Banks et al. |
| 4,699,784 | A | 10/1987 | Shih et al. |
| 4,738,921 | A | 4/1988 | Belagaje et al. |
| 4,755,465 | A | 7/1988 | Gray et al. |
| 4,837,148 | A | 6/1989 | Cregg |
| 4,859,600 | A | 8/1989 | Gray et al. |
| 4,876,197 | A | 10/1989 | Burke et al. |
| 4,880,734 | A | 11/1989 | Burke et al. |
| 4,902,502 | A | 2/1990 | Nitecki et al. |
| 4,904,584 | A | 2/1990 | Shaw |
| 4,929,555 | A | 5/1990 | Cregg et al. |
| 5,021,234 | A | 6/1991 | Ehrenfeld |
| 5,089,398 | A | 2/1992 | Rosenberg et al. |
| 5,122,614 | A | 6/1992 | Zalipsky |
| 5,162,601 | A | 11/1992 | Slightom |
| 5,219,564 | A | 6/1993 | Zalipsky et al. |
| 5,229,490 | A | 7/1993 | Tam |
| 5,231,178 | A | 7/1993 | Holtz et al. |
| 5,252,714 | A | 10/1993 | Harris et al. |
| 5,281,698 | A | 1/1994 | Nitecki |
| 5,290,686 | A | 3/1994 | Kendal et al. |
| 5,324,639 | A | 6/1994 | Brierley et al. |
| 5,324,844 | A | 6/1994 | Zalipsky |
| 5,382,657 | A | 1/1995 | Karasiewicz et al. |
| 5,446,090 | A | 8/1995 | Harris |

(Continued)

FOREIGN PATENT DOCUMENTS

| DE | 3218121 A1 | 11/1983 |
|---|---|---|
| EP | 036 676 A1 | 9/1981 |
| EP | 036 776 A2 | 9/1981 |
| EP | 052 322 A2 | 5/1982 |
| EP | 058 481 A1 | 8/1982 |
| EP | 073 657 A1 | 3/1983 |
| EP | 102 324 A2 | 3/1984 |
| EP | 121 775 A1 | 10/1984 |
| EP | 127 839 A2 | 12/1984 |
| EP | 133 988 A2 | 3/1985 |
| EP | 143 949 A1 | 6/1985 |
| EP | 154 316 A2 | 9/1985 |
| EP | 155 476 A1 | 9/1985 |
| EP | 164 556 A2 | 12/1985 |
| EP | 183 503 A2 | 6/1986 |

(Continued)

OTHER PUBLICATIONS

Duncan, R. "The dawning era of polymer therapeutics," Nat Rev Drug Discov May 2003;2(5):347-60.
Gaertner, HF et RE Offord. "Site-specific attachment of functionalized poly(ethylene glycol) to the amino terminus of proteins," Bioconjug Chem Jan.-Feb. 1996 ;7(1):38-44.
Gu, Z et al. "Chromatographic methods for the isolation of, and refolding of proteins from, Escherichia coli inclusion bodies," Protein Expr Purif. Jun. 2002;25(1):174-9.
Hohsaka, T et M Sisido. "Incorporation of non-natural amino acids into proteins," Curr Opin Chem Biol. Dec. 2002;6 (6):809-15.

(Continued)

Primary Examiner — Christine J Saoud
Assistant Examiner — Jegatheesan Seharaseyon
(74) Attorney, Agent, or Firm — John W. Wallen, III; Kristin S. Eaton

(57) ABSTRACT

Modified human interferon polypeptides and uses thereof are provided, including PEGylated human interferon polypeptides with one or more non-naturally encoded amino acids.

5 Claims, 20 Drawing Sheets

U.S. PATENT DOCUMENTS

| | | |
|---|---|---|
| 5,468,478 A | 11/1995 | Saifer et al. |
| 5,473,034 A | 12/1995 | Yasui et al. |
| 5,476,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,559,213 A | 9/1996 | Hakimi et al. |
| 5,571,709 A | 11/1996 | Devauchelle et al. |
| 5,580,723 A | 12/1996 | Wells et al. |
| 5,583,023 A | 12/1996 | Cerutti et al. |
| 5,602,034 A | 2/1997 | Tekamp-Olson |
| 5,605,827 A | 2/1997 | Jackwood et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| RE35,749 E | 3/1998 | Rosenberg et al. |
| 5,736,625 A | 4/1998 | Callstrom et al. |
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,885 A | 6/1998 | Carrington et al. |
| 5,808,096 A | 9/1998 | Zalipsky |
| 5,824,778 A | 10/1998 | Ishikawa et al. |
| 5,824,784 A | 10/1998 | Kinstler et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,900,461 A | 5/1999 | Harris |
| 5,932,462 A | 8/1999 | Harris et al. |
| 5,939,285 A | 8/1999 | Devauchelle et al. |
| 5,965,393 A | 10/1999 | Hasnain et al. |
| 5,980,948 A | 11/1999 | Goedemoed et al. |
| 5,989,868 A | 11/1999 | Harrison et al. |
| 5,990,237 A | 11/1999 | Bentley et al. |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,083,723 A | 7/2000 | Tekamp-Olson |
| 6,096,304 A | 8/2000 | McCutchen |
| 6,126,944 A | 10/2000 | Pellett et al. |
| 6,129,912 A | 10/2000 | Hortin et al. |
| 6,168,932 B1 | 1/2001 | Uckun et al. |
| 6,183,985 B1 | 2/2001 | Shuster |
| 6,183,987 B1 | 2/2001 | Van De Wiel et al. |
| 6,201,072 B1 | 3/2001 | Rathi et al. |
| 6,214,966 B1 | 4/2001 | Harris |
| 6,225,060 B1 | 5/2001 | Clark et al. |
| 6,245,528 B1 | 6/2001 | Chao |
| 6,261,805 B1 | 7/2001 | Wood |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,515,100 B2 | 2/2003 | Harris |
| 6,521,427 B1 | 2/2003 | Evans |
| 6,552,167 B1 | 4/2003 | Rose |
| 6,586,207 B2 | 7/2003 | Tirrell et al. |
| 6,602,498 B2 | 8/2003 | Shen |
| 6,608,183 B1 | 8/2003 | Cox |
| 6,610,281 B2 | 8/2003 | Harris |
| 6,646,110 B2 | 11/2003 | Nissen et al. |
| 6,927,042 B2 | 8/2005 | Schultz et al. |
| 7,045,337 B2 | 5/2006 | Schultz et al. |
| 7,083,970 B2 | 8/2006 | Schultz et al. |
| 7,270,809 B2 * | 9/2007 | Cox, III ................. 424/85.7 |
| 7,314,613 B2 * | 1/2008 | Patten et al. ............ 424/85.7 |
| 2001/0021763 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0037949 A1 | 3/2002 | Harris et al. |
| 2002/0040076 A1 | 4/2002 | Harris et al. |
| 2002/0042097 A1 | 4/2002 | Tirrell et al. |
| 2002/0052009 A1 | 5/2002 | Hornauer et al. |
| 2002/0052430 A1 | 5/2002 | Harris et al. |
| 2002/0055169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0156047 A1 | 10/2002 | Zhao |
| 2003/0023023 A1 | 1/2003 | Harris et al. |
| 2003/0082575 A1 * | 5/2003 | Schultz et al. ............ 435/6 |
| 2003/0105224 A1 | 6/2003 | Roberts et al. |
| 2003/0105275 A1 | 6/2003 | Bentley et al. |
| 2003/0108885 A1 | 6/2003 | Schultz et al. |
| 2003/0114647 A1 | 6/2003 | Harris et al. |
| 2003/0143596 A1 | 7/2003 | Bentley et al. |
| 2003/0158333 A1 | 8/2003 | Roberts et al. |
| 2003/0162949 A1 | 8/2003 | Cox |
| 2003/0220447 A1 | 11/2003 | Harris |
| 2003/0228274 A1 | 12/2003 | Rose |
| 2004/0001838 A1 | 1/2004 | Zhao et al. |
| 2004/0013637 A1 | 1/2004 | Bentley |
| 2004/0115774 A1 * | 6/2004 | Kochendoerfer et al. ... 435/69.5 |
| 2004/0198637 A1 | 10/2004 | Schultz et al. |
| 2005/0009049 A1 | 1/2005 | Chin et al. |
| 2005/0085619 A1 | 4/2005 | Wilson et al. |
| 2005/0170404 A1 | 8/2005 | Cho et al. |
| 2005/0220762 A1 | 10/2005 | Cho et al. |

FOREIGN PATENT DOCUMENTS

| | | |
|---|---|---|
| EP | 188 256 A2 | 7/1986 |
| EP | 229 108 B1 | 7/1987 |
| EP | 244 234 A2 | 11/1987 |
| EP | 267 851 A2 | 5/1988 |
| EP | 284 044 A1 | 9/1988 |
| EP | 324 274 A1 | 7/1989 |
| EP | 329 203 A1 | 8/1989 |
| EP | 340 986 A2 | 11/1989 |
| EP | 400 472 A2 | 12/1990 |
| EP | 402 378 B1 | 12/1990 |
| EP | 439 508 B1 | 8/1991 |
| EP | 480 480 A2 | 4/1992 |
| EP | 510 356 A1 | 10/1992 |
| EP | 605 963 A1 | 7/1994 |
| EP | 732 403 A1 | 9/1996 |
| EP | 809 996 A2 | 12/1997 |
| EP | 921 131 A1 | 6/1999 |
| EP | 946 736 B1 | 10/1999 |
| JP | 83-118008 A | 1/1985 |
| WO | 88/07082 A1 | 9/1988 |
| WO | 89/01037 A1 | 2/1989 |
| WO | 89/01038 A1 | 2/1989 |
| WO | 90/01556 A1 | 2/1990 |
| WO | 90/02186 A1 | 3/1990 |
| WO | 90/02566 A1 | 3/1990 |
| WO | 90/05785 A1 | 5/1990 |

| | | | |
|---|---|---|---|
| WO | 90/10078 A1 | 9/1990 | |
| WO | 90/10277 A1 | 9/1990 | |
| WO | 90/13540 A1 | 11/1990 | |
| WO | 90/14428 A1 | 11/1990 | |
| WO | 91/00357 A1 | 1/1991 | |
| WO | 92/01801 A1 | 2/1992 | |
| WO | 92/02628 A1 | 2/1992 | |
| WO | 92/16555 A1 | 10/1992 | |
| WO | 92/16619 A1 | 10/1992 | |
| WO | 93/03173 A1 | 2/1993 | |
| WO | 93/15189 A1 | 8/1993 | |
| WO | 93/21259 A1 | 10/1993 | |
| WO | 94/04193 A1 | 3/1994 | |
| WO | 94/09027 A1 | 4/1994 | |
| WO | 94/14758 A1 | 7/1994 | |
| WO | 94/15625 A1 | 7/1994 | |
| WO | 94/17039 A1 | 8/1994 | |
| WO | 94/18247 A1 | 8/1994 | |
| WO | 94/28024 A1 | 12/1994 | |
| WO | 95/00162 A1 | 1/1995 | |
| WO | 95/06058 A1 | 3/1995 | |
| WO | 95/11924 A1 | 5/1995 | |
| WO | 95/13090 A1 | 5/1995 | |
| WO | 95/13312 A1 | 5/1995 | |
| WO | 95/20672 A1 | 8/1995 | |
| WO | 95/33490 A1 | 12/1995 | |
| WO | 96/00080 A1 | 1/1996 | |
| WO | 96/06161 A1 | 2/1996 | |
| WO | 96/07670 A1 | 3/1996 | |
| WO | 96/21469 A1 | 7/1996 | |
| WO | 96/25496 A1 | 8/1996 | |
| WO | 96/29400 A1 | 9/1996 | |
| WO | 96/40791 A1 | 12/1996 | |
| WO | 96/41813 A2 | 12/1996 | |
| WO | 97/03106 A1 | 1/1997 | |
| WO | 97/18832 A1 | 5/1997 | |
| WO | 97/26332 A1 | 7/1997 | |
| WO | 97/32607 A2 | 9/1997 | |
| WO | 98/05363 A2 | 2/1998 | |
| WO | 98/26080 A1 | 6/1998 | |
| WO | 98/32466 A1 | 7/1998 | |
| WO | 98/37208 A1 | 8/1998 | |
| WO | 98/41562 A1 | 9/1998 | |
| WO | 98/48837 A1 | 11/1998 | |
| WO | 99/03887 A1 | 1/1999 | |
| WO | 99/05297 A1 | 2/1999 | |
| WO | 99/07862 A1 | 2/1999 | |
| WO | 99/09193 A1 | 2/1999 | |
| WO | 99/10515 A1 | 3/1999 | |
| WO | 99/31257 A2 | 6/1999 | |
| WO | 99/32134 A1 | 7/1999 | |
| WO | 99/32139 A1 | 7/1999 | |
| WO | 99/32140 A1 | 7/1999 | |
| WO | 99/45130 A1 | 9/1999 | |
| WO | 99/51721 A1 | 10/1999 | |
| WO | 99/67291 A2 | 12/1999 | |
| WO | 00/20032 A1 | 4/2000 | |
| WO | 00/26354 A1 | 5/2000 | |
| WO | 00/55345 A2 | 9/2000 | |
| WO | 00/55353 A1 | 9/2000 | |
| WO | 01/05956 A2 | 1/2001 | |
| WO | 01/27301 A2 | 4/2001 | |
| WO | 01/90390 A1 | 11/2001 | |
| WO | 02/06305 A1 | 1/2002 | |
| WO | 02/085923 A2 | 10/2002 | |
| WO | 02/086075 A2 | 10/2002 | |
| WO | 03/101972 A1 | 12/2003 | |
| WO | 2004/035605 A2 | 4/2004 | |
| WO | 2004/035743 A2 | 4/2004 | |
| WO | 2004/058946 A2 | 7/2004 | |
| WO | 2004/094593 A2 | 11/2004 | |
| WO | WO 2004/094593 A2 | 11/2004 | |
| WO | 2005/007624 A2 | 1/2005 | |
| WO | 2005/007870 A2 | 1/2005 | |
| WO | 2005/019415 A2 | 3/2005 | |
| WO | 2005/035727 A2 | 4/2005 | |
| WO | 2005/074524 A2 | 8/2005 | |
| WO | 2005/074546 A2 | 8/2005 | |
| WO | 2005/074650 A2 | 8/2005 | |
| WO | WO 2005/074524 A2 | 8/2005 | |

OTHER PUBLICATIONS

Lilie, H et al. "Advances in refolding of proteins produced in *E. coli*," Curr Opin Biotechnol. Oct. 1998;9(5):497-501.
Tsumoto, K et al. "Practical considerations in refolding proteins from inclusion bodies," Protein Expr Purif. Mar. 2003;28(1):1-8.
Wang, W. "Instability, stabilization, and formulation of liquid protein pharmaceuticals," Int J Pharm. Aug. 20, 1999;185 (2):129-88.
Abuchowski, A. et al. "Cancer therapy with chemically modified enzymes. I. Antitumor properties of polyethylene glycol-asparaginase conjugates," Cancer Biochem Biophys. Jun. 1984;7(2):175-86.
Altschul, SF et al. "Gapped BLAST and PSI-BLAST: a new generation of protein database search programs," Nucleic Acids Res. Sep. 1, 1997;25(17):3389-402.
Altschul, SF et al. "Basic local alignment search tool," J Mol Biol. Oct. 5, 1990;215(3):403-10.
Amann, E et al., "Vectors bearing a hybrid trp-lac promoter useful for regulated expression of cloned genes in *Escherichia coli*," Gene. Nov. 1983;25(2-3):167-78.
Anderson, JC et al., "Exploring the limits of codon and anticodon size," Chem Biol. Feb. 2002;9(2):237-44.
Andresz, H et al. Abstract of "Chemische Synthese verzweigter Polysaccharide, 5; Kopplung von Oligosacchariden und Amylose an verschiedene Träger durch Hydrazonbindung," Makromol. Chem. 1978;179:301 Abstract.
Arnold, FH. "Protein engineering for unusual environments," Curr Opin Biotechnol. Aug. 1993;4(4):450-5.
Azoulay, M., et al. "Glutamine analogues as Potential Antimalarials," Eur. J. Med. Chem. (1991); 26(2):201-5.
Bain, JD, et al. "Biosynthetic site-specific incorporation of a non-natural amino acid into a polypeptide," J. Am Chem Soc 1989;111(20):8013-8014.
Ballance, DJ et al., "Transformation of *Aspergillus nidulans* by the orotidine-5'-phosphate decarboxylase gene of *Neurospora crassa*," Biochem Biophys Res Commun. Apr 15, 1983;112(1):284-9.
Barany, F. et al., "Genetic disease detection and DNA amplification using cloned thermostable ligase," Proc Natl Acad Sci U S A. Jan. 1, 1991;88(1):189-93.
Barton, DHR et al., "Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives," Tetrahedron (1987) 43:4297-4308.
Bass, S et al., "Mutant Trp repressors with new DNA-binding specificities," Science (1988) 242:240-245.
Batzer, MA et al., "Enhanced evolutionary PCR using oligonucleotides with inosine at the 3'-terminus," Nucleic Acids Res. Sep. 25, 1991;19(18):5081.
Beach, D et al., "Functionally homologous cell cycle control genes in budding and fission yeast," Nature Dec. 1982; 300:706-709.
Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.
Bernstein, FC, et al. "The protein data bank: a computer-based archival file for macromolecular structures," J. Mol. Biol. 1977; 112:535-542.
Boissel, JP et al., "Erythropoietin structure-function relationships. Mutant proteins that test a model of tertiary structure," J Biol Chem. Jul. 25, 1993;268(21):15983-93.
Boles, JO et al. "Bio-incorporation of telluromethionine into buried residues of dihydrofolate reductase," Nat Struct Biol. May 1994;1(5):283-4.
Botstein, D et D Shortle, "Strategies and applications of in vitro mutagenesis," Science. Sep. 20, 1985;229 (4719):1193-201.
Brunner, J. "New photolabeling and crosslinking methods," Annu Rev Biochem. 1993;62:483-514.

Buchner, J. et al., "A method for increasing the yield of properly folded recombinant fusion proteins: Single-chain immunotoxins from renaturation of bacterial inclusion bodies," Anal. Biochem. 1992; 205(2): 263-270.

Bückmann et al. "Functionalization of Poly(ethylene glycol) and Monomethoxy-Poly(ethylene glycol),"Makromol. Chem. 1981;182:1379-84.

Budisa, N et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.

Budisa, N et al., "Bioincorporation of telluromethionine into proteins: a promising new approach for X-ray structure analysis of proteins," J Mol Biol. Jul. 25, 1997;270(4):616-23.

Budisa, N et al., "Toward the experimental codon reassignment in vivo: protein building with an expanded amino acid repertoire," FASEB J. Jan. 1999;13(1):41-51.

Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.

Carbonell, LF et al., "Baculovirus-mediated expression of bacterial genes in dipteran and mammalian cells," J Virol. Oct. 1985;56(1):153-60.

Carrasco, M. and R. Brown, "A Versatile Set of Aminooxy Amino Acids for the Synthesis of Neoglycopeptides," J. Org. Chem. (2003); 68(23): 8853-8858.

Carter, P. "Site-directed mutagenesis," Biochem J. Jul. 1, 1986; 237(1):1-7.

Carter, P et al. "Improved oligonucleotide site-directed mutagenesis using M13 vectors" Nucleic Acids Res. Jun. 25, 1985;13(12):4431-43.

Carter, P. "Improved oligonucleotide-directed mutagenesis using M13 vectors" Methods Enzymol. 1987;154:382-403.

Chaiken, IM. "Semisynthetic peptides and proteins," CRC Crit Rev Biochem. 1981;11(3):255-301.

Chin, JW et al., "Addition of p-azido-L-phenylalanine to the genetic code of *E. coli*," J Am Chem Soc. Aug. 7, 2002;124 (31):9026-7.

Chin, JW et al., "Addition of a photocrosslinking amino acid to the genetic code of *Escherichia coli*," Proc Natl Acad Sci U S A. Aug. 20, 2002;99(17):11020-4. Epub Aug. 1, 2002.

Chin, JW et al., "An expanded eukaryotic genetic code," Science. Aug. 15, 2003;301(5635):964-7.

Chin, JW & P. G. Schultz, "In vivo photocrosslinking with unnatural amino acid mutagenesis," Chembiochem. Nov. 4, 2002; 3(11): 1135-7.

Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985;50(8):1239-1246.

Clark, R et al., "Long-acting growth hormones produced by conjugation with polyethylene glycol," J Biol Chem. Sep. 6, 1996;271(36):21969-77.

Corey, D.R., Schultz, P.G. "Generation of a hybrid sequence-specific single-stranded deoxyribonuclease," Science 1987; 238(4832):1401-1403.

Cornish, VW, et al., "Site-Specific Protein Modification Using a Ketone Handle," J. Am. Chem. Soc. 1996; 118 (34):8150-8151.

Cornish, VW et al., "Probing Protein Structure and Function with an Expanded Genetic Code,"Angew Chem Int Ed Engl,1995;34(6):621-33.

Craig, J.C. et al. "Absolute Configuration of the Enantiomers of 7-Chloro-4 [[4-(diethylamino)-1-methylbutyl]amino] quinoline (Chloroquine)," J. Org. Chem. 1988; 53(6):1167-1170.

Cregg, JM et al., "*Pichia pastoris* as a host system for transformations," Mol Cell Biol. Dec. 1985;5(12):3376-85.

Crick, FHC, et al. "General nature of the genetic code for proteins," Nature. Dec. 30, 1961;192:1227-32.

Dale et al., Oligonucleotide-directed random mutagenesis using the phosphorothioate method, Methods Mol. Biol.1996;57:369-374.

Das, S et al., "Transformation of *Kluyveromyces fragilis*," J Bacteriol. Jun. 1984;158(3):1165-7.

Dawson, P. E. and S. B. H. Kent, "Synthesis of native proteins by chemical ligation," Annu. Rev. Biochem. 2000; 69:923-60.

De Boer, HA et al., "The tac promoter: a functional hybrid derived from the trp and lac promoters," Proc Natl Acad Sci U S A. Jan. 1983;80(1):21-5.

De Louvencourt, L et al., "Transformation of *Kluyveromyces lactis* by killer plasmid DNA," J Bacteriol. May 1983;154(2):737-42.

Tondelli, L. et al. "Poly(ethylene Glycol) Imidazolyl Formates as Oligomeric Drug-Binding Matrices," J. Controlled Release 1985;1(4):251-7.

Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.

Trotter, KM and HA Wood, "Transfection techniques for producing recombinant baculoviruses," in Methods in Molecular Biology—Baculovirus Expression Protocols, vol. 39 (1995); Ed. C.D. Richardson, 97-107.

Tschumper, G. et al., "Sequence of a yeast DNA fragment containing a chromosomal replicator and the TRP1 gene," Gene 1980; 10(2):157-66.

Turcatti, G et al. "Probing the structure and function of the tachykinin neurokinin-2 receptor through biosynthetic incorporation of fluorescent amino acids at specific sites," J Biol Chem. Aug. 16, 1996;271(33):19991-8.

Van Den Berg, JA et al., "*Kluyveromyces* as a host for heterologous gene expression: expression and secretion of prochymosin," Biotechnology (N Y). Feb. 1990;8(2):135-9.

Van Hest, JC and DA Tirrell, "Efficient introduction of alkene functionality into proteins in vivo," FEBS Lett. May 22, 1998;428(1-2):68-70.

Debinski, W et al. "A wide range of human cancers express interleukin 4 (IL4) receptors that can be targeted with chimeric toxin composed of IL4 and *Pseudomonas* exotoxin," J Biol Chem. Jul. 5, 1993;268(19):14065-70.

Deiters, A., et al., "Adding Amino Acids with Novel Reactivity to the Genetic Code of *Saccharomyces cerevisiae*," J. Am. Chem. Soc. 2003; 125(39):11782-11783.

Delgado, C et al., "The uses and properties of PEG-linked proteins," Crit Rev Ther Drug Carrier Syst. 1992;9 (3-4):249-304.

Dennis, MS et al., "Albumin binding as a general strategy for improving the pharmacokinetics of proteins," J Biol Chem. Sep. 20, 2002;277(38):35035-43. Epub Jul. 15, 2002.

Dolphin, CT et al., "Missense mutation in flavin-containing monooxygenase 3 gene, FMO3, underlies fish-odour syndrome," Nat Genet. Dec. 1997;17(4):491-4.

Doring, V et al., "Enlarging the amino acid set of *Escherichia coli* by infiltration of the valine coding pathway," Science. Apr. 20, 2001;292(5516):501-4.

Dougherty, DA. "Unnatural amino acids as probes of protein structure and function," Curr Opin Chem Biol. Dec. 2000;4(6):645-52.

Duewel, H et al., "Incorporation of trifluoromethionine into a phage lysozyme: implications and a new marker for use in protein 19F NMR," Biochemistry. Mar. 18, 1997;36(11):3404-16.

Eghtedarzadeh MK & S Henikoff "Use of oligonucleotides to generate large deletions" Nucleic Acids Res. Jun. 25, 1986;14(12):5115.

Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.

Elliott, S et al., "Yeast-derived recombinant human insulin-like growth factor I: production, purification, and structural characterization," J Protein Chem. Feb. 1990;9(1):95-104.

Ellman, J.A., Mendel, D., Anthony-Cahill, S., Noren, C.J., Schultz, P.G. "Biosynthetic method for introducing unnatural amino acids site-specifically into proteins," Methods in Enz., 1992; 202:301-336.

Ellman, JA, et al. "Site-specific incorporation of novel backbone structures into proteins," Science. Jan. 10, 1992;255 (5041):197-200.

England, P. M., et al., "Backbone mutations in transmembrane domains of a ligand-gated ion channel: implications for the mechanism of gating," Cell. Jan. 8, 1999;96(1):89-98.

Eppstein et al., "Biological Activity of Liposome-Encapsulated Murine Interferon is Mediated by a Cell Membrane Receptor," Proc. Natl. Acad. Sci. U.S.A.(1985); 82: 3688-3692.

Fieschko, JC et al., "Controlled expression and purification of human immune interferon from high-cell-density fermentations of *Saccharomyces cerevisiae*," Biotech. Bioeng. (1987) 29(9):1113-21.

Forster, AC et al., " Programming peptidomimetic syntheses by translating genetic codes designed de novo," Proc Natl Acad Sci U S A. May 27, 2003;100(11):6353-7. Epub May 16, 2003.

Frankel, A et al., "Encodamers: unnatural peptide oligomers encoded in RNA," Chem Biol. Nov. 2003;10 (11):1043-50.

Fraser, MJ et al., "Expression of eucaryotic genes in insect cell cultures," in Vitro Cell. Dev. Biol. 1989; 25:225-235.

Friedman, O.M. & R. Chatterrji. "Synthesis of Derivatives of Glutamine as Model Substrates for Anti-Tumor Agents," J. Am. Chem. Soc. 1959; 81(14):3750-3752.

Fritz HJ et al., "Oligonucleotide-directed construction of mutations: a gapped duplex DNA procedure without enzymatic reactions in vitro," Nucleic Acids Res. Jul. 25, 1988;16(14B):6987-99.

Fromm, M. et al., "Expression of Genes Transferred into Monocot and Dicot Plant Cells by Electroporation," Proc. Natl. Acad. Sci. USA (1985) 82:5824-8.

Furter, R. "Expansion of the genetic code: site-directed p-fluoro-phenylalanine incorporation in *Escherichia coli*," Protein Sci. Feb. 1998;7(2):419-26.

Gaertner, HF et al., "Construction of protein analogues by site-specific condensation of unprotected fragments," Bioconjug Chem. May-Jun. 1992;3(3):262-8.

Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269 (10):7224-30.

Gallivan, JP et al., "Site-specific incorporation of biotinylated amino acids to identify surface-exposed residues in integral membrane proteins," Chem Biol. Oct. 1997;4(10):739-49.

Gellissen, G et al., "Heterologous protein production in yeast," Antonie Van Leeuwenhoek. Aug. 1992;62(1-2):79-93.

Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992;3(2):138-46.

Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.

Gleeson, MA et al., "Transformation of the methylotrophic yeast *Hansenula polymorphica*," J. Gen. Microbiol. (1986) 132:3459-3465.

Goeddel, DV, "Systems for heterologous gene expression," Methods Enzymol. 1990;185:3-7.

Goeddel, DV et al., "Synthesis of human fibroblast interferon by *E. coli*," Nucleic Acids Res. Sep. 25, 1980;8 (18):4057-74.

Goodson RJ et NV Katre. "Site-directed pegylation of recombinant interleukin-2 at its glycosylation site," Biotechnology (N Y). Apr. 1990;8(4):343-6.

Graves, SW et al., "Expression, purification, and initial kinetic characterization of the large subunit of the human mitochondrial DNA polymerase," Biochemistry. Apr. 28, 1998;37(17):6050-8.

Griffin, BA et al., "Specific Covalent Labeling of Recombinant Protein Molecules Inside Live Cells," Science (1998) 281:269-272.

Grundström T et al., "Oligonucleotide-directed mutagenesis by microscale 'shot-gun' gene synthesis," Nucleic Acids Res. May 10, 1985;13(9):3305-16.

Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.

Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.

Hang, HC and CR Bertozzi, "Chemoselective approaches to glycoprotein assembly," Acc Chem Res. Sep. 2001;34 (9):727-36.

Harris, JM et al. "Synthesis and Characterization of Poly(ethylene Glycol) Derivatives," J. Polym. Sci. Chem. Ed. 1984; 22:341-352.

Harris, JM. "Laboratory Synthesis of Polyethylene Glycol Derivatives," JMS-Rev. Macromol. Chem. Phys. 1985;C25 (3): 325-373.

Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.

Henikoff, S and JG Henikoff "Amino Acid Substitution Matrices from Protein Blocks," Proc. Natl. Acad. Sci. USA 1992; 89:10915-9.

Hess, B. et al., "Cooperation of glycolytic enzymes," J. Adv. Enzyme Reg. (1969) 7:149-67.

Hinnen, A et al., "Transformation of yeast," Proc Natl Acad Sci U S A. Apr. 1978;75(4):1929-33.

Hirao, I et al., "An unnatural base pair for incorporating amino acid analogues into proteins," Nat Biotechnol. Feb. 2002;20(2):177-82.

Hitzeman, RA et al., "Isolation and characterization of the yeast 3-phosphoglycerokinase gene (PGK) by an immunological screening technique," J. Biol Chem. Dec. 25, 1980;255(24):12073-80.

Hofmann, K., et H. Bohn. "Studies on polypeptides. XXXVI. The effect of pyrazole-imidazole replacements on the S-protein activating potency of an S-peptide fragment," J. Am Chem, (1966); 88(24):5914-5919.

Hohsaka, T et al., "Efficient Incorporation of Nonnatural Amino Acids with Large Aromatic Groups into Streptavidin in In Vitro Protein Synthesizing Systems," J. Am. Chem. Soc. 1999; 121(1); 34-40.

Hohsaka, T et al., "Incorporation of Two Different Nonnatural Amino Acids Independently into a Single Protein through Extension of the Genetic Code," J. Am. Chem. Soc. 1999; 121(51):12194-12195.

Van Hest, J. C. et al., "Efficient Incorporation of Unsaturated Methionine Analogues into Proteins in Vivo," J. Am. Chem. Soc. 2000 ;122 (7); 1282-1288.

Van Solingen, P. et JB van der Plaat. "Fusion of yeast spheroplasts," J Bacteriol. May 1977;130(2):946-7.

Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985;11(2):141-52.

Vlak, JM et al., "Functional studies on the p10 gene of *Autographa californica* nuclear polyhedrosis virus using a recombinant expressing a p10-beta-galactosidase fusion gene," J Gen Virol. Apr. 1988;69 (Pt 4):765-76.

Wang, Q., et al., "Bioconjugation by Copper(I)-Catalyzed Azide-Alkyne [3 + 2] Cycloaddition," J. Am. Chem. Soc. 2003; 125(11):3192-3193.

Wang, L. et al., "Addition of the keto functional group to the genetic code of *Escherichia coli*," Proc. Natl. Acad. Sci. (2003); 100(1):56-61.

Wang, L et al., "Expanding the genetic code of *Escherichia coli*," Science. Apr. 20, 2001;292(5516):498-500.

Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978;17 (23):4900-7.

Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3):1385-95.

Hsiao, CL et J Carbon, "High-frequency transformation of yeast by plasmids the cloned yeast ARG4 gene," Proc Natl Acad Sci U S A. Aug. 1979;76(8):3829-33.

Huisgen, R. in 1,3-Dipolar Cycloaddition Chemistry, vol. 1, 1984; Ed. Padwa A.; John Wiley and Sons, New York, p. 1-176.

Hwang, KJ et al., "Hepatic uptake and degradation of unilamellar sphingomyelin/cholesterol liposomes: a kinetic study," Proc Natl Acad Sci U S A. Jul. 1980;77(7):4030-4.

Ibba, M et al., "Substrate specificity is determined by amino acid binding pocket size in *Escherichia coli* phenylalanyl-tRNA synthetase," Biochemistry. Jun. 14, 1994;33(23):7107-12.

Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.

Ito, H. et al., "Transformation of intact yeast cells treated with alkali cations," J. Bacteriol. 1983; 153(1):163-8.

Jackson, DY et al. "A designed peptide ligase for total synthesis of ribonuclease A with unnatural catalytic residues," Science. Oct. 14, 1994;266(5183):243-7.

Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.

Jencks, W.P., "Studies on the Mechanism of Oxime and Semicarbazone Formation," J. Am. Chem. Soc.; 1959; 81 (2):475-481.

Joppich, M. et al. "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979;180:1381-4.

Kaiser, ET. "Synthetic approaches to biologically active peptides and proteins including enzymes," Acc Chem Res, (1989); 22(2):47-54.

Kaiser, ET et al. "The chemical modification of enzymatic specificity," Annu Rev Biochem. 1985;54:565-95.

Kaiser, ET and DS Lawrence. "Chemical mutation of enzyme active sites," Science. Nov. 2, 1984;226(4674):505-11.

Karlin, S and SF Altschul "Applications and statistics for multiple high-scoring segments in molecular sequences," Proc Natl Acad Sci U S A. Jun. 15, 1993;90(12):5873-7.

Kayser, B., et al., "Alkyne bridged alpha—amino acids by palladium mediated coupling of alkynes with N-t-Boc-4-iodo-phenylalanine methyl ester," Tetrahedron (1997); 53(7): 2475-2484.

Kelly, JM and MJ Hynes, "Transformation of Aspergillus niger by the amdS gene of Aspergillus nidulans," EMBO J. 1985; 4(2):475-479.

Kiick, K. L. and D. A. Tirrell, "Protein Engineering by In Vivo Incorporation of Non-Natural Amino Acids: Control of Incorporation of Methionine Analogues by Methionyl-tRNA Synthetase," Tetrahedron (2000), 56:9487-9493.

Kiick, KL et al., Incorporation of azides into recombinant proteins for chemoselective modification by the Staudinger ligation, Proc Natl Acad Sci U S A. Jan. 8, 2002;99(1):19-24. Epub Dec. 18, 2001.

Kim, DM and JR Swartz, "Regeneration of adenosine triphosphate from glycolytic intermediates for cell-free protein synthesis," Biotechnol Bioeng. Aug. 20, 2001;74(4):309-16.

Kim, DM and JR Swartz, "Oxalate improves protein synthesis by enhancing ATP supply in a cell-free system derived from Escherichia coli," Biotechnology Letters, 2000; 22:1537-1542.

Kim, DM, and JR Swartz, "Prolonging cell-free protein synthesis by selective reagent additions," Biotechnol Prog. May-Jun. 2000;16(3):385-90.

Kim, DM, and JR Swartz, "Prolonging cell-free protein synthesis with a novel ATP regeneration system," Biotechnol Bioeng. 1999;66(3):180-8.

King, F.E. & Kidd, D.A.A. "A New Synthesis of Glutamine and of gamma-Dipeptides of Glutamic Acid from Phthylated Intermediates," J. Chem. Soc. 1949; 3315-3319.

Kingsman, AJ et al., "Replication in Saccharomyces cerevisiae of plasmid pBR313 carrying DNA from the yeast trpl region," Gene. Oct. 1979;7(2):141-52.

Kitts, PA et al. "Linearization of baculovirus DNA enhances the recovery of recombinant virus expression vectors," Nucleic Acids Res. Oct. 11, 1990;18(19):5667-72.

Klein, TM et al., "High-velocity microprojectiles for delivering nucleic acids into living cells," Nature 1987; 327 (6117):70-73.

Kobayashi, T. et al., "Structural basis for orthogonal tRNA specificities of tyrosyl-tRNA synthetases for genetic code expansion," Nature Structural Biology (2003); 10(6):425-432.

Kogan, TP. "The synthesis of substituted methoxypoly(ethyleneglycol) derivatives suitable for selective protein modification," Synthetic Comm. 1992; 22(16):2417-24.

Kool, ET. "Synthetically modified DNAs as substrates for polymerases," Curr Opin Chem Biol. Dec. 2000;4(6):602-8.

Koskinen, A.M.P. & Rapoport, H. "Synthesis of 4-Substituted Prolines as Conformationally Constrained Amino Acid Analogues," J. Org. Chem. (1989) 54(8):1859-1866.

Kost, TA et al., "Production of a urokinase plasminogen activator-IgG fusion protein (uPA-IgG) in the baculovirus expression system," Gene. Apr. 29, 1997;190(1):139-44.

Kramer, W et al., "The gapped duplex DNA approach to oligonucleotide-directed mutation construction," Nucleic Acids Res. Dec. 21, 1984;12(24):9441-56.

Kramer, W & Fritz HJ. "Oligonucleotide-directed construction of mutations via gapped duplex DNA" Methods Enzymol. 1987;154:350-67.

Kramer, W. et al., "Improved enzymatic in vitro reactions in the gapped duplex DNA approach to oligonucleotide directed construction of mutations," Nucleic Acids Res. Jul. 25, 1988;16(14B):7207.

Kramer, B. et al., "Different base/base mismatches are corrected with different efficiencies by the methyl-directed DNA mismatch-repair system of E. coli," Cell. Oct. 1984;38(3):879-87.

Kreitman, RJ and I. Pastan "Purification and characterization of IL6-PE4E, a recombinant fusion of interleukin 6 with Pseudomonas exotoxin," Bioconjug Chem. Nov.-Dec. 1993;4(6):581-5.

Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.

Kunitani, M. et al., "Reversed-phase chromatography of interleukin-2 muteins," J Chromatogr. May 30, 1986;359:391-402.

Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.

Kunkel, TA "Rapid and efficient site-specific mutagenesis without phenotypic selection," Proc Natl Acad Sci U S A. Jan. 1985;82(2):488-92.

Kunkel, TA et al., "Rapid and efficient site-specific mutagenesis without phenotypic selection," Methods Enzymol. 1987;154:367-82.

Kunze, G et al., "Transformation of the industrially important yeasts Candida maltosa and Pichia guilliermondii," J. Basic Microbiol. 1985; 25:141-4.

Kurtz et al., "Integrative transformation of Candida albicans, using a cloned Candida ADE2 gene," Mol Cell Biol. Jan. 1986;6(1):142-9.

Kurtzhals, P et al., "Albumin binding of insulins acylated with fatty acids: characterization of the ligand-protein interaction and correlation between binding affinity and timing of the insulin effect in vivo," Biochem J. Dec. 15, 1995;312 ( Pt 3):725-31.

Langer, R et al., "Biocompatibility of polymeric delivery systems for macromolecules," J Biomed Mater Res. Mar. 1981;15(2):267-77.

Langer, R. "Controlled release of macromolecules," Chem. Tech. 1982; 12: 98-105.

Liebman, JM et al., "When less is more: enhanced baculovirus production of recombinant proteins at very low multiplicities of infection," Biotechniques. Jan. 1999;26(1):36-8, 40, 42.

Ling, MM et BH Robinson, "Approaches to DNA mutagenesis: an overview" Anal Biochem. Dec. 15, 1997;254 (2):157-78.

Zoller, MJ & Smith M, "Oligonucleotide-directed mutagenesis: a simple method using two oligonucleotide primers and a single-stranded DNA template," Methods Enzymol. 1987;154:329-50.

Mehl, RA et al. "Generation of a bacterium with a 21 amino acid genetic code," J Am Chem Soc. Jan. 29, 2003;125 (4):935-9.

Santoro, SW et al. "An efficient system for the evolution of aminoacyl-tRNA synthetase specificity," Nat Biotechnol. Oct. 2002;20(10):1044-8. Epub Sep. 16, 2002.

Caliceti, P et FM Veronese. "Pharmacokinetic and biodistribution properties of poly(ethylene glycol)-protein conjugates," Adv Drug Deliv Rev. Sep. 26, 2003;55(10):1261-77.

Clark, EDB, "Refolding of recombinant proteins," Curr Opin Biotechnol Apr. 1, 1998;9(2):157-63.

Clark, EDB, "Protein refolding for industrial processes," Curr Opin Biotechnol Apr. 2001;12(2):202-7.

Davis, GD et al., "New fusion protein systems designed to give soluble expression in Escherichia coli," Biotechnol Bioeng Nov. 20, 1999;65(4):382-8.

Wang, L & PG Schultz, "Expanding the genetic code," Chem Commun (Camb). Jan. 7, 2002;1:1-11.

Weissmann, C. "The cloning of interferon and other mistakes." in Interferon 3 1981; ed. I. Gresser; Academic Press, London, 101-134.

Wells, JA et al., "Importance of hydrogen-bond formation in stabilizing the transition state of subtilisin," Phil. Trans. R. Soc. Lond. A 1986; 317: 415-423.

Wells, JA et al., "Cassette mutagenesis: an efficient method for generation of multiple mutations at defined sites," Gene. 1985;34(2-3):315-23.

Woghiren, C et al. "Protected thiol-polyethylene glycol: a new activated polymer for reversible protein modification," Bioconjug Chem. Sep.-Oct. 1993;4(5):314-8.

Wong, SS et LJ Wong, "Chemical crosslinking and the stabilization of proteins and enzymes," Enzyme Microb Technol. Nov. 1992;14(11):866-74.

Wright, K. "Biotechnology: Insect virus as super-vector?," Nature (1986) 321(6072):718.

Liu, H. et al. "A Method for the Generation of Glycoprotein Mimetics," J. Am. Chem. Soc. 2003 125(7): 1702-1703.

Liu, D.R. & Schultz, P.G. "Progress toward the evolution of an organism with an expanded genetic code," Proc Natl Acad Sci U S A. Apr. 27, 1999;96(9):4780-5.

Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.

Lu, T. et al. "Probing ion permeation and gating in a K +channel with backbone mutations in the selectivity filter," Nature Neurosci. Mar. 2001;4(3):239-246.

Luckow, VA and MD Summers, "High level expression of nonfused foreign genes with *Autographa californica* nuclear polyhedrosis virus expression vectors," Virology. May 1989;170(1):31-9.

MA, C et al., "In vitro protein engineering using synthetic tRNA(Ala) with different anticodons," Biochemistry. Aug. 10, 1993;32(31):7939-45.

Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307 (3):755-69.

Mahal, L. K., et al., "Engineering chemical reactivity on cell surfaces through oligosaccharide biosynthesis," Science. May 16, 1997;276(5315):1125-8.

Makrides, SC et al., "Extended in vivo half-life of human soluble complement receptor type 1 fused to a serum albumin-binding receptor," J Pharmacol Exp Ther. Apr. 1996;277(1):534-42.

Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.

Mandecki, W. Oligonucleotide-directed double-strand break repair in plasmids of *Escherichia coli*: a method for site-specific mutagenesis, Proc Natl Acad Sci U S A. Oct. 1986;83(19):7177-81.

Mann, SG and LA King, "Efficient transfection of insect cells with baculovirus DNA using electroporation," J Gen Virol. Dec. 1989;70 (Pt 12):3501-5.

Matsoukas, JM et al., "Differences in backbone structure between angiotensin II agonists and type I antagonists," J Med Chem. Nov. 10, 1995;38(23):4660-9.

McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.

Meggers, E et al., "A Novel Copper-Mediated DNA Base Pair," J. Am. Chem. Soc. 2000; 122(43):10714-10715.

Mehvar, R.,"Modulation of the pharmacokinetics and pharmacodynamics of proteins by polyethylene glycol conjugation" J Pharm Pharm Sci. Jan.-Apr. 2000;3(1):125-36.

Mendel, D, et al. "Site-directed mutagenesis with an expanded genetic code," Annu Rev Biophys Biomol Struct. 1995;24:435-62.

Miller, LK, "Baculoviruses as gene expression vectors," Ann. Rev. Microbiol. 1988; 42:177-99.

Miller, LK. "Insect baculoviruses: powerful gene expression vectors," Bioessays. Oct. 1989;11(4):91-5.

Miller, JC et al. "Flash decaging of tyrosine sidechains in an ion channel," Neuron. Apr. 1998;20(4):619-24.

Minks, C. et al., Noninvasive tracing of recombinant proteins with "fluorophenylalanine-fingers," Anal Biochem. Aug. 15, 2000;284(1)29-34.

Miyanohara, A et al., "Expression of hepatitis B surface antigen gene in yeast," Proc Natl Acad Sci U S A. Jan. 1983;80(1):1-5.

Moore, B. et al., "Quadruplet codons: implications for code expansion and the specification of translation step size," J. Mol. Biol. 2000; 298(2):195-209.

Mosbach, K. et al., "Formation of proinsulin by immobilized *Bacillus subtilis*," Nature Apr. 1983; 302:543-545.

Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.

Nakatsuka, T., et al. "Peptide segment coupling catalyzed by the semisynthetic enzyme thiosubtilisin," J Am Chem Soc, 1987; 109(12): 3808-3810.

Nambiar, KP et al., "Total synthesis and cloning of a gene coding for the ribonuclease S protein," Science (1984) 223: 1299-1301.

Needleman, SB and Wunsch CD, "A general method applicable to the search for similarities in the amino acid sequence of two proteins," J Mol Biol. Mar. 1970;48(3):443-53.

Neet, KE et al. "Properties of thiol-subtilisin. The consequences of converting the active serine residue to cysteine in a serine protease," J Biol Chem. Dec. 25, 1968;243(24):6392-401.

Nielsen, UB, et al., "Therapeutic efficacy of anti-ErbB2 immunoliposomes targeted by a phage antibody selected for cellular endocytosis," Biochim Biophys Acta. Aug. 19, 2002:1591(1-3):109-118.

Nomura, T. et al., "Purification, cDNA Cloning, and Expression of UDP-Gal: Glucosylceramide -1,4-Galactosyltransferase from Rat Brain," J. Biol. Chem. 1998; 273(22):13570-7.

Noren, CJ et al. "A general method for site-specific incorporation of unnatural amino acids into proteins," Science. Apr. 14, 1989;244(4901):182-8.

Nowak, MW et al., "Nicotinic receptor binding site probed with unnatural amino acid incorporation in intact cells," Science. Apr. 21, 1995;268(5209):439-42.

Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.

Ogawa, AK et al., "Rational Design of an Unnatural Base Pair with Increased Kinetic Selectivity," J. Am. Chem. Soc. 2000; 122(36); 8803-8804.

Ohtsuka, E et al., "An alternative approach to deoxyoligonucleotides as hybridization probes by insertion of deoxyinosine at ambiguous codon positions," J Biol Chem. Mar. 10, 1985;260(5):2605-8.

Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.

Padwa, A. "Intermolecular 1,3-Dipolar Cycloadditions," in Comprehensive Organic Synthesis, vol. 4, (1991) Ed. Trost, B. M.; Pergamon, Oxford, 1069-1109.

Palva, I et al., "Secretion of interferon by *Bacillus subtilis*," Gene. May-Jun. 1983;22(2-3):229-35.

Park, JW, et al., "Development of anti-p185HER2 immunoliposomes for cancer therapy," Proc Natl Acad Sci U S A. Feb. 28, 1995;92(5):1327-31.

Park, JW, et al., "Anti-HER2 immunoliposomes: enhanced efficacy attributable to targeted delivery," Clin Cancer Res. Apr. 2002;8(4):1172-81.

Patnaik, R. and JR Swartz, "*E. coli*-based in vitro transcription/translation: in vivo-specific synthesis rates and high yields in a batch system," Biotechniques. May 1998;24(5):862-8.

Pearson, WR and DJ Lipman, "Improved tools for biological sequence comparison," Proc Natl Acad Sci U S A. Apr. 1988;85(8):2444-8.

Pepinsky, RB., et al., "Improved pharmacokinetic properties of a polyethylene glycol-modified form of interferon-beta-1a with preserved in vitro bioactivity," J Pharmacol Exp Ther. Jun. 2001;297(3):1059-66.

Piccirilli, JA et al., "Enzymatic incorporation of a new base pair into DNA and RNA extends the genetic alphabet," Nature 1990; 343:33-37.

Pintar, A et al. "CX, an algorithm that identifies protruding atoms in proteins," Bioinformatics. Jul. 2002;18(7):980-4.

Pitha, J et al. "Detergents linked to polysaccharides: preparation and effects on membranes and cells," Eur J Biochem. Feb. 15, 1979;94(1):11-8.

Polgar, L. and ML Bender. "A new enzyme containing a synthetically formed active site. Thiol-subtilisin." J. Am Chem Soc., 1966; 88(13): 3153-3154.

Pollack, SJ et al. "Introduction of nucleophiles and spectroscopic probes into antibody combining sites," Science. Nov. 18, 1988;242(4881):1038-40.

Preneta, AZ. "Separation on the basis of size: gel permeation chromatography," in Protein Purification Methods, a practical approach, 1989; Eds. Harris & Angal; IRL Press, Oxford; 293-306.

Yelton, MM et al., "Transformation of *Aspergillus nidulans* by using a trpC plasmid," Proc Natl Acad Sci U S A. Mar. 1984;81(5):1470-4.

Yelverton, E et al., "Bacterial synthesis of a novel human leukocyte interferon," Nucleic Acids Res. Feb. 11, 1981;9 (3):731-41.

Zalipsky, S et al. "Attachment of drugs to polyethylene glycols," Eur. Polymer Journal. 1983 19(12):1177-83.

Zalipsky, S. "Functionalized poly(ethylene glycol) for preparation of biologically relevant conjugates," Bioconjug Chem. Mar.-Apr. 1995;6(2):150-65.

Zhang, Z., et al. "A new strategy for the site-specific modification of proteins in vivo," Biochemistry. Jun. 10, 2003;42 (22):6735-46.

Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10 (20):6487-500.

Zoller, MJ & M. Smith, "Oligonucleotide-directed mutagenesis of DNA fragments cloned into M13 vectors" Methods Enzymol. 1983;100:468-500.

Raibaud, O et M Schwartz. "Positive control of transcription initiation in bacteria," Annu Rev Genet. 1984;18:173-206.

Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271 (39):23607-10.

Rivier, J et R McClintock, "Reversed-phase high-performance liquid chromatography of insulins from different species," J Chromatogr. Sep. 23, 1983;268(1):112-9.

Roberts, et al., "Generation of an antibody with enhanced affinity and specificity for its antigen by protein engineering," Nature 1987;328:731-734.

Roberts, RW and JW Szostak, "RNA-peptide fusions for the in vitro selection of peptides and proteins," Proc Natl Acad Sci U S A. Nov. 11, 1997;94(23):12297-302.

Roggenkamp, R. et al., "Transformation of the methylotrophic yeast *Hansenula polymorpha* by autonomous replication and integration vectors," Mol. Genetics and Genomics 1986;202(2):302-8.

Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.

Romanos, MA et al., "Foreign gene expression in yeast: a review," Yeast. Jun. 1992;8(6):423-88.

Rosenthal, GA. "L-canaline: a potent antimetabolite and anti-cancer agent from leguminous plants," Life Sci.1997;60(19):1635-41.

Rossolini, GM et al., "Use of deoxyinosine-containing primers vs degenerate primers for polymerase chain reaction based on ambiguous sequence information," Mol. Cell. Probes 1994; 8:91-98.

Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.

Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.

Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.

Sandler and Karo, "Polyoxyalkylation of hydroxyl compounds," in Polymer Synthesis, vol. 3, 1980; Academic Press, New York, 138-161.

Sartore, L et al., "Enzyme modification by MPEG with an amino acid or peptide as spacer arms," Appl Biochem Biotechnol. Jan. 1991;27(1):45-54.

Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287 (5460):2007-2010.

Sayers, JR et al., "Strand specific cleavage of phosphorothioate-containing DNA by reaction with restriction endonucleases in the presence of ethidium bromide" Nucleic Acids Res. Feb. 11, 1988;16(3):803-14.

Sayers, JR, et al. "5'-3' exonucleases in phosphorothioate-based oligonucleotide-directed mutagenesis," Nucleic Acids Res. Feb. 11, 1988;16(3):791-802.

Schanbacher, FL et al. "Galactosyltransferase Acceptor Specificity of the Lactose Synthetase A Protein," J. Biol. Chem. 1970; 245(19):5057-5061.

Schmidt, M et al., "Baculovirus-mediated large-scale expression and purification of a polyhistidine-tagged rubella virus capsid protein," Protein Expr Purif. Apr. 1998;12(3):323-30.

Schneider, E., et al., "Functional Purification of a Bacterial ATP-Binding Cassette Transporter Protein (MalK) from the Cytoplasmic Fraction of an Overproducing Strain," Protein Expr. Purif. 1995; 6(1):10-14.

Schnolzer, M. and SBH Kent. "Constructing proteins by dovetailing unprotected synthetic peptides: backbone-engineered HIV protease," Science. Apr. 10, 1992;256(5054):221-5.

Scouten, WH. "A survey of enzyme coupling techniques," Methods Enzymol. 1987;135:30-65.

Shao, J and JP Tam, "Unprotected Peptides as Building Blocks for the Synthesis of Peptide Dendrimers with Oxime, Hydrazone, and Thiazolidine Linkages," J. Am. Chem. Soc. 1995; 117(14):3893-3899.

Sharma, N et al., "Efficient introduction of aryl bromide functionality into proteins in vivo," FEBS Lett. Feb. 4, 2000;467 (1):37-40.

Shimatake, H et M Rosenberg, "Purified gamma regulatory protein cll positively activates promoters for lysogenic development," Nature Jul. 1981; 292:128-132.

Shine, J and L Dalgarno, "Determinant of cistron specificity in bacterial ribosomes," Nature. Mar. 6, 1975;254 (5495):34-8.

Sidman, KR et al., "Controlled release of macromolecules and pharmaceuticals from synthetic polypeptides based on glutamic acid," Biopolymers. Jan. 1983;22(1):547-56.

Sieber, V. et al., "Libraries of hybrid proteins from distantly related sequences," Nature Biotechnology, May 2001;19:456-460.

Siffert, W et al., "Association of a human G-protein beta3 subunit variant with hypertension," Nat Genet. Jan. 1998;18(1):45-8.

Sikorski, RS et al., "A System of Shuttle Vectors and Yeast Host Strains Designed for Efficient Manipulation of DNA in *Saccharomyces cerevisiae*," Genetics (1989) 122:19-27.

Sisk, WP et al., "High-level expression and purification of secreted forms of herpes simplex virus type 1 glycoprotein gD synthesized by baculovirus-infected insect cells," J Virol. Feb. 1994;68(2):766-75.

Sjolander, A et al., "The serum albumin-binding region of streptococcal protein G: a bacterial fusion partner with carrier-related properties," J Immunol Methods. Feb. 14, 1997;201(1):115-23.

Smith, M. "In vitro mutagenesis" Ann. Rev. Genet. 1985; 19:423-462.

Smith, GE et al., "Production of human beta interferon in insect cells infected with a baculovirus expression vector," Mol Cell Biol. Dec. 1983;3(12):2156-65.

Stanley, SL et al., "The serine-rich *Entamoeba histolytica* protein is a phosphorylated membrane protein containing O-linked terminal N-acetylglucosamine residues," J Biol Chem. Feb. 24, 1995;270(8):4121-6.

Steitz, JA et al. "Genetic signals and nucleotide sequences in messenger RNA," in Biological Regulation and Development: Gene Expression 1979; ed. R. F. Goldberger; Plenum Press, New York; 349-399.

Stemmer, WPC, "Rapid evolution of a protein in vitro by DNA shuffling," Nature 1994;370(4):389-391.

Stemmer, WP "DNA shuffling by random fragmentation and reassembly: In vitro recombination for molecular evolution," Proc Natl Acad Sci U S A. Oct. 25, 1994;91(22):10747-51.

Studier, FW et BA Moffatt, "Use of bacteriophage T7 RNA polymerase to direct selective high-level expression of cloned genes," J. Mol Biol. May 5, 1986;189(1):113-30.

Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.

Switzer, C et al., "Enzymatic incorporation of a new base pair into DNA and RNA," J. Am. Chem. Soc. 1989; 111 (21):8322-8323.

Tabor, S et CC Richardson, "A bacteriophage T7 RNA polymerase/promoter system for controlled exclusive expression of specific genes," Proc Natl Acad Sci U S A. Feb. 1985;82(4):1074-8.

Tae, EL et al., "Efforts toward Expansion of the Genetic Alphabet: Replication of DNA with Three Base Pairs," J. Am. Chem. Soc. 2001; 123(30):7439-7440.

Tang, Y et al., "Fluorinated Coiled-Coil Proteins Prepared in Vivo Display Enhanced Thermal and Chemical Stability," Angew Chem Int Ed Engl. Apr. 17, 2001;40(8):1494-1496.

Taylor, JW et al., "The use of phosphorothioate-modified DNA in restriction enzyme reactions to prepare nicked DNA," Nucleic Acids Res. Dec. 20, 1985;13(24):8749-64.

Taylor, JW et al., "The rapid generation of oligonucleotide-directed mutations at high frequency using phosphorothioate-modified DNA," Nucleic Acids Res. Dec. 20, 1985;13(24):8765-85.

Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.

Tilburn, J. et al., "Transformation by integration in *Aspergillus nidulans*," Gene. Dec. 1983;26(2-3):205-21.

Wang et al., "Distinct domains of lFNalpha mediate immune and analgesic effects respectively", Journal of Neuroimmunology, Aug. 1, 2008, 108(1-2):64-67.

Wang et al., "Distinct domains of interferon-alpha", Neuroreport, Mar. 26, 2001, 12(4):857-859.

* cited by examiner

Effect of Endotoxin on pSTAT1 Assay (THP-1)

Effect of Endotoxin on Anti-proliferation Assay (Daudi)

Pegasys, BFU-E

Pegasys, CFU-GM

Ribavirin, CFU-GM

SEQUENCE LISTING

<160> NUMBER OF SEQ ID NOS: 23

<210> SEQ ID NO 1
<211> LENGTH: 188
<212> TYPE: PRT
<213> ORGANISM: Homo sapiens

<400> SEQUENCE: 1

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 2
<211> LENGTH: 165
<212> TYPE: PRT
<213> ORGANISM: Homo sapiens

<400> SEQUENCE: 2

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Tyr Ser Pro Cys Ala Trp Glu Val Val Arg
            130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 3
<211> LENGTH: 166
<212> TYPE: PRT
<213> ORGANISM: Homo sapiens

<400> SEQUENCE: 3

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Ser
65                  70                  75                  80

Leu Leu Glu Lys Phe Tyr Thr Glu Leu Tyr Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Arg Leu Arg Arg Lys Glu
                165

<210> SEQ ID NO 4
<211> LENGTH: 77
<212> TYPE: DNA
<213> ORGANISM: Methanococcus jannaschii

<400> SEQUENCE: 4
ccggcggtag ttcagcaggg cagaacggcg gactctaaat ccgcatggcg ctggttcaaa    60
tccggcccgc cggacca                                                   77

<210> SEQ ID NO 5
<211> LENGTH: 88
<212> TYPE: DNA
<213> ORGANISM: Halobacterium sp. NRC-1

<400> SEQUENCE: 5
cccagggtag ccaagctcgg ccaacggcga cggactctaa atccgttctc gtaggagttc    60
gagggttcga atcccttccc tgggacca                                       88

<210> SEQ ID NO 6
<211> LENGTH: 89
<212> TYPE: DNA
<213> ORGANISM: Halobacterium sp. NRC-1

-continued

```
<400> SEQUENCE: 6
gcgagggtag ccaagctcgg ccaacggcga cggacttcct aatccgttct cgtaggagtt    60
cgagggttcg aatccctccc ctcgcacca                                      89

<210> SEQ ID NO 7
<211> LENGTH: 306
<212> TYPE: PRT
<213> ORGANISM: Methanococcus jannaschii

<400> SEQUENCE: 7
```

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

```
<210> SEQ ID NO 8
<211> LENGTH: 306
<212> TYPE: PRT
<213> ORGANISM: Methanococcus jannaschii
```

<400> SEQUENCE: 8

```
Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Gly
            20                  25                  30
Ile Gly Phe Glu Pro Ser Gly Lys Ile His Leu Gly His Tyr Leu Gln
        35                  40                  45
Ile Lys Lys Met Ile Asp Leu Gln Asn Ala Gly Phe Asp Ile Ile Ile
    50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Ser Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Thr Ser His
145                 150                 155                 160
Tyr Leu Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
            180                 185                 190
Asn Pro Val Leu Thr Gly Leu Asp Gly Glu Gly Lys Met Ser Ser Ser
        195                 200                 205
Lys Gly Asn Phe Ile Ala Val Asp Asp Ser Pro Glu Glu Ile Arg Ala
    210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
            260                 265                 270
Leu Glu Ser Leu Phe Lys Asn Lys Glu Leu His Pro Met Asp Leu Lys
        275                 280                 285
Asn Ala Val Ala Glu Glu Leu Ile Lys Ile Leu Glu Pro Ile Arg Lys
    290                 295                 300
Arg Leu
305
```

<210> SEQ ID NO 9
<211> LENGTH: 305
<212> TYPE: PRT
<213> ORGANISM: Methanococcus jannaschii

<400> SEQUENCE: 9

```
Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Ala
            20                  25                  30
Ile Gly Phe Glu Pro Ser Gly Lys Ile His Leu Gly His Tyr Leu Gln
        35                  40                  45
```

```
Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Pro Phe Gln Leu Asp Lys
                100                 105                 110

Asp Tyr Thr Leu Asn Val Tyr Arg Leu Ala Leu Lys Thr Thr Leu Lys
                115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Val Val Cys Ile His Asn
                180                 185                 190

Pro Val Leu Thr Gly Leu Asp Gly Glu Gly Lys Met Ser Ser Ser Lys
                195                 200                 205

Gly Asn Phe Ile Ala Val Asp Asp Ser Pro Glu Glu Ile Arg Ala Lys
210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
                260                 265                 270

Glu Ser Leu Phe Lys Asn Lys Glu Leu His Pro Met Asp Leu Lys Asn
                275                 280                 285

Ala Val Ala Glu Glu Leu Ile Lys Ile Leu Glu Pro Ile Arg Lys Arg
                290                 295                 300

Leu
305

<210> SEQ ID NO 10
<211> LENGTH: 305
<212> TYPE: PRT
<213> ORGANISM: Methanococcus jannaschii

<400> SEQUENCE: 10

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Ala
                 20                  25                  30

Ile Gly Phe Glu Pro Ser Gly Lys Ile His Leu Gly His Tyr Leu Gln
                 35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Pro Phe Gln Leu Asp Lys
                100                 105                 110
```

```
Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
                180                 185                 190

Pro Val Leu Thr Gly Leu Asp Gly Glu Gly Lys Met Ser Ser Ser Lys
                195                 200                 205

Gly Asn Phe Ile Ala Val Asp Asp Ser Pro Glu Glu Ile Arg Ala Lys
        210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
                260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
        290                 295                 300

Leu
305

<210> SEQ ID NO 11
<211> LENGTH: 305
<212> TYPE: PRT
<213> ORGANISM: Methanococcus jannaschii

<400> SEQUENCE: 11

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175
```

```
Met Leu Ala Arg Glu Leu Leu Pro Lys Lys Val Val Cys Ile His Asn
            180                 185                 190
Pro Val Leu Thr Gly Leu Asp Gly Glu Gly Lys Met Ser Ser Ser Lys
        195                 200                 205
Gly Asn Phe Ile Ala Val Asp Asp Ser Pro Glu Glu Ile Arg Ala Lys
    210                 215                 220
Ile Lys Lys Ala Tyr Cys Pro Ala Gly Val Val Glu Gly Asn Pro Ile
225                 230                 235                 240
Met Glu Ile Ala Lys Tyr Phe Leu Glu Tyr Pro Leu Thr Ile Lys Arg
                245                 250                 255
Pro Glu Lys Phe Gly Gly Asp Leu Thr Val Asn Ser Tyr Glu Glu Leu
            260                 265                 270
Glu Ser Leu Phe Lys Asn Lys Glu Leu His Pro Met Asp Leu Lys Asn
        275                 280                 285
Ala Val Ala Glu Glu Leu Ile Lys Ile Leu Glu Pro Ile Arg Lys Arg
    290                 295                 300
Leu
305

<210> SEQ ID NO 12
<211> LENGTH: 306
<212> TYPE: PRT
<213> ORGANISM: Methanococcus jannaschii

<400> SEQUENCE: 12

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Thr
            20                  25                  30
Ile Gly Phe Glu Pro Ser Gly Lys Ile His Leu Gly His Tyr Leu Gln
        35                  40                  45
Ile Lys Lys Met Ile Asp Leu Gln Asn Ala Gly Phe Asp Ile Ile Ile
    50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Asn Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Pro Leu His
145                 150                 155                 160
Tyr Gln Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
            180                 185                 190
Asn Pro Val Leu Thr Gly Leu Asp Gly Glu Gly Lys Met Ser Ser Ser
        195                 200                 205
Lys Gly Asn Phe Ile Ala Val Asp Asp Ser Pro Glu Glu Ile Arg Ala
    210                 215                 220
Lys Ile Lys Lys Ala Tyr Cys Pro Ala Gly Val Val Glu Gly Asn Pro
225                 230                 235                 240
```

```
Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 13
<211> LENGTH: 306
<212> TYPE: PRT
<213> ORGANISM: Methanococcus jannaschii

<400> SEQUENCE: 13

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285
```

```
Asn Ala Val Ala Glu Glu Leu Ile Lys Ile Leu Glu Pro Ile Arg Lys
    290                 295                 300

Arg Leu
305

<210> SEQ ID NO 14
<211> LENGTH: 306
<212> TYPE: PRT
<213> ORGANISM: Methanococcus jannaschii

<400> SEQUENCE: 14

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 15
<211> LENGTH: 306
<212> TYPE: PRT
<213> ORGANISM: Methanococcus jannaschii
```

<400> SEQUENCE: 15

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 16
<211> LENGTH: 306
<212> TYPE: PRT
<213> ORGANISM: Methanococcus jannaschii

<400> SEQUENCE: 16

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45
```

```
Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Phe Gln Leu Asp Lys
             100                 105                 110

Asp Tyr Thr Leu Asn Val Tyr Arg Leu Ala Leu Lys Thr Thr Leu Lys
             115                 120                 125

Arg Ala Arg Arg Ser Met Glu Leu Ile Ala Arg Glu Asp Glu Asn Pro
         130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                 165                 170                 175

His Met Leu Ala Arg Glu Leu Leu Pro Lys Lys Val Val Cys Ile His
             180                 185                 190

Asn Pro Val Leu Thr Gly Leu Asp Gly Glu Gly Lys Met Ser Ser Ser
             195                 200                 205

Lys Gly Asn Phe Ile Ala Val Asp Asp Ser Pro Glu Glu Ile Arg Ala
         210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                 245                 250                 255

Arg Pro Glu Lys Phe Gly Gly Asp Leu Thr Val Asn Ser Tyr Glu Glu
             260                 265                 270

Leu Glu Ser Leu Phe Lys Asn Lys Glu Leu His Pro Met Asp Leu Lys
         275                 280                 285

Asn Ala Val Ala Glu Glu Leu Ile Lys Ile Leu Glu Pro Ile Arg Lys
290                 295                 300

Arg Leu
305

<210> SEQ ID NO 17
<211> LENGTH: 306
<212> TYPE: PRT
<213> ORGANISM: Methanococcus jannaschii

<400> SEQUENCE: 17

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Leu
                 20                  25                  30

Ile Gly Phe Glu Pro Ser Gly Lys Ile His Leu Gly His Tyr Leu Gln
             35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Phe Gln Leu Asp Lys
             100                 105                 110
```

```
Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
        290                 295                 300

Arg Leu
305

<210> SEQ ID NO 18
<211> LENGTH: 306
<212> TYPE: PRT
<213> ORGANISM: Methanococcus jannaschii

<400> SEQUENCE: 18

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175
```

```
His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 19
<211> LENGTH: 306
<212> TYPE: PRT
<213> ORGANISM: Methanococcus jannaschii

<400> SEQUENCE: 19

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240
```

```
Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 20
<211> LENGTH: 306
<212> TYPE: PRT
<213> ORGANISM: Methanococcus jannaschii

<400> SEQUENCE: 20

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285
```

```
Asn Ala Val Ala Glu Glu Leu Ile Lys Ile Leu Glu Pro Ile Arg Lys
            290                 295                 300
Arg Leu
305
```

<210> SEQ ID NO 21
<211> LENGTH: 567
<212> TYPE: DNA
<213> ORGANISM: Homo sapiens

<400> SEQUENCE: 21

```
atggccttga cctttgcttt actggtggcc ctcctggtgc tcagctgcaa gtcaagctgc    60
tctgtgggct gtgatctgcc tcaaacccac agcctgggta gcaggaggac cttgatgctc   120
ctggcacaga tgaggagaat ctctcttttc tcctgcttga aggacagaca tgactttgga   180
tttccccagg aggagtttgg caaccagttc caaaaggctg aaaccatccc tgtcctccat   240
gagatgatcc agcagatctt caatctcttc agcacaaagg actcatctgc tgcttgggat   300
gagaccctcc tagacaaatt ctacactgaa ctctaccagc agctgaatga cctggaagcc   360
tgtgtgatac agggggtggg ggtgacagag actcccctga tgaaggagga ctccattctg   420
gctgtgagga atacttcca aagaatcact ctctatctga agagaagaa atacagccct    480
tgtgcctggg aggttgtcag agcagaaatc atgagatctt tttctttgtc aacaaacttg   540
caagaaagtt taagaagtaa ggaatga                                       567
```

<210> SEQ ID NO 22
<211> LENGTH: 498
<212> TYPE: DNA
<213> ORGANISM: Homo sapiens

<400> SEQUENCE: 22

```
tgtgatctgc ctcaaaccca cagcctgggt agcaggagga ccttgatgct cctggcacag    60
atgaggagaa tctctctttt tcctgcttg aaggacagac atgactttgg atttccccag   120
gaggagtttg gcaaccagtt ccaaaaggct gaaaccatcc ctgtcctcca tgagatgatc   180
cagcagatct tcaatctctt cagcacaaag gactcatctg ctgcttggga tgagaccctc   240
ctagacaaat tctacactga actctaccag cagctgaatg acctggaagc ctgtgtgata   300
cagggggtgg gggtgacaga gactcccctg atgaaggagg actccattct ggctgtgagg   360
aaatacttcc aaagaatcac tctctatctg aagagaaga atacagccc ttgtgcctgg   420
gaggttgtca gagcagaaat catgagatct ttttctttgt caacaaactt gcaagaaagt   480
ttaagaagta aggaatga                                                 498
```

<210> SEQ ID NO 23
<211> LENGTH: 182
<212> TYPE: PRT
<213> ORGANISM: Mus musculus

<400> SEQUENCE: 23

```
Met Leu Pro Val His Leu Phe Leu Val Gly Gly Val Met Leu Ser Cys
1               5                   10                  15
Ser Pro Ala Ser Ser Leu Asp Ser Gly Lys Ser Gly Ser Leu His Leu
            20                  25                  30
Glu Arg Ser Glu Thr Ala Arg Phe Leu Ala Glu Leu Arg Ser Val Pro
        35                  40                  45
Gly His Gln Cys Leu Arg Asp Arg Thr Asp Phe Pro Cys Pro Trp Lys
    50                  55                  60
```

```
Glu Gly Thr Asn Ile Thr Pro Met Thr Leu Gly Glu Thr Thr Ser Cys
 65              70              75              80

Tyr Ser Gln Thr Leu Lys Gln Val Leu His Leu Phe Asp Thr Glu Ala
             85              90              95

Ser Arg Ala Ala Trp His Glu Arg Ala Leu Asp Gln Leu Leu Ser Ser
            100             105             110

Leu Trp Arg Glu Leu Gln Val Leu Lys Arg Pro Arg Glu Gln Gly Gln
        115             120             125

Ser Cys Pro Leu Pro Phe Ala Leu Ala Ile Arg Thr Tyr Phe Arg Gly
    130             135             140

Phe Phe Arg Tyr Leu Lys Ala Lys Ala Tyr Ser Ala Cys Ser Trp Glu
145             150             155             160

Ile Val Arg Val Gln Leu Gln Val Asp Leu Pro Ala Phe Pro Leu Ser
                165             170             175

Ala Arg Arg Gly Pro Arg
            180
```

PEGYLATED HUMAN INTERFERON POLYPEPTIDES

CROSS-REFERENCE TO RELATED APPLICATIONS

This application is a continuation of International Patent Application No. PCT/US2006/021738 filed on Jun. 2, 2006, which is incorporated by reference herein in its entirety and claims the benefit of priority to U.S. provisional patent application 60/687,173 filed Jun. 3, 2005 and U.S. provisional patent application 60/753,375 filed Dec. 21, 2005 entitled "Improved Human Interferon Molecules and Their Uses", the specifications and disclosures of which are incorporated herein in their entirety for all purposes.

FIELD OF THE INVENTION

This invention relates to interferon polypeptides modified with at least one non-naturally encoded amino acid.

BACKGROUND OF THE INVENTION

The growth hormone (GH) supergene family (Bazan, F. *Immunology Today* 11: 350-354 (1990); Mott, H. R. and Campbell, I. D. *Current Opinion in Structural Biology* 5: 114-121 (1995); Silvennoinen, O. and Ihle, J. N. (1996) SIGNALING BY THE HEMATOPOIETIC CYTOKINE RECEPTORS) represents a set of proteins with similar structural characteristics. Each member of this family of proteins comprises a four helical bundle. While there are still more members of the family yet to be identified, some members of the family include the following: growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, gamma interferon, omega interferon, tau interferon, epsilon interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). Members of the GH supergene family have similar secondary and tertiary structures, despite the fact that they generally have limited amino acid or DNA sequence identity. The shared structural features allow new members of the gene family to be readily identified. The general structure of IFNα-2 is shown in FIG. 1.

Interferons are relatively small, single-chain glycoproteins released by cells invaded by viruses or exposed to certain other substances. Interferons are presently grouped into three major classes, designated: 1) leukocyte interferon (interferon-alpha, α-interferon, IFN-α), 2) fibroblast interferon (interferon-beta, β-interferon, IFN-β), and 3) immune interferon (interferon-gamma, γ-interferon, IFN-γ). In response to viral infection, lymphocytes synthesize primarily α-interferon (with omega interferon, IFN-ω), while infection of fibroblasts usually induces production of β-interferon. IFNα and IFNβ share about 20-30 percent amino acid sequence homology. The gene for human IFN-β lacks introns, and encodes a protein possessing 29% amino acid sequence identity with human IFN-α, suggesting that IFN-α and IFN-β genes have evolved from a common ancestor (Taniguchi et al., Nature 285 547-549 (1980)). By contrast, IFN-γ is synthesized by lymphocytes in response to mitogens. IFNα, IFNβ and IFNω are known to induce MHC Class I antigen expression and are referred to as type I interferons, while IFNγ induces MHC Class II antigen expression, and is referred to as type II interferon. Pestka et al. in Annu. Rev. Immunol. (2004) 22:929-79, which is incorporated by reference herein in its entirety, describes class 2 α-helical cytokines including interferons (IFN-α, -β, -ε, -κ, -ω, -δ, -τ, and -γ) as well as interferon-like molecules such as limitin, IL-28A, IL-28B, and IL-29 as well as the ligands, receptors, and signal transduction pathways employed by these molecules. The interferons have different species and many allelic variants. In additional, interferons with novel activities and mutant sequences have been isolated from cells from patients with various diseases.

A large number of distinct genes encoding different species of IFNα have been identified. Alpha interferons fall into two major classes, I and II, each containing a plurality of discrete proteins (Baron et al., Critical Reviews in Biotechnology 10, 179-190 (1990); Nagata et al., Nature 287, 401-408 (1980); Nagata et al., Nature 284, 316-320 (1980); Streuli et al., Science 209, 1343-1347 (1980); Goeddel et al., Nature 290, 20-26 (1981); Lawn et al., Science 212, 1159-1162 (1981); Ullrich et al., J. Mol. Biol. 156, 467-486 (1982); Weissmann et al., Phil. Trans. R. Soc. Lond. B299, 7-28 (1982); Lund et al., Proc. Natl. Acad. Sci. 81, 2435-2439 (1984); Capon et al., Mol. Cell. Biol. 5, 768 (1985)). The various IFN-α species include IFN-αA (IFN-α2), IFN-αB, IFN-αC, IFN-αC1, IFN-αD (IFN-α1), IFN-αE, IFN-αF, IFN-αG, IFN-αH, IFN-αI, IFN-αJ1, IFN-αJ2, IFN-αK, IFN-αL, IFN-α4B, IFN-α5, IFN-α6, IFN-α74, IFN-α76 IFN-α4a), IFN-α88, and alleles thereof. Trotta et al. in "Approval Standards for Alfa Interferon Subtypes" Drug Information Journal 34:1231-1246 (2000), which is incorporated by reference herein in its entirety, describe the members of the human IFN α gene family and proteins and the biological activities of this family including the immunomodulatory, antiproliferative, anti-viral and anti-microbial activities. The interferon proteins mentioned by Trotta et al. include IFN $\alpha_1$ (from $IFN_{A1}$ gene), IFN $\alpha_D$, IFN $\alpha_2$ (IFN $\alpha_{2b}$), IFN $\alpha_A$ (IFN $\alpha_{2a}$), IFN $\alpha_{2c}$, IFN $\alpha_{4a}$ (IFN $\alpha_{76}$), IFN $\alpha_{4b}$, IFN $\alpha_5$, IFN $\alpha_G$, IFN $\alpha_{61}$, IFN $\alpha_6$, IFN $\alpha_K$, IFN $\alpha_{54}$, IFN $\alpha_7$, IFN $\alpha_J$, IFN $\alpha_{J1}$, IFN $\alpha_8$, IFN $\alpha_{B2}$, IFN $\alpha_B$, IFN $\alpha_C$, ΨIFN $\alpha_{10}$, ΨIFN $\alpha_L$, IFN $\alpha_{6L}$, IFN $\alpha_{13}$, IFN $\alpha_{14}$, IFN $\alpha_H$, IFN $\alpha_{H1}$, IFN $\alpha_{16}$, IFN $\alpha_{WA}$, IFN $\alpha_O$, IFN $\alpha_{17}$, IFN $\alpha_1$ (from IFN$\alpha_{A17}$ gene), IFN $\alpha_{88}$, IFN $\alpha_1$ (from IFN$\alpha_{A21}$ gene), IFN $\alpha_F$, and ΨIFN $\alpha_E$. Trotta et al. also discuss the production, characterization, quality assurance, biological activity, and clinical safety and efficacy issues that relate to recombinant versions of proteins in this family. Release tests and physicochemical characterization tests are also discussed. IFN $\alpha_{21}$, IFN$\alpha_4$, IFN$\alpha_{10}$, and IFN $\alpha_3$ are other interferon proteins that have been previously described.

Interferons were originally derived from naturally occurring sources, such as buffy coat leukocytes and fibroblast cells, optionally using inducing agents to increase interferon production. Interferons have also been produced by recombinant DNA technology.

The cloning and expression of recombinant IFNαA (IFNαA, also known as IFNα2) was described by Goeddel et al., Nature 287, 411 (1980). The amino acid sequences of IFNαA, B, C, D, F, G, H, K and L, along with the encoding nucleotide sequences, are described by Pestka in Archiv. Biochem. Biophys. 221, 1 (1983). The cloning and expression of mature IFNβ is described by Goeddel et al., Nucleic Acids Res. 8, 4057 (1980). The cloning and expression of mature IFNγ are described by Gray et al., Nature 295, 503 (1982). IFNω has been described by Capon et al., Mol. Cell. Biol. 5, 768 (1985). IFNτ has been identified and disclosed by Whaley et al., J. Biol. Chem. 269, 10864-8 (1994).

Interferons have a variety of biological activities, including anti-viral, immunoregulatory and anti-proliferative properties, and have been utilized as therapeutic agents for treatment of diseases such as cancer, and various viral diseases. As a class, interferon-α's have been shown to inhibit various types of cellular proliferation, and are especially useful for the treatment of a variety of cellular proliferation disorders frequently associated with cancer, particularly hematologic malignancies such as leukemias. These proteins have shown anti-proliferative activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, E. M. et al. (1984) J. Biol. Response Modifiers 3:580; Oldham, R. K. (1985) Hospital Practice 20:71).

In addition, interferon-α may have important neuroregulatory functions in the CNS. Structural and functional similarities have been shown between IFNα and endorphins. It has been reported that the IFNα molecule contains distinct domains that mediate immune and opioid-like effects and that the μ opioid receptor may be involved in the analgesic effect of IFNα. Analgesic domains of the tertiary structure of interferon-α have been described which locate around the $122^{nd}$ Tyr residue of the molecule and includes the Phe residues 36, 38, and 123 (Wang et al. J. Neuroimmunol. (2000) 108:64-67 and Wang et al. NeuroReport (2001) 12 (4):857-859, which are incorporated by reference herein). Specifically, Wang et al. found that an interferon-α mutant at residue 36 (F36S) resulted in a complete loss of analgesic activity and a reduction of anti-viral activity. Another IFN-α mutant (F38S) resulted in a complete loss of analgesic activity and almost a complete loss of anti-viral activity. Other mutants of IFNα that have been studied include F38L and Y129S. Wang et al. describe these two mutants in studies investigating fever induced by human IFNα, and found that this side effect of IFNα therapy is mediated by IFNα's interaction with opioid receptor and a subsequent induction of prostaglandin $E_2$ (J. of Neuroimmunology (2004) 156:107-112). Modulating the interaction between IFN and opioid receptors may be critical in the development of novel IFN therapeutics to prevent side effects involving this family of receptors. Prostaglandins modulate CNS functions including but not limited to, the generation of fever, the sleep/wake cycle, and the perception of pain. They are produced by the enzymatic activity of cyclooxygenases COX-1 and COX-2.

The administration of IFN-α may also result in a number of neuropsychiatric side effects including depression (Wichers and Maes, Rev. Psychiat. Neurosci. (2004) 29(1):11-17). Wichers and Maes indicate serotonin (5-HT) brain neurotransmission and the induction of the enzyme IDO (indolamine 2,3-dioxygenase) are involved. Other hypotheses involve nitric oxide and soluble ICAM-1 induction by IFN. Modulating the mechanisms by which IFN causes such side effects may be critical in the development of novel IFN therapeutics.

Specific examples of commercially available IFN products include IFNγ-1b (ACTIMMUNE®), IFNβ-1a (AVONEX®, and REBIF®), IFNβ-1b (BETASERON®), IFN alfacon-1 (INFERGEN®), IFNα-2 (INTRON A®), IFNα-2a (ROFERON-A®), Peginterferon alfa-2a (PEGASYS®), and Peginterferon alfa-2b (PEGINTRON®). Some of the problems associated with the production of PEGylated versions of IFN proteins are described in Wang et al. (2002) Adv. Drug Deliv. Rev. 54:547-570; and Pedder, S. C. Semin Liver Dis. 2003;23 Suppl 1:19-22. Wang et al. characterized positional isomers of PEGINTRON®, and Pedder at al. compared PEGASYS® with PEGINTRON® describing the lability of the PEGylation chemistries used and effects upon formulation. PEGASYS® is comprised of nine identifiable isoforms, which specific isoforms differing in anti-viral activity (Foser et al., Pharmacogenomics J 2003; 3:312). Despite the number of IFN products currently available on the market, there is still an unmet need for interferon therapeutics. In particular, interferon therapeutics that modulate one or more side effects found with current IFN therapeutics are of interest.

Covalent attachment of the hydrophilic polymer poly(ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), J. Biol. Chem., 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are composed of various sequences of alpha-amino acids, which have the general structure $H_2N$—CHR—COOH. The alpha amino moiety ($H_2N$—) of one amino acid joins to the carboxyl moiety (—COOH) of an adjacent amino acid to form amide linkages, which can be represented as —(NH—CHR—CO)$_n$—, where the subscript "n" can equal hundreds or thousands. The fragment represented by R can contain reactive sites for protein biological activity and for attachment of PEG derivatives.

For example, in the case of the amino acid lysine, there exists an —$NH_2$ moiety in the epsilon position as well as in the alpha position. The epsilon —$NH_2$ is free for reaction under conditions of basic pH. Much of the art in the field of protein derivatization with PEG has been directed to developing PEG derivatives for attachment to the epsilon —$NH_2$ moiety of lysine residues present in proteins. "Polyethylene Glycol and Derivatives for Advanced PEGylation", Nektar Molecular Engineering Catalog, 2003, pp. 1-17. These PEG derivatives all have the common limitation, however, that they cannot be installed selectively among the often numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as —N(H)—, but many chemically reactive species that react with epsilon —$NH_2$ can also react with —N(H)—. Similarly, the side chain of the amino acid cysteine bears a free sulfhydryl group, represented structurally as —SH. In some instances, the PEG derivatives directed at the epsilon —$NH_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. See, e.g., U.S. Pat. No. 6,610,281 which is incorporated by reference herein, and "Polyethylene Glycol and Derivatives for Advanced PEGylation", Nektar Molecular Engineering Catalog, 2003, pp. 1-17. A cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into bioactive molecules that enables the selective coupling of one or more PEG polymers to the protein while simultaneously being compatible with (i.e., not engaging in undesired side reactions with) sulfhydryls and other chemical functional groups typically found in proteins.

As can be seen from a sampling of the art, many of these derivatives that have been developed for attachment to the side chains of proteins, in particular, the —$NH_2$ moiety on the lysine amino acid side chain and the —SH moiety on the cysteine side chain, have proven problematic in their synthesis and use. Some form unstable linkages with the protein that are subject to hydrolysis and therefore decompose, degrade, or are otherwise unstable in aqueous environments, such as in the bloodstream. See Pedder, S. C. Semin Liver Dis. 2003;23 Suppl 1:19-22 for a discussion of the stability of linkages in PEGINTRON®. Some form more stable linkages, but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results.

In order to overcome the challenges associated with modifying proteins with poly(ethylene glycol) moieties, PEG derivatives have been developed that are more stable (e.g., U.S. Pat. No. 6,602,498, which is incorporated by reference herein) or that react selectively with thiol moieties on molecules and surfaces (e.g., U.S. Pat. No. 6,610,281, which is incorporated by reference herein). There is clearly a need in the art for PEG derivatives that are chemically inert in physiological environments until called upon to react selectively to form stable chemical bonds.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Sacchromyces cerevisiae* (*S. cerevisiae*) (e.g., J. Chin et al., *Science* 301:964-7 (2003)), which has enabled the incorporation of non-genetically encoded amino acids to proteins in vivo. A number of new amino acids with novel chemical, physical or biological properties, including photoaffinity labels and photoisomerizable amino acids, photocrosslinking amino acids (see, e.g., Chin, J. W., et al. (2002) *Proc. Natl. Acad. Sci. U.S.A.* 99:11020-11024; and, Chin, J. W., et al., (2002) *J. Am. Chem. Soc.* 124:9026-9027), keto amino acids, heavy atom containing amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *Chem Bio Chem* 3 (11):1135-1137; J. W. Chin, et al., (2002), *PNAS United States of America* 99:11020-11024; and, L. Wang, & P. G. Schultz, (2002), *Chem. Comm.*, 1:1-11. All references are incorporated by reference in their entirety. These studies have demonstrated that it is possible to selectively and routinely introduce chemical functional groups, such as ketone groups, alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2]cycloaddition reaction in aqueous conditions in the presence of a catalytic amount of copper. See, e.g., Tomoe, et al., (2002) *J. Org. Chem.* 67:3057-3064; and, Rostovtsev, et al., (2002) *Angew. Chem. Int. Ed.* 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of interferon polypeptides, and also addresses the production of an interferon polypeptide with improved biological or pharmacological properties, such as improved therapeutic half-life and/or modulation of one or more biological activities or side effects found with current IFN therapeutics.

BRIEF SUMMARY OF THE INVENTION

This invention provides hIFN polypeptides comprising one or more non-naturally encoded amino acids.

In some embodiments, the hIFN polypeptide comprises one or more post-translational modifications. In some embodiments, the hIFN polypeptide is linked to a linker, polymer, or biologically active molecule. In some embodiments, the hIFN polypeptide is linked to a bifunctional polymer, bifunctional linker, or at least one additional hIFN polypeptide.

In some embodiments, the non-naturally encoded amino acid is linked to a water soluble polymer. In some embodiments, the water soluble polymer comprises a poly(ethylene glycol) moiety. In some embodiments, the non-naturally encoded amino acid is linked to the water soluble polymer with a linker or is bonded to the water soluble polymer. In some embodiments, the poly(ethylene glycol) molecule is a bifunctional polymer. In some embodiments, the bifunctional polymer is linked to a second polypeptide. In some embodiments, the second polypeptide is a hIFN polypeptide. In some embodiments, the hIFN polypeptide comprises one or more naturally-encoded amino acid substitutions, additions, or deletions. In some embodiments, the hIFN polypeptide comprises one or more naturally encoded amino acid substitutions.

In some embodiments, the hIFN polypeptide comprises at least two amino acids linked to a water soluble polymer comprising a poly(ethylene glycol) moiety. In some embodiments, at least one amino acid is a non-naturally encoded amino acid.

In some embodiments, one or more non-naturally encoded amino acids are incorporated at any position in one or more of the following regions corresponding to secondary structures in IFN as follows: 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus) (SEQ ID NO: 2, or the corresponding amino acids in SEQ ID NO: 1 or 3, other interferons, or interferon-like cytokines such as limitin). In some embodiments, one or more non-naturally encoded amino acid are substituted at, but not limited to, one or more of the following positions of hIFN (as in SEQ ID NO: 2, or the corresponding amino acid in SEQ ID NO: 1, 3, or any other IFN polypeptide): before position 1 (i.e., at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, or 166 (i.e. at the carboxyl terminus). In some embodiments, one or more non-naturally encoded amino acids are incorporated in one or more of the following positions in IFN: before position 1 (i.e. at the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus of the protein) (SEQ ID NO: 2, or the corresponding amino acids in SEQ ID NO: 1 or 3). In some embodiments, one or more non-naturally encoded amino acids are incorporated in one or more of the following positions in IFN: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acids in SEQ ID NO: 1 or 3). In some embodiments, the IFN polypeptides of the invention comprise one or more non-naturally encoded amino acids at one or more of the following positions: 100, 106, 107, 108, 111, 113, 114 (SEQ ID NO: 2, or the corresponding amino acids in SEQ ID NO: 1 or 3). In some embodiments, the IFN polypeptides of the invention comprise one or more non-naturally encoded amino acids at one or more of the following positions: 41, 45, 46, 48, 49 (SEQ ID NO: 2, or the corresponding amino acids in SEQ ID NO: 1 or 3). In some embodiments, the IFN polypeptides of the invention comprise one or more non-naturally encoded amino acids at one or more of the following positions: 61, 64, 65, 101, 103, 110, 117, 120, 121, 149 (SEQ ID NO: 2, or the corresponding amino acids in SEQ ID NO: 1 or 3). In some embodiments, the IFN polypeptides of the invention comprise one or more non-naturally encoded amino acids at one or more of the following positions: 6, 9, 12, 13, 16, 96, 156, 159, 160, 161, 162 (SEQ ID NO: 2, or the corresponding amino acids in SEQ ID NO: 1 or 3). In some embodiments, the IFN polypeptides of the invention comprise one or more non-naturally encoded amino acids at one or more of the following positions: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 2, or the corresponding amino acids in SEQ ID NO: 1 or 3). In some embodiments, the IFN polypeptides of the invention comprise one or more non-naturally encoded amino acids at one or more of the following positions: 34, 78, 107 (SEQ ID NO: 2, or the corresponding amino acid in SEQ ID NO: 1, 3, or any other IFN polypeptide). In some embodiments, the non-naturally encoded amino acid at one or more of these or other positions is linked to a water soluble polymer, including but not limited to positions: before position 1 (i.e., at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, or 166 (i.e. at the carboxyl terminus) (SEQ ID NO: 2, or the corresponding amino acid in SEQ ID NO: 1, 3, or any other IFN polypeptide). In some embodiments, the non-naturally encoded amino acid at one or more of these positions is linked to a water soluble polymer, including but not limited to positions: before position 1 (i.e. at the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus) (SEQ ID NO: 2, or the corresponding amino acids in SEQ ID NO: 1 or 3). In some embodiments, the non-naturally encoded amino acid is linked to a water soluble polymer at one or more of the following positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acids in SEQ ID NO: 1 or 3). In some embodiments, the non-naturally encoded amino acid is linked to a water soluble polymer at one or more of the following positions: 100, 106, 107, 108, 111, 113, 114 (SEQ ID NO: 2, or the corresponding amino acids in SEQ ID NO: 1 or 3). In some embodiments, the non-naturally encoded amino acid is linked to a water soluble polymer at one or more of the following positions: 41, 45, 46, 48, 49 (SEQ ID NO: 2, or the corresponding amino acids in SEQ ID NO: 1 or 3). In some embodiments, the non-naturally encoded amino acid is linked to a water soluble polymer at one or more of the following positions: 61, 64, 65, 101, 103, 110, 117, 120, 121, 149 (SEQ ID NO: 2, or the corresponding amino acids in SEQ ID NO: 1 or 3). In some embodiments, the non-naturally encoded amino acid is linked to a water soluble polymer at one or more of the following positions: 6, 9, 12, 13, 16, 96, 156, 159, 160, 161, 162 (SEQ ID NO: 2, or the corresponding amino acids in SEQ ID NO: 1 or 3).

In some embodiments, the one or more non-naturally encoded amino acids at one or more of the following positions is linked to one or more water-soluble polymer: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 2, or the corresponding amino acid in or the corresponding amino acid in SEQ ID NO: 1, 3, or any other IFN polypeptide). In some embodiments, the one or more non-naturally encoded amino acids at one or more of the following positions is linked to one or more water-soluble polymer: 34, 78, 107 (SEQ ID NO: 2, or the corresponding amino acid in SEQ ID NO: 1, 3, or any other IFN polypeptide). In some embodiments, the water soluble polymer is coupled to the IFN polypeptide to a non-naturally encoded amino acid at one or more of the following amino acid positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acid in SEQ ID NO: 1, 3, or any other IFN polypeptide). In some embodiments the water soluble polymer is coupled to the IFN polypeptide at one or more of the following amino acid positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acid in SEQ ID NO: 1, 3, or any other IFN polypeptide). In some embodiments, the non-naturally encoded amino acid at one or more of these positions is linked to one or more water soluble polymers, positions: 34, 78, 107 (SEQ ID NO: 2, or the corresponding amino acid in or the corresponding amino acid in SEQ ID NO: 1, 3, or any other IFN polypeptide). In some embodiments, the IFN polypeptides of the invention comprise one or more non-naturally encoded amino acids at one or more of the following positions providing an antagonist: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 2, or the corresponding amino acid in or the corresponding amino acid in SEQ ID NO: 1, 3, or any other IFN polypeptide); a hIFN polypeptide comprising one of these substitutions may potentially act as a weak antagonist or weak agonist depending on the intended site selected and desired activity. Human IFN antagonists include, but are not limited to, hIFN polypeptides with one or more non-naturally encoded amino acid substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combinations thereof (hIFN; SEQ ID NO: 2 or the corresponding amino acids in SEQ ID NO: 1 or 3, or any other IFN polypeptide).

In some embodiments, one or more non-naturally encoded amino acids are substituted at, but not limited to, one or more of the following positions of hIFN (as in SEQ ID NO: 2, or the corresponding amino acids in SEQ ID NO: 1 or 3, or any other IFN polypeptide): 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 12, 13, 16, 68, 70, 109, 159, 161, 156, 160, 162, 24, 27, 78, 83, 85, 87, 89, 164. In one embodiment, a non-naturally encoded amino acid is substituted at position 38 of hIFN (as in SEQ ID NO: 2, or the corresponding amino acids in SEQ ID NO: 1 or 3, or any other IFN polypeptide). In some embodiments, the non-naturally encoded amino acid at one or more of these or other positions is linked to a water soluble polymer, including but not limited to positions: 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 12, 13, 16, 68, 70, 109, 159, 161, 156, 160, 162, 24, 27, 78, 83, 85, 87, 89, 164 (as in SEQ ID NO: 2, or the corresponding amino acids in SEQ ID NO: 1 or 3, or any other IFN polypeptide).

In some embodiments, one or more non-naturally encoded amino acids are substituted at, but not limited to, one or more of the following positions of hIFN (SEQ ID NO: 2 or the corresponding amino acids in SEQ ID NO: 1 or 3): before position 1 (i.e., at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, or 166 (i.e. at the carboxyl terminus) and one or more natural amino acid substitutions. In some embodiments, the one or more non-naturally encoded amino acids are coupled to a water soluble polymer. In some embodiments, the one or more non-naturally encoded amino acids are coupled to PEG. In one embodiment, the natural amino acid substitution is R149Y. In some embodiments, the natural amino acid substitution is R149E. In some embodiments, the natural amino acid substitution is R149S. In one embodiment, the non-natural amino acid substitution is at position 107 and the natural amino acid substitution is R149Y. In one embodiment, the non-natural amino acid substitution is at position 106 and the natural amino acid substitution is R149Y. In some embodiments, the one or more naturally encoded amino acid substitution is at one or more of the following positions of hIFN (SEQ ID NO:

2 or the corresponding amino acids in SEQ ID NO; 1 or 3), including but not limited to: 10, 16, 13, 79, 83, 85, 86, 87, 90, 91, 93, 94, 96, 120, 121, 124, 125, 128, 149. In some embodiments, the one or more naturally encoded amino acid substitution is one or more of the following substitutions (SEQ ID NO: 2 or the corresponding amino acids in SEQ ID NO: 1 or 3), including but not limited to: G10E, M16R, R13E, T79R, K83Q, K83S, Y85L, T86S, E87S, Q90R, Q91E, N93Q, D94V, E96K, R120K, K121T, Q124R, R125G, L128R, R149Y, R149E, R149S. In some embodiments, the natural amino acid substitution is at position 1 (the N-terminus). In some embodiments, one or more non-naturally encoded amino acids are substituted at one or more of the following positions of hIFN (as in SEQ ID NO: 2, or the corresponding amino acids in other IFN's): 107, 78, 34. In some embodiments, the non-naturally encoded amino acid at one or more of these positions is coupled to a water soluble polymer: 107, 78, 34.

One or more amino acids found in a limitin sequence may be substituted into a hIFN polypeptide (hybrid limitin/hIFN polypeptides). Examples include but are not limited to the natural amino acid substitutions described in the previous paragraph. Alternatively, a set of amino acids found in an interferon polypeptide may be replaced by a set of amino acids found in a limitin sequence. A set of amino acids may comprise contiguous amino acids or amino acids present in different portions of the molecule but are involved in a structural characteristic or biological activity of the polypeptide. The mouse limitin molecule has an improved CFU-GM toxicity profile compared to other IFNα proteins. Alignment of human IFNα-2a with the limitin protein sequence showed 30% amino acid identity. 50% sequence conservation was also observed. In particular, a prominent deletion in the limitin sequence between the C and D helices (in the loop between C and D helices) was observed. The "HV" mutant was generated with the following substitutions in hIFNα-2a (SEQ ID NO: 2): D77-D94 is replaced with the mouse limitin sequence HERALDQLLSSLWRELQV. The "CD" mutant was generated with the following substitutions in hIFNα-2a (SEQ ID NO: 2): V105-D114 with GQSAPLP. This hybrid molecule with the loop region from limitin substituted into the human IFNα-2a protein ("CD" mutant) was found to have equivalent anti-viral activity as the WHO IFN standard. In addition to the one or more limitin amino acids, the hIFN polypeptide may comprise one or more non-naturally encoded amino acids at any one or more positions of the hIFN polypeptide. In some embodiments, the one or more non-naturally encoded amino acids may be linked to a water soluble polymer such as PEG or bonded directly to a water soluble polymer such as PEG. In addition to the natural amino acid substitutions in the HV or the CD mutant, one or more additional natural amino acid substitutions may be found in the hIFN polypeptide.

In some embodiments, the hIFN polypeptide comprises one or more non-naturally encoded amino acids at one or more of the following positions: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide). In some embodiments, the hIFN polypeptide comprises one or more non-naturally encoded amino acids at one or more of the following positions linked to one or more water-soluble polymer: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide). In some embodiments, the hIFN polypeptide comprises one or more non-naturally encoded amino acids at one or more of the following positions linked to one or more water-soluble polymer: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide) and comprises one or more naturally encoded amino acid substitution. In some embodiments, the hIFN polypeptide comprises one or more non-naturally encoded amino acids at one or more of the following positions linked to one or more water-soluble polymer: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide) and comprises one or more of the following naturally encoded amino acid substitutions G10E, M16R, R13E, T79R, K83Q, K83S, Y85L, T86S, E87S, Q90R, Q91E, N93Q, D94V, E96K, R120K, K121T, Q124R, R125G, L128R, R149Y, R149E, R149S.

In some embodiments, the hIFN polypeptide comprises one or more non-naturally encoded amino acids at one or more of the following positions: 6, 16, 37, 45, 46, 78, 87, 89, 107, 108 (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 89, 107, 108 (SEQ ID NO: 2 or the corresponding amino acids in SEQ ID NO: 1 or 3) that is linked to a water soluble polymer. In some embodiments, the hIFN polypeptide comprises one or more non-naturally encoded amino acids at one or more of the following positions: 6, 16, 37, 45, 46, 78, 87, 89, 107, 108 (SEQ ID NO: 2 or the corresponding amino acids in SEQ ID NO: 1 or 3) that is bonded to a water soluble polymer.

In some embodiments, the hIFN polypeptide comprises one or more non-naturally encoded amino acids at one or more of the following positions: 6, 16, 37, 45, 46, 78, 87, 89, 107, 108 and one or more of the following naturally encoded amino acid substitutions: T79R, L80A, K83S, Y85L, Y85S, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 89, 107, 108 that is linked to a water soluble polymer and comprises one or more of the following naturally encoded amino acid substitutions: T79R, L80A, K83S, Y85L, Y85S, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 89, 107, 108 that is bonded to a water soluble polymer and comprises one or more of the following naturally encoded amino acid substitutions: T79R, L80A, K83S, Y85L, Y85S, T86S, E87S, Q91E (SEQ ID NO: 2 or the corresponding amino acids in SEQ ID NO: 1 or 3).

In some embodiments, the hIFN polypeptide comprises one or more non-naturally encoded amino acids at one or more of the following positions: 6, 16, 37, 45, 46, 78, 87, 107, and 108 (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 107, and 108 (SEQ ID NO: 2 or the corresponding amino acids in SEQ ID NO: 1 or 3) that is linked to a water soluble polymer. In some embodiments, the hIFN polypeptide comprises one or more non-naturally encoded amino acids at one or more of the following positions: 6, 16, 37, 45, 46, 78, 87, 107, and 108 (SEQ ID NO: 2 or the corresponding amino acids in SEQ ID NO: 1 or 3) that is bonded to a water soluble polymer.

In some embodiments, the hIFN polypeptide comprises one or more non-naturally encoded amino acids at one or more of the following positions: 6, 16, 37, 45, 46, 78, 87, 107, and 108 and comprises one or more of the following naturally encoded amino acid substitutions: T79R, K83S, Y85L, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 107, and 108 that is linked to a water soluble polymer and comprises one or more of the following naturally encoded amino acid substitutions: T79R, K83S, Y85L, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 107, and 108 that is bonded to a water soluble polymer and comprises one or more of the following naturally encoded amino acid substitutions: T79R, K83S, Y85L, T86S, E87S, Q91E (SEQ ID NO: 2 or the corresponding amino acids in SEQ ID NO: 1 or 3).

In some embodiments, the hIFN polypeptide comprises one or more non-naturally encoded amino acids at one or more of the following positions: 37, 45, 46, 89, and 107 (SEQ ID NO: 2 or the corresponding amino acids in SEQ ID NO: 1 or 3). In some embodiments, the hIFN polypeptide comprises one or more non-naturally encoded amino acids at one or more of the following positions: 37, 45, 46, 89, and 107 (SEQ ID NO: 2 or the corresponding amino acids in SEQ ID NO: 1 or 3) that is linked to a water soluble polymer. In some embodiments, the hIFN polypeptide comprises one or more non-naturally encoded amino acids at one or more of the following positions: 37, 45, 46, 89, and 107 (SEQ ID NO: 2 or the corresponding amino acids in SEQ ID NO: 1 or 3) that is bonded to a water soluble polymer.

In some embodiments, the hIFN polypeptide comprises one or more non-naturally encoded amino acids at one or more of the following positions: 37, 45, 46, 89, and 107 and comprises one or more of the following naturally encoded amino acid substitutions: T79R, L80A, Y85L, Y85S, E87S (SEQ ID NO: 2 or the corresponding amino acids in SEQ ID NO: 1 or 3). In some embodiments, the hIFN polypeptide comprises one or more non-naturally encoded amino acids at one or more of the following positions: 37, 45, 46, 89, and 107 that is linked to a water soluble polymer and comprises one or more of the following naturally encoded amino acid substitutions: T79R, L80A, Y85L, Y85S, E87S (SEQ ID NO: 2 or the corresponding amino acids in SEQ ID NO: 1 or 3). In some embodiments, the hIFN polypeptide comprises one or more non-naturally encoded amino acids at one or more of the following positions: 37, 45, 46, 89, and 107 that is bonded to a water soluble polymer and comprises one or more of the following naturally encoded amino acid substitutions: T79R, L80A, Y85L, Y85S, E87S (SEQ ID NO: 2 or the corresponding amino acids in SEQ ID NO: 1 or 3).

In some embodiments, the hIFN polypeptide comprises one or more non-naturally encoded amino acids at one or more of the following positions: 23, 24, 25, 26, 27, 28, 30, 31, 32, 33, 128, 129, 131, 132, 133, 134, 135, 136, 137, 158, 159, 160, 161, 162, 163, 164, 165 (SEQ ID NO: 2 or the corresponding amino acids in SEQ ID NO: 1 or 3). In some embodiments, the hIFN polypeptide comprises one or more non-naturally encoded amino acids at one or more of the following positions that is linked or bonded to a water soluble polymer: 23, 24, 25, 26, 27, 28, 30, 31, 32, 33, 128, 129, 131, 132, 133, 134, 135, 136, 137, 158, 159, 160, 161, 162, 163, 164, 165 (SEQ ID NO: 2 or the corresponding amino acids in SEQ ID NO: 1 or 3). In some embodiments, the hIFN polypeptide comprises one or more non-naturally encoded amino acids at one or more of the following positions: 23, 24, 27, 31, 128, 131, 134, 158 (SEQ ID NO: 2 or the corresponding amino acids in SEQ ID NO: 1 or 3). In some embodiments, the hIFN polypeptide comprises one or more non-naturally encoded amino acids at one or more of the following positions that is linked or bonded to a water soluble polymer: 23, 24, 27, 31, 128, 131, 134, 158 (SEQ ID NO: 2 or the corresponding amino acids in SEQ ID NO: 1 or 3). In some embodiments, the hIFN polypeptide comprises one or more non-naturally encoded amino acids at one or more of the following positions: 24, 27, 31, 128, 131, 134 (SEQ ID NO: 2 or the corresponding amino acids in SEQ ID NO: 1 or 3). In some embodiments, the hIFN polypeptide comprises one or more non-naturally encoded amino acids at one or more of the following positions that is linked or bonded to a water soluble polymer: 24, 27, 31, 128, 131, 134 (SEQ ID NO: 2 or the corresponding amino acids in SEQ ID NO: 1 or 3).

In some embodiments, the IFN polypeptides of the invention comprise one or more non-naturally encoded amino acids at one or more of the following positions providing an antagonist: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165, or any combination thereof (SEQ ID NO: 2, or the corresponding amino acids in SEQ ID NO: 1 or 3); a hIFN polypeptide comprising one of these substitutions may potentially act as a weak antagonist or weak agonist depending on the site selected and desired activity. Human IFN antagonists include, but are not limited to, those with one or more substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combination thereof (hIFN; SEQ ID NO: 2 or the corresponding amino acids in SEQ ID NO: 1 or 3).

In some embodiments, one or more non-naturally encoded amino acids are substituted at, but not limited to, one or more of the following positions of hIFN (as in SEQ ID NO: 2, or the corresponding amino acids in other IFN's): 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 12, 13, 16, 68, 70, 109, 159, 161, 156, 160, 162, 24, 27, 78, 83, 85, 87, 89, 164. In one embodiment, a non-naturally encoded amino acid is substituted at position 38 of hIFN (as in SEQ ID NO: 2, or the corresponding amino acids in other IFN's). In some embodiments, the non-naturally encoded amino acid at these or other positions is linked to a water soluble polymer, including but not limited to positions: 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 12, 13, 16, 68, 70, 109, 159, 161, 156, 160, 162, 24, 27, 78, 83, 85, 87, 89, 164.

In some embodiments, the hIFN polypeptide comprises one or more non-naturally encoded amino acid and a naturally encoded amino acid substitution. In some embodiments, the non-naturally encoded amino acid present in the hIFN polypeptide is linked to a water soluble polymer and the hIFN polypeptide comprises one or more naturally encoded amino acid substitution.

In some embodiments, the hIFN polypeptide comprises a substitution, addition or deletion that modulates affinity of the hIFN polypeptide for a hIFN polypeptide receptor. In some embodiments, the hIFN polypeptide comprises a substitution, addition, or deletion that increases the stability of the hIFN polypeptide when compared with the stability of the corresponding hIFN without the substitution, addition, or deletion. In some embodiments, the hIFN polypeptide comprises a substitution, addition, or deletion that modulates the immunogenicity of the hIFN polypeptide when compared with the immunogenicity of the corresponding hIFN without the substitution, addition, or deletion. In some embodiments, the hIFN polypeptide comprises a substitution, addition, or deletion that modulates serum half-life or circulation time of the hIFN polypeptide when compared with the serum half-life or circulation time of the corresponding hIFN without the substitution, addition, or deletion.

In some embodiments, the hIFN polypeptide comprises a substitution, addition, or deletion that modulates hIFN polypeptide receptor conformation when compared with hIFN polypeptide receptor conformation with the corresponding hIFN without the substitution, addition, or deletion. In some embodiments, the hIFN polypeptide comprises a substitution, addition, or deletion that modulates one or more downstream signaling events of the hIFN polypeptide receptor when compared to the downstream signaling events of the hIFN polypeptide receptor with the corresponding hIFN without the substitution, addition, or deletion. In some embodiments, the hIFN polypeptide comprises a substitution, addition, or deletion that modulates hIFN polypeptide receptor binding kinetics when compared to hIFN polypeptide receptor binding kinetics with the corresponding hIFN without the substitution, addition, or deletion.

In some embodiments, the hIFN polypeptide comprises a substitution, addition, or deletion that increases the aqueous solubility of the hIFN polypeptide when compared to aqueous solubility of the corresponding hIFN without the substitution, addition, or deletion. In some embodiments, the hIFN polypeptide comprises a substitution, addition, or deletion that increases the solubility of the hIFN polypeptide produced in a host cell when compared to the solubility of the corresponding hIFN without the substitution, addition, or deletion. In some embodiments, the hIFN polypeptide comprises a substitution, addition, or deletion that increases the expression of the hIFN polypeptide in a host cell or increases synthesis in vitro when compared to the expression or synthesis of the corresponding hIFN without the substitution, addition, or deletion. In some embodiments, the hIFN polypeptide comprises a substitution, addition, or deletion that increases protease resistance of the hIFN polypeptide when compared to the protease resistance of the corresponding hIFN without the substitution, addition, or deletion. In some embodiments, the hIFN polypeptide comprises a substitution, addition, or deletion that modulates interaction with one or more members of the opioid family of receptors. In some embodiments, the hIFN polypeptide comprises a substitution, addition, or deletion that modulates 5-HT brain neurotransmission. In some embodiments, the hIFN polypeptide comprises a substitution, addition, or deletion that modulates induction of indoleamine 2,3-dioxygenase (IDO). In some embodiments, the hIFN polypeptide comprises a substitution, addition, or deletion that modulates one or more of the biological activities of IFN, including but not limited to, side effects found with current IFN therapeutics. In some embodiments, the hIFN polypeptide comprises a substitution, addition, or deletion that has modulated toxicity when compared to the toxicity of the corresponding hIFN without the substitution, addition, or deletion. In some embodiments, the hIFN polypeptide comprises a non-naturally encoded amino acid linked to a water soluble polymer that modulates one or more side effects found with IFN. In some embodiments, the hIFN polypeptide comprises a non-naturally encoded amino acid linked to a water soluble polymer and has modulated toxicity. In some embodiments, the hIFN polypeptide comprises a substitution, addition, deletion, or non-naturally encoded amino acid that has modulated anti-viral activity when compared to the anti-viral activity of the corresponding hIFN without the substitution, addition, deletion, or non-naturally encoded amino acid. In some embodiments, the hIFN polypeptide comprises a substitution, addition, deletion, or non-naturally encoded amino acid that has modulated immunogenicity when compared to the immunogenicity of the corresponding hIFN without the substitution, addition, deletion, or non-naturally encoded amino acid. In some embodiments, the hIFN polypeptide comprises a substitution, addition, deletion, or non-naturally encoded amino acid that has modulated anti-tumor activity when compared to the anti-tumor activity of the corresponding hIFN without the substitution, addition, deletion, or non-naturally encoded amino acid. In some embodiments, the hIFN polypeptide comprises a substitution, addition, deletion, or non-naturally encoded amino acid that has modulated anti-infective activity when compared to the anti-infective activity of the corresponding hIFN without the substitution, addition, deletion, or non-naturally encoded amino acid. In some embodiments, the hIFN polypeptide comprises a substitution, addition, deletion, or non-naturally encoded amino acid that has modulated prophylaxis activity for infectious agents when compared to the prophylaxis activity for infectious agents of the corresponding hIFN without the substitution, addition, deletion, or non-naturally encoded amino acid. In some embodiments, the hIFN polypeptide comprises a substitution, addition, deletion, or non-naturally encoded amino acid that has modulated tumor prophylaxis activity when compared to the tumor prophylaxis activity of the corresponding hIFN without the substitution, addition, deletion, or non-naturally encoded amino acid.

In some embodiments the amino acid substitutions in the hIFN polypeptide may be with naturally occurring or non-naturally occurring amino acids, provided that at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

$$\underset{R_3HN}{\overset{(CH_2)_nR_1COR_2}{\bigwedge}}COR_4$$

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

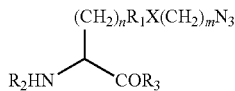

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

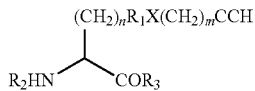

wherein n is 0-10; $R_1$ is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is a hIFN polypeptide agonist, partial agonist, antagonist, partial antagonist, or inverse agonist. In some embodiments, the hIFN polypeptide agonist, partial agonist, antagonist, partial antagonist, or inverse agonist comprises a non-naturally encoded amino acid linked to a water soluble polymer. In some embodiments, the water soluble polymer comprises a poly(ethylene glycol) moiety. In some embodiments, the hIFN polypeptide agonist, partial agonist, antagonist, partial antagonist, or inverse agonist comprises a non-naturally encoded amino acid and one or more post-translational modification, linker, polymer, or biologically active molecule. In some embodiments, the non-naturally encoded amino acid linked to a water soluble polymer is present within the Site II region (the region of the protein encompassing the AC helical-bundle face, amino terminal region of helix A and a portion of helix C) of the hIFN polypeptide. In some embodiments, the hIFN polypeptide comprising a non-naturally encoded amino acid linked to a water soluble polymer prevents dimerization of the hIFN polypeptide receptor by preventing the hIFN polypeptide antagonist from binding to a second hIFN polypeptide receptor molecule.

The present invention also provides isolated nucleic acids comprising a polynucleotide that hybridizes under stringent conditions to SEQ ID NO: 21 or 22 wherein the polynucleotide comprises at least one selector codon. In some embodiments, the selector codon is selected from the group consisting of an amber codon, ochre codon, opal codon, a unique codon, a rare codon, a five-base codon, and a four-base codon.

The present invention also provides methods of making a hIFN polypeptide linked to a water soluble polymer. In some embodiments, the method comprises contacting an isolated hIFN polypeptide comprising a non-naturally encoded amino acid with a water soluble polymer comprising a moiety that reacts with the non-naturally encoded amino acid. In some embodiments, the non-naturally encoded amino acid incorporated into the hIFN polypeptide is reactive toward a water soluble polymer that is otherwise unreactive toward any of the 20 common amino acids. In some embodiments, the non-naturally encoded amino acid incorporated into the hIFN polypeptide is reactive toward a linker, polymer, or biologically active molecule that is otherwise unreactive toward any of the 20 common amino acids.

In some embodiments, the hIFN polypeptide linked to the water soluble polymer is made by reacting a hIFN polypeptide comprising a carbonyl-containing amino acid with a poly(ethylene glycol) molecule comprising an aminooxy, hydrazine, hydrazide or semicarbazide group. In some embodiments, the aminooxy, hydrazine, hydrazide or semicarbazide group is linked to the poly(ethylene glycol) molecule through an amide linkage.

In some embodiments, the hIFN polypeptide linked to the water soluble polymer is made by reacting a poly(ethylene glycol) molecule comprising a carbonyl group with a polypeptide comprising a non-naturally encoded amino acid that comprises an aminooxy, hydrazine, hydrazide or semicarbazide group.

In some embodiments, the hIFN polypeptide linked to the water soluble polymer is made by reacting a hIFN polypeptide comprising an alkyne-containing amino acid with a poly (ethylene glycol) molecule comprising an azide moiety. In some embodiments, the azide or alkyne group is linked to the poly(ethylene glycol) molecule through an amide linkage.

In some embodiments, the hIFN polypeptide linked to the water soluble polymer is made by reacting a hIFN polypeptide comprising an azide-containing amino acid with a poly (ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 0.1 and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some embodiments, the water soluble polymer linked to the hIFN polypeptide comprises a polyalkylene glycol moiety. In some embodiments, the non-naturally encoded amino acid residue incorporated into the hIFN polypeptide comprises a carbonyl group, an aminooxy group, a hydrazide group, a hydrazine, a semicarbazide group, an azide group, or an alkyne group. In some embodiments, the non-naturally encoded amino acid residue incorporated into the hIFN polypeptide comprises a carbonyl moiety and the water soluble polymer comprises an aminooxy, hydrazide, hydrazine, or semicarbazide moiety. In some embodiments, the non-naturally encoded amino acid residue incorporated into the hIFN polypeptide comprises an alkyne moiety and the water soluble polymer comprises an azide moiety. In some embodiments, the non-naturally encoded amino acid residue incorporated into the hIFN polypeptide comprises an azide moiety and the water soluble polymer comprises an alkyne moiety.

The present invention also provides compositions comprising a hIFN polypeptide comprising a non-naturally encoded amino acid and a pharmaceutically acceptable carrier. In some embodiments, the non-naturally encoded amino acid is linked to a water soluble polymer.

The present invention also provides cells comprising a polynucleotide encoding the hIFN polypeptide comprising a selector codon. In some embodiments, the cells comprise an orthogonal RNA synthetase and/or an orthogonal tRNA for substituting a non-naturally encoded amino acid into the hIFN polypeptide.

The present invention also provides methods of making a hIFN polypeptide comprising a non-naturally encoded amino acid. In some embodiments, the methods comprise culturing cells comprising a polynucleotide or polynucleotides encoding a hIFN polypeptide, an orthogonal RNA synthetase and/or an orthogonal tRNA under conditions to permit expression of the hIFN polypeptide; and purifying the hIFN polypeptide from the cells and/or culture medium.

The present invention also provides methods of increasing therapeutic half-life, serum half-life or circulation time of hIFN polypeptides. The present invention also provides methods of modulating immunogenicity of hIFN polypeptides. The present invention also provides methods of modulating toxicity of hIFN polypeptides. The present invention also provides methods of modulating side effects of current IFN therapeutics. In some embodiments, the methods comprise substituting a non-naturally encoded amino acid for any one or more amino acids in naturally occurring hIFN polypeptides and/or linking the hIFN polypeptide to a linker, a polymer, a water soluble polymer, or a biologically active molecule.

The present invention also provides methods of treating a patient in need of such treatment with an effective amount of a hIFN molecule of the present invention. In some embodiments, the methods comprise administering to the patient a therapeutically-effective amount of a pharmaceutical composition comprising a hIFN polypeptide comprising a non-naturally-encoded amino acid and a pharmaceutically acceptable carrier. In some embodiments, the non-naturally encoded amino acid is linked to a water soluble polymer.

The present invention also provides hIFN polypeptides comprising a sequence shown in SEQ ID NO: 1, 2, 3 or any other hIFN polypeptide sequence or interferon-like cytokine such as limitin, except that at least one amino acid is substituted by a non-naturally encoded amino acid. In some embodiments, the non-naturally encoded amino acid is linked to a water soluble polymer. In some embodiments, the water soluble polymer comprises a poly(ethylene glycol) moiety. In some embodiments, the non-naturally encoded amino acid comprises a carbonyl group, an aminooxy group, a hydrazide group, a hydrazine group, a semicarbazide group, an azide group, or an alkyne group.

The present invention also provides pharmaceutical compositions comprising a pharmaceutically acceptable carrier and a hIFN polypeptide comprising the sequence shown in SEQ ID NO: 1, 2, 3 or any other IFN polypeptide sequence or interferon-like cytokine such as limitin, wherein at least one amino acid is substituted by a non-naturally encoded amino acid. In some embodiments, the non-naturally encoded amino acid comprises a saccharide moiety. In some embodiments, the water soluble polymer is linked to the polypeptide via a saccharide moiety. In some embodiments, a linker, polymer, or biologically active molecule is linked to the hIFN polypeptide via a saccharide moiety.

The present invention also provides a hIFN polypeptide comprising a water soluble polymer linked by a covalent bond to the hIFN polypeptide at a single amino acid. In some embodiments, the water soluble polymer comprises a poly(ethylene glycol) moiety. In some embodiments, the amino acid covalently linked to the water soluble polymer is a non-naturally encoded amino acid present in the polypeptide.

The present invention provides a hIFN polypeptide comprising at least one linker, polymer, or biologically active molecule, wherein said linker, polymer, or biologically active molecule is attached to the polypeptide through a functional group of a non-naturally encoded amino acid ribosomally incorporated into the polypeptide. In some embodiments, the polypeptide is monoPEGylated. The present invention also provides a hIFN polypeptide comprising a linker, polymer, or biologically active molecule that is attached to one or more non-naturally encoded amino acid wherein said non-naturally encoded amino acid is ribosomally incorporated into the polypeptide at pre-selected sites.

In another embodiment, conjugation of the hIFN polypeptide comprising one or more non-naturally occurring amino acids to another molecule, including but not limited to PEG, provides substantially purified hIFN due to the unique chemical reaction utilized for conjugation to the non-natural amino acid. Conjugation of hIFN comprising one or more non-naturally encoded amino acids to another molecule, such as PEG, may be performed with other purification techniques performed prior to or following the conjugation step to provide substantially pure hIFN.

DEFINITIONS

Figure 1:
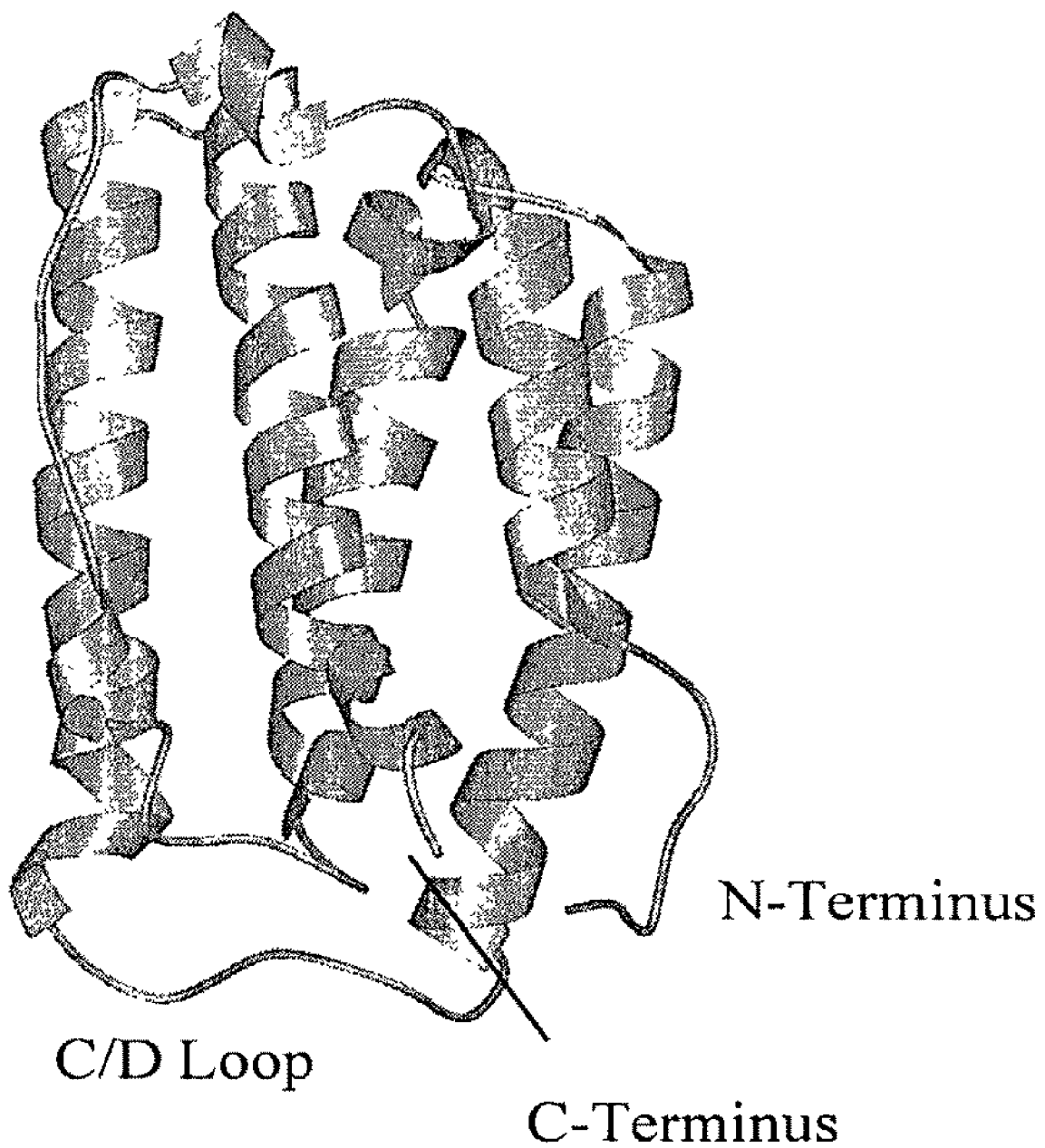
FIG. 1—A diagram of the general structure for the four helical bundle protein Interferon alpha-2 (IFNα-2) is shown.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "hIFN" is a reference to one or more such proteins and includes equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to a hIFN polypeptide that may be substantially or essentially free of components that normally accompany or interact with the protein as found in its naturally occurring environment, i.e. a native cell, or host cell in the case of recombinantly produced hIFN polypeptides. hIFN polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the hIFN polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the hIFN polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" hIFN polypeptide as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the hIFN polypeptide has been secreted, including medium either before or after a proliferation step. The term also may encompass buffers or reagents that contain host cell lysates, such as in the case where the hIFN polypeptide is produced intracellularly and the host cells are lysed or disrupted to release the hIFN polypeptide.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used hereinwith respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N->2, 3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

As used herein, "interferon" or "IFN" shall include those polypeptides and proteins that have at least one biological activity of an interferon, including but not limited to IFNα, IFNβ, IFNγ, IFNω, IFNε, or IFNτ or interferon-like cytokines such as limitin (such as those described in U.S. Pat. Nos. 4,414,150; 4,456,748; 4,727,138; 4,762,791, 4,929,554; 5,096,705; 4,695,623; 4,614,651; 4,678,751; 4,925,793; 5,460,811; 5,120,832; 4,780,530; 4,908,432; 4,970,161; 4,973,479; 4,975,276; 5,098,703; 5,278,286; 5,661,009; 6,372,206; 6,433,144; 6,472,512; 6,572,853; 6,703,225; 6,200,780; 6,299,869; 6,300,475; 6,323,006; 6,350,589; 5,705,363; 5,738,845; 5,789,551; 6,117,423; 6,174,996; 5,540,923; 5,541,293; 5,541,312; 5,554,513; 5,593,667 which are incorporated by reference herein), as well as IFN analogs, IFN isoforms, IFN mimetics, IFN fragments, hybrid IFN proteins, fusion proteins, oligomers and multimers, homologues, glycosylation pattern variants, variants, splice variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. Specific examples of IFN include, but are not limited to, IFNγ-1b (ACTIMMUNE®), IFNβ-1a (AVONEX®, and REBIF®), IFNβ-1b (BETASERON®), consensus IFN, IFN alfacon-1 (INFERGEN®), IFNα-2 (INTRON A®), IFNα-2a (ROFERON-A®), Peginterferon alfa-2a (PEGASYS®), Peginterferon alfa-2b (PEGINTRON®), IFN analog, IFN mutants, altered glycosylated human IFN, and PEG conjugated IFN analogs. Specific examples of cells modified for expression of endogenous human IFN are described in Devlin et al., J. Leukoc. Biol. 41:306 (1987); U.S. Pat. Nos. 6,610,830; 6,482,613; 6,489, 144; 6,159,712; 5,814,485; 5,710,027; 5,595,888; 4,966,843; which are incorporated by reference herein. See also, U.S. Pat. Nos. 6,716,606; 6,379,661; 6,004,548; 5,830,705; 5,582, 823; 4,810,643; and 6,242,218, which are incorporated by reference herein, for expression of GH family members.

The term "human IFN (hIFN)" or "hIFN polypeptide" refers to interferon or IFN as described above, as well as a polypeptide that retains at least one biological activity of a naturally-occurring hIFN. The term "hIFN polypeptides" or "hIFN" also includes the pharmaceutically acceptable salts and prodrugs, and prodrugs of the salts, polymorphs, hydrates, solvates, biologically-active fragments, biologically-active variants and stereoisomers of the naturally-occurring human IFN as well as agonist, mimetic, and antagonist variants of the naturally-occurring human IFN and polypeptide fusions thereof. Examples of hIFN polypeptides include, but are not limited to, those described in U.S. Pat. Nos. 4,604,284; 5,582,824; 6,531,122; 6,204,022; 6,120,762; 6,046,034; 6,036,956; 5,939,286; 5,908,626; 5,780,027; 5,770,191; 5,723,125; 5,594,107; 5,378,823; 4,898,931; 4,892,743, which are incorporated by reference herein. Fusions comprising additional amino acids at the amino terminus, carboxyl terminus, or both, are encompassed by the term "hIFN polypeptide." Exemplary fusions include, but are not limited to, e.g., methionyl IFN in which a methionine is linked to the N-terminus of hIFN resulting from the recombinant expression of the mature form of hIFN lacking the secretion signal peptide or portion thereof, fusions for the purpose of purification (including but not limited to, to polyhistidine or affinity epitopes), fusions with serum albumin binding peptides and fusions with serum proteins such as serum albumin. Also the term "hIFN polypeptide" also includes hybrid molecules that have one or more amino acid substitutions from limitin or other interferon-like cytokines. U.S. Pat. No. 5,750,373, which is incorporated by reference herein, describes a method for selecting novel proteins such as growth hormone and antibody fragment variants having altered binding properties for their respective receptor molecules. The method comprises fusing a gene encoding a protein of interest to the carboxy terminal domain of the gene III coat protein of the filamentous phage M13. The naturally-occurring hIFN nucleic acid and amino acid sequences for full-length and mature forms are known, as are variants such as single amino acid variants or splice variants.

Consensus interferon is a recombinant type 1 interferon containing 166 amino acids. Consensus IFN was derived by scanning the sequences of several natural alpha interferons and assigning the most frequently observed amino acid in each corresponding position. Consensus IFN, when compared on an equal mass basis with IFNα-2a and α-2b in in vitro assays, typically displays 5-10 times higher biological activity (Blatt et al. J. Interferon Cytokine Res. 1996; 16:489-99).

Modified hIFN polypeptides may exhibit one or more properties or biological activities found with a different interferon molecule. For example, a hIFN polypeptide that was generated from an IFNα-2a amino acid sequence and that comprises one or more non-naturally encoded amino acid that is unPEGylated or PEGylated may exhibit one or more biological activity that is found with IFNβ. One such activity may be anti-proliferative activity.

For the complete full-length naturally-occurring IFNα-2a amino acid sequence as well as the mature naturally-occurring IFNα-2a amino acid sequence, see SEQ ID NO: 1, and SEQ ID NO: 2, respectively, herein. In some embodiments, hIFN polypeptides of the invention are substantially identical to SEQ ID NO: 1, SEQ ID NO: 2, SEQ ID NO: 3, or any other sequence of an interferon polypeptide or interferon-like cytokine such as limitin. Nucleic acid molecules encoding hIFN mutants and mutant hIFN polypeptides are well known and include, but are not limited to, those disclosed in U.S. Pat. Nos. 6,331,525; 6,069,133; 5,955,307; 5,869,293; 5,831,062; 5,081,022; 5,004,689; 4,738,931; 4,686,191; which are incorporated by reference herein. Examples of hIFN mutants include those disclosed in U.S. Pat. Nos. 6,514,729 and 5,582, 824, which are incorporated by reference herein.

Interferons have a variety of biological activities, including anti-viral, immunoregulatory and anti-proliferative properties, and have been utilized as therapeutic agents for treatment of diseases such as cancer, and various viral diseases. Interferon-α's have been shown to inhibit various types of cellular proliferation, and are especially useful for the treatment of a variety of cellular proliferation disorders frequently associated with cancer, particularly hematologic malignancies such as leukemias. These proteins have shown anti-proliferative activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, E. M. et al. (1984) J. Biol. Response Modifiers 3:580; Oldham, R. K. (1985) Hospital Practice 20:71).

IFNα's are useful against various types of viral infections (Finter, N. B. et al. (1991) Drugs 42 (5):749). Interferon-α's have shown activity against human papillomavirus infection, Hepatitis B, and Hepatitis C infections (Finter, N. B. et al., 1991, supra; Kashima, H. et al. (1988) Laryngoscope 98:334; Dusheiko, G. M. et al. (1986) J. Hematology 3 (Supple. 2):S199; Davis, G L et al. (1989) N. England J. Med. 321: 1501). The role of interferons and interferon receptors in the pathogenesis of certain autoimmune and inflammatory diseases has also been investigated (Benoit, P. et al. (1993) J. Immunol. 150 (3):707). In addition, interferon-α has been approved for use for the treatment of diseases such as hairy cell leukemia, renal cell carcinoma, basal cell carcinoma, malignant melanoma, AIDS-related Kaposi's sarcoma, multiple myeloma, chronic myelogenous leukemia, non-Hodgkin's lymphoma, laryngeal papillomatosis, mycosis fungoides, condyloma acuminata, chronic hepatitis B, hepatitis C, chronic hepatitis D, and chronic non-A, non-B/C hepatitis.

Interferons have been implicated in the pathogenesis of various autoimmune diseases, such as systemic lupus erythematoses, Behcet's disease, and insulin-dependent diabetes mellitus (IDDM, also referred to as type I diabetes). It has been demonstrated in a transgenic mouse model that β cell expression of IFN-α can cause insulitis and IDDM, and IFN-α antagonists (including antibodies) have been proposed for the treatment of IDDM (WO 93/04699, published Mar. 18, 1993). Impaired IFN-γ and IFN-α production has been observed in multiple sclerosis (MS) patients. IFN-α has been detected in the serum of many AIDS patients, and it has been reported that the production of IFN-γ is greatly suppressed in suspensions of mitogen-stimulated mononuclear cells derived from AIDS patients. For a review see, for example, Chapter 16, "The Presence and Possible Pathogenic Role of Interferons in Disease", In: Interferons and other Regulatory Cytokines, Edward de Maeyer (1988, John Wiley and Sons publishers). Alpha and beta interferons have been used in the treatment of the acute viral disease herpes zoster (T. C. Merigan et al, N. Engl. J. Med, 298, 981-987 (1978); E. Heidemann et al., Onkologie 7, 210-212 (1984)), chronic viral infections, e.g. hepatitis C and hepatitis B infections (R. L. Knobler et al., Neurology 34(10): 1273-9 (1984); M. A. Faerkkilae et al., Act. Neural. Sci. 69, 184-185 (1985)), rIFNα-2a (ROFERON®, Roche) is an injection formulation indicated in use for the treatment of hairy cell leukemia and AIDS-related Kaposi's sarcoma. Recombinant IFNα-2b (INTRON A®, Schering) has been approved for the treatment of hairy cell leukemia, selected cases of condylomata acuminata, AIDS-related Kaposi's sarcoma, chronic hepatitis C, and chronic hepatitis B infections in certain patients. Compositions of multiple subtypes of IFNα are also used to treat a variety of diseases (MULTIFERON®, Viragen, Inc.). IFNγ1b (ACTIMMUNE®, Intermune Pharmaceuticals, Inc.) is commercially available for the treatment of chronic granulomatous disease and malignant osteopetrosis.

The biologic activities of type I IFNs have been disclosed and are known in the art, and can be found, for example, in Pfeffer, Semin. Oncol. 24 (suppl 9), S9-63-S9-69 (1997) and U.S. Pat. Nos. 6,436,391; 6,372,218; 6,270,756; 6,207,145; 6,086,869; 6,036,949; 6,013,253; 6,007,805; 5,980,884; 5,958,402; 5,863,530; 5,849,282; 5,846,526; 5,830,456; 5,824,300; 5,817,307; 5,780,021; 5,624,895; 5,480,640; 5,268,169; 5,208,019; 5,196,191; 5,190,751; 5,104,653; 5,019,382; 4,959,210; which are incorporated by reference herein. A related application is U.S. patent application entitled "Modified Human Interferon Polypeptides and Their Uses" published as US 2005/0220762 on Oct. 6, 2005, which is incorporated by reference herein.

IFNα's are members of the diverse helical-bundle superfamily of cytokine genes (Sprang, S. R. et al. (1993) Curr. Opin. Struct. Biol. 3:815-827). The human interferon α's are encoded by a family of over 20 tandemly duplicated nonallelic genes that share 85-98% sequence identity at the amino acid level (Henco, K. et al. (1985) J. Mol. Biol. 185:227-260). Human IFNβ is a regulatory polypeptide with a molecular weight of about 22 kDa consisting of 166 amino acid residues. It can be produced by most cells in the body, in particular fibroblasts, in response to viral infection or exposure to other agents. It binds to a multimeric cell surface receptor, and productive receptor binding results in a cascade of intracellular events leading to the expression of IFNβ inducible genes which in turn produces effects which can be classified as anti-viral, anti-proliferative and immunomodulatory.

The amino acid sequence of human IFNβ is known and was reported for example by Taniguchi, Gene 10:11-15, 1980, and in EP 83069, EP 41313 and U.S. Pat. No. 4,686,191 which are incorporated by reference herein. Crystal structures have been reported for human and murine IFNβ, respectively (Proc. Natl. Acad. Sci. USA 94:11813-11818, 1997; J. Mol. Biol. 253:187-207, 1995; U.S. Pat. Nos. 5,602,232; 5,460, 956; 5,441,734; 4,672,108; which are incorporated by reference herein). They have been reviewed in Cell Mol. Life. Sci. 54:1203-1206, 1998. Variants of IFNβ have been reported (WO 95/25170, U.S. Pat. Nos. 6,572,853, 5,545,723, 4,914, 033, EP 260350, U.S. Pat. Nos. 4,588,585, 4,769,233, Stewart et al, DNA Vol. 6 no. 2 1987 pp. 119-128, Runkel et al, 1998, J. Biol. Chem. 273, No. 14, pp. 8003-8008, which are incorporated by reference herein). Expression of IFNβ in CHO cells has been reported (U.S. Pat. Nos. 4,966,843, 5,376,567 and 5,795,779, which are incorporated by reference herein). IFNβ molecules with a particular glycosylation pattern and methods for their preparation have been reported (EP 287075 and EP 529300).

Commercial preparations of IFNβ are sold under the names BETASERON® (also termed interferon β1b, which is non-glycosylated, produced using recombinant bacterial cells, has a deletion of the N-terminal methionine residue and the C17S mutation), and AVONEX® and REBIF® (also termed interferon β1a, which is glycosylated, produced using recombinant mammalian cells) for treatment of patients with multiple sclerosis, have shown to be effective in reducing the exacerbation rate, and more patients remain exacerbation-free for prolonged periods of time as compared with placebo-treated patients. Furthermore, the accumulation rate of disability is reduced (Neurol. 51:682-689, 1998).

Comparison of IFNβ1a and β1b with respect to structure and function has been presented in Pharmaceut. Res. 15:641-649, 1998. IFNβ has been shown to delay the progression of multiple sclerosis, a relapsing then progressive inflammatory degenerative disease of the central nervous system. IFNβ may have inhibitory effects on the proliferation of leukocytes and antigen presentation. IFNβ may modulate the profile of cytokine production towards an anti-inflammatory phenotype. IFNβ can reduce T-cell migration by inhibiting the activity of T-cell matrix metalloproteases. These activities are likely to act in concert to account for the mechanism of IFNβ in MS (Neurol. 51:682-689, 1998).

IFNβ may be used for the treatment of osteosarcoma, basal cell carcinoma, cervical dysplasia, glioma, acute myeloid leukemia, multiple myeloma, Hodgkin's disease, breast carcinoma, melanoma, and viral infections such as papilloma virus, viral hepatitis, herpes genitalis, herpes zoster, herpetic keratitis, herpes simplex, viral encephalitis, cytomegalovirus pneumonia, and rhinovirus, Various side effects are associated with the use of current preparations of IFNβ, including injection site reactions, fever, chills, myalgias, arthralgias, and other flu-like symptoms (Clin. Therapeutics, 19:883-893, 1997).

Given the multitude of side effects with current IFNβ products, their association with frequent injection, the risk of developing neutralizing antibodies impeding the desired therapeutic effect of IFNβ, and the potential for obtaining more optimal therapeutic IFNβ levels with concomitant enhanced therapeutic effect, there is clearly a need for improved IFNβ-like molecules.

Additional side effects found in patients receiving interferon therapy include flu-like symptoms such as fatigue, headache, and fever, anorexia, myelosuppression, and neutropenia. Side effects such as these can require cessation of treatment or a reduction of dosage. See Jonasch, E. Oncologist 2001; 6:34-55, which is incorporated by reference. IFNα2a therapy has other associated toxicities including thrombocytopenia. Among the most common side effects of IFNα current therapy are pyrexia, headache, rigors, and myalgia. Side effects that lead to dose reductions are most commonly hematological consequences of bone marrow suppression, including anemia and neutropenia. Adverse effects of IFNs are problematic even with IFN/ribavirin combination therapy; the combined use of a PEGylated interferonα (PEGASYS® or PEGINTRON®) and Ribavirin (COPEGUS®) is the current standard of care in HCV therapy. Moreover, patients with HCV genotype 1 (1a or 1b) have been shown to be much less likely to respond to combination therapy than HCV genotype 2 or 3. Also, these combination regimens are found to be remarkably less effective in patients with a high viral load. Thus, there is clearly a need for improved IFN-like therapeutics.

Other interferons (IFN-ε, IFN-κ, IFN-δ, IFN-τ) and four interferon-like cytokines (limitin, IL-28A, IL-28B, IL-29) have been described. The interaction of interferons and interferon-like molecules with receptor molecules as well as their biological activities and clinical applications are described by Pestka, S. et al. in "Interferons, interferon-like cytokines, and their receptors," Immunol Rev. 2004 December; 202:8-32, which is incorporated by reference herein. Type I receptor chains IFNαR1 and IFNαR2 are utilized by a number of the interferons including IFN-α, IFN-β, and limitin. The gene encoding sequence of IFNαR1 was originally cloned by Uze et al. Cell 1990; 60:225, which is incorporated by reference herein. It is a 110 kDa protein, whereas IFNαR2 occurs in two different forms. The two forms of IFNαR2 are from the same gene and are generated as differentially spliced products (Lutfalla et al. EMBO J. 1995; 14:5100; Domanski et al. J. Biol. Chem. 1995; 270:21606; and Novick et al. Cell 1994; 77:391, which are incorporated by reference herein). The short form (IFNAR2b) has a molecular mass of 51 kDa and the long form (IFNAR2c) is 90-100 kDa. Thus, two forms of the receptor complex thus exist, with IFNαR1 associating with IFNAR2b or IFNAR2c. Colamonici et al. J. Biol. Chem. 1994; 269: 5660, which is incorporated by reference herein, have shown that both types of receptor transduce signals and mediate the biological effects of interferons. IFNs utilize the Jak-Stat signal transduction pathway in addition to other pathways.

Limitin (Interferon-zeta) has been found only in mice and was isolated based on its ability to inhibit the proliferation of a myelomonocytic leukemia cell line (Oritani, K. et al. Nature Medicine 2000 6 (6):659-666, which is incorporated herein by reference). Limitin (SEQ ID NO: 23) has been shown to kill or arrest the proliferation of certain lympho-hematopoietic cell lines (B lymphopoiesis), but showed little influence on erythropoiesis or myelopoiesis. Sequence analysis of the 182 amino acid protein has shown homology to IFN-α and IFN-β (31.9% and 25.9% identical in 166 overlapping amino acids) and a hydrophobic set of residues at the amino terminus. Kawamoto et al. J Virol. 2003 September; 77 (17):9622-31, which is incorporated by reference, describe studies of the antiviral activity of limitin with encephalomyocarditis virus (EMCV) and herpes simplex virus (HSV) infected cells, and plaque formation in mouse hepatitis virus (MHV) infected cells.

Differences between limitin and interferons such as IFNα have been discussed, including, but not limited to, differences in signal transduction pathways for antiviral effects, in the antiviral effects themselves, and in myelosuppressive effects. See Kawamoto et al. J. Virol. 2003 September; 77 (17):9622-31. Kawamoto et al. Experimental Hematology 2004; 32:797-805, which is incorporated by reference herein, describes differences found between limitin and IFN-α in assays measuring antiviral, immunomodulatory, antitumor, and myelosuppressive activity and in an in vivo study. Limitin was found to separate anti-viral activity from bone marrow toxicity.

Thirteen different alpha interferons transmit distinct signals through a single paired α/β two chain receptor complex. Modulating of components involved in one or more signaling pathways mediated through the same receptor complex may provide optimization of the antiviral effects of hIFN polypeptides, and modulation of toxic side effects. A number of molecules are involved with downstream signaling pathways. Antisense oligonucleotides to CrkL and CrkII that inhibited protein expression of these molecules were used by Platanias et al. and were found to reverse the inhibition of IFNα or IFNγ on proliferation of bone marrow cells (CFU-GM and BFU-E). IFNα is known to activate the STAT1 pathway, and knockout mouse studies point to the importance of the STAT1 signaling cascade in fighting viral infections. Durbin et al. (Cell. 1996 Feb. 9; 84 (3):443-50) have shown that mice homozygous for a STAT1 knockout develop spontaneous viral infections unless they are raised in a sterile environment. In addition, signaling through STAT5 and CrkL ultimately lead to activation of the RAP1 protein which may be necessary for producing growth-inhibitory signals. The phosphorylation of STAT3 may also be measured.

Various references disclose modification of polypeptides by polymer conjugation or glycosylation. The term "hIFN polypeptide" includes polypeptides conjugated to a polymer such as PEG and may be comprised of one or more additional derivitizations of cysteine, lysine, or other residues. In addition, the hIFN polypeptide may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

Polymer modification of native IFNβ or a C17S variant thereof has been reported (EP 229108, U.S. Pat. No. 5,382, 657; EP 593868; U.S. Pat. No. 4,917,888 and WO 99/55377, which are incorporated by reference herein). U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. Examples of PEGylated IFN molecules include those disclosed in U.S. Pat. Nos. 6,524,570; 6,250,469; 6,180,096; 6,177,074; 6,042,822; 5,981,709; 5,951,974; 5,908,621; 5,738,846; 5,711,944; 5,382,657, which are incorporated by reference herein. IFNβ is mentioned as one example of a polypeptide belonging to the growth hormone superfamily. WO 00/23114 discloses glycosylated and pegylated IFNβ. WO 00/23472 discloses IFNβ fusion proteins. WO 00/26354 discloses a method of producing a glycosylated polypeptide variant with reduced allergenicity, which as compared to a corresponding parent polypeptide comprises at least one additional glycosylation site. IFNβ is disclosed as one example among many polypeptides that can be modified according to the technology described in U.S. Pat. No. 5,218,092, which is incorporated by reference herein. U.S. Pat. No. 5,218,092, which is incorporated by reference herein, discloses modification of granulocyte colony stimulating factor (G-CSF) and other polypeptides so as to introduce at least one additional carbohydrate chain as compared to the native polypeptide.

The term "hIFN polypeptide" also includes glycosylated hIFN, such as but not limited to, polypeptides glycosylated at any amino acid position, N-linked or O-linked glycosylated forms of the polypeptide. These forms included, but are not limited to, a polypeptide with an O-linked glycosylation site at position 129 of SEQ ID NO: 1, or the equivalent position of SEQ ID NO: 2 or 3, or any other IFN polypeptide (Adolf et al., Biochem. J. 276:511 (1991)).

Variants containing single nucleotide changes are also considered as biologically active variants of hIFN polypeptide. In addition, splice variants are also included. The term "hIFN polypeptide" also includes hIFN polypeptide heterodimers, homodimers, heteromultimers, or homomultimers of any one or more hIFN polypeptides or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

All references to amino acid positions in hIFN described herein are based on the position in SEQ ID NO: 2, unless otherwise specified (i.e., when it is stated that the comparison is based on SEQ ID NO: 1, 3, or other hIFN sequence or interferon-like cytokine such as limitin). Those of skill in the art will appreciate that amino acid positions corresponding to positions in SEQ ID NO: 1, 2, 3, or any other IFN sequence or interferon-like cytokine such as limitin can be readily identified in any other hIFN molecule or interferon-like cytokine such as limitin such as hIFN fusions, variants, fragments, etc. For example, sequence alignment programs such as BLAST can be used to align and identify a particular position in a protein that corresponds with a position in SEQ ID NO: 1, 2, 3, or other IFN sequence or interferon-like cytokine such as limitin. Substitutions, deletions or additions of amino acids described herein in reference to SEQ ID NO: 1, 2, 3, or other IFN sequence are intended to also refer to substitutions, deletions or additions in corresponding positions in hIFN fusions, variants, fragments, interferon-like cytokines such as limitin, etc. described herein or known in the art and are expressly encompassed by the present invention.

The term "hIFN polypeptide" or "hIFN" encompasses hIFN polypeptides comprising one or more amino acid substitutions, additions or deletions. hIFN polypeptides of the present invention may be comprised of modifications with one or more natural amino acids in conjunction with one or more non-natural amino acid modification. For example, a hIFN polypeptide may comprise a non-naturally encoded amino acid substitution as well as a natural amino acid substitution for the first amino acid at the N-terminus. Exemplary substitutions in a wide variety of amino acid positions in naturally-occurring hIFN polypeptides have been described, including but not limited to substitutions that modulate one or more of the biological activities of the hIFN polypeptide, such as but not limited to, increase agonist activity, increase solubility of the polypeptide, decrease protease susceptibility, convert the polypeptide into an antagonist, etc. and are encompassed by the term "hIFN polypeptide."

Human IFN antagonists include, but are not limited to, those with substitutions at: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165, or any combination thereof (SEQ ID NO: 2, or the corresponding amino acid in SEQ ID NO: 1, 3, or any other IFN sequence); a hIFN polypeptide comprising one of these substitutions may potentially act as a weak antagonist or weak agonist depending on the site selected and the desired activity. Human IFN antagonists include, but are not limited to, those with substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combination thereof (hIFN; SEQ ID NO: 2 or the corresponding amino acids in SEQ ID NO: 1 or 3). In some embodiments, hIFN antagonists comprise at least one substitution in the regions 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus) that cause IFN to act as an antagonist. In other embodiments, the exemplary sites of incorporation of a non-naturally encoded amino acid include residues within the amino terminal region of helix A and a portion of helix C. In other embodiments, the above-listed substitutions are combined with additional substitutions that cause the hIFN polypeptide to be a hIFN antagonist. In some embodiments, the hIFN antagonist comprises a non-naturally encoded amino acid linked to a water soluble polymer that is present in a receptor binding region of the hIFN molecule.

In some embodiments, the hIFN polypeptides further comprise an addition, substitution or deletion that modulates biological activity of the hIFN polypeptide. For example, the additions, substitutions or deletions may modulate one or more properties or activities of hIFN. For example, the additions, substitutions or deletions may modulate affinity for the hIFN polypeptide receptor, modulate (including but not limited to, increases or decreases) receptor dimerization, modulate downstream signaling events post hIFN receptor binding, stabilize receptor dimers, modulate circulating half-life, modulate therapeutic half-life, modulate stability of the polypeptide, modulate cleavage by proteases, modulate dose, modulate release or bio-availability, modulate one or more side effects found with current IFN therapeutics, modulate toxicity, facilitate purification, or improve or alter a particular route of administration. Similarly, hIFN polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "hIFN polypeptide" also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, small organic compounds, water soluble polymers of a variety of lengths such as poly(ethylene glycol) or polydextran, or polypeptides of various lengths.

A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671, 958, 4,659,839, 4,414,148, 4,699,784; 4,680,338; and 4,569, 789 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to hIFN and its receptor or hIFN.

Where substituent groups are specified by their conventional chemical formulas, written from left to right, they equally encompass the chemically identical substituents that would result from writing the structure from right to left, for example, the structure —CH$_2$O— is equivalent to the structure —OCH$_2$—.

The term "substituents" includes but is not limited to "non-interfering substituents". "Non-interfering substituents" are those groups that yield stable compounds. Suitable non-interfering substituents or radicals include, but are not limited to, halo, C$_1$-C$_{10}$ alkyl, C$_2$-C$_{10}$ alkenyl, C$_2$-C$_{10}$ alkynyl, C$_1$-C$_{10}$ alkoxy, C$_1$-C$_{12}$ aralkyl, C$_1$-C$_{12}$ alkaryl, C$_3$-C$_{12}$ cycloalkyl, C$_3$-C$_{12}$ cycloalkenyl, phenyl, substituted phenyl, toluoyl, xylenyl, biphenyl, C$_2$-C$_{12}$ alkoxyalkyl, C$_2$-C$_{12}$ alkoxyaryl, C$_7$-C$_{12}$ aryloxyalkyl, C$_7$-C$_{12}$ oxyaryl, C$_1$-C$_6$ alkylsulfinyl, C$_1$-C$_{10}$ alkylsulfonyl, —(CH$_2$)$_m$—O—(C$_1$-C$_{10}$ alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C$_1$-C$_{10}$ alkyl), —C(O)—(C$_1$-C$_{10}$ alkyl), C$_2$-C$_{10}$ alkyl thioalkyl, —C(O)O—(C$_1$-C$_{10}$ alkyl), —OH, —SO$_2$, =S, —COOH, —NR$_2$, carbonyl, —C(O)—(C$_1$-C$_{10}$ alkyl)-CF$_3$, —C(O)—CF3, —C(O)NR2, —(C$_1$-C$_{10}$ aryl)-S—(C$_6$-C$_{10}$ aryl), —C(O)—(C$_1$-C$_{10}$ aryl), —(CH$_2$)$_m$—O—(—(CH$_2$)$_m$—O—(C$_1$-C$_{10}$ alkyl) wherein each m is from 1 to 8, —C(O)NR$_2$, —C(S)NR$_2$, —SO$_2$NR$_2$, —NRC(O) NR$_2$, —NRC(S)NR$_2$, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —CH$_2$CH$_2$— and —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

As used herein, the term "water soluble polymer" refers to any polymer that is soluble in aqueous solvents. Linkage of water soluble polymers to hIFN polypeptides can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered receptor dimerization or multimerization, modulated toxicity, and modulation of one or more the biological activities of IFN including side effects found with current IFN therapeutics. The water soluble polymer may or may not have its own biological activity, and may be utilized as a linker for attaching hIFN to other substances, including but not limited to one or more hIFN polypeptides, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly(alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (including but not limited to from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such a radical. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, but are not limited to: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified hIFN relative to its non-modified form. Serum half-life is measured by taking blood samples at various time points after administration of hIFN, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of hIFN, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown on the molecule by enzymes such as proteases, or an increase or decrease in another parameter or mechanism of action of the non-modified molecule.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins: Structures and Molecular Properties* (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1997) *Nuc. Acids Res.* 25:3389-3402, and Altschul et al. (1990) *J. Mol. Biol.* 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) *Proc. Natl. Acad. Sci. USA* 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, PNA, or other nucleic acid mimics, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Laboratory Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "non-eukaryote" refers to non-eukaryotic organisms. For example, a non-eukaryotic organism can belong to the Eubacteria (including but not limited to, *Escherichia coli*, *Thermus thermophilus*, *Bacillus stearothermophilus*, *Pseudomonas fluorescens*, *Pseudomonas aerugi-* nosa, *Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment.

The term "effective amount" as used herein refers to that amount of the modified non-natural amino acid polypeptide being administered which will relieve to some extent one or more of the symptoms of the disease, condition or disorder being treated. Compositions containing the modified non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In prophylactic applications, compositions containing the modified non-natural amino acid polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein, including photolabile groups such as Nvoc and MeNvoc. Other protecting groups known in the art may also be used in or with the methods and compositions described herein.

By way of example only, blocking/protecting groups may be selected from:

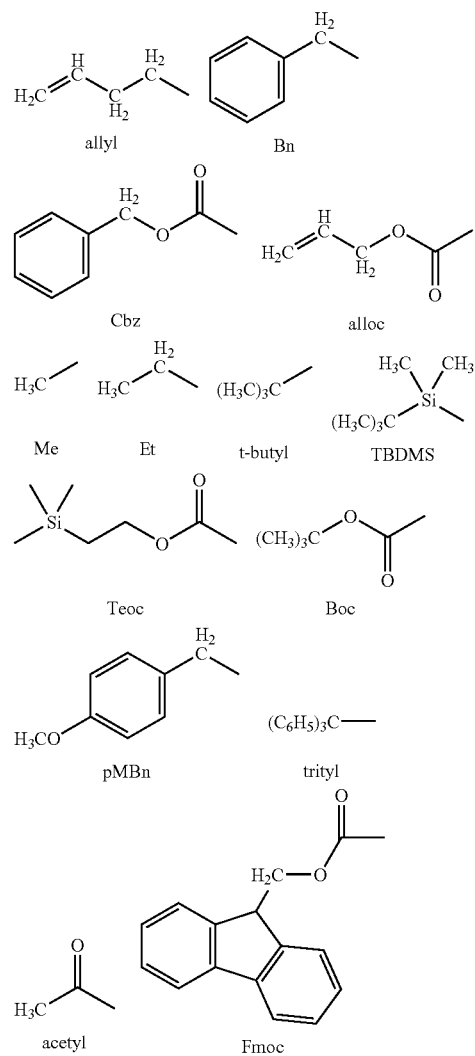

Other protecting groups are described in Greene and Wuts, Protective Groups in Organic Synthesis, 3rd Ed., John Wiley & Sons, New York, N.Y., 1999, which is incorporated herein by reference in its entirety.

In therapeutic applications, compositions containing the modified non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Non-naturally encoded amino acid polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labelled compounds described herein, for example those into which radioactive isotopes such as $^3H$ and $^{14}C$ are incorporated, may be useful in drug and/or substrate tissue distribution assays. Further, substitution with isotopes such as deuterium, i.e., $^2H$, can afford certain therapeutic advantages resulting from greater metabolic stability, for example increased in vivo half-life or reduced dosage requirements.

All isomers including but not limited to diastereomers, enantiomers, and mixtures thereof are considered as part of the compositions described herein. In additional or further embodiments, the non-naturally encoded amino acid polypeptides are metabolized upon administration to an organism in need to produce a metabolite that is then used to produce a desired effect, including a desired therapeutic effect. In further or additional embodiments are active metabolites of non-naturally encoded amino acid polypeptides.

In some situations, non-naturally encoded amino acid polypeptides may exist as tautomers. In addition, the non-naturally encoded amino acid polypeptides described herein can exist in unsolvated as well as solvated forms with pharmaceutically acceptable solvents such as water, ethanol, and the like. The solvated forms are also considered to be disclosed herein. Those of ordinary skill in the art will recognize that some of the compounds herein can exist in several tautomeric forms. All such tautomeric forms are considered as part of the compositions described herein.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction

Interferon molecules comprising at least one unnatural amino acid are provided in the invention. In certain embodiments of the invention, the hIFN polypeptide with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2]cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified hIFN polypeptide of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell. A linker, polymer, water soluble polymer, or other molecule may attach the molecule to the polypeptide. The molecule may be linked directly to the polypeptide.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on members of the GH supergene family, in particular hIFN, comprising at least one non-naturally encoded amino acid. Introduction of at least one non-naturally encoded amino acid into hIFN can allow for the application of conjugation chemistries that involve specific chemical reactions, including, but not limited to, with one or more non-naturally encoded amino acids while not reacting with the commonly occurring 20 amino acids. In some embodiments, hIFN comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the non-naturally encoded amino acid. Known chemistry methodologies of a wide variety are suitable for use in the present invention to incorporate a water soluble polymer into the protein. Such methodologies include but are not limited to a Huisgen [3+2]cycloaddition reaction (see, e.g., Padwa, A. in *Comprehensive Organic Synthesis Vol.* 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176) with, including but not limited to, acetylene or azide derivatives, respectively.

Because the Huisgen [3+2]cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tornoe, et al., (2002) *J. Org. Chem.* 67:3057-3064; and, Rostovtsev, et al., (2002) *Angew. Chem. Int. Ed.* 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2]cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more importantly, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2]cycloaddition product.

It is well established in the art that PEG can be used to modify the surfaces of biomaterials (see, e.g., U.S. Pat. No. 6,610,281; Mehvar, R., J. Pharm Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2]cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives containing sulfonyl acid halides, halogen atoms and other leaving groups are known to those of ordinary skill in the art. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are known to those of ordinary skill in the art.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives is well established to practitioners in the art.

The invention also provides a method for the selective modification of proteins to add other substances to the modified protein, including but not limited to water soluble polymers such as PEG and PEG derivatives containing an azide or acetylene moiety. The azide- and acetylene-containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II. Growth Hormone Supergene Family

The following proteins include those encoded by genes of the growth hormone (GH) supergene family (Bazan, F., *Immunology Today* 11: 350-354 (1990); Bazan, J. F. *Science* 257: 410-413 (1992); Mott, H. R. and Campbell, I. D., *Current Opinion in Structural Biology* 5: 114-121 (1995); Silvennoinen, O. and Ihle, J. N., SIGNALLING BY THE HEMATOPOIETIC CYTOKINE RECEPTORS (1996)): growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor (CNTF), leukemia inhibitory factor (LIF), alpha interferon, beta interferon, epsilon interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified and the non-natural amino acid methods and compositions described herein similarly applied. Given the extent of structural homology among the members of the GH supergene family, non-naturally encoded amino acids may be incorporated into any members of the GH supergene family using the present invention. Each member of this family of proteins comprises a four helical bundle. The general structure of family member IFNα-2 is shown in FIG. 1.

Structures of a number of cytokines, including G-CSF (Zink et al., FEBS Lett. 314:435 (1992); Zink et al., Biochemistry 33:8453 (1994); Hill et al., Proc. Natl. Acad. Sci. USA 90:5167 (1993)), GM-CSF (Diederichs, K., et al. *Science* 154: 1779-1782 (1991); Walter et al., *J. Mol. Biol.* 224:1075-1085 (1992)), IL-2 (Bazan, J. F. and McKay, D. B. *Science* 257: 410-413 (1992)), IL-4 (Redfield et al., *Biochemistry* 30: 11029-11035 (1991); Powers et al., *Science* 256:1673-1677 (1992)), and IL-5 (Milburn et al., *Nature* 363: 172-176 (1993)) have been determined by X-ray diffraction and NMR studies and show striking conservation with the GH structure, despite a lack of significant primary sequence homology. IFN is considered to be a member of this family based upon modeling and other studies (Lee et al., J. Interferon Cytokine Res. 15:341 (1995); Murgolo et al., Proteins 17:62 (1993); Radhakrishnan et al., Structure 4:1453 (1996); Klaus et al., J. Mol. Biol. 274:661 (1997)). EPO is considered to be a member of this family based upon modeling and mutagenesis studies (Boissel et al., *J. Biol. Chem.* 268: 15983-15993 (1993); Wen et al., J. Biol. Chem. 269: 22839-22846 (1994)). All of the above cytokines and growth factors are now considered to comprise one large gene family.

In addition to sharing similar secondary and tertiary structures, members of this family share the property that they must oligomerize cell surface receptors to activate intracellular signaling pathways. Some GH family members, including but not limited to; GH and EPO, bind a single type of receptor and cause it to form homodimers. Other family members, including but not limited to, IL-2, IL-4, and IL-6, bind more than one type of receptor and cause the receptors to form heterodimers or higher order aggregates (Davis et al., (1993), *Science* 260: 1805-1808; Paonessa et al., (1995), EMBO J. 14: 1942-1951; Mott and Campbell, *Current Opinion in Structural Biology* 5: 114-121 (1995)). Mutagenesis studies have shown that, like GH, these other cytokines and growth factors contain multiple receptor binding sites, typically two, and bind their cognate receptors sequentially (Mott and Campbell, *Current Opinion in Structural Biology* 5: 114-121 (1995); Matthews et al., (1996) *Proc. Natl. Acad. Sci. USA* 93: 9471-9476). Like GH, the primary receptor binding sites for these other family members occur primarily in the four alpha helices and the A-B loop. The specific amino acids in the helical bundles that participate in receptor binding differ amongst the family members. Most of the cell surface receptors that interact with members of the GH supergene family are structurally related and comprise a second large multi-gene family. See, e.g. U.S. Pat. No. 6,608,183, which is incorporated by reference herein.

A general conclusion reached from mutational studies of various members of the GH supergene family is that the loops joining the alpha helices generally tend to not be involved in receptor binding. In particular the short B-C loop appears to be non-essential for receptor binding in most, if not all, family members. For this reason, the B-C loop may be substituted with non-naturally encoded amino acids as described herein in members of the GH supergene family. The A-B loop, the C-D loop (and D-E loop of interferon/IL-10-like members of the GH superfamily) may also be substituted with a non-naturally-occurring amino acid. Amino acids proximal to helix A and distal to the final helix also tend not to be involved in receptor binding and also may be sites for introducing non-naturally-occurring amino acids. In some embodiments, a non-naturally encoded amino acid is substituted at any position within a loop structure, including but not limited to, the first 1, 2, 3, 4, 5, 6, 7, or more amino acids of the A-B, B-C, C-D or D-E loop. In some embodiments, one or more non-naturally encoded amino acids are substituted within the last 1, 2, 3, 4, 5, 6, 7, or more amino acids of the A-B, B-C, C-D or D-E loop.

Certain members of the GH family, including but not limited to, EPO, IL-2, IL-3, IL-4, IL-6, G-CSF, GM-CSF, TPO, IL-10, IL-12 p35, IL-13, IL-15 and beta interferon contain N-linked and/or O-linked sugars. The glycosylation sites in the proteins occur almost exclusively in the loop regions and not in the alpha helical bundles. Because the loop regions generally are not involved in receptor binding and because they are sites for the covalent attachment of sugar groups, they may be useful sites for introducing non-naturally-occurring amino acid substitutions into the proteins. Amino acids that comprise the N- and O-linked glycosylation sites in the proteins may be sites for non-naturally-occurring amino acid substitutions because these amino acids are surface-exposed. Therefore, the natural protein can tolerate bulky sugar groups attached to the proteins at these sites and the glycosylation sites tend to be located away from the receptor binding sites.

Additional members of the GH supergene family are likely to be discovered in the future. New members of the GH supergene family can be identified through computer-aided secondary and tertiary structure analyses of the predicted protein sequences, and by selection techniques designed to identify molecules that bind to a particular target. Members of the GH supergene family typically possess four or five amphipathic helices joined by non-helical amino acids (the loop regions). The proteins may contain a hydrophobic signal sequence at their N-terminus to promote secretion from the cell. Such later discovered members of the GH supergene family also are included within this invention. A related application is International Patent Application entitled "Modified Four Helical Bundle Polypeptides and Their Uses" published as WO 05/074650 on Aug. 18, 2005, which is incorporated by reference herein.

Thus, the description of the growth hormone supergene family is provided for illustrative purposes and by way of example only and not as a limit on the scope of the methods, compositions, strategies and techniques described herein. Further, reference to GH and IFN polypeptides in this application is intended to use the generic term as an example of any member of the GH supergene family. Thus, it is understood that the modifications and chemistries described herein with reference to hIFN polypeptides or protein can be equally applied to any member of the GH supergene family, including those specifically listed herein.

III. General Recombinant Nucleic Acid Methods for Use with the Invention

In numerous embodiments of the present invention, nucleic acids encoding a hIFN polypeptide of interest will be isolated, cloned and often altered using recombinant methods. Such embodiments are used, including but not limited to, for protein expression or during the generation of variants, derivatives, expression cassettes, or other sequences derived from a hIFN polypeptide. In some embodiments, the sequences encoding the polypeptides of the invention are operably linked to a heterologous promoter. Isolation of hIFN and production of IFN in host cells are described in, e.g., U.S. Pat. Nos. 6,489,144; 6,410,697; 6,159,712; 5,955,307; 5,814,485; 5,710,027; 5,595,888; 5,391,713; 5,244,655; 5,196,323; 5,066,786; 4,966,843; 4,894,330; 4,364,863, which are incorporated by reference herein.

A nucleotide sequence encoding a hIFN polypeptide comprising a non-naturally encoded amino acid may be synthesized on the basis of the amino acid sequence of the parent polypeptide, including but not limited to, having the amino acid sequence shown in SEQ ID NO: 2 (hIFN), and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Nail. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001);

Kriegler, *Gene Transfer and Expression. A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes or polynucleotides that include selector codons for production of proteins that include unnatural amino acids, orthogonal tRNAs, orthogonal synthetases, and pairs thereof.

Various types of mutagenesis are used in the invention for a variety of purposes, including but not limited to, to produce novel synthetases or tRNAs, to mutate tRNA molecules, to mutate polynucleotides encoding synthetases, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, tertiary, or quaternary structure, crystal structure or the like.

The texts and examples found herein describe these procedures. Additional information is found in the following publications and references cited within: Ling et al., *Approaches to DNA mutagenesis: an overview, Anal Biochem.* 254 (2): 157-178 (1997); Dale et al., *Oligonucleotide-directed random mutagenesis using the phosphorothioate method, Methods Mol. Biol.* 57:369-374 (1996); Smith, *In vitro mutagenesis, Ann. Rev. Genet.* 19:423-462 (1985); Botstein & Shortle, *Strategies and applications of in vitro mutagenesis, Science* 229:1193-1201 (1985); Carter, *Site-directed mutagenesis, Biochem. J.* 237:1-7 (1986); Kunkel, *The efficiency of oligonucleotide directed mutagenesis*, in *Nucleic Acids & Molecular Biology* (Eckstein, F. and Lilley, D. M. J. eds., Springer Verlag, Berlin) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Bass et al., *Mutant Trp repressors with new DNA-binding specificities, Science* 242:240-245 (1988); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); Zoller & Smith, *Oligonucleotide-directed mutagenesis: a simple method using two oligonucleotide primers and a single-stranded DNA template, Methods in Enzymol.* 154:329-350 (1987); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8785 (1985); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Sayers et al., *5'-3' Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Improved enzymatic in vitro reactions in the gapped duplex DNA approach to oligonucleotide-directed construction of mutations, Nucl. Acids Res.* 16: 7207 (1988); Fritz et al., *Oligonucleotide-directed construction of mutations: a gapped duplex DNA procedure without enzymatic reactions in vitro, Nucl. Acids Res.* 16: 6987-6999 (1988); Kramer et al., *Different base/base mismatches are corrected with different efficiencies by the methyl-directed DNA mismatch-repair system of E. coli, Cell* 38:879-887 (1984); Carter et al., *Improved oligonucleotide site-directed mutagenesis using M13 vectors, Nucl. Acids Res.* 13: 4431-4443 (1985); Carter, *Improved oligonucleotide-directed mutagenesis using M13 vectors, Methods in Enzymol.* 154: 382-403 (1987); Eghtedarzadeh & Henikoff, *Use of oligonucleotides to generate large deletions, Nucl. Acids Res.* 14: 5115 (1986); Wells et al., *Importance of hydrogen-bond formation in stabilizing the transition state of subtilisin, Phil. Trans. R. Soc. Lond.* A 317: 415-423 (1986); Nambiar et al., *Total synthesis and cloning of a gene coding for the ribonuclease S protein, Science* 223: 1299-1301 (1984); Sakmar and Khorana, *Total synthesis and expression of a gene for the alpha-subunit of bovine rod outer segment guanine nucleotide-binding protein (transducin), Nucl. Acids Res.* 14: 6361-6372 (1988); Wells et al., *Cassette mutagenesis: an efficient method for generation of multiple mutations at defined sites, Gene* 34:315-323 (1985); Grundström et al., *Oligonucleotide-directed mutagenesis by microscale 'shotgun' gene synthesis, Nucl. Acids Res.* 13: 3305-3316 (1985); Mandecki, *Oligonucleotide-directed double-strand break repair in plasmids of Escherichia coli: a method for site-specific mutagenesis, Proc. Natl. Acad. Sci. USA*, 83:7177-7181 (1986); Arnold, *Protein engineering for unusual environments, Current Opinion in Biotechnology* 4:450-455 (1993); Sieber, et al., Nature Biotechnology, 19:456-460 (2001); W. P. C. Stemmer, *Nature* 370, 389-91 (1994); and, I. A. Lorimer, I. Pastan, *Nucleic Acids Res.* 23, 3067-8 (1995). Additional details on many of the above methods can be found in *Methods in Enzymology* Volume 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically according to the solid phase phosphoramidite triester method described by Beaucage and Caruthers, Tetrahedron Letts. 22 (20):1859-1862, (1981) e.g., using an automated synthesizer, as described in Needham-VanDevanter et al., Nucleic Acids Res., 12:6159-6168 (1984).

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. The vector can be, for example, in the form of a plasmid, a cosmid, a phage, a bacterium, a virus, a naked polynucleotide, or a conjugated polynucleotide. The vectors are introduced into cells and/or microorganisms by standard methods including electroporation (Fromm et al., Proc. Natl. Acad. Sci. USA 82, 5824 (1985)), infection by viral vectors, high velocity ballistic penetration by small particles with the nucleic acid either within the matrix of small beads or particles, or on the surface (Klein et al., Nature 327, 70-73 (1987)), and/or the like.

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, Gene 8:81 (1979); Roberts, et al., Nature, 328:731 (1987); Schneider, E., et al., Protein Expr. Purif. 6 (1):10-14 (1995); Ausubel, Sambrook, Berger (all supra). A catalogue of bacteria and bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, N.Y. In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding at least a portion of the hIFN polypeptide.

In one embodiment, the methods involve the use of a selector codon that is a stop codon for the incorporation of one or more unnatural amino acids in vivo. For example, an O-tRNA is produced that recognizes the stop codon, including but not limited to, UAG, and is aminoacylated by an O—RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5'-3' *Exonucleases in phosphorothioate-based oligonucleotide-directed mutagenesis*. Nucleic Acids Res, 16:791-802. When the O—RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNAArg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.*, 25:4685 (1997). Components of the present invention can be generated to use these rare codons in vivo.

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology*, 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.*, 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.*, 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.*, 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology*, 20:177-182. See, also, Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.*, 121:11585-6; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See, Meggers et al., (2000) *J. Am. Chem. Soc.*, 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of ordinary skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as a hIFN polypeptide may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of a polypeptide are known to those of ordinary skill in the art, such as those described in U.S. Pat. No. 6,608,183, which is incorporated by reference herein, and standard mutagenesis techniques.

IV. Non-Naturally Encoded Amino Acids

A very wide variety of non-naturally encoded amino acids are suitable for use in the present invention. Any number of non-naturally encoded amino acids can be introduced into a hIFN polypeptide. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a hIFN polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2]cycloaddition product.

The generic structure of an alpha-amino acid is illustrated as follows (Formula I):

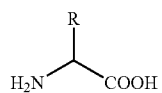

I

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Pat. No. 7,045,337 and U.S. Patent Application Publication 2003/0108885, which are incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

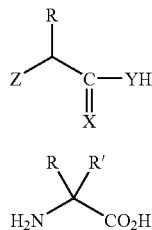

wherein Z typically comprises OH, NH₂, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) *Incorporation of azides into recombinant proteins for chemoselective modification by the Staudinger ligation, PNAS* 99:19-24, which is incorporated by reference herein, for additional methionine analogs.

In one embodiment, compositions of a hIFN polypeptide that include an unnatural amino acid (such as p-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2]cycloaddition reaction.

A non-natural amino acid incorporated into a polypeptide at the amino terminus can be composed of an R group that is any substituent other than one used in the twenty natural amino acids and a $2^{nd}$ reactive group different from the NH₂ group normally present in α-amino acids (see Formula I). A similar non-natural amino acid can be incorporated at the carboxyl terminus with a $2^{nd}$ reactive group different from the COOH group normally present in α-amino acids (see Formula I).

The unnatural amino acids of the invention may be selected or designed to provide additional characteristics unavailable in the twenty natural amino acids. For example, unnatural amino acid may be optionally designed or selected to modify the biological properties of a protein, e.g., into which they are incorporated. For example, the following properties may be optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Chemical Synthesis of Unnatural Amino Acids

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.*, 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et at. (1988) *Absolute Configuration of the Enantiomers of 7-Chloro-4 [[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 50:1239-1246; Barton et al., (1987) *Synthesis of Novel alpha-Amino-Acids and Derivatives Using Radical Chemistry. Synthesis of L- and D-alpha-Amino-Adipic Acids, L-alpha-aminopimelic Acid and Appropriate Unsaturated Derivatives. Tetrahedron* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, U.S. Patent Publication No. US 2004/0198637 entitled "Protein Arrays," which is incorporated by reference herein.

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

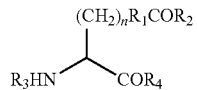

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one of ordinary skill in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et al., *Bioconjug. Chem.* 3: 262-268 (1992); Geoghegan, K. & Stroh, J., *Bioconjug. Chem.* 3:138-146 (1992); Gaertner et al., *J. Biol. Chem.* 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., *J. Am. Chem. Soc.* 81, 475-481 (1959); Shao, J. and Tam, J. P., *J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Am. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

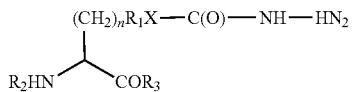

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the alphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one of ordinary skill in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., *J. Am. Chem. Soc.* 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., *J. Am. Chem. Soc.* 117:3893-3899 (1995); H. Hang and C. Bertozzi, *Acc. Chem. Res.* 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

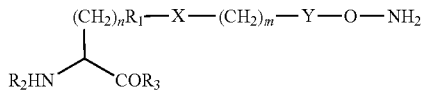

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J. Org. Chem.* 68: 8853-8858 (2003). Certain aminooxy-containing amino acids, such as L-2-amino-4-(aminooxy)butyric acid), have been isolated from natural sources (Rosenthal, G., Life Sci. 60: 1635-1641 (1997). Other aminooxy-containing amino acids can be prepared by one of ordinary skill in the art.

D. Azide and Alkyne Reactive Groups

The unique reactivity of azide and alkyne functional groups makes them extremely useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2]cycloaddition reaction to generate the corresponding triazole. See, e.g., Chin J., et al., *Science* 301:964-7 (2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing hIFN polypeptide can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., *J. Am. Chem. Soc.* 125, 3192-3193 (2003); Tornoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2]cycloaddition reaction between an azide and an alkyne is desired, the hIFN polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azidophenylalanine).

Exemplary water soluble polymers containing an aryl ester and a phosphine moiety can be represented as follows:

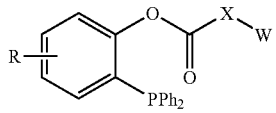

wherein X can be O, N, S or not present, Ph is phenyl, W is a water soluble polymer and R can be H, alkyl, aryl, substituted alkyl and substituted aryl groups. Exemplary R groups include but are not limited to —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

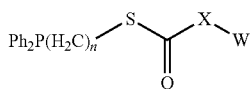

wherein n is 1-10; X can be O, N, S or not present, Ph is phenyl, and W is a water soluble polymer.

Exemplary alkyne-containing amino acids can be represented as follows:

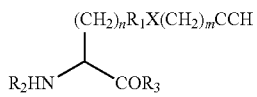

wherein n is 0-10; R$_1$ is an alkyl, aryl, substituted alkyl, or substituted aryl or not present; X is O, N, S or not present; m is 0-10, R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the acetylene moiety is positioned in the para position relative to the alkyl side chain. In some embodiments, n is 1, R$_1$ is phenyl, X is O, m is 1 and the propargyloxy group is positioned in the para position relative to the alkyl side chain (i.e., O-propargyl-tyrosine). In some embodiments, n is 1, R$_1$ and X are not present and m is 0 (i.e., propargylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53 (7): 2475-2484 (1997). Other alkyne-containing amino acids can be prepared by one of ordinary skill in the art.

Exemplary azide-containing amino acids can be represented as follows:

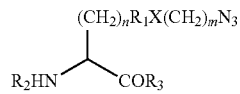

wherein n is 0-10; R$_1$ is an alkyl, aryl, substituted alkyl, substituted aryl or not present; X is O, N, S or not present; m is 0-10; R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the azide moiety is positioned para to the alkyl side chain. In some embodiments, n is 0-4 and R$_1$ and X are not present, and m=0. In some embodiments, n is 1, R$_1$ is phenyl, X is O, m is 2 and the β-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of ordinary skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J. Am. Chem. Soc.* 1995, 117 (14) 3893-3899. In some embodiments, beta-substituted aminothiol amino acids can be incorporated into hIFN polypeptides and then reacted with water soluble polymers comprising an aldehyde functionality. In some embodiments, a water soluble polymer, drug conjugate or other payload can be coupled to a hIFN polypeptide comprising a beta-substituted aminothiol amino acid via formation of the thiazolidine.

Cellular Uptake of Unnatural Amino Acids

Unnatural amino acid uptake by a cell is one issue that is typically considered when designing and selecting unnatural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., U.S. Patent Publication No. US 2004/0198637 entitled "Protein Arrays" which is incorporated by reference herein; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at maxygen.com), is optionally used to develop novel enzymes and pathways. See, e.g., Stemmer (1994), *Rapid evolution of a protein in vitro by DNA shuffling, Nature* 370 (4):389-391; and, Stemmer, (1994), *DNA shuffling by random fragmentation and reassembly. In vitro recombination for molecular evolution, Proc. Natl. Acad. Sci. USA.,* 91:10747-10751. Similarly DesignPath™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, those identified through functional genomics, and molecular evolution and design. Diversa Corporation (available on the World Wide Web at diversa.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution (e.g. liver), modulating immunogenicity, modulating protease resistance, etc. Alterations in signal transduction may be achieved through site specific PEGylation of hIFN. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology,* 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man)$_2$-Man-GlcNAc-GlcNAc)) to an asparagine by a GlcNAc-asparagine linkage. See Table 1 which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 1

EXAMPLES OF OLIGOSACCHARIDES THROUGH GlcNAc-LINKAGE

| Type | Base Structure |
|---|---|
| High-mannose | Manα1-6\\Manα1-6\\Manα1-3/  Manβ1-4GlcNAcβ1-4GlcNAcβ1-Asn  /Manα1-3 |
| Hybrid | Manα1-6\\  Manβ1-4GlcNAcβ1-4GlcNAcβ1-Asn  GlcNAcβ1-2—Manα1-3/ |
| Complex | GlcNAcβ1-2—Manα1-6\\  Manβ1-4GlcNAcβ1-4GlcNAcβ1-Asn  GlcNAcβ1-2—Manα1-3/ |
| Xylose | Manα1-6\\  Manβ1-4GlcNAcβ1-4GlcNAcβ1-Asn  /Xylβ1-2 |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like. U.S. Pat. Nos. 4,963,495 and 6,436,674, which are incorporated herein by reference, detail constructs designed to improve secretion of hGH polypeptides.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *J. Am. Chem. Soc.,* 118:8150-8151; Mahal, et al., (1997) *Science,* 276:1125-1128; Wang, et al., (2001) *Science* 292:498-500; Chin, et al., (2002) *J. Am. Chem. Soc.* 124:9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* 301:964-7, all of which are incorporated by reference herein. This allows the selective labeling of virtually any protein with a host of reagents including fluorophores, crosslinking agents, saccharide derivatives and cytotoxic molecules. See also, U.S. Pat. No. 6,927,042 entitled "Glycoprotein synthesis," which is incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation, PNAS* 99:19-24.

This invention provides another highly efficient method for the selective modification of proteins, which involves the genetic incorporation of unnatural amino acids, including but not limited to, containing an azide or alkynyl moiety into proteins in response to a selector codon. These amino acid side chains can then be modified by, including but not limited to, a Huisgen [3+2]cycloaddition reaction (see, e.g., Padwa, A. in *Comprehensive Organic Synthesis,* Vol. 4, (1991) Ed. Trost, B. M., Pergamon, Oxford, p. 1069-1109; and, Huisgen, R. in *1,3-Dipolar Cycloaddition Chemistry,* (1984) Ed. Padwa, A., Wiley, New York, p. 1-176) with, including but not limited to, alkynyl or azide derivatives, respectively. Because this method involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tomoe, et al., (2002) *J. Org. Chem.* 67:3057-3064; and, Rostovtsev, et al., (2002) *Angew. Chem. Int. Ed.* 41:2596-2599. Another method that can be used is the ligand exchange on a bisarsenic compound with a tetracysteine motif, see, e.g., Griffin, et al., (1998) *Science* 281:269-272.

A molecule that can be added to a protein of the invention through a [3+2]cycloaddition includes virtually any molecule with an azide or alkynyl derivative. Molecules include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like.

These molecules can be added to an unnatural amino acid with an alkynyl group, including but not limited to, p-propargyloxyphenylalanine, or azido group, including but not limited to, p-azido-phenylalanine, respectively.

V. In vivo Generation of hIFN Polypeptides Comprising Non-genetically-encoded Amino Acids The hIFN polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Pat. No. 7,045,337 (Ser. No. 10/126,927) and U.S. Patent Application Publication 2003/0108885 (Ser. No. 10/126,931) which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O—RS). Typically, the O—RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42 (22): 6735-6746 (2003). Exemplary O—RS, or portions thereof, are encoded by polynucleotide sequences and include amino acid sequences disclosed in U.S. Pat. No. 7,045,337 and U.S. Patent Application Publication 2003/0108885, each incorporated herein by reference. Corresponding O-tRNA molecules for use with the O—RSs are also described in U.S. Pat. No. 7,045,337 (Ser. No. 10/126,927) and U.S. Patent Application Publication 2003/0108885 (Ser. No. 10/126,931) which are incorporated by reference herein.

An example of an azide-specific O-tRNA/aminoacyl-tRNA synthetase system is described in Chin, J. W., et al., *J. Am. Chem. Soc.* 124:9026-9027 (2002). Exemplary O—RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Patent Application Publication 2003/0108885 (Ser. No. 10/126,931) which is incorporated by reference herein. Exemplary O-tRNA sequences suitable for use in the present invention include, but are not limited to, nucleotide sequences SEQ ID NOs: 1-3 as disclosed in U.S. Patent Application Publication 2003/0108885 (Ser. No. 10/126,931) which is incorporated by reference herein. Other examples of O-tRNA/aminoacyl-tRNA synthetase pairs specific to particular non-naturally encoded amino acids are described in U.S. Pat. No. 7,045,337 (Ser. No. 10/126,927) which is incorporated by reference herein. O—RS and O-tRNA that incorporate both keto- and azide-containing amino acids in *S. cerevisiae* are described in Chin, J. W., et al., *Science* 301:964-967 (2003).

Several other orthogonal pairs have been reported. Glutaminyl (see, e.g., Liu, D. R., and Schultz, P. G. (1999) *Proc. Natl. Acad. Sci. U.S.A.* 96:4780-4785), aspartyl (see, e.g., Pastrnak, M., et al., (2000) *Helv. Chim. Acta* 83:2277-2286), and tyrosyl (see, e.g., Ohno, S., et al., (1998) *J. Biochem. (Tokyo, Jpn.)* 124:1065-1068; and, Kowal, A. K., et al., (2001) *Proc. Natl. Acad. Sci. U.S.A.* 98:2268-2273) systems derived from *S. cerevisiae* tRNA's and synthetases have been described for the potential incorporation of unnatural amino acids in *E. coli*. Systems derived from the *E. coli* glutaminyl (see, e.g., Kowal, A. K., et al., (2001) *Proc. Natl. Acad. Sci. U.S.A.* 98:2268-2273) and tyrosyl (see, e.g., Edwards, H., and Schimmel, P. (1990) *Mol. Cell. Biol.* 10:1633-1641) synthetases have been described for use in *S. cerevisiae*. The *E. coli* tyrosyl system has been used for the incorporation of 3-iodo-L-tyrosine in vivo, in mammalian cells. See, Sakamoto, K., et al., (2002) *Nucleic Acids Res.* 30:4692-4699.

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the hIFN polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O-RSs, O-tRNAs, and orthogonal O-tRNA/O—RS pairs that can be used to incorporate a non-naturally encoded amino acid are described in Wang, L., et al., *Science* 292: 498-500 (2001); Chin, J. W., et al., *J. Am. Chem. Soc.* 124:9026-9027 (2002); Zhang, Z. et al., *Biochemistry* 42: 6735-6746 (2003). Methods and compositions for the in vivo incorporation of non-naturally encoded amino acids are described in U.S. Pat. No. 7,045,337 (Ser. No. 10/126,927) which is incorporated by reference herein. Methods for selecting an orthogonal tRNA-tRNA synthetase pair for use in in vivo translation system of an organism are also described in U.S. Pat. No. 7,045,337 (Ser. No. 10/126,927) and U.S. Patent Application Publication 2003/0108885 (Ser. No. 10/126,931) which are incorporated by reference herein. PCT Publication No. WO 04/035743 entitled "Site Specific Incorporation of Keto Amino Acids into Proteins," which is incorporated by reference herein in its entirety, describes orthogonal RS and tRNA pairs for the incorporation of keto amino acids. PCT Publication No. WO 04/094593 entitled "Expanding the Eukaryotic Genetic Code," which is incorporated by reference herein in its entirety, describes orthogonal RS and tRNA pairs for the incorporation of non-naturally encoded amino acids in eukaryotic host cells.

Methods for producing at least one recombinant orthogonal aminoacyl-tRNA synthetase (O—RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T thermophilus*, or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O—RS; wherein the at least one recombinant O—RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O—RS. For example, a CAT identification protocol optionally acts as a positive selection and/or a negative screening in determination of appropriate O—RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant O—RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a eubacterium, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O—RS, wherein the at least one recombinant O—RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia Coli*, a fungi, a yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O—RS) can further comprise: (d) isolating the at least one recombinant O—RS; (e) generating a second set of O—RS (optionally mutated) derived from the at least one recombinant O—RS; and, (f) repeating steps (b) and (c) until a mutated O—RS is obtained that comprises an ability to preferentially aminoacylate the O-tRNA. Optionally, steps (d)-(f) are repeated, including but not limited to, at least about two times. In one aspect, the second set of mutated O—RS derived from at least one recombinant O—RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS(O—RS), thereby providing at least one recombinant O-tRNA; wherein the at least one recombinant O-tRNA recognizes a selector codon and is not efficiency recognized by the RS from the second organism and is preferentially aminoacylated by the O—RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii, Methanobacterium thermoautotrophicum, Escherichia coli, Halobacterium*, etc.), eukaryotes, mammals, fungi, yeasts, archaebacteria, eubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS(O—RS) can include: introducing a positive selection or screening marker gene, wherein the positive marker gene comprises a drug resistance gene (including but not limited to, β-lactamase gene, comprising at least one of the selector codons, such as at least one amber stop codon) or a gene essential to the organism, or a gene that leads to detoxification of a toxic agent, along with the O—RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least one recombinant tRNA is aminoacylated by the O—RS and inserts an amino acid into a translation product encoded by the positive marker gene, in response to the at least one selector codons. In another embodiment, the concentration of the selection and/or screening agent is varied.

Methods for generating specific O-tRNA/O—RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS(O—RS), thereby providing at least one recombinant O-tRNA. The at least one recombinant O-tRNA recognizes a selector codon and is not efficiency recognized by the RS from the second organism and is preferentially aminoacylated by the O—RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O—RS pair, wherein the at least one specific O-tRNA/O—RS pair comprises at least one recombinant O—RS that is specific for the non-naturally encoded amino acid and the at least one recombinant O-tRNA. Specific O-tRNA/O—RS pairs produced by the methods are included. For example, the specific O-tRNA/O—RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii, Methanobacterium thermoautotrophicum, Halobacterium, Escherichia coli, A. fulgidus, P. furiosus, P. horikoshii, A. pernix, T thermophilus*, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methanococcus jannaschii, Methanobacterium thermoautotrophicum, Halobacterium, Escherichia coli, A. fulgidus, Halobacterium, P. furiosus, P. horikoshii, A. pernix, T thermophilus*, or the like. Alternatively, the second organism can be a eukaryotic organism, including but not limited to, a yeast, an animal cell, a plant cell, a fungus, a mammalian cell, or the like. In various embodiments the first and second organisms are different.

VI. Location of Non-naturally-occurring Amino Acids in hIFN Polypeptides

The present invention contemplates incorporation of one or more non-naturally-occurring amino acids into hIFN polypeptides. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids and/or inserting the non-naturally-occurring amino acid in a location that is not required for activity.

Regions of hIFN can be illustrated as follows, wherein the amino acid positions in hIFN are according to SEQ ID NO:2: 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix) 137-155 (E helix) 156-165 (C-terminus).

A variety of biochemical and structural approaches can be employed to select the desired sites for substitution with a non-naturally encoded amino acid within the hIFN polypeptide. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing a hIFN molecule having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of hIFN polypeptides can be identified using point mutation analysis, alanine scanning or homolog scanning methods known in the art. See, e.g., Di Marco et al., Biochem Biophys Res Corn 202:1445 (1994); Walter et al., Cancer Biotherapy & Radiopharm. 13:143 (1998); Runkel et al., J. B. C. 273:8003 (1998) for IFN. U.S. Pat. Nos. 5,580,723; 5,834,250; 6,013,478; 6,428,954; and 6,451,561, which are incorporated by reference herein, describe methods for the systematic analysis of the structure and function of polypeptides such as hGH by identifying active domains which influence the activity of the polypeptide with a target substance. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. Alternatively, residues that modulate one or more of the biological activities of IFN including side effects found with current IFN therapeutics may be good candidates for substitution with a non-naturally encoded amino acid. Such side effects include but are not limited to, neutropenia. Alternatively, residues that modulate toxicity may be good candidates for substitution with a non-naturally encoded amino acid. Such residues may include, but are not limited to, residues that interact with one or more members of the opioid family of receptors and/or residues to modulate the induction of indoleamine 2,3-dioxygenase. Residues that improve antiviral activity may be good candidates for substitution with a non-naturally encoded amino acid. Chimeric hIFN polypeptides may be designed incorporating regions or sites from limitin into IFNα to provide an improved hIFN polypeptide with retained or improved antiviral activity and/or modulated side effects and/or modulated toxicity. One or more residues in hIFN may be substituted with one or more residues found in limitin. One or more residues in the C-D loop may be good candidates for substitution with a non-naturally encoded amino acid or other modifications, including but not limited to, substitution of residues in IFN with residues found in limitin. A majority of the residues in the C-D loop of hIFN may be substituted with residues found in limitin. Suitable residues from limitin for substitution into hIFN may be determined by performing a comparison between the sequences, three-dimensional structure, secondary structure, one or more biological activities, or receptor binding of limitin and hIFN.

It is readily apparent to those of ordinary skill in the art that any means, technique, or method for selecting a position for substitution with a non-natural amino acid into any polypeptide is suitable for use in the present invention.

The structure and activity of naturally-occurring mutants of hIFN polypeptides that contain deletions can also be examined to determine regions of the protein that are likely to be tolerant of substitution with a non-naturally encoded amino acid. In a similar manner, protease digestion and monoclonal antibodies can be used to identify regions of hIFN that are responsible for binding the hIFN receptor. Once residues that are likely to be intolerant to substitution with non-naturally encoded amino acids have been eliminated, the impact of proposed substitutions at each of the remaining positions can be examined from the three-dimensional crystal structure of the hIFN and its binding proteins. X-ray crystallographic and NMR structures of hIFN are also available in the Protein Data Bank (including 1RH2 and 1ITF) (PDB, available on the World Wide Web at rcsb.org), a centralized database containing three-dimensional structural data of large molecules of proteins and nucleic acids, as well as U.S. Pat. Nos. 5,602,232; 5,460,956; 5,441,734; 4,672,108, which are incorporated by reference herein. Models may be made investigating the secondary and tertiary structure of polypeptides, if three-dimensional structural data is not available. Thus, those of ordinary skill in the art can readily identify amino acid positions that can be substituted with non-naturally encoded amino acids.

In some embodiments, the hIFN polypeptides of the invention comprise one or more non-naturally occurring amino acids positioned in a region of the protein that does not disrupt the helices or beta sheet secondary structure of the polypeptide.

Exemplary residues of incorporation of a non-naturally encoded amino acid may be those that are excluded from potential receptor binding regions (including but not limited to, Site I and Site II), may be fully or partially solvent exposed, have minimal or no hydrogen-bonding interactions with nearby residues, may be minimally exposed to nearby reactive residues, and may be in regions that are highly flexible (including but not limited to, C-D loop) or structurally rigid (including but not limited to, B helix) as predicted by the three-dimensional crystal structure, secondary, tertiary, or quaternary structure of the hIFN polypeptide, bound or unbound to its receptor. Residues of incorporation of a non-naturally encoded amino acid may be those that modulate one or more of the biological activities of IFN including side effects found with current IFN therapeutics. Residues of incorporation of a non-naturally encoded amino acid may be those that modulate toxicity. Such residues include, but are not limited to, residues that are involved with binding to one or more members of the opioid receptor family and/or residues that modulate induction of indoleamine 2,3-dioxygenase.

In some embodiments, one or more non-naturally encoded amino acid are incorporated or substituted in one or more of the following regions corresponding to secondary structures in IFN wherein the amino acid positions in hIFN are according to SEQ ID NO: 2:

1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix) 137-155 (E helix) 156-165 (C-terminus).

In some embodiments, one or more non-naturally encoded amino acid are substituted at, but not limited to, one or more of the following positions of hIFN (as in SEQ ID NO: 2, or the corresponding amino acid in SEQ ID NO: 1, 3, or any other IFN polypeptide): before position 1 (i.e., at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, or 166 (i.e. at the carboxyl terminus). In some embodiments, one or more non-naturally encoded amino acids are incorporated in one or more of the following positions in IFN: before position 1 (i.e. at the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus of the protein) (as in SEQ ID NO: 2, or the corresponding amino acids in other IFN's). In some embodiments, one or more non-naturally encoded amino acids are incorporated in one or more of the following positions in IFN: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acids in SEQ ID NO: 1 or 3). In some embodiments, the IFN polypeptides of the invention comprise one or more non-naturally encoded amino acids at one or more of the following positions: 100, 106, 107, 108, 111, 113, 114 (SEQ ID NO: 2, or the corresponding amino acids in other IFN's). In some embodiments, the IFN polypeptides of the invention comprise one or more non-naturally encoded amino acids at one or more of the following positions: 41, 45, 46, 48, 49 (SEQ ID NO: 2, or the corresponding amino acids in other IFN's). In some embodiments, the IFN polypeptides of the invention comprise one or more non-naturally encoded amino acids at one or more of the following positions: 61, 64, 65, 101, 103, 110, 117, 120, 121, 149 (SEQ ID NO: 2, or the corresponding amino acids in other IFN's). In some embodiments, the IFN polypeptides of the invention comprise one or more non-naturally encoded amino acids at one or more of the following positions: 6, 9, 12, 13, 16, 96, 156, 159, 160, 161, 162 (SEQ ID NO: 2, or the corresponding amino acids in other IFN's). In some embodiments, the IFN polypeptides of the invention comprise one or more non-naturally occurring amino acids at one or more of the following positions: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 2, or the corresponding amino acids in other IFN's). In some embodiments, the IFN polypeptides of the invention comprise one or more non-naturally encoded amino acids at one or more of the following positions: 34, 78, 107 (SEQ ID NO: 2, or the corresponding amino acid in SEQ ID NO: 1, 3, or any other IFN polypeptide). In some embodiments, the non-naturally encoded amino acid at one or more of these or other positions is linked to a water soluble polymer, including but not limited to positions: before position 1 (i.e., at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, or 166 (i.e. at the carboxyl terminus) (SEQ ID NO: 2, or the corresponding amino acid in SEQ ID NO: 1, 3, or any other IFN polypeptide). In some embodiments, the non-naturally encoded amino acid at these or other positions is linked to a water soluble polymer, including but not limited to positions: before position 1 (i.e. the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. the carboxyl terminus) (SEQ ID NO: 2, or the corresponding amino acids in other IFN's). In some embodiments, the water soluble polymer is coupled at one or more amino acid positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acid in SEQ ID NO: 1, 3, or any other IFN polypeptide). In some embodiments, the non-naturally encoded amino acid is linked to a water soluble polymer at one or more of the following positions: 100, 106, 107, 108, 111, 113, 114 (SEQ ID NO: 2, or the corresponding amino acids in SEQ ID NO: 1 or 3). In some embodiments, the non-naturally encoded amino acid is linked to a water soluble polymer at one or more of the following positions: 41, 45, 46, 48, 49 (SEQ ID NO: 2, or the corresponding amino acids in SEQ ID NO: 1 or 3). In some embodiments, the non-naturally encoded amino acid is linked to a water soluble polymer at one or more of the following positions: 61, 64, 65, 101, 103, 110, 117, 120, 121, 149 (SEQ ID NO: 2, or the corresponding amino acids in SEQ ID NO: 1 or 3). In some embodiments, the non-naturally encoded amino acid is linked to a water soluble polymer at one or more of the following positions: 6, 9, 12, 13, 16, 96, 156, 159, 160, 161, 162 (SEQ ID NO: 2, or the corresponding amino acids in SEQ ID NO: 1 or 3).

In some embodiments, the one or more non-naturally encoded amino acids at one or more of the following positions is linked to one or more water-soluble polymer: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 2, or the corresponding amino acid in or the corresponding amino acid in SEQ ID NO: 1, 3, or any other IFN polypeptide). In some embodiments, the one or more non-naturally encoded amino acids at one or more of the following positions is linked to one or more water-soluble polymer: 34, 78, 107 (SEQ ID NO: 2, or the corresponding amino acid in SEQ ID NO: 1, 3, or any other IFN polypeptide). In some embodiments, the water soluble polymer is coupled to the IFN polypeptide to a non-naturally encoded amino acid at one or more of the following amino acid positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acid in SEQ ID NO: 1, 3, or any other IFN polypeptide). In some embodiments the water soluble polymer is coupled to the IFN polypeptide at one or more of the following amino acid positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acid in SEQ ID NO: 1, 3, or any other IFN polypeptide). In some embodiments, the non-naturally encoded amino acid at one or more of these positions is linked to one or more water soluble polymers, positions: 34, 78, 107 (SEQ ID NO: 2, or the corresponding amino acid in or the corresponding amino acid in SEQ ID NO: 1, 3, or any other IFN polypeptide). In some embodiments, the IFN polypeptides of the invention comprise one or more non-naturally encoded amino acids at one or more of the following positions providing an antagonist: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 2, or the corresponding amino acid in or the corresponding amino acid in SEQ ID NO: 1, 3, or any other IFN polypeptide); a hIFN polypeptide comprising one of these substitutions may potentially act as a weak antagonist or weak agonist depending on the intended site selected and desired activity. Human IFN antagonists include, but are not limited to, hIFN polypeptides with one or more non-naturally encoded amino acid substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combinations thereof (hIFN; SEQ ID NO: 2 or the corresponding amino acids in SEQ ID NO: 1 or 3, or any other IFN polypeptide).

In some embodiments, one or more non-naturally encoded amino acids are substituted at, but not limited to, one or more of the following positions of hIFN (as in SEQ ID NO: 2, or the corresponding amino acids in SEQ ID NO: 1 or 3, or any other IFN polypeptide): 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 12, 13, 16, 68, 70, 109, 159, 161, 156, 160, 162, 24, 27, 78, 83, 85, 87, 89, 164. In one embodiment, a non-naturally encoded amino acid is substituted at position 38 of hIFN (as in SEQ ID NO: 2, or the corresponding amino acids in SEQ ID NO: 1 or 3, or any other IFN polypeptide). In some embodiments, the non-naturally encoded amino acid at one or more of these or other positions is linked to a water soluble polymer, including but not limited to positions: 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 12, 13, 16, 68, 70, 109, 159, 161, 156, 160, 162, 24, 27, 78, 83, 85, 87, 89, 164 (as in SEQ ID NO: 2, or the corresponding amino acids in SEQ ID NO: 1 or 3, or any other IFN polypeptide).

In some embodiments, one or more non-naturally encoded amino acids are substituted at, but not limited to, one or more of the following positions of hIFN (SEQ ID NO: 2 or the corresponding amino acids in SEQ ID NO: 1 or 3): before position 1 (i.e., at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, or 166 (i.e. at the carboxyl terminus) and one or more natural amino acid substitutions. In some embodiments, the one or more non-naturally encoded amino acids are coupled to a water soluble polymer. In some embodiments, the one or more non-naturally encoded amino acids are coupled to PEG. In one embodiment, the natural amino acid substitution is R149Y. In some embodiments, the natural amino acid substitution is R149E. In some embodiments, the natural amino acid substitution is R149S. In one embodiment, the non-natural amino acid substitution is at position 107 and the natural amino acid substitution is R149Y. In one embodiment, the non-natural amino acid substitution is at position 106 and the natural amino acid substitution is R149Y. In some embodiments, the one or more naturally encoded amino acid substitution is at one or more of the following positions of hIFN (SEQ ID NO: 2 or the corresponding amino acids in SEQ ID NO: 1 or 3), including but not limited to: 10, 16, 13, 79, 83, 85, 86, 87, 90, 91, 93, 94, 96, 120, 121, 124, 125, 128, 149. In some embodiments, the one or more naturally encoded amino acid substitution is one or more of the following substitutions (SEQ ID NO: 2 or the corresponding amino acids in SEQ ID NO: 1 or 3), including but not limited to: G10E, M16R, R13E, T79R, K83Q, K83S, Y85L, T86S, E87S, Q90R, Q91E, N93Q, D94V, E96K, R120K, K121T, Q124R, R125G, L128R, R149Y, R149E, R149S. In some embodiments, the natural amino acid substitution is at position 1 (the N-terminus). In some embodiments, one or more non-naturally encoded amino acids are substituted at one or more of the following positions of hIFN (as in SEQ ID NO: 2, or the corresponding amino acids in other IFN's): 107, 78, 34. In some embodiments, the non-naturally encoded amino acid at one or more of these positions is coupled to a water soluble polymer: 107, 78, 34.

One or more amino acids found in a limitin sequence may be substituted into a hIFN polypeptide (hybrid limitin/hIFN polypeptides). Examples include but are not limited to the natural amino acid substitutions described in the previous paragraph. Alternatively, a set of amino acids found in an interferon polypeptide may be replaced by a set of amino acids found in a limitin sequence. A set of amino acids may comprise contiguous amino acids or amino acids present in different portions of the molecule but are involved in a structural characteristic or biological activity of the polypeptide. The mouse limitin molecule has an improved CFU-GM toxicity profile compared to other IFN$\alpha$ proteins. Alignment of human IFN$\alpha$-2a with the limitin protein sequence showed 30% amino acid identity. 50% sequence conservation was also observed. In particular, a prominent deletion in the limitin sequence between the C and D helices (in the loop between C and D helices) was observed. The "HV" mutant was generated with the following substitutions in hIFN$\alpha$-2a (SEQ ID NO: 2): D77-D94 is replaced with the mouse limitin sequence HERALDQLLSSLWRELQV. The "CD" mutant was generated with the following substitutions in hIFN$\alpha$-2a (SEQ ID NO: 2): V105-D114 with GQSAPLP. This hybrid molecule with the loop region from limitin substituted into the human IFN$\alpha$-2a protein ("CD" mutant) was found to have equivalent anti-viral activity as the WHO IFN standard. In addition to the one or more limitin amino acids, the hIFN polypeptide may comprise one or more non-naturally encoded amino acids at any one or more positions of the hIFN polypeptide. In some embodiments, the one or more non-naturally encoded amino acids may be linked to a water soluble polymer such as PEG or bonded directly to a water soluble polymer such as PEG. In addition to the natural amino acid substitutions in the HV or the CD mutant, one or more additional natural amino acid substitutions may be found in the hIFN polypeptide.

In some embodiments, the hIFN polypeptide comprises one or more non-naturally encoded amino acids at one or more of the following positions: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide). In some embodiments, the hIFN polypeptide comprises one or more non-naturally encoded amino acids at one or more of the following positions linked to one or more water-soluble polymer: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide). In some embodiments, the hIFN polypeptide comprises one or more non-naturally encoded amino acids at one or more of the following positions linked to one or more water-soluble polymer: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide) and comprises one or more naturally encoded amino acid substitution. In some embodiments, the hIFN polypeptide comprises one or more non-naturally encoded amino acids at one or more of the following positions linked to one or more water-soluble polymer: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide) and comprises one or more of the following naturally encoded amino acid substitutions G10E, M16R, R13E, T79R, K83Q, K83S, Y85L, T86S, E87S, Q90R, Q91E, N93Q, D94V, E96K, R120K, K121T, Q124R, R125G, L128R, R149Y, R149E, R149S.

In some embodiments, the hIFN polypeptide comprises one or more non-naturally encoded amino acids at one or more of the following positions: 6, 16, 37, 45, 46, 78, 87, 89, 107, 108 (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 89, 107, 108 (SEQ ID NO: 2 or the corresponding amino acids in SEQ ID NO: 1 or 3) that is linked to a water soluble polymer. In some embodiments, the hIFN polypeptide comprises one or more non-naturally encoded amino acids at one or more of the following positions: 6, 16, 37, 45, 46, 78, 87, 89, 107, 108 (SEQ ID NO: 2 or the corresponding amino acids in SEQ ID NO: 1 or 3) that is bonded to a water soluble polymer.

In some embodiments, the hIFN polypeptide comprises one or more non-naturally encoded amino acids at one or more of the following positions: 6, 16, 37, 45, 46, 78, 87, 89, 107, 108 and one or more of the following naturally encoded amino acid substitutions: T79R, L80A, K83S, Y85L, Y85S, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 89, 107, 108 that is linked to a water soluble polymer and comprises one or more of the following naturally encoded amino acid substitutions: T79R, L80A, K83S, Y85L, Y85S, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 89, 107, 108 that is bonded to a water soluble polymer and comprises one or more of the following naturally encoded amino acid substitutions: T79R, L80A, K83S, Y85L, Y85S, T86S, E87S, Q91E (SEQ ID NO: 2 or the corresponding amino acids in SEQ ID NO: 1 or 3).

In some embodiments, the hIFN polypeptide comprises one or more non-naturally encoded amino acids at one or more of the following positions: 6, 16, 37, 45, 46, 78, 87, 107, and 108 (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 107, and 108 (SEQ ID NO: 2 or the corresponding amino acids in SEQ ID NO: 1 or 3) that is linked to a water soluble polymer. In some embodiments, the hIFN polypeptide comprises one or more non-naturally encoded amino acids at one or more of the following positions: 6, 16, 37, 45, 46, 78, 87, 107, and 108 (SEQ ID NO: 2 or the corresponding amino acids in SEQ ID NO: 1 or 3) that is bonded to a water soluble polymer.

In some embodiments, the hIFN polypeptide comprises one or more non-naturally encoded amino acids at one or more of the following positions: 6, 16, 37, 45, 46, 78, 87, 107, and 108 and comprises one or more of the following naturally encoded amino acid substitutions: T79R, K83S, Y85L, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 107, and 108 that is linked to a water soluble polymer and comprises one or more of the following naturally encoded amino acid substitutions: T79R, K83S, Y85L, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 107, and 108 that is bonded to a water soluble polymer and comprises one or more of the following naturally encoded amino acid substitutions: T79R, K83S, Y85L, T86S, E87S, Q91E (SEQ ID NO: 2 or the corresponding amino acids in SEQ ID NO: 1 or 3).

In some embodiments, the hIFN polypeptide comprises one or more non-naturally encoded amino acids at one or more of the following positions: 37, 45, 46, 89, and 107 (SEQ ID NO: 2 or the corresponding amino acids in SEQ ID NO: 1 or 3). In some embodiments, the hIFN polypeptide comprises one or more non-naturally encoded amino acids at one or more of the following positions: 37, 45, 46, 89, and 107 (SEQ ID NO: 2 or the corresponding amino acids in SEQ ID NO: 1 or 3) that is linked to a water soluble polymer. In some embodiments, the hIFN polypeptide comprises one or more non-naturally encoded amino acids at one or more of the following positions: 37, 45, 46, 89, and 107 (SEQ ID NO: 2 or the corresponding amino acids in SEQ ID NO: 1 or 3) that is bonded to a water soluble polymer.

In some embodiments, the hIFN polypeptide comprises one or more non-naturally encoded amino acids at one or more of the following positions: 37, 45, 46, 89, and 107 and comprises one or more of the following naturally encoded amino acid substitutions: T79R, L80A, Y85L, Y85S, E87S (SEQ ID NO: 2 or the corresponding amino acids in SEQ ID NO: 1 or 3). In some embodiments, the hIFN polypeptide comprises one or more non-naturally encoded amino acids at one or more of the following positions: 37, 45, 46, 89, and 107 that is linked to a water soluble polymer and comprises one or more of the following naturally encoded amino acid substitutions: T79R, L80A, Y85L, Y85S, E87S (SEQ ID NO: 2 or the corresponding amino acids in SEQ ID NO: 1 or 3). In some embodiments, the hIFN polypeptide comprises one or more non-naturally encoded amino acids at one or more of the following positions: 37, 45, 46, 89, and 107 that is bonded to a water soluble polymer and comprises one or more of the following naturally encoded amino acid substitutions: T79R, L80A, Y85L, Y85S, E87S (SEQ ID NO: 2 or the corresponding amino acids in SEQ ID NO: 1 or 3).

In some embodiments, the hIFN polypeptide comprises one or more non-naturally encoded amino acids at one or more of the following positions: 23, 24, 25, 26, 27, 28, 30, 31, 32, 33, 128, 129, 131, 132, 133, 134, 135, 136, 137, 158, 159, 160, 161, 162, 163, 164, 165 (SEQ ID NO: 2 or the corresponding amino acids in SEQ ID NO: 1 or 3). In some embodiments, the hIFN polypeptide comprises one or more non-naturally encoded amino acids at one or more of the following positions that is linked or bonded to a water soluble polymer: 23, 24, 25, 26, 27, 28, 30, 31, 32, 33, 128, 129, 131, 132, 133, 134, 135, 136, 137, 158, 159, 160, 161, 162, 163, 164, 165 (SEQ ID NO: 2 or the corresponding amino acids in SEQ ID NO: 1 or 3). In some embodiments, the hIFN polypeptide comprises one or more non-naturally encoded amino acids at one or more of the following positions: 23, 24, 27, 31, 128, 131, 134, 158 (SEQ ID NO: 2 or the corresponding amino acids in SEQ ID NO: 1 or 3). In some embodiments, the hIFN polypeptide comprises one or more non-naturally encoded amino acids at one or more of the following positions that is linked or bonded to a water soluble polymer: 23, 24, 27, 31, 128, 131, 134, 158 (SEQ ID NO: 2 or the corresponding amino acids in SEQ ID NO: 1 or 3). In some embodiments, the hIFN polypeptide comprises one or more non-naturally encoded amino acids at one or more of the following positions: 24, 27, 31, 128, 131, 134 (SEQ ID NO: 2 or the corresponding amino acids in SEQ ID NO: 1 or 3). In some embodiments, the hIFN polypeptide comprises one or more non-naturally encoded amino acids at one or more of the following positions that is linked or bonded to a water soluble polymer: 24, 27, 31, 128, 131, 134 (SEQ ID NO: 2 or the corresponding amino acids in SEQ ID NO: 1 or 3).

In some embodiments, the IFN polypeptides of the invention comprise one or more non-naturally encoded amino acids at one or more of the following positions providing an antagonist: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165, or any combination thereof (SEQ ID NO: 2, or the corresponding amino acids in other IFN's); a hIFN polypeptide comprising one of these substitutions may potentially act as a weak antagonist or weak agonist depending on the site selected and the desired activity. Human IFN antagonists include, but are not limited to, those with one or more substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combination thereof (hIFN; SEQ ID NO: 2 or the corresponding amino acids in SEQ ID NO: 1 or 3).

In some embodiments, one or more non-naturally encoded amino acids are substituted at, but not limited to, one or more of the following positions of hIFN (as in SEQ ID NO: 2, or the corresponding amino acids in other IFN's): 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 16, 68, 70, 109, 159, 161, 156, 160, 162, 12, 13, 24, 27, 78, 83, 85, 87, 89, 164. In one embodiment, a non-naturally encoded amino acid is substituted at position 38 of hIFN (as in SEQ ID NO: 2, or the corresponding amino acids in other IFN's). In some embodiments, the non-naturally occurring amino acid at these or other positions is linked to a water soluble polymer, including but not limited to positions: 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 12, 13, 16, 68, 70, 109, 159, 161, 156, 160, 162, 24, 27, 78, 83, 85, 87, 89, 164.

In some embodiments, the hIFN polypeptide comprises one or more non-naturally encoded amino acid and a naturally encoded amino acid substitution. In some embodiments, the non-naturally encoded amino acid present in the hIFN polypeptide is linked to a water soluble polymer and the hIFN polypeptide comprises one or more naturally encoded amino acid substitution.

A wide variety of non-naturally encoded amino acids can be substituted for, or incorporated into, a given position in a hIFN polypeptide. In general, a particular non-naturally encoded amino acid is selected for incorporation based on an examination of the three dimensional crystal structure of a hIFN polypeptide with its receptor, a preference for conservative substitutions (i.e., aryl-based non-naturally encoded amino acids, such as p-acetylphenylalanine or O-propargyltyrosine substituting for Phe, Tyr or Trp), and the specific conjugation chemistry that one desires to introduce into the hIFN polypeptide (e.g., the introduction of 4-azidophenylalanine if one wants to effect a Huisgen [3+2]cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the hIFN polypeptide to affect other biological traits of the hIFN polypeptide. In some cases, the other additions, substitutions or deletions may increase the stability (including but not limited to, resistance to proteolytic degradation) of the hIFN polypeptide or increase affinity of the hIFN polypeptide for its receptor. In some cases, the other additions, substitutions or deletions may increase the solubility (including but not limited to, when expressed in *E. coli* or other host cells) of the hIFN polypeptide. In some embodiments additions, substitutions or deletions may increase the polypeptide solubility following expression in *E. coli* or other recombinant host cells. In some embodiments sites are selected for substitution with a naturally encoded or non-natural amino acid in addition to another site for incorporation of a non-natural amino acid that results in increasing the polypeptide solubility following expression in *E. coli* recombinant host cells. In some embodiments, the hIFN polypeptides comprise another addition, substitution or deletion that modulates affinity for the hIFN polypeptide receptor, modulates (including but not limited to, increases or decreases) receptor dimerization, modulated downstream signaling events after hIFN receptor binding, stabilizes receptor dimers, modulates circulating half-life, modulates release or bio-availability, facilitates purification, or improves or alters a particular route of administration. hIFN polypeptides of the invention may modulate one or more of the biological activities of IFN including side effects found with current IFN therapeutics. hIFN polypeptides of the invention may modulate toxicity found with current IFN therapeutics. Similarly, hIFN polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or membranes, prodrug release or activation, hIFN size reduction, or other traits of the polypeptide.

In some embodiments, the substitution of a non-naturally encoded amino acid generates a hIFN antagonist. A subset of exemplary sites for incorporation of one or more non-naturally encoded amino acid include: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (as in SEQ ID NO: 2, or the corresponding amino acids in other IFNs). Another subset of exemplary sites for incorporation of a non-naturally encoded amino acid include: 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, (hIFN; SEQ ID NO: 2 or the corresponding amino acids in SEQ ID NO: 1 or 3). In some embodiments, hIFN antagonists comprise at least one substitution in the regions 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus) that cause IFN to act as an antagonist. In other embodiments, the exemplary sites of incorporation of a non-naturally encoded amino acid include residues within the amino terminal region of helix A and a portion of helix C. In other embodiments, the above-listed substitutions are combined with additional substitutions that cause the hIFN polypeptide to be a hIFN antagonist. In some embodiments, the hIFN antagonist comprises a non-naturally encoded amino acid linked to a water soluble polymer that is present in a receptor binding region of the hIFN molecule.

In some cases, 1, 2, 3, 4, 5, 6, 7, 8, 9, 10, or more amino acids are substituted with one or more non-naturally-encoded amino acids. In some cases, the hIFN polypeptide further includes 1, 2, 3, 4, 5, 6, 7, 8, 9, 10, or more substitutions of one or more non-naturally encoded amino acids for naturally-occurring amino acids. In some embodiments, one or more residues in the following regions of hIFN are substituted with one or more non-naturally encoded amino acids: 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus). In some cases, one or more non-naturally encoded residues are linked to one or more lower molecular weight linear or branched PEGs (approximately~5-20 kDa in mass or less), thereby enhancing binding affinity and comparable serum half-life relative to the species attached to a single, higher molecular weight PEG.

Sites for incorporation in hIFN of one or more non-naturally encoded amino acids include combinations of the following residues (as in SEQ ID NO: 2, or the corresponding amino acids in other IFN's or interferon-like cytokines): before position 1 (i.e. at the N-terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus of the protein) or any combination thereof. Sites for incorporation in hIFN of one or more non-naturally encoded amino acids include combinations of the following residues (as in SEQ ID NO: 2, or the corresponding amino acids in other IFN's or interferon-like cytokines): 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 16, 68, 70, 109, 159, 161, 156, 160, 162, 12, 13, 24, 27, 78, 83, 85, 87, 89, 164.

VII. Expression in Non-eukaryotes and Eukaryotes

To obtain high level expression of a cloned hIFN polynucleotide, one typically subclones polynucleotides encoding a hIFN polypeptide of the invention into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. and Ausubel et al.

Bacterial expression systems for expressing hIFN polypeptides of the invention are available in, including but not limited to, *E. coli, Bacillus* sp., *Pseudomonas fluorescens, Pseudomonas aeruginosa, Pseudomonas putida*, and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are known to those of ordinary skill in the art and are also commercially available. In cases where orthogonal tRNAs and aminoacyl tRNA synthetases (described above) are used to express the hIFN polypeptides of the invention, host cells for expression are selected based on their ability to use the orthogonal components. Exemplary host cells include Gram-positive bacteria (including but not limited to *B. brevis, B. subtilis,* or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O-RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 µg/liter, at least 50 µg/liter, at least 75 µg/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

I. Expression Systems, Culture, and Isolation hIFN polypeptides may be expressed in any number of suitable expression systems including, for example, yeast, insect cells, mammalian cells, and bacteria. A description of exemplary expression systems is provided below.

Yeast As used herein, the term "yeast" includes any of the various yeasts capable of expressing a gene encoding a hIFN polypeptide. Such yeasts include, but are not limited to, ascosporogenous yeasts (Endomycetales), basidiosporogenous yeasts and yeasts belonging to the Fungi imperfecti (Blastomycetes) group. The ascosporogenous yeasts are divided into two families, Spermophthoraceae and Saccharomycelaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium*, and *Filobasidiella*. Yeasts belonging to the Fungi Imperfecti (Blastomycetes) group are divided into two families, Sporobolomycetaceae (e.g., genera *Sporobolomyces* and *Bullera*) and Cryptococcaceae (e.g., genus *Candida*).

Of particular interest for use with the present invention are species within the genera *Pichia, Kluyveromyces, Saccharomyces, Schizosaccharomyces, Hansenula, Torulopsis,* and *Candida*, including, but not limited to, *P. pastoris, P. guillerimondii, S. cerevisiae, S. carlsbergensis, S. diastaticus, S. douglasii, S. kluyveri, S. norbensis, S. oviformis, K. lactis, K. fragilis, C. albicans, C. maltosa,* and *H. polymorpha*.

The selection of suitable yeast for expression of hIFN polypeptides is within the skill of one of ordinary skill in the art. In selecting yeast hosts for expression, suitable hosts may include those shown to have, for example, good secretion capacity, low proteolytic activity, good secretion capacity, good soluble protein production, and overall robustness. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a hIFN polypeptide, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., GENETICS (1989) 122:19; Ito et al., J. BACTERIOL. (1983) 153:163; Hinnen et al., PROC. NATL. ACAD. SCI. USA (1978) 75:1929); *C. albicans* (Kurtz et al., MOL. CELL. BIOL. (1986) 6:142); *C. maltosa* (Kunze et al., J. BASIC MICROBIOL. (1985) 25:141); *H. polymorpha* (Gleeson et al., J. GEN. MICROBIOL. (1986) 132:3459; Roggenkamp et al., MOL. GENETICS AND GENOMICS (1986) 202:302); *K. fragilis* (Das et al., J. BACTERIOL. (1984) 158:1165); *K. lactis* (De Louvencourt et al., J. BACTERIOL. (1983) 154:737; Van den Berg et al., BIOTECHNOLOGY (NY) (1990) 8:135); *P. guillerimondii* (Kunze et al., J. BASIC MICROBIOL. (1985) 25:141); *P. pastoris* (U.S. Pat. Nos. 5,324,639; 4,929,555; and 4,837,148; Cregg et al., MOL. CELL. BIOL. (1985) 5:3376); *Schizosaccharomyces pombe* (Beach et al., NATURE (1982) 300:706); and *Y. lipolytica; A. nidulans* (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); *A. niger* (Kelly and Hynes, EMBO J. (1985) 4:475-479); *T. reesia* (EP 0 244 234); and filamentous fungi such as, e.g., *Neurospora, Penicillium, Tolypocladium* (WO 91/00357), each incorporated by reference herein.

Control sequences for yeast vectors are well known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehyde-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Miyanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:12073); and other glycolytic enzymes, such as pyruvate decarboxylase, triosephosphate isomerase, and phosphoglucose isomerase (Holland et al., BIOCHEMISTRY (1978) 17:4900; Hess et al., J. ADV. ENZYME REG. (1969) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2µ plasmid origin is suitable for yeast. A suitable selection gene for use in yeast is the trp1 gene present in the yeast plasmid. See Tschumper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are known to those of ordinary skill in the art, and typically include, but are not limited to, either the transformation of spheroplasts or of intact yeast host cells treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are known to those of ordinary skill in the art.

See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,749; PCT Published Patent Applications WO 99/07862; WO 98/37208; and WO 98/26080; European Patent Applications EP 0 946 736; EP 0 732 403; EP 0 480 480; WO 90/10277; EP 0 340 986; EP 0 329 203; EP 0 324 274; and EP 0 164 556. See also Gellissen et al., Antonie Van Leeuwenhoek (1992) 62 (1-2): 79-93; Romanos et al., Yeast (1992) 8 (6):423-488; Goeddel, Methods in Enzymology (1990) 185:3-7, each incorporated by reference herein.

The yeast host strains may be grown in fermentors during the amplification stage using standard feed batch fermentation methods known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. Protein Chem. (1990) 9:95; and Fieschko et al., Biotech. Bioeng. (1987) 29:1113, incorporated by reference herein.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein.

Baculovirus-Infected Insect Cells The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a hIFN polypeptide, are included in the progeny intended by this definition.

The selection of suitable insect cells for expression of hIFN polypeptides is known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those of ordinary skill in the art and fully described in Summers and Smith, Texas Agricultural Experiment Station Bulletin No. 1555 (1987), herein incorporated by reference. See also, Richardson, 39 Methods in molecular Biology: Baculovirus Expression Protocols (1995); Ausubel et al., Current Protocols in Molecular Biology 16.9-16.11 (1994); King and Possee, The Baculovirus System: A Laboratory Guide (1992); and O'Reilly et al., Baculovirus Expression Vectors: A Laboratory Manual (1992).

Indeed, the production of various heterologous proteins using baculovirus/insect cell expression systems is known to those of ordinary skill in the art. See, e.g., U.S. Pat. Nos. 6,368,825; 6,342,216; 6,338,846; 6,261,805; 6,245,528; 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032; WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/02628; WO 92/01801; WO 90/14428; WO 90/10078; WO 90/02566; WO 90/02186; WO 90/01556; WO 89/01038; WO 89/01037; WO 88/07082, which are incorporated by reference herein.

Vectors that are useful in baculovirus/insect cell expression systems are known in the art and include, for example, insect expression and transfer vectors derived from the baculovirus *Autographa californica* nuclear polyhedrosis virus (AcNPV), which is a helper-independent, viral expression vector. Viral expression vectors derived from this system usually use the strong viral polyhedrin gene promoter to drive expression of heterologous genes. See generally, O'Reilly et al., Baculovirus Expression Vectors: A Laboratory Manual (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller, Ann. Rev. Micro- BIOL. (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, VIROLOGY 170:31 (1989). Other commercially available vectors include, for example, PBlueBac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN No. 1555 (1987); Smith et al., MOL. CELL. BIOL. (1983) 3:2156; Luckow and Summers, VIROLOGY (1989) 170:31. For example, the insertion can be into a gene such as the polyhedrin gene, by homologous double crossover recombination; insertion can also be into a restriction enzyme site engineered into the desired baculovirus gene. See Miller et al., BIOESSAYS (1989) 11 (4):91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26 (1):36; Graves et al., BIOCHEMISTRY (1998) 37:6050; Nomura et al., J. BIOL. CHEM. (1998) 273 (22):13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271 (37):22376; Reverey et al., J. BIOL. CHEM. (1996) 271 (39):23607-10; Stanley et al., J. BIOL. CHEM. (1995) 270:4121; Sisk et al., J. VIROL. (1994) 68 (2):766; and Peng et al., BIOTECHNIQUES (1993) 14 (2):274. Commercially available liposomes include, for example, CELLFECTIN® and LIPOFECTIN® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18 (19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., *The Regulation of Baculovirus Gene Expression* in THE MOLECULAR BIOLOGY OF BACULOVIRUSES (1986); EP 0 127 839 and 0 155 476) and the gene encoding the p10 protein (Vlak et al., J. GEN. VIROL. (1988) 69:765).

The newly formed baculovirus expression vector is packaged into an infectious recombinant baculovirus and subsequently grown plaques may be purified by techniques known to those of ordinary skill in the art. See Miller et al., BIOESSAYS (1989) 11 (4):91; SUMMERS AND SMITH, TEXAS AGRICULTURAL EXPERIMENT STATION BULLETIN No. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL-8910), *Drosophila melanogaster* (ATCC No. 1963), *Spodoptera frugiperda*, and *Trichoplusia ni*. See Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ BTI-TN-5B1-4 (*Trichopulsia ni*).

Cells and culture media are commercially available for both direct and fusion expression of heterologous polypeptides in a baculovirus/expression, and cell culture technology is generally known to those of ordinary skill in the art.

*E. Coli, Pseudomonas* species, and other Prokaryotes Bacterial expression techniques are known to those of ordinary skill in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981) 9:731; U.S. Pat. No. 4,738,921; EP Pub. Nos. 036 776 and 121 775, which are incorporated by reference herein]. The β-galactosidase (bla) promoter system [Weissmann (1981) "The cloning of interferon and other mistakes," In Interferon 3 (Ed. I. Gresser)], bacteriophage lambda PL [Shimatake et al., NATURE (1981) 292:128] and T5 [U.S. Pat. No. 4,689,406, which are incorporated by reference herein] promoter systems also provide useful promoter sequences. Preferred methods of the present invention utilize strong promoters, such as the T7 promoter to induce hIFN polypeptides at high levels. Examples of such vectors are known to those of ordinary skill in the art and include the pET29 series from Novagen, and the pPOP vectors described in WO99/05297, which is incorporated by reference herein. Such expression systems produce high levels of hIFN polypeptides in the host without compromising host cell viability or growth parameters. pET19 (Novagen) is another vector known in the art.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433, which is incorporated by reference herein]. For example, the tac promoter is a hybrid trp-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189:113; Tabor et al., Proc Natl. Acad. Sci. (1985) 82:1074]. In addition, a hybrid promoter can also be comprised of a bacteriophage promoter and an E. coli operator region (EP Pub. No. 267 851).

In addition to a functioning promoter sequence, an efficient ribosome binding site is also useful for the expression of foreign genes in prokaryotes. In E. coli, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of E. coli 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in Escherichia coli", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a hIFN polypeptide, are included in the progeny intended by this definition.

The selection of suitable host bacteria for expression of hIFN polypeptides is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. Other examples of suitable E. coli hosts include, but are not limited to, strains of BL21, DH10B, or derivatives thereof. In another embodiment of the methods of the present invention, the E. coli host is a protease minus strain including, but not limited to, OMP– and LON–. The host cell strain may be a species of Pseudomonas, including but not limited to, Pseudomonas fluorescens, Pseudomonas aeruginosa, and Pseudomonas putida. Pseudomonas fluorescens biovar 1, designated strain MB101, is known to be useful for recombinant production and is available for therapeutic protein production processes. Examples of a Pseudomonas expression system include the system available from The Dow Chemical Company as a host strain (Midland, Mich. available on the World Wide Web at dow.com). U.S. Pat. Nos. 4,755,465 and 4,859,600, which are incorporated by reference herein, describe the use of Pseudomonas strains as a host cell for hGH production.

Once a recombinant host cell strain has been established (i.e., the expression construct has been introduced into the host cell and host cells with the proper expression construct are isolated), the recombinant host cell strain is cultured under conditions appropriate for production of hIFN polypeptides. As will be apparent to one of skill in the art, the method of culture of the recombinant host cell strain will be dependent on the nature of the expression construct utilized and the identity of the host cell. Recombinant host strains are normally cultured using methods that are known to those of ordinary skill in the art. Recombinant host cells are typically cultured in liquid medium containing assimilatable sources of carbon, nitrogen, and inorganic salts and, optionally, containing vitamins, amino acids, growth factors, and other proteinaceous culture supplements known to those of ordinary skill in the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the hIFN polypeptide accumulates intracellularly) or harvesting of culture supernatant in either batch or continuous formats. For production in prokaryotic host cells, batch culture and cell harvest are preferred.

The hIFN polypeptides of the present invention are normally purified after expression in recombinant systems. Voss et al. Biochem J. (1994) 298:719-725; Rosendahl et al. Bioconjugate Chem (2005) 16:200-207; Swaminathan et al. Protein Expression and Purification (1999) 15:236-242; and Neves et al. Protein Expression and Purification (2004) 35:353-359, which are incorporated by reference herein, describe methods of expression, purification, isolation and characterization of recombinant interferons. The hIFN polypeptide may be purified from host cells or culture medium by a variety of methods known to the art. hIFN polypeptides produced in bacterial host cells may be poorly soluble or insoluble (in the form of inclusion bodies). In one embodiment of the present invention, amino acid substitutions may readily be made in the hIFN polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the E. coli host cells to release the inclusion bodies of the hIFN polypeptides. When handling inclusion bodies of hIFN polypeptide, it may be advantageous to minimize the homogenization time on repetitions in order to maximize the yield of inclusion bodies without loss due to factors such as solubilization, mechanical shearing or proteolysis.

Insoluble or precipitated hIFN polypeptide may then be solubilized using any of a number of suitable solubilization agents known to the art. The hIFN polypeptide may be solubilized with urea or guanidine hydrochloride. The volume of the solubilized hIFN polypeptide-BP should be minimized so that large batches may be produced using conveniently manageable batch sizes. This factor may be significant in a large-scale commercial setting where the recombinant host may be grown in batches that are thousands of liters in volume. In addition, when manufacturing hIFN polypeptide in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the hIFN polypeptide inclusion bodies in place of the harsher denaturing agent guanidine hydrochloride. The use of urea significantly reduces the risk of damage to stainless steel equipment utilized in the manufacturing and purification process of hIFN polypeptide while efficiently solubilizing the hIFN polypeptide inclusion bodies.

In the case of soluble hIFN protein, the hIFN may be secreted into the periplasmic space or into the culture medium. In addition, soluble hIFN may be present in the cytoplasm of the host cells. It may be desired to concentrate soluble hIFN prior to performing purification steps. Standard techniques known to those of ordinary skill in the art may be used to concentrate soluble hIFN from, for example, cell lysates or culture medium. In addition, standard techniques known to those of ordinary skill in the art may be used to disrupt host cells and release soluble hIFN from the cytoplasm or periplasmic space of the host cells.

When hIFN polypeptide is produced as a fusion protein, the fusion sequence may be removed. Removal of a fusion sequence may be accomplished by enzymatic or chemical cleavage. Enzymatic removal of fusion sequences may be accomplished using methods known to those of ordinary skill in the art. The choice of enzyme for removal of the fusion sequence will be determined by the identity of the fusion, and the reaction conditions will be specified by the choice of enzyme as will be apparent to one of ordinary skill in the art. Chemical cleavage may be accomplished using reagents known to those of ordinary skill in the art, including but not limited to, cyanogen bromide, TEV protease, and other reagents. The cleaved hIFN polypeptide may be purified from the cleaved fusion sequence by methods known to those of ordinary skill in the art. Such methods will be determined by the identity and properties of the fusion sequence and the hIFN polypeptide, as will be apparent to one of ordinary skill in the art. Methods for purification may include, but are not limited to, size-exclusion chromatography, hydrophobic interaction chromatography, ion-exchange chromatography or dialysis or any combination thereof.

The hIFN polypeptide may also be purified to remove DNA from the protein solution. DNA may be removed by any suitable method known to the art, such as precipitation or ion exchange chromatography, but may be removed by precipitation with a nucleic acid precipitating agent, such as, but not limited to, protamine sulfate. The hIFN polypeptide may be separated from the precipitated DNA using standard well known methods including, but not limited to, centrifugation or filtration. Removal of host nucleic acid molecules is an important factor in a setting where the hIFN polypeptide is to be used to treat humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Human hIFN polypeptides of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the hIFN polypeptide of the present invention includes separating deamidated, clipped, acetylated, and oxidized forms of the hIFN polypeptide variant from the intact form.

Any of the following exemplary procedures can be employed for purification of hIFN polypeptides of the invention: affinity chromatography; anion- or cation-exchange chromatography (using, including but not limited to, DEAE SEPHAROSE); chromatography on silica; High Performance Liquid Chromatography (HPLC); reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction. "Protein Purification" (1998) Janson et Ryden eds. (A. John Wiley and Sons, Inc. Publishers) describe various methods of chromatography and electrophoresis as well as modifications that can be performed within each method for optimization of purification schemes.

Proteins of the present invention, including but not limited to, proteins comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods known to those of ordinary skill in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins comprising unnatural amino acids) are used as purification reagents, including but not limited to, for affinity-based purification of proteins comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production.

In addition to other references noted herein, a variety of purification/protein folding methods are known to those of ordinary skill in the art, including, but not limited to, those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana, (1997) *Bioseparation of Proteins*, Academic Press, Inc.; Bollag et al. (1996) *Protein Methods*, 2nd Edition Wiley-Liss, NY; Walker, (1996) *The Protein Protocols Handbook* Humana Press, NJ, Harris and Angal, (1990) *Protein Purification Applications: A Practical Approach* IRL Press at Oxford, Oxford, England; Harris and Angal, *Protein Purification Methods: A Practical Approach* IRL Press at Oxford, Oxford, England; Scopes, (1993) *Protein Purification: Principles and Practice 3rd Edition* Springer Verlag, NY; Janson and Ryden, (1998) *Protein Purification: Principles, High Resolution Methods and Applications, Second Edition* Wiley-VCH, NY; and Walker (1998), *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins can possess a conformation different from the desired conformations of the relevant polypeptides. In one aspect of the invention, the expressed protein or polypeptide is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are known to those of ordinary skill in the art (see, the references above, and Debinski, et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of hIFN polypeptide, the hIFN polypeptide thus produced may be misfolded and thus lacks or has reduced biological activity. The bioactivity of the protein may be restored by "refolding". In general, misfolded hIFN polypeptide is refolded by solubilizing (where the hIFN polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. hIFN polypeptide may be refolded using standard methods known in the art, such as those described in U.S. Pat. Nos. 4,511,502, 4,511,503, and 4,512,922, which are incorporated by reference herein. The hIFN polypeptide may also be cofolded with other proteins to form heterodimers or heteromultimers.

After refolding, the hIFN may be further purified. Purification of hIFN may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, hIFN may be exchanged into different buffers and/or concentrated by any of a variety of methods known to the art, including, but not limited to, diafiltration and dialysis. hIFN that is provided as a single purified protein may be subject to aggregation and precipitation.

The purified hIFN may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 98% pure, or at least 99% or greater pure. Regardless of the exact numerical value of the purity of the hIFN, the hIFN is sufficiently pure for use as a pharmaceutical product or for further processing, such as conjugation with a water soluble polymer such as PEG.

Certain hIFN molecules may be used as therapeutic agents in the absence of other active ingredients or proteins (other than excipients, carriers, and stabilizers, serum albumin and the like), or they may be complexed with another protein or a polymer.

General Purification Methods Any one of a variety of isolation steps may be performed on the cell lysate, extract, culture medium, inclusion bodies, periplasmic space of the host cells, cytoplasm of the host cells, or other material, comprising hIFN polypeptide or on any hIFN polypeptide mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERFRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, Monitor pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the present invention, for example, the hIFN polypeptide may be reduced and denatured by first denaturing the resultant purified hIFN polypeptide in urea, followed by dilution into TRIS buffer containing a reducing agent (such as DTT) at a suitable pH. In another embodiment, the hIFN polypeptide is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured hIFN polypeptide mixture may then be further isolated or purified.

As stated herein, the pH of the first hIFN polypeptide mixture may be adjusted prior to performing any subsequent isolation steps. In addition, the first hIFN polypeptide mixture or any subsequent mixture thereof may be concentrated using techniques known in the art. Moreover, the elution buffer comprising the first hIFN polypeptide mixture or any subsequent mixture thereof may be exchanged for a buffer suitable for the next isolation step using techniques known to those of ordinary skill in the art.

Ion Exchange Chromatography In one embodiment, and as an optional, additional step, ion exchange chromatography may be performed on the first hIFN polypeptide mixture. See generally ION EXCHANGE CHROMATOGRAPHY: PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Anion or cation exchange column chromatography may be performed on the hIFN polypeptide at any stage of the purification process to isolate substantially purified hIFN polypeptide. The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing.

Following adsorption of the hIFN polypeptide to the cation exchanger matrix, substantially purified hIFN polypeptide may be eluted by contacting the matrix with a buffer having a sufficiently high pH or ionic strength to displace the hIFN polypeptide from the matrix. Suitable buffers for use in high pH elution of substantially purified hIFN polypeptide include, but are not limited to, citrate, phosphate, formate, acetate, HEPES, and MES buffers ranging in concentration from at least about 5 mM to at least about 100 mM.

Reverse-Phase Chromatography RP-HPLC may be performed to purify proteins following suitable protocols that are known to those of ordinary skill in the art. See, e.g., Pearson et al., ANAL BIOCHEM. (1982) 124:217-230 (1982); Rivier et al., J. CHROM. (1983) 268:112-119; Kunitani et al., J. CHROM. (1986) 359:391-402. RP-HPLC may be performed on the hIFN polypeptide to isolate substantially purified hIFN polypeptide. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{18}$, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. The Source RP column is another example of a RP-HPLC column.

A suitable elution buffer containing an ion pairing agent and an organic modifier such as methanol, isopropanol, tetrahydrofuran, acetonitrile or ethanol, may be used to elute the hIFN polypeptide from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

Hydrophobic Interaction Chromatography Purification Techniques Hydrophobic interaction chromatography (HIC) may be performed on the hIFN polypeptide. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, N.J.).

Briefly, prior to loading, the HIC column may be equilibrated using standard buffers known to those of ordinary skill in the art, such as an acetic acid/sodium chloride solution or HEPES containing ammonium sulfate. Ammonium sulfate may be used as the buffer for loading the HIC column. After loading the hIFN polypeptide, the column may then washed using standard buffers and conditions to remove unwanted materials but retaining the hIFN polypeptide on the HIC column. The hIFN polypeptide may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the hIFN molecules. The eluant may then be concentrated, for example, by filtration such as diafiltration or ultrafiltration. Diafiltration may be utilized to remove the salt used to elute the hIFN polypeptide.

Other Purification Techniques Yet another isolation step using, for example, gel filtration (GEL FILTRATION: PRINCIPLES AND METHODS (Cat. No. 18-1022-18, Amersham Biosciences, Piscataway, N.J.) which is incorporated by reference herein, hydroxyapatite chromatography (suitable matrices include, but are not limited to, HA-Ultrogel, High Resolution (Calbiochem), CHT Ceramic Hydroxyapatite (BioRad), Bio-Gel HTP Hydroxyapatite (BioRad)), HPLC, expanded bed adsorption, ultrafiltration, diafiltration, lyophilization, and the like, may be performed on the first hIFN polypeptide mixture or any subsequent mixture thereof, to remove any excess salts and to replace the buffer with a suitable buffer for the next isolation step or even formulation of the final drug product.

The yield of hIFN polypeptide, including substantially purified hIFN polypeptide, may be monitored at each step described herein using techniques known to those of ordinary skill in the art. Such techniques may also be used to assess the yield of substantially purified hIFN polypeptide following the last isolation step. For example, the yield of hIFN polypeptide may be monitored using any of several reverse phase high pressure liquid chromatography columns, having a variety of alkyl chain lengths such as cyano RP-HPLC, $C_{18}$RP-HPLC; as well as cation exchange HPLC and gel filtration HPLC.

In specific embodiments of the present invention, the yield of hIFN after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the hIFN in the starting material for each purification step.

Purity may be determined using standard techniques, such as SDS-PAGE, or by measuring hIFN polypeptide using Western blot and ELISA assays. For example, polyclonal antibodies may be generated against proteins isolated from negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of hIFN polypeptide from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The hIFN polypeptide fractions which are within the IPC limits are pooled.

DEAE Sepharose (Pharmacia) material consists of diethylaminoethyl (DEAE)-groups which are covalently bound to the surface of Sepharose beads. The binding of hIFN polypeptide to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and hIFN polypeptide is eluted with a buffer with increased ionic strength. The column is packed with DEAE Sepharose fast flow. The column volume is adjusted to assure a hIFN polypeptide load in the range of 3-10 mg hIFN polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, hIFN polypeptide is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at −70° C.

Additional methods that may be employed include, but are not limited to, steps to remove endotoxins. Endotoxins are lipopoly-saccharides (LPSs) which are located on the outer membrane of Gram-negative host cells, such as, for example, *Escherichia coli*. Methods for reducing endotoxin levels are known to one of ordinary skill in the art and include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Modifications or additional methods may be required to remove contaminants such as co-migrating proteins from the polypeptide of interest. Methods for measuring endotoxin levels are known to one of ordinary skill in the art and include, but are not limited to, Limulus Amebocyte Lysate (LAL) assays. The EndosafeTM-PTS assay is a colorimetric, single tube system that utilizes cartridges preloaded with LAL reagent, chromogenic substrate, and control standard endotoxin along with a handheld spectrophotometer. Alternate methods include, but are not limited to, a Kinetic LAL method that is turbidimetric and uses a 96 well format.

A wide variety of methods and procedures can be used to assess the yield and purity of a hIFN protein comprising one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one of ordinary skill in the art.

Additional methods include, but are not limited to: SDS-PAGE coupled with protein staining methods, immunoblotting, matrix assisted laser desorption/ionization-mass spectrometry (MALDI-MS), liquid chromatography/mass spectrometry, isoelectric focusing, analytical anion exchange, chromatofocusing, and circular dichroism.

VIII. Expression in Alternate Systems

Several strategies have been employed to introduce unnatural amino acids into proteins in non-recombinant host cells, mutagenized host cells, or in cell-free systems. These systems are also suitable for use in making the hIFN polypeptides of the present invention. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem,* 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.,* 1995, 34:621 (1995); C. J. Noren, S. J. Anthony-Cahill, M. C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.,* 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.,* 284:29 (2000); trifluoromethionine has been used to replace methionine in bacteriophage T4 lysozyme to study its interaction with chitooligosaccharide ligands by $^{19}F$ NMR, see, e.g., H. Duewel, E. Daub, V. Robinson and J. F. Honek, *Biochemistry,* 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.,* 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.,* 9:1665 (1990); J. O. Boles, K. Lewinski, M. Kunkle, J. D. Odom, B. Dunlap, L. Lebioda and M. Hatada, *Nat. Struct. Biol.,* 1:283 (1994); N. Budisa, B. Steipe, P. Demange, C. Eckerskorn, J. Kellermann and R. Huber, *Eur. J. Biochem.,* 230:788 (1995); and, N. Budisa, W. Karnbrock, S. Steinbacher, A. Humm, L. Prade, T. Neuefeind, L. Moroder and R. Huber, *J. Mol. Biol.,* 270:616 (1997). Methionine analogs with alkene or alkyne functionalities have also been incorporated efficiently, allowing for additional modification of proteins by chemical means. See, e.g., J. C. van Hest and D. A. Tirrell, *FEBS Lett.,* 428:68 (1998); J. C. van Hest, K. L. Kiick and D. A. Tirrell, *J. Am. Chem. Soc.,* 122:1282 (2000); and, K. L. Kiick and D. A. Tirrell, *Tetrahedron,* 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry,* 33:7107 (1994). An *Escherichia coli* strain harboring this mutant PheRS allows the incorporation of p-Cl-phenylalanine or p-Br-phenylalanine in place of phenylalanine See, e.g., M. Ibba and H. Hennecke, *FEBS Lett.,* 364:272 (1995); and, N. Sharma, R. Furter, P. Kast and D. A. Tirrell, *FEBS Lett.,* 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.,* 275: 40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation.

If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science,* 292:501 (2001). ValRS can misaminoacylate tRNAVal with Cys, Thr, or aminobutyrate (Abu); these non-cognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature,* 192: 1227-1232 (1961); Hofmann, K., Bohn, H. *Studies on polypeptides. XXVI. The effect of pyrazole-imidazole replacements on the S-protein activating potency of an S-peptide fragment, J. Am. Chem,* 88 (24):5914-5919 (1966); Kaiser, E. T. *Synthetic approaches to biologically active peptides and proteins including enyzmes, Acc Chem Res,* 22:47-54 (1989); Nakatsuka, T., Sasaki, T., Kaiser, E. T. *Peptide segment coupling catalyzed by the semisynthetic enzyme thiosubtilisin, J Am Chem Soc,* 109:3808-3810 (1987); Schnolzer, M., Kent, S B H. *Constructing proteins by dovetailing unprotected synthetic peptides: backbone-engineered HIV protease, Science,* 256 (5054):221-225 (1992); Chaiken, I. M. *Semisynthetic peptides and proteins, CRC Crit. Rev Biochem,* 11 (3):255-301 (1981); Offord, R. E. *Protein engineering by chemical means? Protein Eng.,* 1 (3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 266 (5183): 243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 238 (4832): 1401-1403 (1987); Kaiser, E. T., Lawrence D. S., Rokita, S. E. *The chemical modification of enzymatic specificity, Annu Rev Biochem,* 54:565-595 (1985); Kaiser, E. T., Lawrence, D. S. *Chemical mutation of enzyme active sites, Science,* 226 (4674):505-511 (1984); Neet, K. E., Nanci A, Koshland, D. E. *Properties of thiol-subtilisin, J. Biol. Chem.,* 243 (24):6392-6401 (1968); Polgar, L. B. et M. L. Bender, *A new enzyme containing a synthetically formed active site. Thiol-subtilisin. J. Am. Chem Soc,* 88:3153-3154 (1966); and, Pollack, S. J., Nakayama, G. Schultz, P. G. *Introduction of nucleophiles and spectroscopic probes into antibody combining sites, Science,* 242 (4881):1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem,* 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci,* 83 (22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am. Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.,* vol. 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. *5'-3' Exonucleases in phosphorothioate-based olignoucleotide-directed mutagensis, Nucleic Acids Res,* 16 (3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [³H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10 (6):425-432; and, Ellman, J. A., Mendel, D., Schultz, P. G. *Site-specific incorporation of novel backbone structures into proteins, Science,* 255 (5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. Ace. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA.

Ribozymes can be generated by in vitro selection using a partially randomized r24mini conjugated with tRNA$^{ASn}_{C-CCG}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Immobilization on a substrate may be used to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing *E. coli* lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Lu et al. in Mol. Cell. 2001 October; 8 (4):759-69 describe a method in which a protein is chemically ligated to a synthetic peptide containing unnatural amino acids (expressed protein ligation).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science*, 268:439 (1995); and, D. A. Dougherty, *Curr. Opin. Chem. Biol.*, 4:645 (2000). A *Xenopus* oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.*, 271:19991 (1996); the incorporation of biotinylated amino acids to identify surface-exposed residues in ion channels, see, e.g., J. P. Gallivan, H. A. Lester and D. A. Dougherty, *Chem. Biol.*, 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, *Cell,* 96:89 (1999); and, T. Lu, A. Y. Ting, J. Mainland, L. Y. Jan, P. G. Schultz and J. Yang, *Nat. Neurosci.*, 4:239 (2001).

The ability to incorporate unnatural amino acids directly into proteins in vivo offers a wide variety of advantages including but not limited to, high yields of mutant proteins, technical ease, the potential to study the mutant proteins in cells or possibly in living organisms and the use of these mutant proteins in therapeutic treatments and diagnostic uses. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.* 7:419 (1998).

It may also be possible to obtain expression of a hIFN polynucleotide of the present invention using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/ BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, *Biotechnology and Bioengineering,* 74:309-316 (2001); Kim, D. M. and J. R. Swartz, *Biotechnology Letters,* 22, 1537-1542, (2000); Kim, D. M., and J. R. Swartz, *Biotechnology Progress,* 16, 385-390, (2000); Kim, D. M., and J. R. Swartz, *Biotechnology and Bioengineering,* 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of hIFN polypeptides comprising a non-naturally encoded amino acid includes the mRNA-peptide fusion technique. See, e.g., R. Roberts and J. Szostak, *Proc. Natl. Acad. Sci.* (*USA*) 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of hIFN polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl. Acad. Sci.* (*USA*) 100:6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 (α or β), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

IX. Macromolecular Polymers Coupled to hIFN Polypeptides

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide;

a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to hIFN polypeptides of the present invention to modulate biological properties of the hIFN polypeptide, and/or provide new biological properties to the hIFN molecule. These macromolecular polymers can be linked to the hIFN polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the molecular weight of the polymer is 30,000 Da. In some embodiments, the molecular weight of the polymer is 40,000 Da.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated hIFN polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. For therapeutic use of the end-product preparation, the polymer will be pharmaceutically acceptable.

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG: hIFN polypeptide conjugates, the term "therapeutically effective amount" refers to an amount which gives a decrease in viral levels that provides benefit to a patient. The amount will vary from one individual to another and will depend upon a number of factors, including the overall physical condition of the patient and the underlying cause of the condition. The amount of hIFN polypeptide used for therapy gives an acceptable decrease in viral level. A therapeutically effective amount of the present compositions may be readily ascertained by one of ordinary skill in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods known to those of ordinary skill in the art (Sandier and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the hIFN polypeptide by the formula:

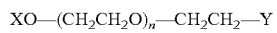

$$XO-(CH_2CH_2O)_n-CH_2CH_2-Y$$

where n is 2 to 10,000 and X is H or a terminal modification, including but not limited to, a $C_{1-4}$ alkyl, a protecting group, or a terminal functional group.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a hIFN polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the hIFN polypeptide to form a Huisgen [3+2]cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the hIFN polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). The molecular weight of PEG may be of a wide range, including but not limited to, between about 100 Da and about 100,000 Da or more. PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, PEG is between about 100 Da and 50,000 Da. In some embodiments, PEG is between about 100 Da and 40,000 Da. In some embodiments, PEG is between about 1,000 Da and 40,000 Da. In some embodiments, PEG is between about 5,000 Da and 40,000 Da. In some embodiments, PEG is between about 10,000 Da and 40,000 Da. In some embodiments, the molecular weight of the PEG is 30,000 Da. In some embodiments, the molecular weight of the PEG is 40,000 Da. Branched chain PEGs, including but not limited to, PEG molecules with each chain having a MW ranging from 1-100 kDa (including but not limited to, 1-50 kDa or 5-20 kDa) can also be used. The molecular weight of each chain of the branched chain PEG may be, including but not limited to, between about 1,000 Da and about 100,000 Da or more. The molecular weight of each chain of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of each chain of the branched chain PEG is between about 1,000 Da and 50,000 Da. In some embodiments, the molecular weight of each chain of the branched chain PEG is between about 1,000 Da and 40,000 Da. In some embodiments, the molecular weight of each chain of the branched chain PEG is between about 5,000 Da and 40,000 Da. In some embodiments, the molecular weight of each chain of the branched chain PEG is between about 5,000 Da and 20,000 Da. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2]cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the hIFN polypeptide variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —$CH_2CH_2O$—($CH_2CH_2O$)$_n$—$CH_2CH_2$—, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone. The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and 50,000 Da. In some embodiments, the molecular weight of PEG is between about 100 Da and 40,000 Da. In some embodiments, the molecular weight of PEG is between about 1,000 Da and 40,000 Da. In some embodiments, the molecular weight of PEG is between about 5,000 Da and 40,000 Da. In some embodiments, the molecular weight of PEG is between about 10,000 Da and 40,000 Da. In some embodiments, the molecular weight of PEG is 30,000 Da. In some embodiments, the molecular weight of PEG is 40,000 Da.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462; 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(—YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

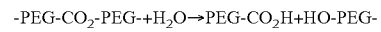

-PEG-CO$_2$-PEG-+H$_2$O→PEG-CO$_2$H+HO-PEG-

It is understood by those of ordinary skill in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and 50,000 Da. In some embodiments, the molecular weight of each chain of the polymer backbone is between about 100 Da and 40,000 Da. In some embodiments, the molecular weight of each chain of the polymer backbone is between about 1,000 Da and 40,000 Da. In some embodiments, the molecular weight of each chain of the polymer backbone is between about 5,000 Da and 40,000 Da. In some embodiments, the molecular weight of each chain of the polymer backbone is between about 10,000 Da and 40,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

X-A-POLY-B—N=N=N wherein:
N=N=N is an azide moiety;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those of ordinary skill in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Biotechnology (NY) 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900, 461). All of the above references and patents are incorporated herein by reference.

In certain embodiments of the present invention, the polymer derivatives of the invention comprise a polymer backbone having the structure:

X—CH$_2$CH$_2$O—(CH$_2$CH$_2$O)$_n$—CH$_2$CH$_2$—N=N=N wherein:
X is a functional group as described above; and
n is about 20 to about 4000.

In another embodiment, the polymer derivatives of the invention comprise a polymer backbone having the structure:

X—CH$_2$CH$_2$O—(CH$_2$CH$_2$O)$_n$—CH$_2$CH$_2$—O—(CH$_2$)$_m$—W—N=N=N wherein:
W is an aliphatic or aromatic linker moiety comprising between 1-10 carbon atoms;
n is about 20 to about 4000; and
X is a functional group as described above. m is between 1 and 10.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

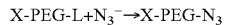

X-PEG-L+N$_3^-$→X-PEG-N$_3$

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below:

X-PEG-M+N-linker-N=N=N→PG-X-PEG-linker-N=N=N wherein:
PEG is poly(ethylene glycol) and X is a capping group such as alkoxy or a functional group as described above; and
M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

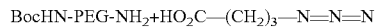

BocHN-PEG-NH$_2$+HO$_2$C—(CH$_2$)$_3$—N=N=N

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

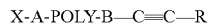

X-A-POLY-B—C≡C—R wherein:
R can be either H or an alkyl, alkene, alkyoxy, or aryl or substituted aryl group;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

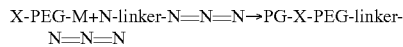

In another embodiment of the present invention, the polymer derivatives comprise a polymer backbone having the structure:

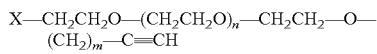

wherein:
X is a functional group as described above;
n is about 20 to about 4000; and
m is between 1 and 10.
Specific examples of each of the heterobifunctional PEG polymers are shown below.

The acetylene-containing PEG derivatives of the invention can be prepared using methods known to those of ordinary skill in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

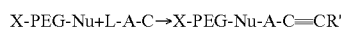

As shown, a preferred polymer backbone for use in the reaction has the formula X-PEG-Nu, wherein PEG is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

wherein:
PEG is poly(ethylene glycol) and X is a capping group such as alkoxy or a functional group as described above; and
R' is either H, an alkyl, alkoxy, aryl or aryloxy group or a substituted alkyl, alkoxyl, aryl or aryloxy group.
In the example above, the leaving group L should be sufficiently reactive to undergo SN2-type displacement when contacted with a sufficient concentration of the acetylene anion. The reaction conditions required to accomplish SN2 displacement of leaving groups by acetylene anions are known to those of ordinary skill in the art.

Purification of the crude product can usually be accomplished by methods known in the art including, but are not limited to, precipitation of the product followed by chromatography, if necessary.

Water soluble polymers can be linked to the hIFN polypeptides of the invention. The water soluble polymers may be linked via a non-naturally encoded amino acid incorporated in the hIFN polypeptide or any functional group or substituent of a non-naturally encoded or naturally encoded amino acid, or any functional group or substituent added to a non-naturally encoded or naturally encoded amino acid. Alternatively, the water soluble polymers are linked to a hIFN polypeptide incorporating a non-naturally encoded amino acid via a naturally-occurring amino acid (including but not limited to, cysteine, lysine or the amine group of the N-terminal residue). In some cases, the hIFN polypeptides of the invention comprise 1, 2, 3, 4, 5, 6, 7, 8, 9, 10 non-natural amino acids, wherein one or more non-naturally-encoded amino acid(s) are linked to water soluble polymer(s) (including but not limited to, PEG and/or oligosaccharides). In some cases, the hIFN polypeptides of the invention further comprise 1, 2, 3, 4, 5, 6, 7, 8, 9, 10, or more naturally-encoded amino acid(s) linked to water soluble polymers. In some cases, the hIFN polypeptides of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the hIFN polypeptide relative to the unconjugated form.

The number of water soluble polymers linked to a hIFN polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of hIFN is increased at least about 10, 20, 30, 40, 50, 60, 70, 80, 90 percent, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, a hIFN polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

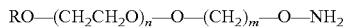

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

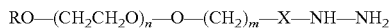

where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure:

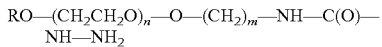
RO—(CH$_2$CH$_2$O)$_n$—O—(CH$_2$)$_m$—NH—C(O)—
NH—NH$_2$ where R is a simple alkyl (methyl, ethyl, propyl, etc.), m is 2-10 and n is 100-1,000.

In another embodiment of the invention, a hIFN polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

RO—(CH$_2$CH$_2$O)$_n$—O—(CH$_2$)$_2$—NH—C(O)(CH$_2$)$_m$—
O—NH$_2$ where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

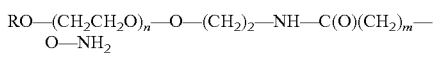
RO—(CH$_2$CH$_2$O)$_n$—O—(CH$_2$)$_2$—NH—C(O)(CH$_2$)$_m$—
X—NH—NH$_2$ where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure:

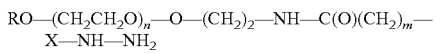
RO—(CH$_2$CH$_2$O)$_n$—O—(CH$_2$)$_2$—NH—C(O)(CH$_2$)$_m$—
NH—C(O)—NH—NH$_2$ where R is a simple alkyl (methyl, ethyl, propyl, etc.), m is 2-10 and n is 100-1,000.

In another embodiment of the invention, a hIFN polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, may be from 5-20 kDa.

In another embodiment of the invention, a hIFN polypeptide comprising a non-naturally encoded amino acid is modified with a PEG derivative having a branched structure. For instance, in some embodiments, the hydrazine- or hydrazide-terminal PEG derivative will have the following structure:

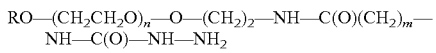
[RO—(CH$_2$CH$_2$O)$_n$—O—(CH$_2$)$_2$—NH—C(O)]$_2$CH
(CH$_2$)$_m$—X—NH—NH$_2$ where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure:

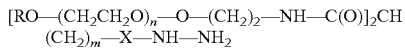
[RO—(CH$_2$CH$_2$O)$_n$—O—(CH$_2$)$_2$—C(O)—NH—
CH$_2$—CH$_2$]$_2$CH—X—(CH$_2$)$_m$—NH—C(O)—
NH—NH$_2$ where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

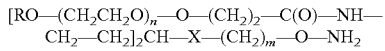
[RO—(CH$_2$CH$_2$O)$_n$—O—(CH$_2$)$_2$—C(O)—NH—
CH$_2$—CH$_2$]$_2$CH—X—(CH$_2$)$_m$—O—NH$_2$ where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the hIFN polypeptide can modulate the binding of the hIFN polypeptide to the hIFN polypeptide receptor at Site 1. In some embodiments, the linkages are arranged such that the hIFN polypeptide binds the hIFN polypeptide receptor at Site 1 with a $K_d$ of about 400 nM or lower, with a $K_d$ of 150 nM or lower, and in some cases with a $K_d$ of 100 nM or lower, as measured by an equilibrium binding assay, such as that described in Spencer et al., *J. Biol. Chem.,* 263:7862-7867 (1988) for hGH.

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), Protein Immobilisation. Fundamental and Applications, Marcel Dekker, N.Y.; S. S. Wong, (1992), Chemistry of Protein Conjugation And Crosslinking, CRC Press, Boca Raton; G. T. Hermanson et al., (1993), Immobilized Affinity Ligand Techniques, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, M*acromol. Chem. Phys. C*25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese et al., *App. Biochem. Biotech.* 11: 141-52 (1985)). All references and patents cited are incorporated by reference herein.

PEGylation (i.e., addition of any water soluble polymer) of hIFN polypeptides containing a non-naturally encoded amino acid, such as p-azido-L-phenylalanine, is carried out by any convenient method. For example, hIFN polypeptide is PEGylated with an alkyne-terminated mPEG derivative. Briefly, an excess of solid mPEG(5000)-O—$CH_2$—C≡CH is added, with stirring, to an aqueous solution of p-azido-L-Phe-containing hIFN polypeptide at room temperature. Typically, the aqueous solution is buffered with a buffer having a $pK_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated hIFN polypeptide variants from free mPEG(5000)—O—$CH_2$—C≡CH and any high-molecular weight complexes of the pegylated hIFN polypeptide which may form when unblocked PEG is activated at both ends of the molecule, thereby crosslinking hIFN polypeptide variant molecules. The conditions during hydrophobic interaction chromatography are such that free mPEG(5000)-O—CH$_2$—C≡CH flows through the column, while any crosslinked PEGylated hIFN polypeptide variant complexes elute after the desired forms, which contain one hIFN polypeptide variant molecule conjugated to one or more PEG groups. Suitable conditions vary depending on the relative sizes of the crosslinked complexes versus the desired conjugates and are readily determined by those of ordinary skill in the art. The eluent containing the desired conjugates is concentrated by ultrafiltration and desalted by diafiltration.

If necessary, the PEGylated hIFN polypeptide obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta, A Z in PROTEIN PURIFICATION METHODS, A PRACTICAL APPROACH (Harris & Angal, Eds.) IRL Press 1989, 293-306). The purity of the hGH-PEG conjugate can be assessed by proteolytic degradation (including but not limited to, trypsin cleavage) followed by mass spectrometry analysis. Pepinsky R B., et al., *J. Pharmcol. & Exp. Ther.* 297 (3):1059-66 (2001).

A water soluble polymer linked to an amino acid of a hIFN polypeptide of the invention can be further derivatized or substituted without limitation.

Azide-containing PEG Derivatives

In another embodiment of the invention, a hIFN polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure:

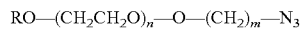

where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

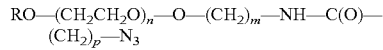

where R is a simple alkyl (methyl, ethyl, propyl, etc.), m is 2-10, p is 2-10 and n is 100-1,000 (i.e., average molecular weight is between 5-40 kDa).

In another embodiment of the invention, a hIFN polypeptide comprising a alkyne-containing amino acid is modified with a branched PEG derivative that contains a terminal azide moiety, with each chain of the branched PEG having a MW ranging from 10-40 kDa and may be from 5-20 kDa. For instance, in some embodiments, the azide-terminal PEG derivative will have the following structure:

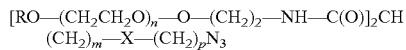

where R is a simple alkyl (methyl, ethyl, propyl, etc.), m is 2-10, p is 2-10, and n is 100-1,000, and X is optionally an O, N, S or carbonyl group (C═O), in each case that can be present or absent.

Alkyne-containing PEG Derivatives

In another embodiment of the invention, a hIFN polypeptide is modified with a PEG derivative that contains an alkyne moiety that will react with an azide moiety present on the side chain of the non-naturally encoded amino acid.

In some embodiments, the alkyne-terminal PEG derivative will have the following structure:

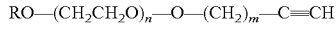

where R is a simple alkyl (methyl, ethyl, propyl, etc.), m is 2-10 and n is 100-1,000 (i.e., average molecular weight is between 5-40 kDa).

In another embodiment of the invention, a hIFN polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

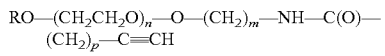

where R is a simple alkyl (methyl, ethyl, propyl, etc.), m is 2-10, p is 2-10 and n is 100-1,000.

In another embodiment of the invention, a hIFN polypeptide comprising an azide-containing amino acid is modified with a branched PEG derivative that contains a terminal alkyne moiety, with each chain of the branched PEG having a MW ranging from 10-40 kDa and may be from 5-20 kDa. For instance, in some embodiments, the alkyne-terminal PEG derivative will have the following structure:

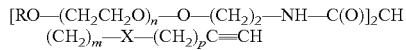

where R is a simple alkyl (methyl, ethyl, propyl, etc.), m is 2-10, p is 2-10, and n is 100-1,000, and X is optionally an O, N, S or carbonyl group (C═O), or not present.

Phosphine-containing PEG Derivatives

In another embodiment of the invention, a hIFN polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

In some embodiments, the PEG derivative will have the structure:

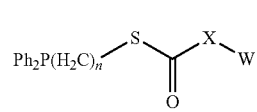

wherein n is 1-10; X can be O, N, S or not present, Ph is phenyl, and W is a water soluble polymer.

In some embodiments, the PEG derivative will have the structure:

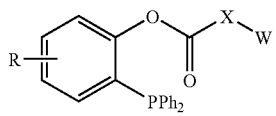

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2$R', —$S(O)_2$NR'R", —CN and —$NO_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

Other Peg Derivatives and General PEGylation Techniques

Other exemplary PEG molecules that may be linked to hIFN polypeptides, as well as PEGylation methods include those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Enhancing Affinity for Serum Albumin

Various molecules can also be fused to the hIFN polypeptides of the invention to modulate the half-life of hIFN polypeptides in serum. In some embodiments, molecules are linked or fused to hIFN polypeptides of the invention to enhance affinity for endogenous serum albumin in an animal.

For example, in some cases, a recombinant fusion of a hIFN polypeptide and an albumin binding sequence is made. Exemplary albumin binding sequences include, but are not limited to, the albumin binding domain from streptococcal protein G (see. e.g., Makrides et al., *J. Pharmacol. Exp. Ther.* 277:534-542 (1996) and Sjolander et al., *J, Immunol. Methods* 201:115-123 (1997)), or albumin-binding peptides such as those described in, e.g., Dennis, et al., *J. Biol. Chem.* 277:35035-35043 (2002).

In other embodiments, the hIFN polypeptides of the present invention are acylated with fatty acids. In some cases, the fatty acids promote binding to serum albumin. See, e.g., Kurtzhals, et al., *Biochem. J.* 312:725-731 (1995).

In other embodiments, the hIFN polypeptides of the invention are fused directly with serum albumin (including but not limited to, human serum albumin). Those of skill in the art will recognize that a wide variety of other molecules can also be linked to hIFN in the present invention to modulate binding to serum albumin or other serum components.

X. Glycosylation of hIFN Polypeptides

The invention includes hIFN polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to hIFN polypeptides either in vivo or in vitro. In some embodiments of the invention, a hIFN polypeptide comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the hIFN polypeptide. See, e.g., H. Liu, et al. *J. Am. Chem. Soc.* 125: 1702-1703 (2003).

In some embodiments of the invention, a hIFN polypeptide comprising a carbonyl-containing non-naturally encoded amino acid is modified directly with a glycan with defined structure prepared as an aminooxy derivative. One of ordinary skill in the art will recognize that other functionalities, including azide, alkyne, hydrazide, hydrazine, and semicarbazide, can be used to link the saccharide to the non-naturally encoded amino acid.

In some embodiments of the invention, a hIFN polypeptide comprising an azide or alkynyl-containing non-naturally encoded amino acid can then be modified by, including but not limited to, a Huisgen [3+2]cycloaddition reaction with, including but not limited to, alkynyl or azide derivatives, respectively. This method allows for proteins to be modified with extremely high selectivity.

XI. GH Supergene Family Member Dimers and Multimers

The present invention also provides for GH supergene family member combinations (including but not limited to hIFN and hIFN analogs) such as homodimers, heterodimers, homomultimers, or heteromultimers (i.e., trimers, tetramers, etc.) where a GH supergene family member polypeptide such as hIFN containing one or more non-naturally encoded amino acids is bound to another GH supergene family member or variant thereof or any other polypeptide that is a non-GH supergene family member or variant thereof, either directly to the polypeptide backbone or via a linker. Due to its increased molecular weight compared to monomers, the GH supergene family member, such as hIFN, dimer or multimer conjugates may exhibit new or desirable properties, including but not limited to different pharmacological, pharmacokinetic, pharmacodynamic, modulated therapeutic half-life, or modulated plasma half-life relative to the monomeric GH supergene family member. In some embodiments, the GH supergene family member, such as hIFN, dimers of the invention will modulate the dimerization of the GH supergene family member receptor. In other embodiments, the GH supergene family member dimers or multimers of the present invention will act as a GH supergene family member receptor antagonist, agonist, or modulator.

In some embodiments, one or more of the hIFN molecules present in a hIFN containing dimer or multimer comprises a non-naturally encoded amino acid linked to a water soluble polymer that is present within the Site II binding region. As such, each of the hIFN molecules of the dimer or multimer are accessible for binding to the hIFN polypeptide receptor via the Site I interface but are unavailable for binding to a second hIFN polypeptide receptor via the Site II interface. Thus, the hIFN polypeptide dimer or multimer can engage the Site I binding sites of each of two distinct hIFN polypeptide receptors but, as the hIFN molecules have a water soluble polymer attached to a non-genetically encoded amino acid present in the Site II region, the hIFN polypeptide receptors cannot engage the Site II region of the hIFN polypeptide ligand and the dimer or multimer acts as a hIFN polypeptide antagonist. In some embodiments, one or more of the hIFN molecules present in a hIFN polypeptide containing dimer or multimer comprises a non-naturally encoded amino acid linked to a water soluble polymer that is present within the Site I binding region, allowing binding to the Site II region. Alternatively, in some embodiments one or more of the hIFN molecules present in a hIFN polypeptide containing dimer or multimer comprises a non-naturally encoded amino acid linked to a water soluble polymer that is present at a site that is not within the Site I or Site II binding region, such that both are available for binding. In some embodiments a combination of hIFN molecules is used having Site I, Site II, or both available for binding. A combination of hIFN molecules wherein at least one has Site I available for binding, and at least one has Site II available for binding may provide molecules having a desired activity or property. In addition, a combination of hIFN molecules having both Site I and Site II available for binding may produce a super-agonist hIFN molecule.

In some embodiments, the GH supergene family member polypeptides are linked directly, including but not limited to, via an Asn-Lys amide linkage or Cys-Cys disulfide linkage. In some embodiments, the linked GH supergene family member polypeptides, and/or the linked non-GH supergene family member, will comprise different non-naturally encoded amino acids to facilitate dimerization, including but not limited to, an alkyne in one non-naturally encoded amino acid of a first hIFN polypeptide and an azide in a second non-naturally encoded amino acid of a second GH supergene family member polypeptide will be conjugated via a Huisgen [3+2] cycloaddition. Alternatively, a first GH supergene family member, and/or the linked non-GH supergene family member, polypeptide comprising a ketone-containing non-naturally encoded amino acid can be conjugated to a second GH supergene family member polypeptide comprising a hydroxylamine-containing non-naturally encoded amino acid and the polypeptides are reacted via formation of the corresponding oxime.

Alternatively, the two GH supergene family member polypeptides, and/or the linked non-GH supergene family member, are linked via a linker. Any hetero- or homo-bifunctional linker can be used to link the two GH supergene family members, and/or the linked non-GH supergene family member, polypeptides, which can have the same or different primary sequence. In some cases, the linker used to tether the GH supergene family member, and/or the linked non-GH supergene family member, polypeptides together can be a bifunctional PEG reagent. The linker may have a wide range of molecular weight or molecular length. Larger or smaller molecular weight linkers may be used to provide a desired spatial relationship or conformation between the GH superfamily member and the linked entity. Linkers having longer or shorter molecular length may also be used to provide a desired space or flexibility between the GH superfamily member and the linked entity. Similarly, a linker having a particular shape or conformation may be utilized to impart a particular shape or conformation to the GH superfamily member or the linked entity, either before or after the GH superfamily member reaches its target. This optimization of the spatial relationship between the GH superfamily member and the linked entity may provide new, modulated, or desired properties to the molecule.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more GH supergene family member, such as hIFN, formed by reactions with water soluble activated polymers that have the structure:

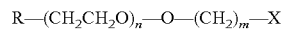

wherein n is from about 5 to 3,000, m is 2-10, X can be an azide, an alkyne, a hydrazine, a hydrazide, an aminooxy group, a hydroxylamine, an acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

XII. Measurement of hIFN Polypeptide Activity and Affinity of hIFN Polypeptide for the hIFN Polypeptide Receptor The hIFN receptor can be prepared as described in U.S. Pat. Nos. 6,566,132; 5,889,151; 5,861,258; 5,731,169; 5,578,707, which is incorporated by reference herein. hIFN polypeptide activity can be determined using standard or known in vitro or in vivo assays. For example, cells or cell lines that modulate growth or MHC Class I or II antigen production in response to hIFN or bind hIFN (including but not limited to, cells containing active IFN receptors such as human lymphoblastoid Daudi cells, or recombinant IFN receptor producing cells) can be used to monitor hIFN receptor binding. For a non-PEGylated or PEGylated hIFN polypeptide comprising a non-natural amino acid, the affinity of the hormone for its receptor can be measured by using techniques known in the art such as a BIAcore™ biosensor (Pharmacia). In vivo animal models as well as human clinical trials for testing hIFN activity include those described in, e.g., Kontsek et al., Acta Virol. 43:63 (1999); Youngster et al., Current Pharma Design 8:2139 (2002); Kozlowski et al., BioDrugs 15:419 (2001); U.S. Pat. Nos. 6,180,096; 6,177,074; 6,042,822; 5,981,709; 5,951,974; 5,908,621; 5,711,944; 5,738,846, which are incorporated by reference herein.

Regardless of which methods are used to create the present hIFN analogs, the analogs are subject to assays for biological activity. Tritiated thymidine assays may be conducted to ascertain the degree of cell division. Other biological assays, however, may be used to ascertain the desired activity. Biological assays such as assaying for the ability to inhibit viral replication, also provides indication of IFN activity. See Bailon et al., Bioconj. Chem. 12:195 (2001); Forti et al., Meth. Enzymol. 119:533 (1986); Walter et al., Cancer Biother. & Radiopharm. 13:143 (1998); DiMarco et al., BioChem. Biophys. Res. Com. 202:1445 (1994); Foser et al. Pharmacogenomics Journal 3:312-319 (2003); and U.S. Pat. Nos. 4,675,282; 4,241,174; 4,514,507; 4,622,292; 5,766,864, which are incorporated by reference herein. Assays such as those described by Oritani et al. Nature Medicine 2000 6 (6):659-666; Kawamoto et al. Experimental Hematology 2004 32:797-805; and Kawamoto et al. J. Virol. 2003 September; 77 (17):9622-31 may be also used to assess the biological activity and potential side effects of hIFN polypeptides of the invention.

Platanias et al. in Experimental Hematology 1999; 27:1583-1592, which is incorporated by reference herein, discuss signaling pathways activated by interferons including the Jak-Stat pathway, the insulin receptor substrate (IRS)/PI-3'-kinase pathway, and the activation of CBL and the Crk-signaling pathway. The importance of the Vav proto-oncogene and its role in IFN-dependent growth inhibition and the role of tyrosine phosphatases in type I IFN signaling, as well as molecules critical to signaling cascades with the type II interferon receptor were discussed. Assays evaluating signaling and pathways downstream from interferon receptor binding may be used to evaluate hIFN polypeptides of the invention, including studies described in Platanias et al. in Experimental Hematology 1999 27:1315-1321, which is incorporated by reference herein, that investigate two members of the Crk-family of proteins, CrkL and CrkII.

To assess the effect of hIFN polypeptides on normal myeloid (CFU-GM) and erythroid progenitors (BFU-E), colony formation assays such as those described by Kawamoto et al. Experimental Hematology 2004 32:797-805 or Giron-Michel et al. Leukemia 2002 16:1135-1142, incorporated by reference herein, may be used. Clonal proliferation of megakaryocytes may also be performed. There exists a correlation between colony formation assays and bone marrow toxicity. In vivo effects on normal hematopoiesis may be measured in, for example, peripheral blood or bone marrow of mice after injection with hIFN polypeptides or effects on body temperature in mice may be measured as described by Kawamoto et al. Oligoadenylate synthetase mRNA may also be used as a biomarker for antiviral activity (branched DNA assay).

Viral replication assays or in vivo studies may be performed with hIFN polypeptides of the invention to screen for anti-viral activity. Viral replication assays are known to those skilled in the art and may involve HCV (Hepatitis C Virus), VSV (Vesicular Stomatitis Virus), or EMCV (Encephalomyocarditis Virus). HCV replicon assays involving human WISH or Huh-7 cells may be performed with RNA expression measured by various methods including, but not limited to, RT-PCR, Real Time PCR, or branched DNA methods. Different HCV genotypes may be used, including but not limited to, HCV genotypes 1a and 1b. The reduction of cytopathic effect (CPE) of cells such as baby hamster kidney BHK21 cells infected with VSV may also be measured with hIFN polypeptides. Various cell lines and calculation algorithms may be used to determine potency in CPE assays. Comparisons are made with known reference standards and international units may be calculated. Other assays include, but are not limited to, assays that involve HCV replication in specific cell lines and human foreskin fibroblast cells infected with EMCV (Trotta et al., Drug Information Journal (2000); 34:1231-1246), which is incorporated by reference herein.

Other in vitro assays may be used to ascertain biological activity. In general, the test for biological activity should provide analysis for the desired result, such as increase or decrease in biological activity (as compared to non-altered IFN), different biological activity (as compared to non-altered IFN), receptor affinity analysis, or serum half-life analysis.

It was previously reported that Daudi cells will bind $^{125}$I-labeled murine IFN and that this binding can be competed for by addition of unlabeled IFN (See e.g. U.S. Pat. Nos. 5,516, 515; 5,632,988). The ability of natural IFN and hIFN to compete for binding of $^{125}$I-IFN to human and murine leukemic cells is tested. Highly purified natural IFN (>95% pure; 1 µg) is iodinated [Tejedor, et al., Anal. Biochem., 127, 143 (1982)], and is separated from reactants by gel filtration and ion exchange chromatography. The specific activity of the natural $^{125}$I-IFN may be approximately 100 µCi/µg protein.

Trotta et al. Drug Information Journal 2000; 34:1231-1246, which is incorporated by reference herein, discuss the numerous biological activities of IFNα including immunomodulatory, antiproliferative, antiviral, and antimicrobial activities. Different human IFN α species exhibit varied relative levels of biological activities despite the high degree of amino acid sequence homology. Assays known those skilled in the art to measure immunomodulatory, antiproliferative, antiviral, and antimicrobial activities of one or more IFN α species may be used to evaluate hIFN polypeptides of the invention.

In vitro assays that measure secretion of prostaglandins, e.g., PGE2, may be performed to evaluate hIFN polypeptides of the invention. Prostaglandins modulate a number of CNS functions such as the generation of fever and the perception of pain, and one of the side effects of current IFN therapies is fever.

Transcriptional activity of monoPEGylated interferon-α-2a isomers is described in Foser et al. Pharmacogenomics Journal 2003; 3:312-319, which is incorporated by reference herein in its entirety, using oligonucleotide array transcript analysis. Similar assays may be performed with hIFN polypeptides of the invention. Cell lines that may be used in gene expression studies include but are not limited to, melanoma cell lines such as ME15. ME15 or similar cell lines may also be used to investigate functional properties of hIFN polypeptides of the invention. Alternate assays to DNA microarrays may be performed with hIFN polypeptides of the invention to provide mRNA profiling data, differential gene expression information, or altered gene expression data (change in the level of a transcription or translation products). Cellular arrays may also be performed. DNA microarray or DNA chip studies involve assembling PCR products of a group of genes or all genes within a genome on a solid surface in a high density format or array. General methods for array construction and use are available (see Schena M, Shalon D, Davis R W, Brown P O., Quantitative monitoring of gene expression patterns with a complementary DNA microarray. Science. Oct. 20, 1995; 270 (5235): 467-70). A DNA microarray allows the analysis of gene expression patterns or profile of many genes to be performed simultaneously by hybridizing the DNA microarray comprising these genes or PCR products of these genes with cDNA probes prepared from the sample to be analyzed. DNA microarray or "chip" technology permits examination of gene expression on a genomic scale, allowing transcription levels of many genes to be measured simultaneously. Methods and materials for various arrays and similar analyses are known to those of ordinary skill in the art.

The above compilation of references for assay methodologies is not exhaustive, and those skilled in the art will recognize other assays useful for testing for the desired end result. Alterations to such assays are known to those of ordinary skill in the art.

XIII. Measurement of Potency, Functional In Vivo Half-Life, Toxicity, and Pharmacokinetic Parameters An important aspect of the invention is the prolonged biological half-life that is obtained by construction of the hIFN polypeptide with or without conjugation of the polypeptide to a water soluble polymer moiety. The rapid decrease of hIFN polypeptide serum concentrations has made it important to evaluate biological responses to treatment with conjugated and non-conjugated hIFN polypeptide and variants thereof. The conjugated and non-conjugated hIFN polypeptide and variants thereof of the present invention may have prolonged serum half-lives also after subcutaneous or i.v. administration, making it possible to measure by, e.g. ELISA method or by a primary screening assay. ELISA or RIA kits from either BioSource International (Camarillo, Calif.) or Diagnostic Systems Laboratories (Webster, Tex.) may be used. Another example of an assay for the measurement of in vivo half-life of IFN or variants thereof is described in Kozlowski et al., BioDrugs 15:419 (2001); Bailon et al., Bioconj. Chem. 12:195 (2001); Youngster et al., Current Pharm. Design 8:2139 (2002); U.S. Pat. Nos. 6,524,570; 6,250,469; 6,180,096; 6,177,074; 6,042,822; 5,981,709; 5,591,974; 5,908,621; 5,738,846, which are incorporated by reference herein. Measurement of in vivo biological half-life is carried out as described herein.

The potency and functional in vivo half-life of a hIFN polypeptide comprising a non-naturally encoded amino acid can be determined according to the protocol described in U.S. Pat. Nos. 5,711,944; 5,382,657, which are incorporated by reference herein.

Pharmacokinetic parameters for a hIFN polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a hIFN polypeptide comprising a non-naturally encoded amino acid not conjugated to a water soluble polymer and about 4 days for a hIFN polypeptide comprising a non-naturally encoded amino acid and conjugated to a water soluble polymer. Pharmacokinetic data for hIFN polypeptides is well-studied in several species and can be compared directly to the data obtained for hIFN polypeptides comprising a non-naturally encoded amino acid. See Mordenti J., et al., *Pharm. Res.* 8 (11):1351-59 (1991) for studies related to hGH.

Pharmacokinetic parameters can also be evaluated in a primate, e.g., cynomolgus monkeys. Typically, a single injection is administered either subcutaneously or intravenously, and serum hIFN levels are monitored over time.

Uno et al., which is incorporated by reference herein, in *J Interferon Cytokine Res.* 1998 December; 18 (12):1011-8 describe the induction of 2',5' oligoadenylate synthetase in THP-1 cells in response to IFN. In particular, the assay described is sensitive to IFNα and may be useful as a bioassay for serum interferon.

Animal models used to study antiviral activity of hIFN polypeptides include, but are not limited to, the chimpanzee HCV (Purcell R H, FEMS Microbiol Rev. 1994 July; 14 (3):181-91), the HCV-Trimera mouse (Ilan E et al. J Infect Dis. 2002 Jan. 15; 185 (2):153-61), and the Alb-uPA transgenic mouse models (Mercer D F et al. Nat. Med. 2001 August; 7 (8):927-33; Kneteman, N et al (2003) 10th HCV Meeting Kyoto Japan, P-187), all of which are incorporated by reference herein. Other animal models may be used to evaluate side effects such as fever, depression, and pain threshold.

hIFN polypeptides of the invention may be evaluated using a human bone marrow NOD/SCID reconstitution model. Variations to this protocol are known to one of ordinary skill in the art. With this model, the transplantation protocol is as follows: NOD/SCID mice are housed under sterile conditions in microisolator cages. Just before and for 2 months after total body irradiation mice receive acidified $H_2O$ (pH=3). The NOD/SCID mice are sublethally irradiated 325-350 cGy using a 137Cs γ-irradiator (approximately 1 cGy/min). Cells are transplanted with human MNC (mononuclear cells from bone marrow or cord blood) by i.v. injection on the day of irradiation. For the reconstitution analysis, at 6-8 weeks post-injection mice are bled through the tail vein, or retro-orbitally, collected into heparinized vacutubes. Peripheral blood cells are analyzed by FACS using anti-human CD45 and anti-mouse CD45 to assess reconstitution. Mice with >0.1% human cells in the peripheral blood are considered positive.

The mice are treated with PEGASYS® or hIFN polypeptide with a dosing regimen. Various dosing regimens may be used. Mice are s.c. injected with drug vs. buffer, weekly dosing. On week 4, the animals are sacrificed and peripheral blood, spleen, liver, and bone marrow are harvested for analysis. The samples are processed in the following manner: Peripheral blood is collected into heparinized vacutubes. The spleen and liver are removed and a single cell suspension generated. Tibia and femur bone marrow is harvested. Levels of PEGASYS® or hIFN polypeptide are measured in blood and tissue by methods including but not limited to, ELISA. Peled et al. in Science (1999) 283:845-848 and Kim et al. in Stem Cells (1999) 17:286-294 discuss the repopulating cells of SCID mice.

Cynomolgus monkeys are used to evaluate in vivo activity and bone marrow toxicity of hIFN polypeptides. Induction of 2',5'-Oligoadenylate synthetase (2'5'-OAS) is measured in monkeys and reflects activity of hIFN polypeptides. Bone marrow toxicity is evaluated by measuring circulating blood cells, including but not limited to neutrophils, RBCs, and platelets as well as potentially collecting and evaluating bone marrow.

Additional animal models for evaluating hIFN polypeptides of the invention include animal models studying depression. Capuron, L et al. in Am. J. Psychiatry 2003; 160:1342-1344 present clinical data suggesting a correlation between IFN-α, the HPA axis, and depression. During the first twelve weeks of IFN-α therapy, the plasma concentrations of adrenocorticotropic hormone (ACTH), cortisol, and interleukin-6 (IL-6) were measured in patients both immediately before and one, two, and three hours after administration. The patients were also evaluated for symptoms of major depression during the course of the study. It was found that patients who subsequently met symptom criteria for major depression exhibited higher ACTH and cortisol responses (but not IL-6 responses) to the initial administration of IFN-α than patients who did not meet the symptom criteria.

Yamano, M. et al. JPET 2000; 292:181-187, which is incorporated by reference herein, discusses Sumiferon, a lymphoblastoid preparation of human IFN-α (Sumitomo Pharmaceuticals), and YM643 (IFN-alphacon-1; Amgen) and their effects on mice. Upon dosing i.v. both compounds induced immobility, a depression-like behavior, in mice, as measured by the Tail Suspension Test (TST) in a dose-dependent manner. Similar results were achieved by s.c. and i.c.v. injection, although dose levels and general dosing regimens differed. Imipramine (a tricyclic anti-depressant and down-regulator of the HPA axis) was found to significantly reduce IFN-induced immobility, whereas indomethacin (a cyclooxygenase inhibitor) and naloxone (an opioid receptor antagonist) did not reduce the observed IFN-induced immobility. Yamano et al. also showed that the CRF antagonist CP-154, 526 blocks IFN-induced immobility and does so in a dose-dependent manner, implicating the involvement of the HPA axis in IFN-α induced depression.

The Tail Suspension Test is an alternative to the "behavioral despair" or swim test in which an animal is forced to swim in a particular area without an escape. With the Tail Suspension Test, the animal is suspended from its tail for defined length of time, e.g., six minutes, and cannot escape. During the test, various measurements are taken including but not limited to, the number of times each animal enters into an escape behavior (called an event) e.g. struggling episodes, the duration of the event, and the average strength of each event. Tail Suspension Test equipment is available, for example, from Lafayette Instrument (Lafayette, Ind.).

Other studies involve animal models of other side effects found with current IFN therapies, such as neutropenia. Animal studies performed may be performed in combination with Ribavirin or another compound.

The specific activity of hIFN polypeptides in accordance with this invention can be determined by various assays known in the art. The biological activity of the hIFN polypeptide muteins, or fragments thereof, obtained and purified in accordance with this invention can be tested by methods described or referenced herein or known to those of ordinary skill in the art.

XIV. Administration and Pharmaceutical Compositions

The polypeptides or proteins of the invention (including but not limited to, hIFN, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are known to those of ordinary skill in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods known to those of ordinary skill in the art. In particular, dosages can be initially determined by activity, stability or other suitable measures of unnatural herein to natural amino acid homologues (including but not limited to, comparison of a hIFN polypeptide modified to include one or more unnatural amino acids to a natural amino acid hIFN polypeptide), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

hIFN polypeptides of the invention may be administered by any conventional route suitable for proteins or peptides, including, but not limited to parenterally, e.g. injections including, but not limited to, subcutaneously or intravenously or any other form of injections or infusions. Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art. The hIFN polypeptide comprising a non-naturally encoded amino acid, may be used alone or in combination with other suitable components such as a pharmaceutical carrier.

The hIFN polypeptide comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of hIFN can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, G-CSF, GM-CSF, IFNs, interleukins, antibodies, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or, including but not limited to, to inhibit infection by a pathogen, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors or pharmaceutical formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acid polypeptides at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human hIFN polypeptides of the invention can be administered directly to a mammalian subject. Administration is by any of the routes normally used for introducing hIFN polypeptide to a subject. The hIFN polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampoules and vials. hIFN polypeptides of the invention can be prepared in a mixture in a unit dosage injectable form (including but not limited to, solution, suspension, or emulsion) with a pharmaceutically acceptable carrier. hIFN polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3 (9) 26-30 (1990) and Arakawa et al. Pharm. Res. 8 (3):285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235, 710 and 6,001,800, which are incorporated by reference herein, describe the preparation of recombinant erythropoietin by spray drying.

The pharmaceutical compositions of the invention may comprise a pharmaceutically acceptable carrier, excipient, or stabilizer. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences,* 17th ed. 1985)).

Suitable carriers include, but are not limited to, buffers containing succinate, phosphate, borate, HEPES, citrate, histidine, imidazole, acetate, bicarbonate, and other organic acids; antioxidants including but not limited to, ascorbic acid;

low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, asparagine, arginine, histidine or histidine derivatives, methionine, glutamate, or lysine; monosaccharides, disaccharides, and other carbohydrates, including but not limited to, trehalose, sucrose, glucose, mannose, or dextrins; chelating agents including but not limited to, EDTA and edentate disodium; divalent metal ions including but not limited to, zinc, cobalt, or copper; sugar alcohols including but not limited to, mannitol or sorbitol; salt-forming counter ions including but not limited to, sodium and sodium chloride; and/or nonionic surfactants including but not limited to Tween™ (including but not limited to, Tween 80 (polysorbate 80) and Tween 20 (polysorbate 20), Pluronics™ and other pluronic acids, including but not limited to, and other pluronic acids, including but not limited to, pluronic acid F68 (poloxamer 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize PEGylated hIFN against one or more stresses including but not limited to stress that results from agitation. Some of the above may be referred to as "bulking agents." Some may also be referred to as "tonicity modifiers." Antimicrobial preservatives may also be applied for product stability and antimicrobial effectiveness; suitable preservatives include but are not limited to, benzyl alcohol, bezalkonium chloride, metacresol, methyl/propyl parabene, cresol, and phenol, or a combination thereof.

Formulations of interferon molecules, including but not limited to, interferon alpha and PEGylated forms of interferon alpha are described in U.S. Pat. Nos. 5,762,923; 5,766,582; and 5,935,566, which are incorporated by reference herein in their entirety. Methods for manufacture and to test stability of interferon molecules are also described. Allen et al. International Journal of Pharmaceutics (1999) 187:259-272 also discusses the formulation of a hybrid interferon-α molecule and degradation products found under various conditions such as high and low pH.

hIFN polypeptides of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 267-277 (1981); Langer, *Chem. Tech.*, 12: 98-105 (1982), ethylene vinyl acetate (Langer et al., supra) or poly-D-(−)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (Sidman et al., *Biopolymers*, 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. All references and patents cited are incorporated by reference herein.

Liposomally entrapped hIFN polypeptides can be prepared by methods described in, e.g., DE 3,218,121; Eppstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. Composition and size of liposomes are well known or able to be readily determined empirically by one of ordinary skill in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591 (1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the hIFN polypeptide of the present invention administered parenterally per dose is in the range of about 0.01 µg/kg/day to about 100 µg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available hIFN polypeptide products approved for use in humans. Generally, a PEGylated hIFN polypeptide of the invention can be administered by any of the routes of administration described above.

XV. Therapeutic Uses of hIFN Polypeptides of the Invention

The hIFN polypeptides of the invention are useful for treating a wide range of disorders.

An agonist hIFN variant may act to stimulate the immune system of a mammal by increasing its immune function, whether the increase is due to antibody mediation or cell mediation, and whether the immune system is endogenous to the host treated with the hIFN polypeptide or is transplanted from a donor to the host recipient given the hIFN polypeptide (as in bone marrow transplants). "Immune disorders" include any condition in which the immune system of an individual has a reduced antibody or cellular response to antigens than normal, including those individuals with small spleens with reduced immunity due to drug (e.g., chemotherapeutic) treatments. Examples individuals with immune disorders include, e.g., elderly patients, individuals undergoing chemotherapy or radiation therapy, individuals recovering from a major illness, or about to undergo surgery, individuals with AIDS, Patients with congenital and acquired B-cell deficiencies such as hypogammaglobulinemia, common varied agammaglobulinemia, and selective immunoglobulin deficiencies (e.g., IgA deficiency, patients infected with a virus such as rabies with an incubation time shorter than the immune response of the patient; and individuals with hereditary disorders such as diGeorge syndrome. IFNα's exhibit many immunomodulatory activities, see Zoon et al., (1986) In, The Biology of the Interferon System. Cantell and Schellenkens, Eds., Martinus Nyhoff Publishers, Amsterdam).

Administration of the hIFN products of the present invention results in any of the activities demonstrated by commercially available IFN preparations in humans. The pharmaceutical compositions containing hIFN may be formulated at a strength effective for administration by various means to a human patient experiencing disorders that may be affected by IFN agonists or antagonists, such as but not limited to, antiproliferatives, anti-inflammatory, or antivirals are used, either alone or as part of a condition or disease.

The hIFN of the present invention may thus be used to interrupt or modulate a viral replication cycle, modulate inflammation, or as anti-proliferative agents. Among the conditions treatable by the present invention include HCV, HBV, and other viral infections, tumor cell growth or viability, and multiple sclerosis. The invention also provides for administration of a therapeutically effective amount of another active agent such as an anti-cancer chemotherapeutic agent. The amount to be given may be readily determined by one skilled in the art based upon therapy with hIFN.

Although IFNs were first discovered by virologists, their first clinical use (in 1979) was as therapeutic agents for myeloma (Joshua et al., (1997) Blood Rev. 11 (4):191-200). IFNα's have since been shown to be efficacious against a myriad of diseases of viral, malignant, angiogenic, allergic, inflammatory, and fibrotic origin (Tilg, (1997) Gastroenterology. 112 (3):1017-1021). It has also proven efficacious in the treatment of metastatic renal carcinoma and chronic myeloid leukemia (Williams and Linch, (1997) Br. J. Hosp. Med. 57 (9):436-439). Clinical uses of IFNs are reviewed in Gresser (1997) J. Leukoc. Biol. 61 (5):567-574 and Pfeffer (1997) Semin. Oncol. 24 (3 Suppl. 9):S9-S63S969, which are incorporated by reference herein.

Average quantities of the hIFN may vary and in particular should be based upon the recommendations and prescription of a qualified physician. The exact amount of hIFN is a matter of preference subject to such factors as the exact type of condition being treated, the condition of the patient being treated, as well as the other ingredients in the composition. The invention also provides for administration of a therapeutically effective amount of another active agent. The amount to be given may be readily determined by one of ordinary skill in the art based upon therapy with hIFN.

Pharmaceutical compositions of the invention may be manufactured in a conventional manner.

EXAMPLES

The following examples are offered to illustrate, but do not to limit the claimed invention.

Example 1

This example describes one of the many potential sets of criteria for the selection of preferred sites of incorporation of non-naturally encoded amino acids into hIFN.

This example demonstrates how preferred sites within the hIFN polypeptide were selected for introduction of a non-naturally encoded amino acid. The crystal structure with PDB ID 1RH2 and the NMR structure 1ITF (twenty-four different NMR structures) were used to determine preferred positions into which one or more non-naturally encoded amino acids could be introduced. The coordinates for these structures are available from the Protein Data Bank (PDB) or via The Research Collaboratory for Structural Bioinformatics PDB available on the World Wide Web at rcsb.org.

Sequence numbering used in this example is according to the amino acid sequence of mature hIFN shown in SEQ ID NO: 2. The following criteria were used to evaluate each position of hIFN for the introduction of a non-naturally encoded amino acid: the residue (a) should not interfere with binding of hIFN based on structural analysis of crystallographic structures of hIFN conjugated with hIFN receptor, b) should not be affected by alanine scanning mutagenesis, (c) should be surface exposed and exhibit minimal van der Waals or hydrogen bonding interactions with surrounding residues, (d) should be either deleted or variable in hIFN variants, (e) would result in conservative changes upon substitution with a non-naturally encoded amino acid and (f) could be found in either highly flexible regions (including but not limited to CD loop) or structurally rigid regions (including but not limited to *Helix* B). Publications used in site evaluation include: Bioconj. Chemistry 2001 (12) 195-202; Current Pharmaceutical Design 2002 (8) 2139-2157; Neuroreport 2001 (12), 857-859; BBRC 1994 (202) 1445-1451; Cancer Biotherapy+Radiopharmaceuticals 1998 (vol 13) 143-153; Structure 1996 (14) 1453-1463; JMB 1997 (274) 661-675. In addition, further calculations were performed on the hIFN molecule, utilizing the Cx program (Pintar et al. *Bioinformatics*, 18, pp 980) to evaluate the extent of protrusion for each protein atom. In some embodiments, one or more non-naturally encoded amino acid are substituted at, but not limited to, one or more of the following positions of hIFN (as in SEQ ID NO: 2, or the corresponding amino acid in SEQ ID NO: 1, 3, or any other IFN polypeptide): before position 1 (i.e., at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, or 166 (i.e. at the carboxyl terminus). In some embodiments, one or more non-naturally encoded amino acid are substituted at, but not limited to, one or more of the following positions of hIFN (as in SEQ ID NO: 2, or the corresponding amino acid in SEQ ID NO: 1, 3, or any other IFN polypeptide): before position 1 (i.e., at the N-terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, or 166 (i.e. at the carboxyl terminus). In some embodiments, one or more non-naturally encoded amino acids are incorporated in one or more of the following positions in IFN: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acids in SEQ ID NO: 1 or 3). In some embodiments, the IFN polypeptides of the invention comprise one or more non-naturally encoded amino acids at one or more of the following positions: 100, 106, 107, 108, 111, 113, 114 (SEQ ID NO: 2, or the corresponding amino acid in or the corresponding amino acid in SEQ ID NO: 1, 3, or any other IFN polypeptide). In some embodiments, the IFN polypeptides of the invention comprise one or more non-naturally encoded amino acids at one or more of the following positions: 41, 45, 46, 48, 49 (SEQ ID NO: 2, or the corresponding amino acid in or the corresponding amino acid in SEQ ID NO: 1, 3, or any other IFN polypeptide). In some embodiments, the IFN polypeptides of the invention comprise one or more non-naturally encoded amino acids at one or more of the following positions: 61, 64, 65, 101, 103, 110, 117, 120, 121, 149 (SEQ ID NO: 2, or the corresponding amino acid in or the corresponding amino acid in SEQ ID NO: 1, 3, or any other IFN polypeptide). In some embodiments, the IFN polypeptides of the invention comprise one or more non-naturally encoded amino acids at one or more of the following positions: 6, 9, 12, 13, 16, 96, 156, 159, 160, 161, 162 (SEQ ID NO: 2, or the corresponding amino acid in or the corresponding amino acid in SEQ ID NO: 1, 3, or any other IFN polypeptide). In some embodiments, the IFN polypeptides of the invention comprise one or more non-naturally encoded amino acids at one or more of the following positions: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 2, or the corresponding amino acid in or the corresponding amino acid in SEQ ID NO: 1, 3, or any other IFN polypeptide). In some embodiments, the IFN polypeptides of the invention comprise one or more non-naturally encoded amino acids at one or more of the following positions: 34, 78, 107 (SEQ ID NO: 2, or the corresponding amino acid in SEQ ID NO: 1, 3, or any other IFN polypeptide). In some embodiments, the non-naturally encoded amino acid at one or more of these or other positions is linked to a water soluble polymer, including but not limited to positions: before position 1 (i.e., at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, or 166 (i.e. at the carboxyl terminus) (SEQ ID NO: 2, or the corresponding amino acid in SEQ ID NO: 1, 3, or any other IFN polypeptide). In some embodiments, the non-naturally encoded amino acid at one or more of these positions is linked to one or more water soluble polymers, including but not limited to positions: before position 1 (i.e. the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus) (SEQ ID NO: 2, or the corresponding amino acid in or the corresponding amino acid in SEQ ID NO: 1, 3, or any other IFN polypeptide). In some embodiments, the non-naturally encoded amino acid is linked to a water soluble polymer at one or more of the following positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acids in SEQ ID NO: 1 or 3). In some embodiments, the one or more non-naturally encoded amino acids at one or more of the following positions is linked to one or more water-soluble polymer: 100, 106, 107, 108, 111, 113, 114 (SEQ ID NO: 2, or the corresponding amino acid in or the corresponding amino acid in SEQ ID NO: 1, 3, or any other IFN polypeptide). In some embodiments, the one or more non-naturally encoded amino acids at one or more of the following positions is linked to one or more water-soluble polymer: 41, 45, 46, 48, 49 (SEQ ID NO: 2, or the corresponding amino acid in or the corresponding amino acid in SEQ ID NO: 1, 3, or any other IFN polypeptide). In some embodiments, the one or more non-naturally encoded amino acids at one or more of the following positions is linked to one or more water-soluble polymer: 61, 64, 65, 101, 103, 110, 117, 120, 121, 149 (SEQ ID NO: 2, or the corresponding amino acid in or the corresponding amino acid in SEQ ID NO: 1, 3, or any other IFN polypeptide). In some embodiments, the one or more non-naturally encoded amino acids at one or more of the following positions is linked to one or more water-soluble polymer: 6, 9, 12, 13, 16, 96, 156, 159, 160, 161, 162 (SEQ ID NO: 2, or the corresponding amino acid in or the corresponding amino acid in SEQ ID NO: 1, 3, or any other IFN polypeptide). In some embodiments, the one or more non-naturally encoded amino acids at one or more of the following positions is linked to one or more water-soluble polymer: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 2, or the corresponding amino acid in or the corresponding amino acid in SEQ ID NO: 1, 3, or any other IFN polypeptide). In some embodiments, the one or more non-naturally encoded amino acids at one or more of the following positions is linked to one or more water-soluble polymer: 34, 78, 107 (SEQ ID NO: 2, or the corresponding amino acid in SEQ ID NO: 1, 3, or any other IFN polypeptide). In some embodiments, the water soluble polymer is coupled to the IFN polypeptide to a non-naturally encoded amino acid at one or more of the following amino acid positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acid in SEQ ID NO: 1, 3, or any other IFN polypeptide). In some embodiments the water soluble polymer is coupled to the IFN polypeptide at one or more of the following amino acid positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 2, or the corresponding amino acid in SEQ ID NO: 1, 3, or any other IFN polypeptide). In some embodiments, the non-naturally encoded amino acid at one or more of these positions is linked to one or more water soluble polymers, positions: 34, 78, 107 (SEQ ID NO: 2, or the corresponding amino acid in or the corresponding amino acid in SEQ ID NO: 1, 3, or any other IFN polypeptide). In some embodiments, the IFN polypeptides of the invention comprise one or more non-naturally encoded amino acids at one or more of the following positions providing an antagonist: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 2, or the corresponding amino acid in or the corresponding amino acid in SEQ ID NO: 1, 3, or any other IFN polypeptide); a hIFN polypeptide comprising one of these substitutions may potentially act as a weak antagonist or weak agonist depending on the intended site selected and desired activity. Human IFN antagonists include, but are not limited to, hIFN polypeptides with one or more non-naturally encoded amino acid substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combinations thereof (hIFN; SEQ ID NO: 2 or the corresponding amino acids in SEQ ID NO: 1 or 3, or any other IFN polypeptide).

In some embodiments, one or more non-naturally encoded amino acids are substituted at, but not limited to, one or more of the following positions of hIFN (as in SEQ ID NO: 2, or the corresponding amino acids in SEQ ID NO: 1 or 3, or any other IFN polypeptide): 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 12, 13, 16, 68, 70, 109, 159, 161, 156, 160, 162, 24, 27, 78, 83, 85, 87, 89, 164. In one embodiment, a non-naturally encoded amino acid is substituted at position 38 of hIFN (as in SEQ ID NO: 2, or the corresponding amino acids in SEQ ID NO: 1 or 3, or any other IFN polypeptide). In some embodiments, the non-naturally encoded amino acid at one or more of these or other positions is linked to a water soluble polymer, including but not limited to positions: 31, 134, 34, 38, 129, 36, 122, 37, 121, 41, 125, 124, 149, 117, 39, 118, 120, 107, 108, 106, 100, 111, 113, 114, 41, 45, 46, 48, 49, 61, 64, 65, 101, 103, 102, 110, 117, 120, 121, 149, 96, 6, 9, 12, 13, 16, 68, 70, 109, 159, 161, 156, 160, 162, 24, 27, 78, 83, 85, 87, 89, 164 (as in SEQ ID NO: 2, or the corresponding amino acids in SEQ ID NO: 1 or 3, or any other IFN polypeptide).

In some embodiments, one or more non-naturally encoded amino acids are substituted at, but not limited to, one or more of the following positions of hIFN (SEQ ID NO: 2 or the corresponding amino acids in SEQ ID NO: 1 or 3): before position 1 (i.e., at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, or 166 (i.e. at the carboxyl terminus) and one or more natural amino acid substitutions. In some embodiments, the one or more non-naturally encoded amino acids are coupled to a water soluble polymer. In some embodiments, the one or more non-naturally encoded amino acids are coupled to PEG. In one embodiment, the natural amino acid substitution is R149Y. In some embodiments, the natural amino acid substitution is R149E. In some embodiments, the natural amino acid substitution is R149S. In one embodiment, the non-natural amino acid substitution is at position 107 and the natural amino acid substitution is R149Y. In one embodiment, the non-natural amino acid substitution is at position 106 and the natural amino acid substitution is R149Y. In some embodiments, the one or more naturally encoded amino acid substitution is at one or more of the following positions of hIFN (SEQ ID NO: 2 or the corresponding amino acids in SEQ ID NO: 1 or 3), including but not limited to: 10, 16, 13, 79, 83, 85, 86, 87, 90, 91, 93, 94, 96, 120, 121, 124, 125, 128, 149. In some embodiments, the one or more naturally encoded amino acid substitution is one or more of the following substitutions (SEQ ID NO: 2 or the corresponding amino acids in SEQ ID NO: 1 or 3), including but not limited to: G10E, M16R, R13E, T79R, K83Q, K83S, Y85L, T86S, E87S, Q90R, Q91E, N93Q, D94V, E96K, R120K, K121T, Q124R, R125G, L128R, R149Y, R149E, R149S. In some embodiments, the natural amino acid substitution is at position 1 (the N-terminus). In some embodiments, one or more non-naturally encoded amino acids are substituted at one or more of the following positions of hIFN (as in SEQ ID NO: 2, or the corresponding amino acids in other IFN's): 107, 78, 34. In some embodiments, the non-naturally encoded amino acid at one or more of these positions is coupled to a water soluble polymer: 107, 78, 34.

One or more amino acids found in a limitin sequence may be substituted into a hIFN polypeptide (hybrid limitin/hIFN polypeptides). Examples include but are not limited to the natural amino acid substitutions described in the previous paragraph. Alternatively, a set of amino acids found in an interferon polypeptide may be replaced by a set of amino acids found in a limitin sequence. A set of amino acids may comprise contiguous amino acids or amino acids present in different portions of the molecule but are involved in a structural characteristic or biological activity of the polypeptide. The mouse limitin molecule has an improved CFU-GM toxicity profile compared to other IFNα proteins. Alignment of human IFNα-2a with the limitin protein sequence showed 30% amino acid identity. 50% sequence conservation was also observed. In particular, a prominent deletion in the limitin sequence between the C and D helices (in the loop between C and D helices) was observed. The "HV" mutant was generated with the following substitutions in hIFNα-2a (SEQ ID NO: 2): D77-D94 is replaced with the mouse limitin sequence HERALDQLLSSLWRELQV. The "CD" mutant was generated with the following substitutions in hIFNα-2a (SEQ ID NO: 2): V105-D114 with GQSAPLP. This hybrid molecule with the loop region from limitin substituted into the human IFNα-2a protein ("CD" mutant) was found to have equivalent anti-viral activity as the WHO IFN standard. In addition to the one or more limitin amino acids, the hIFN polypeptide may comprise one or more non-naturally encoded amino acids at any one or more positions of the hIFN polypeptide. In some embodiments, the one or more non-naturally encoded amino acids may be linked to a water soluble polymer such as PEG or bonded directly to a water soluble polymer such as PEG. In addition to the natural amino acid substitutions in the HV or the CD mutant, one or more additional natural amino acid substitutions may be found in the hIFN polypeptide.

In some embodiments, the hIFN polypeptide comprises one or more non-naturally encoded amino acids at one or more of the following positions: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide). In some embodiments, the hIFN polypeptide comprises one or more non-naturally encoded amino acids at one or more of the following positions linked to one or more water-soluble polymer: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide). In some embodiments, the hIFN polypeptide comprises one or more non-naturally encoded amino acids at one or more of the following positions linked to one or more water-soluble polymer: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide) and comprises one or more naturally encoded amino acid substitution. In some embodiments, the hIFN polypeptide comprises one or more non-naturally encoded amino acids at one or more of the following positions linked to one or more water-soluble polymer: 6, 16, 34, 39, 45, 46, 64, 65, 68, 78, 85, 87, 101, 107, 108, 111, 114, 118, 124, 125, 145, 146, 153, 156, 96, 149 (SEQ ID NO: 2, or the corresponding amino acid in or the corresponding amino acid in SEQ ID NO: 1, 3, or any other IFN polypeptide) and comprises one or more of the following naturally encoded amino acid substitutions G10E, M16R, R13E, T79R, K83Q, K83S, Y85L, T86S, E87S, Q90R, Q91E, N93Q, D94V, E96K, R120K, K121T, Q124R, R125G, L128R, R149Y, R149E, R149S.

In some embodiments, the hIFN polypeptide comprises one or more non-naturally encoded amino acids at one or more of the following positions: 6, 16, 37, 45, 46, 78, 87, 89, 107, 108 (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 89, 107, 108 (SEQ ID NO: 2 or the corresponding amino acids in SEQ ID NO: 1 or 3) that is linked to a water soluble polymer. In some embodiments, the hIFN polypeptide comprises one or more non-naturally encoded amino acids at one or more of the following positions: 6, 16, 37, 45, 46, 78, 87, 89, 107, 108 (SEQ ID NO: 2 or the corresponding amino acids in SEQ ID NO: 1 or 3) that is bonded to a water soluble polymer.

In some embodiments, the hIFN polypeptide comprises one or more non-naturally encoded amino acids at one or more of the following positions: 6, 16, 37, 45, 46, 78, 87, 89, 107, 108 and one or more of the following naturally encoded amino acid substitutions: T79R, L80A, K83S, Y85L, Y85S, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 89, 107, 108 that is linked to a water soluble polymer and comprises one or more of the following naturally encoded amino acid substitutions: T79R, L80A, K83S, Y85L, Y85S, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 89, 107, 108 that is bonded to a water soluble polymer and comprises one or more of the following naturally encoded amino acid substitutions: T79R, L80A, K83S, Y85L, Y85S, T86S, E87S, Q91E (SEQ ID NO: 2 or the corresponding amino acids in SEQ ID NO: 1 or 3).

In some embodiments, the hIFN polypeptide comprises one or more non-naturally encoded amino acids at one or more of the following positions: 6, 16, 37, 45, 46, 78, 87, 107, and 108 (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 107, and 108 (SEQ ID NO: 2 or the corresponding amino acids in SEQ ID NO: 1 or 3) that is linked to a water soluble polymer. In some embodiments, the hIFN polypeptide comprises one or more non-naturally encoded amino acids at one or more of the following positions: 6, 16, 37, 45, 46, 78, 87, 107, and 108 (SEQ ID NO: 2 or the corresponding amino acids in SEQ ID NO: 1 or 3) that is bonded to a water soluble polymer.

In some embodiments, the hIFN polypeptide comprises one or more non-naturally encoded amino acids at one or more of the following positions: 6, 16, 37, 45, 46, 78, 87, 107, and 108 and comprises one or more of the following naturally encoded amino acid substitutions: T79R, K83S, Y85L, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 107, and 108 that is linked to a water soluble polymer and comprises one or more of the following naturally encoded amino acid substitutions: T79R, K83S, Y85L, T86S, E87S, Q91E (SEQ ID NO: 2 or the corresponding amino acids in SEQ ID NO: 1 or 3). In some embodiments, the hIFN polypeptide comprises one or more non-naturally encoded amino acids at one or more of the following positions: 6, 16, 37, 45, 46, 78, 87, 107, and 108 that is bonded to a water soluble polymer and comprises one or more of the following naturally encoded amino acid substitutions: T79R, K83S, Y85L, T86S, E87S, Q91E (SEQ ID NO: 2 or the corresponding amino acids in SEQ ID NO: 1 or 3).

In some embodiments, the hIFN polypeptide comprises one or more non-naturally encoded amino acids at one or more of the following positions: 37, 45, 46, 89, and 107 (SEQ ID NO: 2 or the corresponding amino acids in SEQ ID NO: 1 or 3). In some embodiments, the hIFN polypeptide comprises one or more non-naturally encoded amino acids at one or more of the following positions: 37, 45, 46, 89, and 107 (SEQ ID NO: 2 or the corresponding amino acids in SEQ ID NO: 1 or 3) that is linked to a water soluble polymer. In some embodiments, the hIFN polypeptide comprises one or more non-naturally encoded amino acids at one or more of the following positions: 37, 45, 46, 89, and 107 (SEQ ID NO: 2 or the corresponding amino acids in SEQ ID NO: 1 or 3) that is bonded to a water soluble polymer.

In some embodiments, the hIFN polypeptide comprises one or more non-naturally encoded amino acids at one or more of the following positions: 37, 45, 46, 89, and 107 and comprises one or more of the following naturally encoded amino acid substitutions: T79R, L80A, Y85L, Y85S, E87S (SEQ ID NO: 2 or the corresponding amino acids in SEQ ID NO: 1 or 3). In some embodiments, the hIFN polypeptide comprises one or more non-naturally encoded amino acids at one or more of the following positions: 37, 45, 46, 89, and 107 that is linked to a water soluble polymer and comprises one or more of the following naturally encoded amino acid substitutions: T79R, L80A, Y85L, Y85S, E87S (SEQ ID NO: 2 or the corresponding amino acids in SEQ ID NO: 1 or 3). In some embodiments, the hIFN polypeptide comprises one or more non-naturally encoded amino acids at one or more of the following positions: 37, 45, 46, 89, and 107 that is bonded to a water soluble polymer and comprises one or more of the following naturally encoded amino acid substitutions: T79R, L80A, Y85L, Y85S, E87S (SEQ ID NO: 2 or the corresponding amino acids in SEQ ID NO: 1 or 3).

In some embodiments, the hIFN polypeptide comprises one or more non-naturally encoded amino acids at one or more of the following positions: 23, 24, 25, 26, 27, 28, 30, 31, 32, 33, 128, 129, 131, 132, 133, 134, 135, 136, 137, 158, 159, 160, 161, 162, 163, 164, 165 (SEQ ID NO: 2 or the corresponding amino acids in SEQ ID NO: 1 or 3). In some embodiments, the hIFN polypeptide comprises one or more non-naturally encoded amino acids at one or more of the following positions that is linked or bonded to a water soluble polymer: 23, 24, 25, 26, 27, 28, 30, 31, 32, 33, 128, 129, 131, 132, 133, 134, 135, 136, 137, 158, 159, 160, 161, 162, 163, 164, 165 (SEQ ID NO: 2 or the corresponding amino acids in SEQ ID NO: 1 or 3). In some embodiments, the hIFN polypeptide comprises one or more non-naturally encoded amino acids at one or more of the following positions: 23, 24, 27, 31, 128, 131, 134, 158 (SEQ ID NO: 2 or the corresponding amino acids in SEQ ID NO: 1 or 3). In some embodiments, the hIFN polypeptide comprises one or more non-naturally encoded amino acids at one or more of the following positions that is linked or bonded to a water soluble polymer: 23, 24, 27, 31, 128, 131, 134, 158 (SEQ ID NO: 2 or the corresponding amino acids in SEQ ID NO: 1 or 3). In some embodiments, the hIFN polypeptide comprises one or more non-naturally encoded amino acids at one or more of the following positions: 24, 27, 31, 128, 131, 134 (SEQ ID NO: 2 or the corresponding amino acids in SEQ ID NO: 1 or 3). In some embodiments, the hIFN polypeptide comprises one or more non-naturally encoded amino acids at one or more of the following positions that is linked or bonded to a water soluble polymer: 24, 27, 31, 128, 131, 134 (SEQ ID NO: 2 or the corresponding amino acids in SEQ ID NO: 1 or 3).

Example 2

This example details cloning and expression of a modified hIFN polypeptide in *E. coli*.

This example demonstrates how a hIFN polypeptide including a non-naturally encoded amino acid can be expressed in *E. Coli*. See Nagata et. al., Nature, vol. 284, 316-320 (1980) and U.S. Pat. No. 4,364,863, which is incorporated by reference. cDNA encoding the full length hIFN and the mature form of hIFN lacking the N-terminal signal sequence are shown in SEQ ID NO: 21 and SEQ ID NO: 22, respectively. The full length and mature hIFN encoding cDNA is inserted into the pBAD HISc, pET20b, and pET19b expression vectors following optimization of the sequence for cloning and expression without altering amino acid sequence.

An introduced translation system that comprises an orthogonal tRNA (O-tRNA) and an orthogonal aminoacyl tRNA synthetase (O-RS) is used to express hIFN containing a non-naturally encoded amino acid. The O-RS preferentially aminoacylates the O-tRNA with a non-naturally encoded amino acid. In turn the translation system inserts the non-naturally encoded amino acid into hIFN, in response to an encoded selector codon.

The transformation of *E. coli* with plasmids containing the modified hIFN gene and the orthogonal aminoacyl tRNA synthetase/tRNA pair (specific for the desired non-naturally encoded amino acid) allows the site-specific incorporation of non-naturally encoded amino acid into the hIFN polypeptide. The transformed *E. coli*, grown at 37° C. in media containing between 0.01-100 mM of the particular non-naturally encoded amino acid, expresses modified hIFN with high fidelity and efficiency. The His-tagged hIFN containing a non-naturally encoded amino acid is produced by the *E. coli* host cells as inclusion bodies or aggregates. The aggregates are solubilized and affinity purified under denaturing conditions in 6M guanidine HCl. Refolding is performed by dialysis at 4° C. overnight in 50 mM TRIS-HCl, pH 8.0, 40 µM $CuSO_4$, and 2% (w/v) Sarkosyl. The material is then dialyzed against 20 mM TRIS-HCl, pH 8.0, 100 mM NaCl, 2 mM $CaCl_2$, followed by removal of the His-tag. See Boissel et al., (1993) 268:15983-93. Methods for purification of hIFN are well known in the art and are confirmed by SDS-PAGE, Western Blot analyses, or electrospray-ionization ion trap mass spectrometry and the like.

To generate hIFN polypeptides with a 6 His tag at the N terminus, hIFN nucleotide sequences were cloned downstream of the tag. The transformation of *E. Coli* (BL21 (DE3)) with constructs containing the hIFN polynucleotide sequence and the orthogonal aminoacyl tRNA synthetase/tRNA pair (specific for the desired non-naturally encoded amino acid) allowed site-specific incorporation of non-naturally encoded amino acid (p-acetyl-phenylalanine) into the hIFN polypeptide.

Example 3

This example details introduction of a carbonyl-containing amino acid and subsequent reaction with an aminooxy-containing PEG.

This Example demonstrates a method for the generation of a hIFN polypeptide that incorporates a ketone-containing non-naturally encoded amino acid that is subsequently reacted with an aminooxy-containing PEG of approximately 5,000 MW. Each of the residues identified according to the criteria of Example 1, including but not limited to, 100, 106,

TABLE 2

O-RS and O-tRNA sequences.

| | | |
|---|---|---|
| SEQ ID NO: 4 | *M. jannaschii* mtRNA$_{CUA}^{Tyr}$ | tRNA |
| SEQ ID NO: 5 | HLAD03; an optimized amber supressor tRNA | tRNA |
| SEQ ID NO: 6 | HL325A; an optimized AGGA frameshift supressor tRNA | tRNA |
| SEQ ID NO: 7 | Aminoacyl tRNA synthetase for the incorporation of p-azido-L-phenylalanine p-Az-PheRS(6) | RS |
| SEQ ID NO: 8 | Aminoacyl tRNA synthetase for the incorporation of p-benzoyl-L-phenylalanine p-BpaRS(1) | RS |
| SEQ ID NO: 9 | Aminoacyl tRNA synthetase for the incorporation of propargyl-phenylalanine Propargyl-PheRS | RS |
| SEQ ID NO: 10 | Aminoacyl tRNA synthetase for the incorporation of propargyl-phenylalanine Propargyl-PheRS | RS |
| SEQ ID NO: 11 | Aminoacyl tRNA synthetase for the incorporation of propargyl-phenylalanine Propargyl-PheRS | RS |
| SEQ ID NO: 12 | Aminoacyl tRNA synthetase for the incorporation of p-azido-phenylalanine p-Az-PheRS(1) | RS |
| SEQ ID NO: 13 | Aminoacyl tRNA synthetase for the incorporation of p-azido-phenylalanine p-Az-PheRS(3) | RS |
| SEQ ID NO: 14 | Aminoacyl tRNA synthetase for the incorporation of p-azido-phenylalanine p-Az-PheRS(4) | RS |
| SEQ ID NO: 15 | Aminoacyl tRNA synthetase for the incorporation of p-azido-phenylalanine p-Az-PheRS(2) | RS |
| SEQ ID NO: 16 | Aminoacyl tRNA synthetase for the incorporation of p-acetyl-phenylalanine (LW1) | RS |
| SEQ ID NO: 17 | Aminoacyl tRNA synthetase for the incorporation of p-acetyl-phenylalanine (LW5) | RS |
| SEQ ID NO: 18 | Aminoacyl tRNA synthetase for the incorporation of p-acetyl-phenylalanine (LW6) | RS |
| SEQ ID NO: 19 | Aminoacyl tRNA synthetase for the incorporation of p-azido-phenylalanine (AzPheRS-5) | RS |
| SEQ ID NO: 20 | Aminoacyl tRNA synthetase for the incorporation of p-azido-phenylalanine (AzPheRS-6) | RS |

107, 108, 111, 113, 114 (hIFN) is separately substituted with a non-naturally encoded amino acid having the following structure:

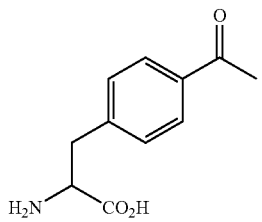

The sequences utilized for site-specific incorporation of p-acetyl-phenylalanine into hIFN are SEQ ID NO: 2 (hIFN), and SEQ ID NO: 4 (muttRNA), and 16, 17 or 18 (TyrRS LW1, 5, or 6) described in Example 2 above.

Once modified, the hIFN polypeptide variant comprising the carbonyl-containing amino acid is reacted with an aminooxy-containing PEG derivative of the form:

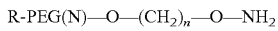

where R is methyl, n is 3 and N is approximately 5,000 MW. The purified hIFN containing p-acetylphenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. *J. Am. Chem. Soc.* 1959, 81, pp 475). The PEG-hIFN is then diluted into appropriate buffer for immediate purification and analysis.

Example 4

Conjugation with a PEG consisting of a hydroxylamine group linked to the PEG via an amide linkage.

A PEG reagent having the following structure is coupled to a ketone-containing non-naturally encoded amino acid using the procedure described in Example 3:

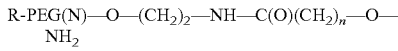

where R=methyl, n=4 and N is approximately 20,000 MW. The reaction, purification, and analysis conditions are as described in Example 3.

Example 5

This example details the introduction of two distinct non-naturally encoded amino acids into hIFN polypeptides.

This example demonstrates a method for the generation of a hIFN polypeptide that incorporates non-naturally encoded amino acid comprising a ketone functionality at two positions among the residues identified according to Example 1, wherein X* represents a non-naturally encoded amino acid. The hIFN polypeptide is prepared as described in Examples 1 and 2, except that the selector codon is introduced at two distinct sites within the nucleic acid.

Example 6

This example details conjugation of hIFN polypeptide to a hydrazide-containing PEG and subsequent in situ reduction.

A hIFN polypeptide incorporating a carbonyl-containing amino acid is prepared according to the procedure described in Examples 2 and 3. Once modified, a hydrazide-containing PEG having the following structure is conjugated to the hIFN polypeptide:

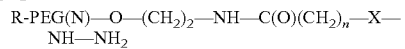

where R=methyl, n=2 and N=10,000 MW and X is a carbonyl (C=O) group. The purified hIFN containing p-acetylphenylalanine is dissolved at between 0.1-10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 1 to 100-fold excess of hydrazide-containing PEG, and the corresponding hydrazone is reduced in situ by addition of stock 1M NaCNBH$_3$ (Sigma Chemical, St. Louis, Mo.), dissolved in H$_2$O, to a final concentration of 10-50 mM. Reactions are carried out in the dark at 4° C. to RT for 18-24 hours. Reactions are stopped by addition of 1 M Tris (Sigma Chemical, St. Louis, Mo.) at about pH 7.6 to a final Tris concentration of 50 mM or diluted into appropriate buffer for immediate purification.

Example 7

This example details introduction of an alkyne-containing amino acid into a hIFN polypeptide and derivatization with mPEG-azide.

Any of the residues of hIFN identified according to Example 1, including but not limited to, 100, 106, 107, 108, 111, 113, 114 are substituted with this non-naturally encoded amino acid:

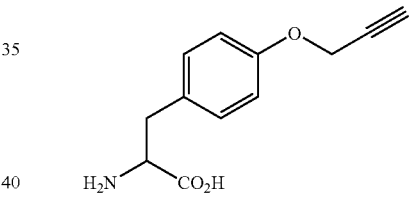

The sequences utilized for site-specific incorporation of p-propargyl-tyrosine into hIFN are SEQ ID NO: 2 (hIFN), SEQ ID NO: 4 (muttRNA, *M. jannaschii* mtRNAT$_{CUA}^{Tyr}$), and 9, 10 or 11 described in Example 2 above. The hIFN polypeptide containing the propargyl tyrosine is expressed in *E. coli* and purified using the conditions described in Example 3.

The purified hIFN containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of CuSO$_4$ and Cu wire are then added to the reaction mixture. After the mixture is incubated (including but not limited to, about 4 hours at room temperature or 37° C., or overnight at 4° C.), H$_2$O is added and the mixture is filtered through a dialysis membrane. The sample can be analyzed for the addition.

In this Example, the PEG has the following structure:

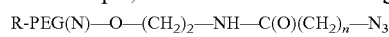

where R is methyl, n is 4 and N is 10,000 MW.

Example 8

This example details substitution of a large, hydrophobic amino acid in a hIFN polypeptide with propargyl tyrosine.

A Phe, Trp or Tyr residue present within one the following regions of hIFN: 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus), (as in SEQ ID NO: 2 or the corresponding amino acids of other IFN polypeptides), is substituted with the following non-naturally encoded amino acid as described in Example 7:

Once modified, a PEG is attached to the hIFN polypeptide variant comprising the alkyne-containing amino acid. The PEG will have the following structure:

Me-PEG(N)—O—(CH$_2$)$_2$—N$_3$ and coupling procedures would follow those in Example 7. This generates a hIFN polypeptide variant comprising a non-naturally encoded amino acid that is approximately isosteric with one of the naturally-occurring, large hydrophobic amino acids and which is modified with a PEG derivative at a distinct site within the polypeptide.

Example 9

This example details generation of a hIFN polypeptide homodimer, heterodimer, homomultimer, or heteromultimer separated by one or more PEG tinkers.

The alkyne-containing hIFN polypeptide variant produced in Example 7 is reacted with a bifunctional PEG derivative of the form:

N$_3$—(CH$_2$)$_n$—C(O)—NH—(CH$_2$)$_2$—O-PEG(N)—O—(CH$_2$)$_2$—NH—C(O)—(CH$_2$)$_n$—N$_3$ where n is 4 and the PEG has an average MW of approximately 5,000, to generate the corresponding hIFN polypeptide homodimer where the two hIFN molecules are physically separated by PEG. In an analogous manner a hIFN polypeptide may be coupled to one or more other polypeptides to form heterodimers, homomultimers, or heteromultimers. Coupling, purification, and analyses will be performed as in Examples 7 and 3.

Example 10

This example details coupling of a saccharide moiety to a hIFN polypeptide.

One residue of the following is substituted with the non-natural encoded amino acid below: 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165 (as in SEQ ID NO: 2, or the corresponding amino acids of other IFN polypeptides).

Once modified, the hIFN polypeptide variant comprising the carbonyl-containing amino acid is reacted with a β-linked aminooxy analogue of N-acetylglucosamine (GlcNAc). The hIFN polypeptide variant (10 mg/mL) and the aminooxy saccharide (21 mM) are mixed in aqueous 100 mM sodium acetate buffer (pH 5.5) and incubated at 37° C. for 7 to 26 hours. A second saccharide is coupled to the first enzymatically by incubating the saccharide-conjugated hIFN polypeptide (5 mg/mL) with UDP-galactose (16 mM) and β-1,4-galacytosyltransferase (0.4 units/mL) in 150 mM HEPES buffer (pH 7.4) for 48 hours at ambient temperature (Schanbacher et al. *J. Biol. Chem.* 1970, 245, 5057-5061).

Example 11

This example details generation of a PEGylated hIFN polypeptide antagonist.

One of the following residues, 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165, (hIFN; SEQ ID NO: 2 or the corresponding amino acids in SEQ ID NO: 1 or 3) is substituted with the following non-naturally encoded amino acid as described in Example 3; a hIFN polypeptide comprising one of these substitutions may potentially act as a weak antagonist or weak agonist depending on the site selected and the desired activity. One of the following residues, 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, (hIFN; SEQ ID NO: 2 or the corresponding amino acids in SEQ ID NO: 1 or 3) is substituted with the following non-naturally encoded amino acid as described in Example 3.

Once modified, the hIFN polypeptide variant comprising the carbonyl-containing amino acid will be reacted with an aminooxy-containing PEG derivative of the form:

R-PEG(N)—O—(CH$_2$)$_n$—O—NH$_2$ where R is methyl, n is 4 and N is 20,000 MW to generate a hIFN polypeptide antagonist comprising a non-naturally encoded amino acid that is modified with a PEG derivative at a single site within the polypeptide. Coupling, purification, and analyses are performed as in Example 3.

Example 12

Generation of a hIFN Polypeptide Homodimer, Heterodimer, Homomultimer, or Heteromultimer in which the hIFN Molecules are Linked Directly A hIFN polypeptide variant comprising the alkyne-containing amino acid can be directly coupled to another hIFN polypeptide variant comprising the azido-containing amino acid, each of which comprise non-naturally encoded amino acid substitutions at the sites described in, but not limited to, Example 10. This will generate the corresponding hIFN polypeptide homodimer where the two hIFN polypeptide variants are physically joined. In an analogous manner a hIFN polypeptide may be coupled to one or more other polypeptides to form heterodimers, homomultimers, or heteromultimers. Coupling, purification, and analyses are performed as in Examples 3, 6, and 7.

Example 13

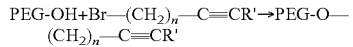

A B

The polyalkylene glycol (P—OH) is reacted with the alkyl halide (A) to form the ether (B). In these compounds, n is an integer from one to nine and R' can be a straight- or branched-chain, saturated or unsaturated C1, to C20 alkyl or heteroalkyl group. R' can also be a C3 to C7 saturated or unsaturated cyclic alkyl or cyclic heteroalkyl, a substituted or unsubstituted aryl or heteroaryl group, or a substituted or unsubstituted alkaryl (the alkyl is a C1 to C20 saturated or unsaturated alkyl) or heteroalkaryl group. Typically, PEG-OH is polyethylene glycol (PEG) or monomethoxy polyethylene glycol (mPEG) having a molecular weight of 800 to 40,000 Daltons (Da).

Example 14

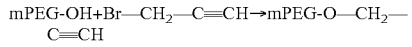

mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI were then added to the solution and the resulting mixture was heated to reflux for 2 hours. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford propargyl-O-PEG.

Example 15

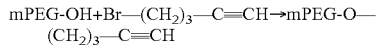

The mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 5-bromo-1-pentyne (0.53 mL, 5 mmol, Aldrich) and a catalytic amount of KI were then added to the mixture. The resulting mixture was heated to reflux for 16 hours. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford the corresponding alkyne. 5-chloro-1-pentyne may be used in a similar reaction.

Example 16

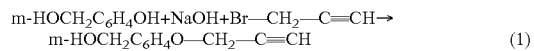 (1)

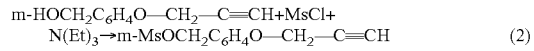 (2)

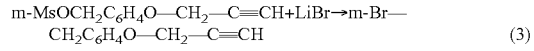 (3)

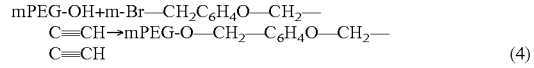 (4)

To a solution of 3-hydroxybenzylalcohol (2.4 g, 20 mmol) in THF (50 mL) and water (2.5 mL) was first added powdered sodium hydroxide (1.5 g, 37.5 mmol) and then a solution of propargyl bromide, dissolved as an 80% weight solution in xylene (3.36 mL, 30 mmol). The reaction mixture was heated at reflux for 6 hours. To the mixture was added 10% citric acid (2.5 mL) and the solvent was removed under vacuum. The residue was extracted with ethyl acetate (3×15 mL) and the combined organic layers were washed with saturated NaCl solution (10 mL), dried over $MgSO_4$ and concentrated to give the 3-propargyloxybenzyl alcohol.

Methanesulfonyl chloride (2.5 g, 15.7 mmol) and triethylamine (2.8 mL, 20 mmol) were added to a solution of compound 3 (2.0 g, 11.0 mmol) in $CH_2Cl_2$ at 0° C. and the reaction was placed in the refrigerator for 16 hours. A usual work-up afforded the mesylate as a pale yellow oil. This oil (2.4 g, 9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous $Na_2SO_4$, and concentrated to give the desired bromide.

mPEG-OH 20 kDa (1.0 g, 0.05 mmol, Sunbio) was dissolved in THF (20 mL) and the solution was cooled in an ice bath. NaH (6 mg, 0.25 mmol) was added with vigorous stirring over a period of several minutes followed by addition of the bromide obtained from above (2.55 g, 11.4 mmol) and a catalytic amount of KI. The cooling bath was removed and the resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a white precipitate, which was collected to yield the PEG derivative.

Example 17

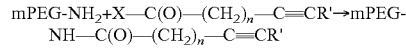

The terminal alkyne-containing poly(ethylene glycol) polymers can also be obtained by coupling a poly(ethylene glycol) polymer containing a terminal functional group to a reactive molecule containing the alkyne functionality as shown above. n is between 1 and 10. R' can be H or a small alkyl group from C1 to C4.

Example 18

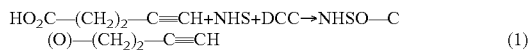
(1)

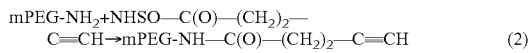
(2)

4-pentynoic acid (2.943 g, 3.0 mmol) was dissolved in CH$_2$Cl$_2$ (25 mL). N-hydroxysuccinimide (3.80 g, 3.3 mmol) and DCC (4.66 g, 3.0 mmol) were added and the solution was stirred overnight at room temperature. The resulting crude NHS ester 7 was used in the following reaction without further purification.

mPEG-NH$_2$ with a molecular weight of 5,000 Da (mPEG-NH$_2$, 1 g, Sunbio) was dissolved in THF (50 mL) and the mixture was cooled to 4° C. NHS ester 7 (400 mg, 0.4 mmol) was added portion-wise with vigorous stirring. The mixture was allowed to stir for 3 hours while warming to room temperature. Water (2 mL) was then added and the solvent was removed under vacuum. To the residue was added CH$_2$Cl$_2$ (50 mL) and the organic layer was separated, dried over anhydrous Na$_2$SO$_4$, and the volume was reduced to approximately 2 mL. This CH$_2$Cl$_2$ solution was added to ether (150 mL) drop-wise. The resulting precipitate was collected and dried in vacuo.

Example 19

This Example represents the preparation of the methane sulfonyl ester of poly(ethylene glycol), which can also be referred to as the methanesulfonate or mesylate of poly(ethylene glycol). The corresponding tosylate and the halides can be prepared by similar procedures.

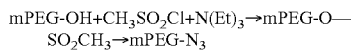

The mPEG-OH (MW=3,400, 25 g, 10 mmol) in 150 mL of toluene was azeotropically distilled for 2 hours under nitrogen and the solution was cooled to room temperature. 40 mL of dry CH$_2$Cl$_2$ and 2.1 mL of dry triethylamine (15 mmol) were added to the solution. The solution was cooled in an ice bath and 1.2 mL of distilled methanesulfonyl chloride (15 mmol) was added dropwise. The solution was stirred at room temperature under nitrogen overnight, and the reaction was quenched by adding 2 mL of absolute ethanol. The mixture was evaporated under vacuum to remove solvents, primarily those other than toluene, filtered, concentrated again under vacuum, and then precipitated into 100 mL of diethyl ether. The filtrate was washed with several portions of cold diethyl ether and dried in vacuo to afford the mesylate.

The mesylate (20 g, 8 mmol) was dissolved in 75 ml of THF and the solution was cooled to 4° C. To the cooled solution was added sodium azide (1.56 g, 24 mmol). The reaction was heated to reflux under nitrogen for 2 hours. The solvents were then evaporated and the residue diluted with CH$_2$Cl$_2$ (50 mL). The organic fraction was washed with NaCl solution and dried over anhydrous MgSO$_4$. The volume was reduced to 20 ml and the product was precipitated by addition to 150 ml of cold dry ether.

Example 20

(1)

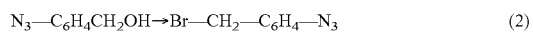
(2)

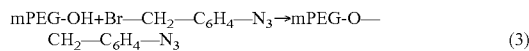
(3)

4-azidobenzyl alcohol can be produced using the method described in U.S. Pat. No. 5,998,595, which is incorporated by reference herein. Methanesulfonyl chloride (2.5 g, 15.7 mmol) and triethylamine (2.8 mL, 20 mmol) were added to a solution of 4-azidobenzyl alcohol (1.75 g, 11.0 mmol) in CH$_2$Cl$_2$ at 0° C. and the reaction was placed in the refrigerator for 16 hours. A usual work-up afforded the mesylate as a pale yellow oil. This oil (9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous Na$_2$SO$_4$, and concentrated to give the desired bromide.

mPEG-OH 20 kDa (2.0 g, 0.1 mmol, Sunbio) was treated with NaH (12 mg, 0.5 mmol) in THF (35 mL) and the bromide (3.32 g, 15 mmol) was added to the mixture along with a catalytic amount of KI. The resulting mixture was heated to reflux for 12 hours. Water (1.0 mL) was added to the mixture and the solvent was removed under vacuum. To the residue was added CH$_2$Cl$_2$ (25 mL) and the organic layer was separated, dried over anhydrous Na$_2$SO$_4$, and the volume was reduced to approximately 2 mL. Dropwise addition to an ether solution (150 mL) resulted in a precipitate, which was collected to yield mPEG-O—CH$_2$—C$_6$H$_4$—N$_3$.

Example 21

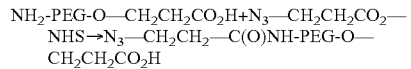

NH$_2$-PEG-O—CH$_2$CH$_2$CO$_2$H (MW 3,400 Da, 2.0 g) was dissolved in a saturated aqueous solution of NaHCO$_3$ (10 mL) and the solution was cooled to 0° C. 3-azido-1-N-hydroxysuccinimido propionate (5 equiv.) was added with vigorous stirring. After 3 hours, 20 mL of H$_2$O was added and the mixture was stirred for an additional 45 minutes at room temperature. The pH was adjusted to 3 with 0.5 N H$_2$SO$_4$ and NaCl was added to a concentration of approximately 15 wt %. The reaction mixture was extracted with CH$_2$Cl$_2$ (100 mL×3), dried over Na$_2$SO$_4$ and concentrated. After precipitation with cold diethyl ether, the product was collected by filtration and dried under vacuum to yield the omega-carboxy-azide PEG derivative.

Example 22

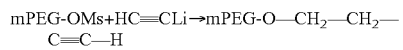

To a solution of lithium acetylide (4 equiv.), prepared as known in the art and cooled to −78° C. in THF, is added dropwise a solution of mPEG-OMs dissolved in THF with vigorous stirring. After 3 hours, the reaction is permitted to warm to room temperature and quenched with the addition of 1 mL of butanol. 20 mL of $H_2O$ is then added and the mixture was stirred for an additional 45 minutes at room temperature. The pH was adjusted to 3 with 0.5 N $H_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the 1-(but-3-ynyloxy)-methoxy-polyethylene glycol (mPEG).

Example 23

The azide- and acetylene-containing amino acids were incorporated site-selectively into proteins using the methods described in L. Wang, et al., (2001), Science 292:498-500, J. W. Chin et al., Science 301:964-7 (2003)), J. W. Chin et al., (2002), Journal of the American Chemical Society 124:9026-9027; J. W. Chin, & P. G. Schultz, (2002), Chem Bio Chem 11:1135-1137; J. W. Chin, et al., (2002), PNAS United States of America 99:11020-11024: and, L. Wang, & P. G. Schultz, (2002), Chem. Comm. 1-10. Once the amino acids were incorporated, the cycloaddition reaction was carried out with 0.01 mM protein in phosphate buffer (PB), pH 8, in the presence of 2 mM PEG derivative, 1 mM $CuSO_4$, and ~1 mg Cu-wire for 4 hours at 37° C.

The synthesis of p-Acetyl-D,L-phenylalanine (pAF) and m-PEG-hydroxylamine derivatives is performed as described below. The racemic pAF is synthesized using the previously described procedure in Zhang, Z., Smith, B. A. C., Wang, L., Brock, A., Cho, C. & Schultz, P. G., Biochemistry, (2003) 42, 6735-6746. To synthesize the m-PEG-hydroxylamine derivative, the following procedures are completed. To a solution of (N-t-Boc-aminooxy)acetic acid (0.382 g, 2.0 mmol) and 1,3-Diisopropylcarbodiimide (0.16 mL, 1.0 mmol) in dichloromethane (DCM, 70 mL), which is stirred at room temperature (RT) for 1 hour, methoxy-polyethylene glycol amine (m-PEG-$NH_2$, 7.5 g, 0.25 mmol, Mt. 30 K, from BioVectra) and Diisopropylethylamine (0.1 mL, 0.5 mmol) are added. The reaction is stirred at RT for 48 hours, and then is concentrated to about 100 mL. The mixture is added dropwise to cold ether (800 mL). The t-Boc-protected product precipitated out and is collected by filtering, washed by ether 3×100 mL. It is further purified by re-dissolving in DCM (100 mL) and precipitating in ether (800 mL) twice. The product is dried in vacuum, confirmed by NMR and Nihydrin test.

The deBoc of the protected product (7.0 g) obtained above is carried out in 50% TFA/DCM (40 mL) at 0° C. for 1 hour and then at RT for 1.5 hour. After removing most of TFA in vacuum, the TFA salt of the hydroxylamine derivative is converted to the HCl salt by adding 4N HCl in dioxane (1 mL) to the residue. The precipitate is dissolved in DCM (50 mL) and re-precipitated in ether (800 mL). The final product is collected by filtering, washed with ether 3×100 mL, dried in vacuum, stored under nitrogen. Other PEG (5K, 20K) hydroxylamine derivatives can be synthesized using the same procedure.

Example 24 hIFN polypeptides were isolated according to the following protocol. Variations to the refolding method have also been performed to isolate hIFN polypeptides of the invention, modifying the composition of the buffer that receives the solubilized IFN. Additional modifications such as the addition of $Cu^{++}$ or other mild oxidizing agents during or after the procedure, altering denaturing agents or reducing agents, altering the pH to assess refolding efficiency at various pHs may be performed. Column-based refolding methods using HIC, dye-based, size-exclusion, or ion-exchange resins may be used for refolding. Other modifications to such methods are known to those of ordinary skill in the art.

To generate hIFN polypeptides with a 6 His tag at the N terminus, hIFN nucleotide sequences were cloned downstream of the tag. The transformation of E. coli (BL21 (DE3)) with constructs containing the hIFN polynucleotide sequence and the orthogonal aminoacyl tRNA synthetase/tRNA pair (specific for the desired non-naturally encoded amino acid) allowed site-specific incorporation of non-naturally encoded amino acid (p-acetyl-phenylalanine) into the hIFN polypeptide.

Inclusion Body Preparation and Refolding

Fresh or frozen E. coli host cell pellets were resuspended in approximately 10 mL/g of 20 mM Tris pH 7.5, 200 mM NaCl, 1 mM EDTA. The pellets were sonicated six times for 30 seconds with 1 minute incubations on ice between each sonication. 1 mg/mL lysozyme and DNase I were added to each sonicated sample, and the samples were incubated for 30 minutes at room temperature.

The samples were centrifuged at 12,000 rpm for 10 minutes at 4° C., and the supernatants for each sample were removed for analysis. The pellets were washed three times with 40 ml of chilled IB Wash Buffer 1 (20 mM Tris, pH 7.5, 100 mM NaCl, 1 mM EDTA, 1% Triton) by detaching them from the sides of the tubes and resuspending the pellets by sonication for 30 seconds. In between each wash, the samples were centrifuged at 12,000 rpm for 5 minutes at 4° C. The pellets were then resuspended/washed twice with 40 ml of chilled IB Wash Buffer 2 (20 mM Tris, pH 7.5, 100 mM NaCl, 1 mM EDTA). In between each wash, the samples were centrifuged at 12,000 rpm for 5 minutes at 4° C.

After the two sets of washes, the pellets were solubilized by douncing in 5-20 ml of Solubilization Buffer (50 mM Tris, pH 7.5, 8M Gdn-HCl). The minimum amount of buffer necessary to completely solubilize each pellet was used. Samples were then centrifuged at 12,000 for 15 minutes at 4° C. to remove any insoluble particles, and the supernatants were transferred into fresh tubes.

An aliquot was taken from each sample, and the aliquots were diluted 20× in Solubilization Buffer, and the OD280 for each sample was measured to determine protein concentration. The Extinction coefficient at 280 nm is 22,500 M−1 or 1.17 mg/ml −1.

The inclusion bodies were aliquoted into 3-5 ml aliquots and stored at −80° C. 0.15 mg/ml IFN final (5 mg/mL solution in 6-8M GndHCl, pH 8) were injected in three aliquots into a fast-stirring buffer (20-50 mM Tris HCl, pH 8.2, 0.5 M L-arginine, 10% Glycerol or Sucrose) (plus 200-250 mM Gnd from solubilized IFN) at 4° C. The injections were performed under the surface of the solution to avoid foaming. After injection, slow stirring was used for approximately 16-24 hours at 4° C. After the completion of the refolding reaction, the samples were processed further.

The samples were concentrated with Amicon Stirring cells (YM-10 membrane) to approximately 1-1.5 mg/ml (15-30 ml). The samples were then dialyzed against 30 mM Tris, pH 7.8, 20 mM NaCl, 5% glycerol overnight at 4° C. The samples were diluted to 50 ml with Q HP Buffer A (10 mM Tris, pH 7.5), and purification was performed on a 5 ml Q HP AKTA column using a gradient of 0-30% B (10 mM Tris, pH 7.5, 1 M NaCl) over fifteen column volumes. The column was washed with 2.5 M NaCl, followed by 1M NaCl/1M NaOH. SDS-PAGE analysis was performed on the column fractions, and the fractions containing monomeric refolded hIFN polypeptides were pooled. The pH of each pool was adjusted by adding 1/20 volume of 1M NaAc, pH 4.5, and each pool was dialyzed overnight against 20 mM NaAc, pH 4, 20 mM NaCl, 5% glycerol. The hIFN polypeptides were concentrated to >1 mg/ml for PEGylation.

PEGylation

Figure 19:
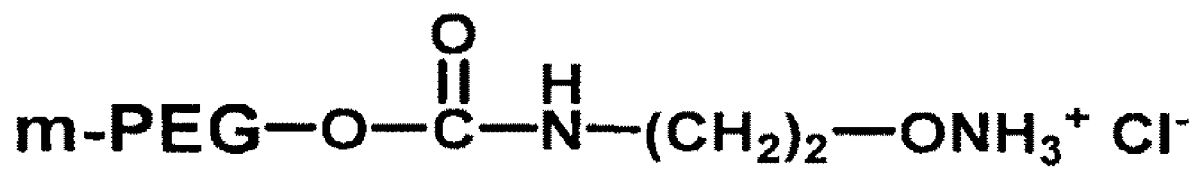
FIG. 19—A diagram is shown of the structure of linear, 30 kDa monomethoxy-poly(ethylene glycol)-2-aminooxy ethylamine carbamate hydrochloride.

Oxyamino-derivatized 30K PEG is added to hIFN polypeptide at a 1:12 molar ratio (30 mg/mg IFN/ml), and the mixture is incubated at 28° C. for 16-48 hours. FIG. 19 shows the 30K PEG used in the conjugation.

Isolation of PEGylated hIFN Polypeptides

PEGylated hIFN polypeptides were isolated using the Source Q 30 column. The buffers used with this column were Buffer A (10 mM Tris, pH 8.0); Buffer B (10 mM Tris, pH 8.0; 1M NaCl); and Sanitization Buffer (1M NaOH; 1M NaCl). The fractions of PEGylated hIFN were pooled, dialyzed against the following storage buffer: 20 mM NaAcetate, pH 6, 0.005% Tween, 125 mM NaCl. The samples were then concentrated to >8 microM and stored at 4° C.

Buffer lines were primed and washed with the appropriate buffers, and the column and sample line were sanitized with 30-40 mL Sanitization Buffer. The sample line was rinsed with Buffer A to remove any traces of Sanitization Buffer, and the line was primed for sample addition. The column was equilibrated with 5-10 column volumes of Buffer A, until parameters such as UV and Conductivity were stable.

A sample of PEGylated hIFN polypeptide was injected onto the column, and the column was washed with 4 column volumes of Buffer A. The gradient used was the following: 0-20% Buffer B for 20 column volumes; 100% Buffer B for 4 column volumes. 1-1.5 mL fractions were collected from the column and were analyzed by SDS-PAGE to determine fractions for pooling. PEG monomer fractions were pooled. The column was prepared for the next sample by the sanitizing column and sample line with 30-40 mL Sanitization Buffer.

Example 25

This example details the measurement of hIFN activity and affinity of hIFN polypeptides for the hIFN receptor.

Biacore Studies (Receptor Binding Affinity)

The sequence for the IFNAR2 extracellular domain (consisting of 206 amino acids ending with sequence LLPPGQ) was amplified from clone MHS1011-61064 (OpenBiosystems, Huntsville, Ala.). This insert was cloned into the pET20 expression vector (Novagen) downstream of the T7 promoter. Protein expression was induced with 0.4 mM IPTG in BL21 (DE3) cells (Novagen).

Since the expressed protein was insoluble, the inclusion bodies were purified from lysed cells and solubilized in 6M GndCl. A 5 ml aliquot (50 mg amount) was reduced with 10 mM DTT for 45 minutes at 37° C. Then the mixture was injected into 200 ml of refolding buffer which consisted of 50 mM Tris pH 8, 20 mM NaCl, 0.5 M Arginine, 10% glycerol at 4° C. and incubated overnight with gentle stirring.

The refolding reaction was then concentrated to 25 ml using an Amicon stirring cell, and dialyzed overnight against 20 mM Tris, pH 8, 20 mM NaCl, 10% glycerol. Monomeric refolded IFNAR ECD was purified on HP Q Sepharose using the AKTA FPLC system (Amersham). Purified IFNAR2 ECD was immobilized on CM5 Biacore chip using a lysine-specific coupling procedure recommended by the manufacturer. About 200 RUs of functional protein were immobilized. Various concentrations of IFN variants in HBS-EP buffer (Biacore) were injected at a flow rate of 50 mcl/minute over the flowcell containing immobilized IFNAR2, and a control flowcell containing immobilized bovine serum albumin. Sensograms generated were fit to the 1:1 interaction model to calculate $k_{on}$, $k_{off}$ and $K_d$ values using BiaEvaluation software (Biacore). N-terminal 6-His hIFN polypeptides comprising the non-naturally encoded amino acid p-acetyl-phenylalanine (pAF) were tested, as well as PEGylated hIFN polypeptides comprising pAF after isolation via the methods described in Example 25. Controls utilized in these studies included IFNαA obtained from Sigma, N-6 His tagged wild-type IFN, and PEGASYS®. Data collected for hIFN polypeptides is shown in Table 3. Non-PEGylated hIFN polypeptide with a para-acetylphenylalanine substitution at position 149 of SEQ ID NO: 2 showed altered binding kinetics in this assay (faster $k_{off}$).

TABLE 3

Binding parameters for IFNα-2a:IFNAR2 interaction, as determined by SPR

| IFNα2A | $k_{on}$, × 10$^{-6}$ 1/M * s | $k_{off}$, 1/s | $K_d$, nM |
|---|---|---|---|
| SIGMA WT IFN | 1.9 | 0.02 | 11 |
| N-6His WT IFN | 3.5 | 0.02 | 6 |
| PEGASYS ® | 0.1 | 0.03 | 300 |
| 6His K31pAF | 1.3 | 0.07 | 52 |
| 6His K31pAF-30K PEG | 0.09 | 0.07 | 830 |
| 6His H34pAF | 3.7 | 0.014 | 4 |
| 6His H34pAF-30K PEG | 0.14 | 0.02 | 140 |
| 6His E107pAF | 4.2 | 0.019 | 4.8 |
| 6His E107pAF-30K PEG | 0.1 | 0.025 | 240 |
| 6His F38L | 2.8 | 0.053 | 18 |
| 6His F38S | 1.7 | 0.07 | 42 |
| 6His G37pAF | 2.4 | 0.027 | 12 |
| 6His G37pAF-30K PEG | 0.12 | 0.049 | 410 |
| 6His E41pAF | 1.9 | 0.031 | 16 |
| 6His E41pAF-30K PEG | 0.079 | 0.044 | 560 |
| 6His R125pAF | 1.3 | 0.025 | 19 |
| 6His R125pAF-30K PEG | 0.055 | 0.018 | 330 |
| 6His F36S | 0.01 | 0.013 | 1300 |
| 6His P39pAF | 1.3 | 0.023 | 17 |
| 6His P39pAF-30K PEG | 0.076 | 0.034 | 440 |
| 6His N65pAF | 2.4 | 0.015 | 7 |
| 6His N65pAF-30K PEG | 0.17 | 0.026 | 150 |
| 6His T106pAF | 2.1 | 0.015 | 7.5 |
| 6His T106pAF-30K PEG | 0.15 | 0.022 | 140 |
| 6His L117pAF | 1.9 | 0.015 | 8 |
| 6His L117pAF-30K PEG | 0.15 | 0.021 | 140 |
| 6His R12pAF | 1.75 | 0.014 | 7.9 |
| 6His R12pAF-30K PEG | 0.049 | 0.0165 | 340 |
| 6His Y122S | 0.031 | 0.01 | 300 |
| 6His F27pAF | 3.4 | 0.026 | 7.9 |
| 6His F27pAF-30K PEG | 0.045 | 0.0094 | 210 |
| 6His L110pAF | 4.3 | 0.056 | 12.8 |
| 6His L110pAF-30K PEG | 0.16 | 0.026 | 160 |
| 6His E113pAF | 1.0 | 0.02 | 19 |
| 6His E113pAF-30K PEG | 0.15 | 0.024 | 150 |
| 6His K134pAF | 3.4 | 0.036 | 10 |
| 6His K134pAF-30K PEG | 0.095 | 0.025 | 270 |
| 6His N45pAF | 2.4 | 0.0155 | 6.5 |
| 6His N45pAF-30K PEG | 0.134 | 0.034 | 250 |
| 6His I100pAF | 1.9 | 0.0177 | 9.5 |
| 6His I100pAF-30K PEG | 0.132 | 0.03 | 225 |
| 6His E78pAF | 2.4 | 0.015 | 7 |
| 6His E78pAF-30K PEG | 0.147 | 0.025 | 170 |
| 6His Y89pAF | 2 | 0.018 | 9 |
| 6His Y89pAF-30K PEG | 0.164 | 0.027 | 167 |
| 6His I24pAF | 2.2 | 0.011 | 5 |
| 6His I24pAF-30K PEG | 0.094 | 0.016 | 170 |
| 6His M16pAF | 1.4 | 0.024 | 18 |
| 6His M16pAF-30K PEG | 0.075 | 0.034 | 460 |
| 6His R13pAF | 1.3 | 0.018 | 14 |
| 6His R13pAF-30K PEG | 0.049 | 0.027 | 550 |
| 6His L9pAF | 1.25 | 0.017 | 14 |
| 6His L9pAF-30K PEG | 0.1 | 0.03 | 300 |
| 6His R120pAF | 4.4 | 0.018 | 4 |
| 6His R120pAF-30K PEG | 0.093 | 0.026 | 280 |

TABLE 3-continued

Binding parameters for IFNα-2a:IFNAR2 interaction, as determined by SPR

| IFNα2A | $k_{on}, \times 10^{-6}$ 1/M * s | $k_{off}$, 1/s | $K_d$, nM |
|---|---|---|---|
| 6His R149pAF | 2.1 | 0.16 | 75 |
| 6His R149pAF-30K PEG | 0.018 | 0.11 | >5000 |
| 6His E159pAF | 6.7 | 0.023 | 3.5 |
| 6His E159pAF-30K PEG | 0.1 | 0.0165 | 160 |
| 6His K49pAF | 3.6 | 0.035 | 10 |
| 6His K49pAF-30K PEG | 0.23 | 0.038 | 170 |
| 6His Q46pAF | 3.4 | 0.08 | 24 |
| 6His Q46pAF-30K PEG | ND | | |
| 6His Q48pAF | 4.6 | 0.078 | 17 |
| 6His Q48pAF-30K PEG | 0.37 | 0.037 | 100 |
| 6His Q61pAF | 0.8 | 0.018 | 21 |
| 6His Q61pAF-30K PEG | 0.24 | 0.034 | 142 |
| 6His E96pAF | 4.8 | 0.057 | 12 |
| 6His E96pAF-30K PEG | 0.09 | 0.026 | 280 |
| 6His G102pAF | 3.2 | 0.085 | 27 |
| 6His G102pAF-30K PEG | 0.12 | 0.026 | 210 |
| 6His V103pAF | 4.4 | 0.062 | 14 |
| 6His V103pAF-30K PEG | 0.15 | 0.027 | 180 |
| 6His P109pAF | 5.1 | 0.086 | 17 |
| 6His P109pAF-30K PEG | 0.16 | 0.03 | 190 |
| 6His K164pAF | 1.3 | 0.025 | 19 |
| 6His K164pAF-30K PEG | 0.075 | 0.035 | 460 |

Measurement of Phosphorylated STAT1

To assess the biological activity of modified hIFNα2a polypeptides, an assay measuring phosphorylation of STAT1, a signal transducer and activator of transcription family member, was performed using the human monocytic leukemia THP-1 cells. Activation of STAT1 has been shown to be essential for the antiviral activity of IFNs (Durbin J E et al. Cell 1996 84:443-450). The human monocyte line THP-1 was purchased from ATCC (Manassas, Va.) and was routinely passaged in RPMI 1640, sodium pyruvate, penicillin, streptomycin, 10% heat-inactivated fetal bovine serum and 50 uM 2-mercaptoethanol. The cells were maintained at 37° C. in a humidified atmosphere of 5% $CO_2$.

Figure 2:
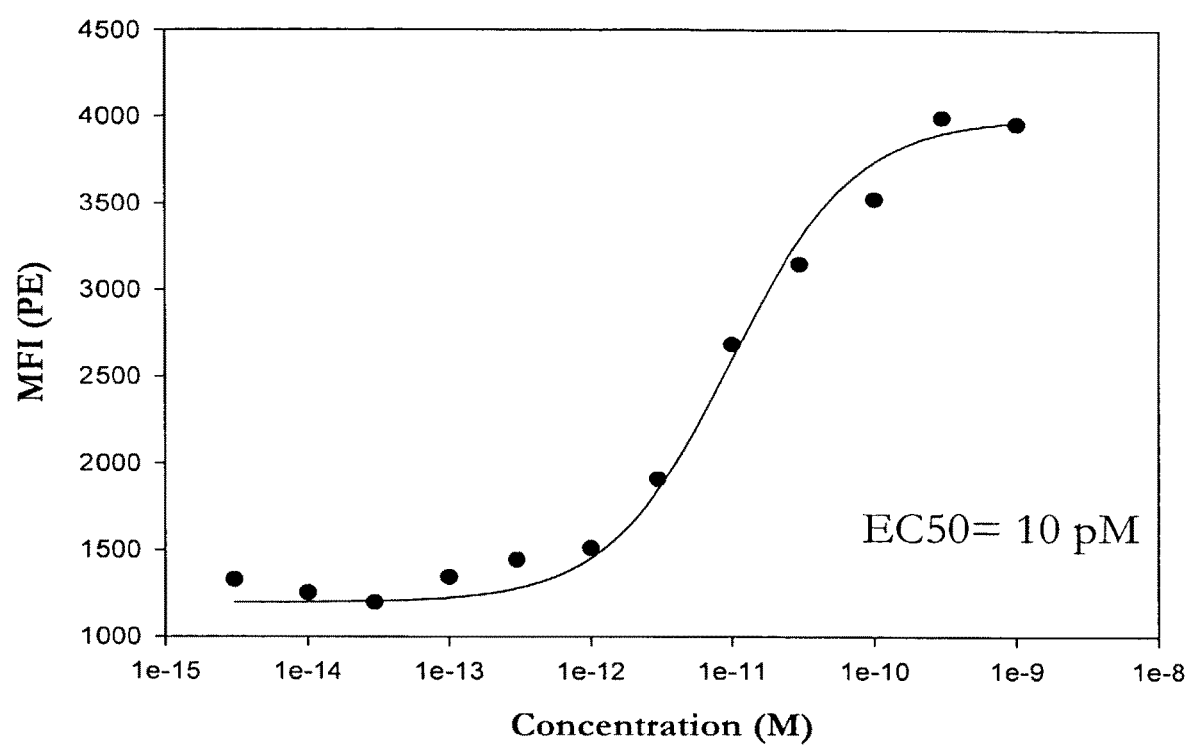
FIG. 2—A diagram of results obtained from the pSTAT1 assay is shown.

The THP-1 cells were starved overnight in assay media containing 1% heat inactivated charcoal/dextran treated fetal bovine serum before stimulation with increasing concentrations of hIFN polypeptides for 30 minutes at 37° C. All stimulated cells were fixed for permeabilization and stained with the appropriate phospho-antibody as suggested by manufacturer (Cell Signaling Technology, Beverly, Mass.). Sample acquisition was performed on the FACS Array with acquired data analyzed on the Flowjo software (Tree Star, Inc., Ashland, Oreg.). $EC_{50}$ values were derived from dose response curves plotted with mean fluorescent intensity against protein concentration utilizing SigmaPlot. (FIG. 2)

Figure 3:
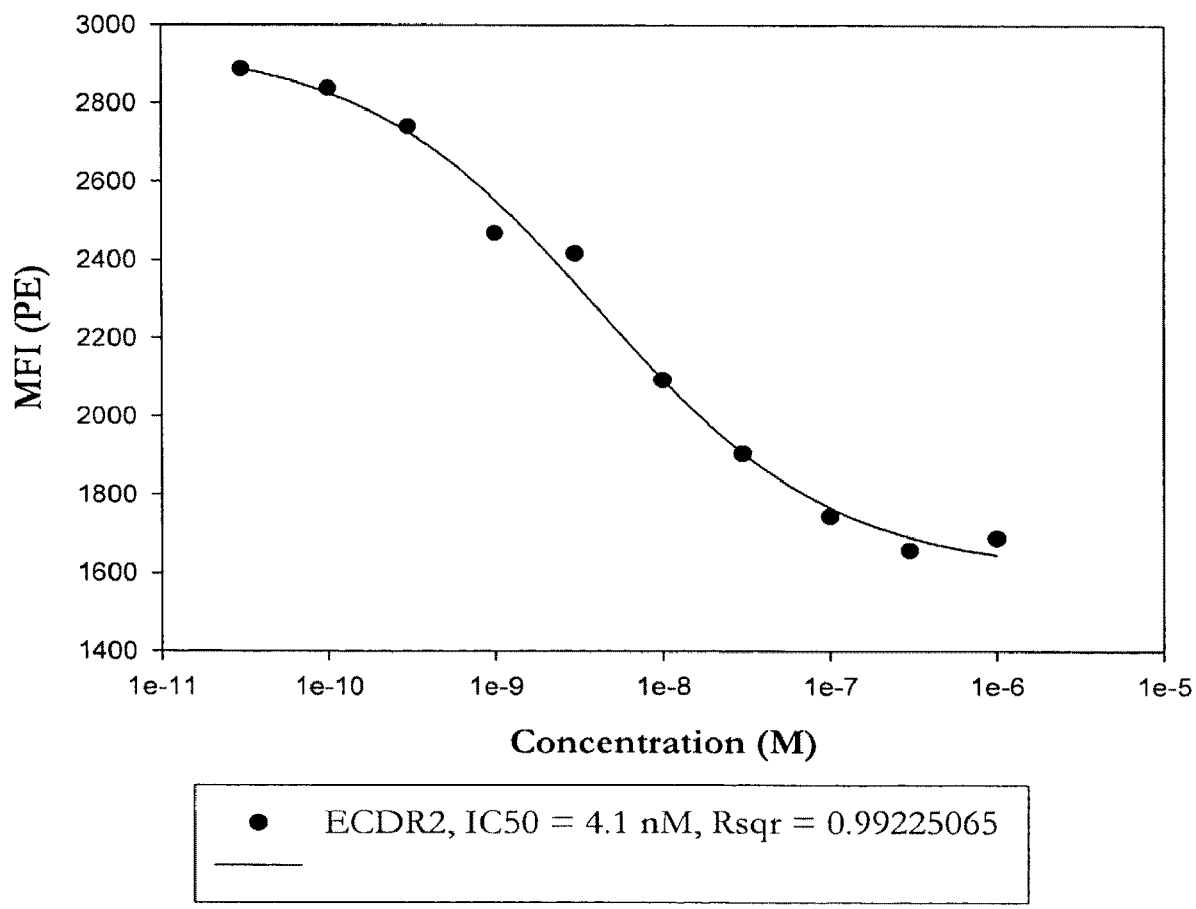
FIG. 3—A diagram showing the specificity of the pSTAT1 assay is shown.

Additional controls were performed to confirm that the IFN induced phosphorylation of STAT1 was selective for the IFNα receptor 2 (IFNAR2). Serum starved THP-1 were pre-incubated with increasing concentrations of IFNAR2 extracellular domain (ECDR2) for 15 minutes at 37° C. before the addition of IFN at an $EC_{80}$ dose. The extracellular domain of the IFNα receptor 2 was found to compete effectively against IFNαA stimulated STAT1 phosphorylation indicating that IFNαA induced phosphorylation of STAT1 is selective for the IFNAR2. FIG. 3 shows that ECDR2 competes with IFNαA induced pSTAT activity.

Figure 4:
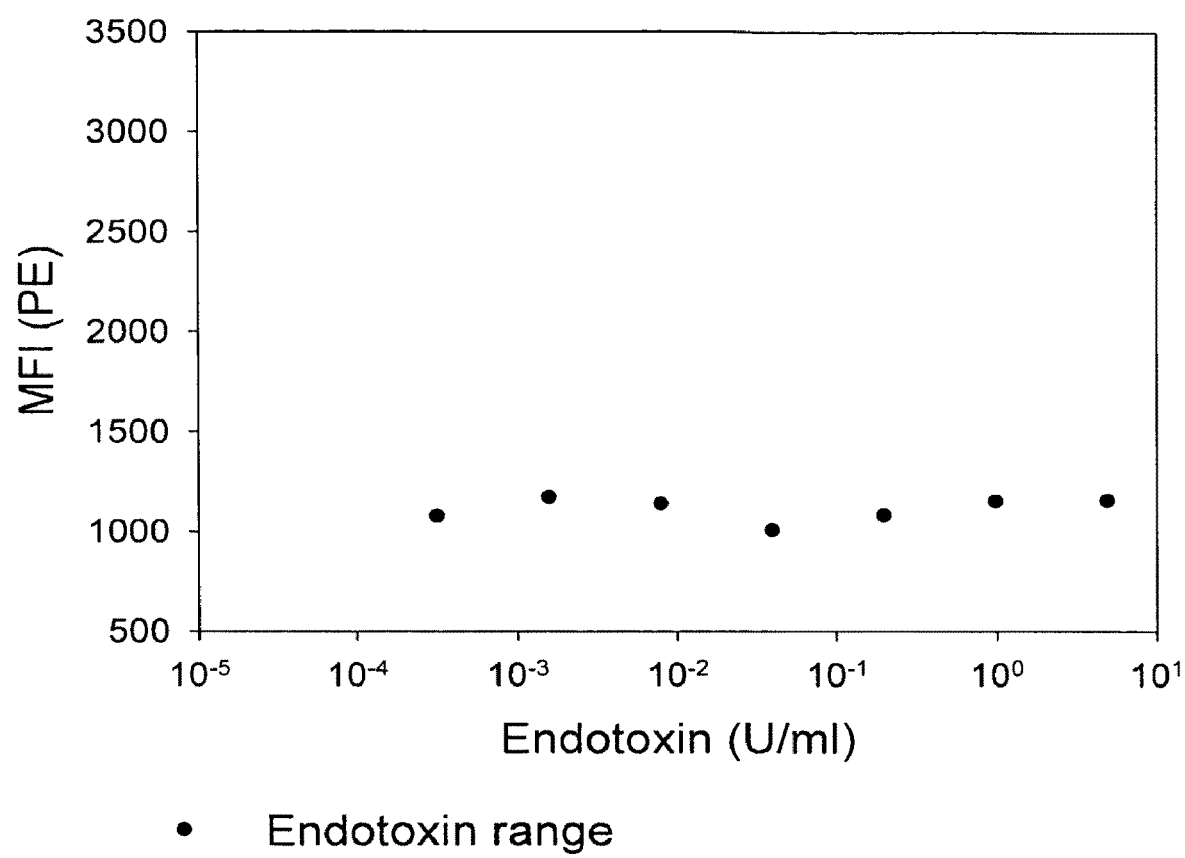
FIG. 4—A diagram of the effect of endotoxin on the pSTAT1 assay is shown.

A potential contaminant after purification of hIFN polypeptides is endotoxin. To determine if endotoxin affects the phosphorylation of STAT1, a range of endotoxin levels were tested in this cellular assay. FIG. 4 shows that endotoxin did not have a substantial effect on the assay at the levels tested. The endotoxin concentration range tested (as shown) provided comparable MFI (PE) to a control sample containing no endotoxin.

Alternatively, phosphorylation of STAT1 may be measured with RayBio® Cell-Based Stat1 (Tyr701) ELISA kit (Raybiotech, Norcross, Ga.). With this kit, the assay is performed in 96 well plates and has a colorimetric readout measurable by a spectrophotometric plate reader.

Measurement of Anti-Proliferative Activity hIFN polypeptides were also assayed for anti-proliferative activity. A prominent effect of IFNα's is their ability to inhibit cell growth, which is of major importance in determining anti-tumor action. The human lymphoblastoid Daudi cell line has proven to be extremely sensitive to IFNα's, and it has been used to measure antiproliferative activity in many IFNα's and derived hybrid polypeptides (Meister et al., J Gen Virol. (1986) August; 67 (Pt 8):1633-43). Use of this cell line has been facilitated by its ability to be grown in suspension cultures (Evinger and Pestka, (1981) Methods Enzymol. 79:362-368).

The human Daudi B cell line was purchased from ATCC (Manassas, Va.) and grown in RPMI 1640 supplemented with sodium pyruvate, penicillin, streptomycin (Invitrogen, Carlsbad, San Diego) and 10% heat inactivated fetal bovine serum (Hyclone, Logan, Utah). The cell culture was maintained at 37° C. in a humidified atmosphere of 5% $CO_2$.

Figure 5:
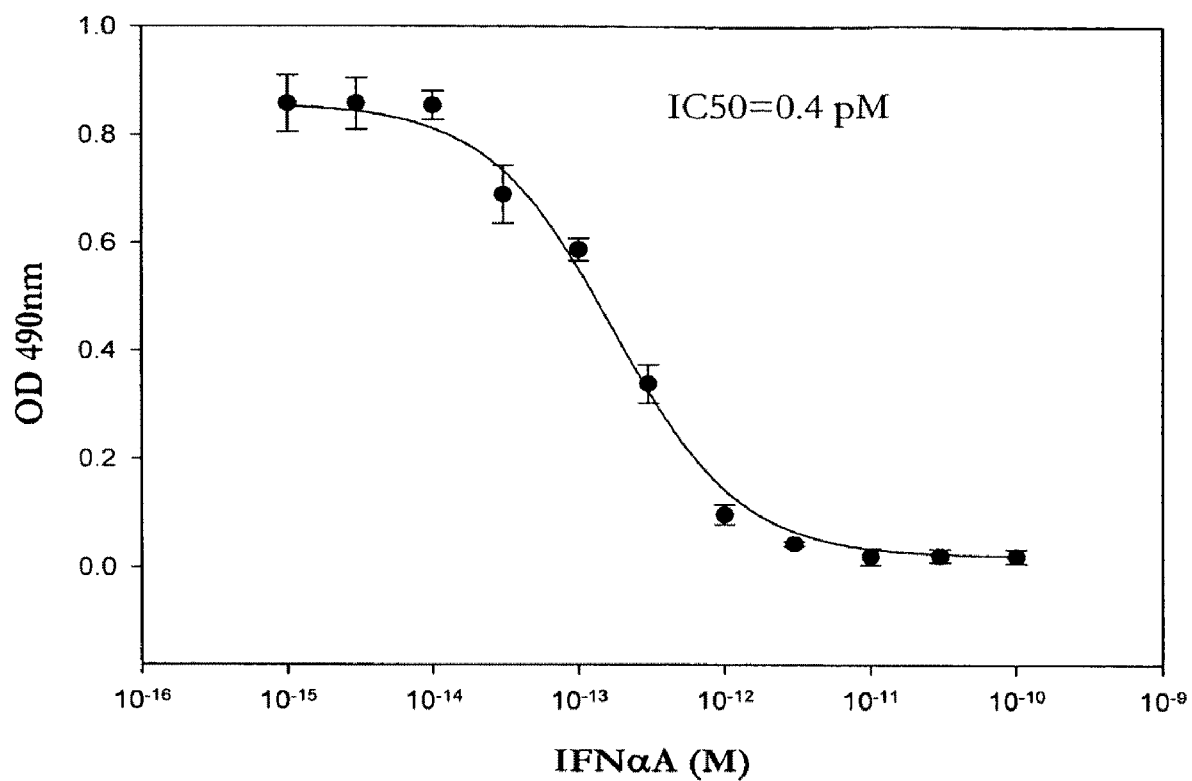
FIG. 5—A diagram of results obtained from an anti-proliferation assay is shown.

The Daudi cells were plated at a density of $1 \times 10^4$ cells/well in a flat-bottom, 96-well plate. The cells were activated with increasing concentration of IFNα2A in triplicates per dose concentration. Following a 4-day incubation period at 37° C. with 5% $CO_2$, 40 ul of CellTiter 96 Aqueous One solution Reagent (Promega Corporation, Madison, Wis.) was added to each well, and the culture was allowed to incubate for an additional 3 hours. Absorbance was read at 490 nm using a Spectromax. $EC_{50}$s were obtained from dose response curves plotted with $OD_{490}$ nm (average of triplicates) against protein concentration with SigmaPlot. See FIG. 5.

Figure 6:
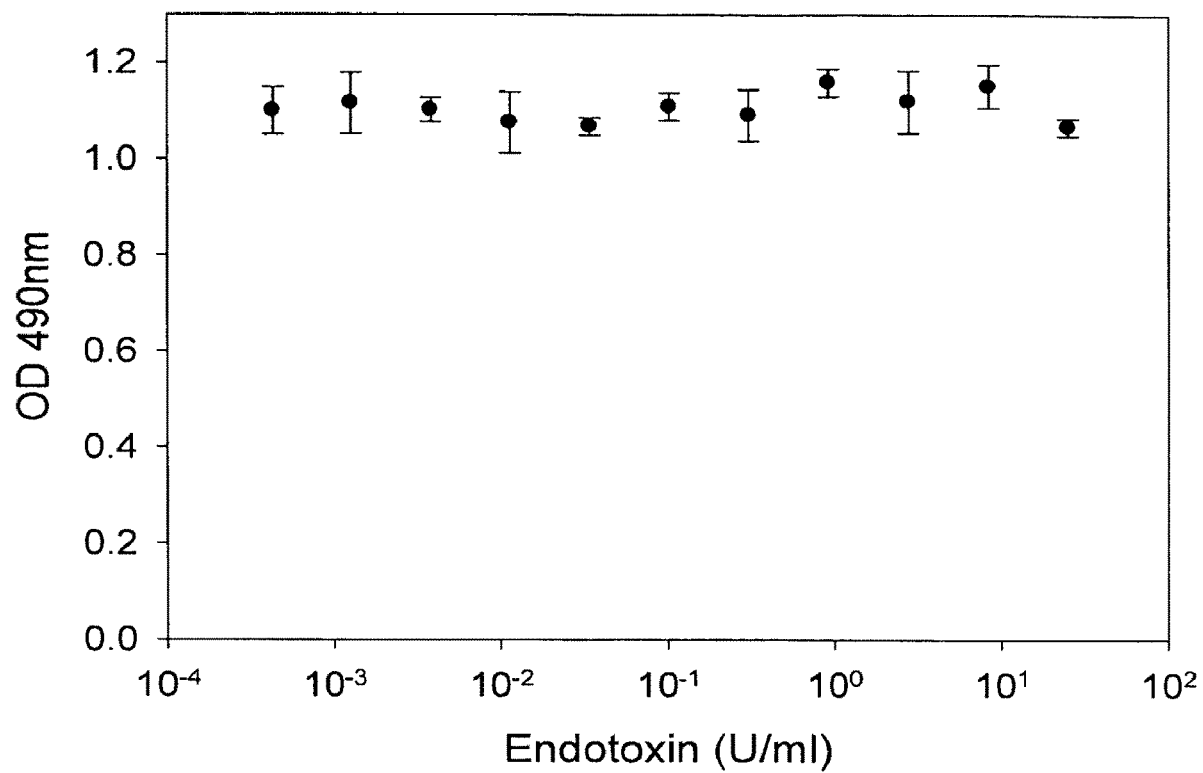
FIG. 6—A diagram of the effect of endotoxin on the anti-proliferation assay is shown.

Since a potential contaminant after purification of hIFN polypeptides is endotoxin, a range of endotoxin levels were tested in the anti-proliferation assay. FIG. 6 shows that endotoxin did not have a substantial affect on the assay at the levels tested.

Measurement of Phosphorylated Tyk2

Figure 8:
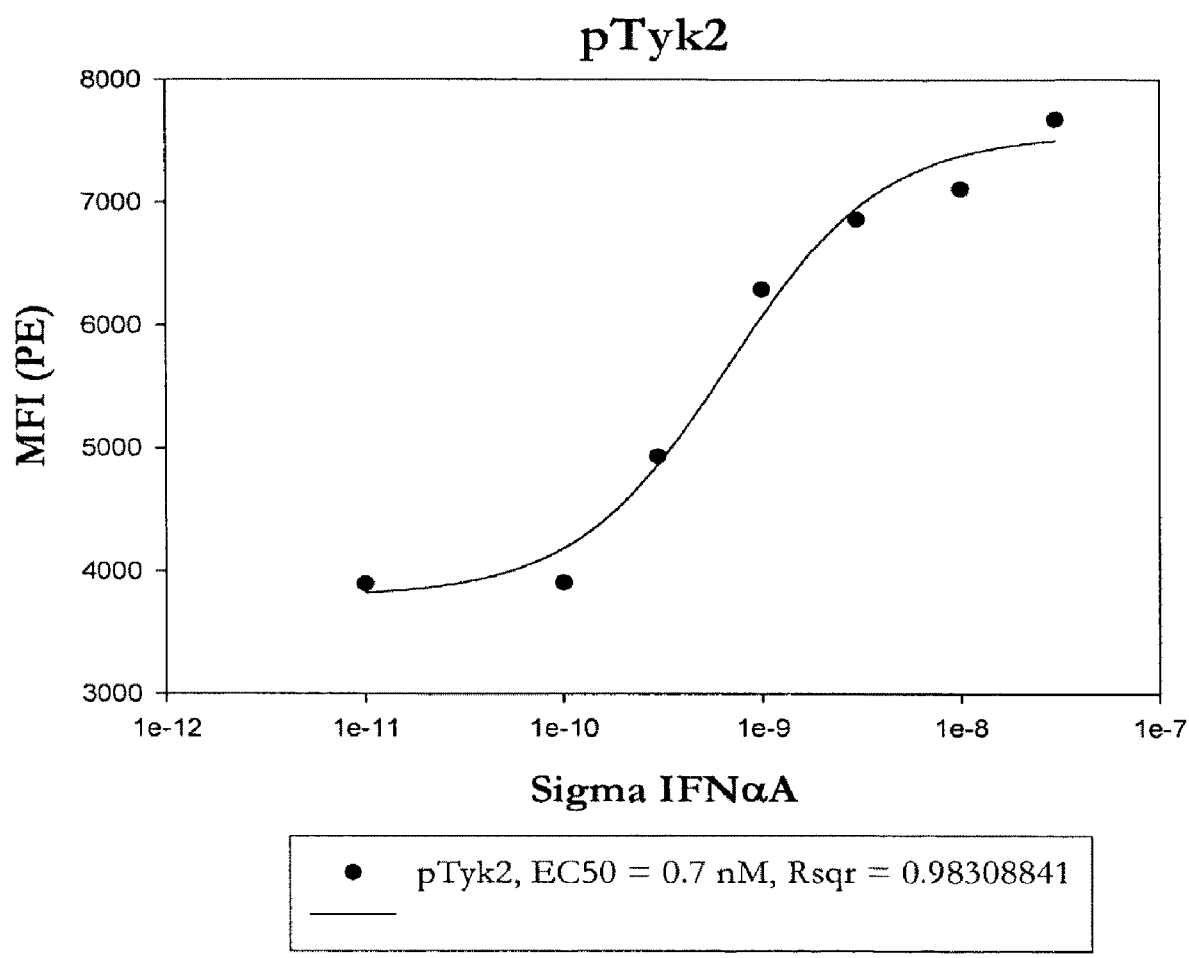
FIG. 8—A diagram of Tyk2 phosphorylation in U266 cells is shown.

Kawamoto et al. in Experimental Hematology 2004 32:797-805 and Ishida et al. Experimental Hematology 2005 33:495-503, which are incorporated by reference herein, discuss signaling differences between limitin and IFN-α involving Tyk2, CrkL, CrkII, and Daxx and side effects of IFN. Assays measuring phosphorylation of CrkL, CrkII and Tyk2 may be used to evaluate hIFN polypeptides of the invention. Evaluating the phosphorylation of CrkII in U-266 may be performed as described by Platanias et al. in Experimental Hematology 1999; 27:1315-1321, which is incorporated by reference herein. For measuring the phosphorylation of Tyk2, the human U266B1 cells (ATCC, Manassas, Va.) were maintained in RPMI 1640 supplemented with sodium pyruvate, penicillin, streptomycin (Invitrogen, Carlsbad, San Diego) and 15% heat inactivated fetal bovine serum. The cell culture was maintained at 37° C. in a humidified atmosphere of 5% $CO_2$. Serum starved U266 cells were activated at 37° C. with IFNα2A for 5 minutes when measuring Tyk2. All stimulated cells were fixed, permeabilized and stained with the appropriate phospho-antibody as suggested by the manufacturer (Cell Signaling Technology, Beverly, Mass.). Sample acquisition was performed on the FACS Array with acquired data analyzed on the Flowjo software (Tree Star Inc., Ashland, Oreg.). $EC_{50}$ values were derived from dose response curves plotted with mean fluorescent intensity against protein concentration utilizing SigmaPlot. Competition assays with the extracellular domain of IFNAR2 are useful for determining specificity. See FIG. 8 for Tyk2.

Table 4 and 5 summarize data obtained with hIFN polypeptides that are IFNα2a variants. pSTAT1 data, anti-proliferation data, $K_d$ values obtained from affinity studies with the extracellular domain of IFNAR2 are shown. hIFN polypeptides comprising the non-naturally encoded amino acid p-acetyl-phenylalanine (pAF) were tested, as well as PEGylated hIFN polypeptides comprising pAF. Controls utilized in these studies included WHO IFNα2A, IFNαA obtained from Sigma, and PEGASYS®.

TABLE 4

| IFNα2A Variants | pSTAT1 EC50 (pM) | Proliferation IC50 (pM) | Kd (nM) |
|---|---|---|---|
| WHO IFNα2A | 16.0 ± 5.3 (n = 3) | 0.26 ± 0.05 (n = 4) | ND |
| Sigma IFNαA | 14.1 ± 1.7 (n = 3) | 0.33 ± 0.17 (n = 5) | 11 |
| Infergen | ND | 0.23 + 0.04 (n = 2) | |
| PEGASYS ® | 478.7 ± 183.2 (n = 12) | 11.3 ± 2.2 (n = 8) | 300 |
| 6His-IFNα2A | 17.6 (n = 1) | 0.3 ± 0.4 (n = 3) | 6 |
| 6His IFNα-2a + limitin loop (pool) | 62.7 | 0.54 | |
| 6HisC1G/C98 IFNα-2a + limitin loop (pool) | 30.0 | 0.90 | |
| 6His IFNα-2a + limitin loop (select) | | | 10 |
| 6HisC1G/C98 IFNα-2a + limitin loop (select) | 34.8 | | 11 |
| 6His-F36S | ND | 64.3 (n = 1) | 1300 |
| 6His-F38L | 13 (n = 1) | 0.2 (n = 1) | 18 |
| 6His-F38S | 18 (n = 1) | 0.2 (n = 1) | 42 |
| 6His-L9pAF | ND | 0.5 (n = 1) | 14 |
| 6His-L9pAF-30K | 430 (n = 1) | 12.00 (n = 1) | 300 |
| 6His-R12pAF | ND | 0.6 (n = 1) | 8 |
| 6His-R12pAF-30K | 660 (n = 1) | 16.7 ± 3.0 (n = 2) | 340 |
| 6His-R13pAF | ND | 0.5 (n = 1) | 14 |
| 6His-R13pAF-30K | 807 (n = 1) | >32.55 + 1.2 (n = 2) | 550 |
| 6His-M16pAF | ND | 0.35 (n = 1) | 18 |
| 6His-M16pAF-30K | 202 (n = 1) | 8.3 (n = 1) | 460 |
| 6His-I24pAF | ND | 0.19 (n = 1) | 5 |
| 6His-I24pAF-30K | 35 (n = 1) | 2.2 (n = 1) | 170 |
| 6His-F27pAF | ND | 0 3 (n = 1) | 8 |
| 6His-F27pAF-30K | 316 (n = 1) | 5.6 (n = 1) | 210 |
| 6His-K31pAF | 49 (n = 1) | 0.6 ± 0.1 (n = 2) | 52 |
| 6His-K31pAF-30K | 299 ± 34 (n = 2) | 4.8 ± 2.3 (n = 2) | 830 |
| 6His-H34pAF | 120 ± 122 (n = 2) | 0.2 (n = 1) | 4 |
| 6His-H34pAF-30K | 161 ± 175 (n = 3) | 0.9 ± 0.1 (n = 2) | 140 |
| 6His-G37pAF | 21.8 (n = 1) | 0.3 (n = 1) | 12 |
| 6His-G37pAF-30K | 193 (n = 1) | 2.2 (n = 1) | 410 |
| 6His-P39pAF | ND | 0.3 (n = 1) | 17 |
| 6His-P39pAF-30K | 253.3 ± 241.2 (n = 3) | 12.8 ± 1.4 (n = 2) | 440 |
| 6His-E41pAF | 19.0 (n = 1) | 0.2 (n = 1) | 16 |
| 6His-E41pAF-30K | 120.5 + 31.8 (n = 2) | 2.6 (n = 1) | 560 |
| 6His-N45pAF | ND | 0.5 (n = 1) | 7 |
| 6His-N45pAF-30K | 87 (n = 1) | 7.1 ± 0.7 (n = 2) | 250 |
| 6His-Q48pAF | | 0.24 | 17 |
| 6His-Q48PAF-30K | 119 | 3.00 | 100 |
| 6His-K49pAF | | 0.13 | 10 |
| 6His-K49pAF-30K | 134 | 3.20 | 170 |
| 6His-Q61pAF | | 1.50 | 21 |
| 6His-Q61pAF-30K | >88900 | no inhibition | 140 |
| 6His-N65pAF | 11 7 (n = 1) | 0.7 (n = 1) | 7 |
| 6His-N65pAF-30K | >2865 ± 2908 (n = 2) | 146 (n = 1) | 150 |
| 6His-E78pAF | ND | 0.13 (n = 1) | 7 |
| 6His-E78pAF-30K | 45.0 (n = 1) | 1.9 ± 0.1 (n = 2) | 170 |
| 6His-Y89pAF | ND | 0.13 (n = 1) | 9 |
| 6His-Y89pAF-30K | 244 (n = 1) | 4.4 ± 0.8 (n = 2) | 167 |
| 6His-E96pAF | | 0.55 | 12 |
| 6His-E96pAF-30K | 2190 | 21.1 | 280 |
| 6His-I100pAF | ND | 0.4 (n = 1) | 10 |
| 6His-I100pAF-30K | 130 (n = 1) | 2.4 ± 0.1 (n = 2) | 225 |
| 6His-G102pAF | | 1.4 | 27 |
| 6His-G102pAF-30K | 981 | 5.4 | 210 |
| 6His-V103pAF | | 0.6 | 14 |
| 6His-V103pAF-30K | 190 | 3.6 | 180 |
| 6His-T106pAF | ND | 0.08 (n = 1) | 8 |
| 6His-T106pAF-30K | 136 (n = 1) | 1.7 (n = 1) | 140 |
| 6His-E107pAF | 30.8 (n = 1) | 0.2 (n = 1) | 5 |
| 6His-E107pAF-30K | 106.7 ± 41.5 (n = 2) | 3.1 ± 0.4 (n = 2) | 240 |
| 6His-E107pAF-B2 | | 0.2 (n = 1) | |
| 6His-E107pAF-30K-B2 | 34.8 (n = 1) | 3.0 (n = 1) | 250 |

TABLE 4-continued

| IFNα2A Variants | pSTAT1 EC50 (pM) | Proliferation IC50 (pM) | Kd (nM) |
|---|---|---|---|
| 6His-P109pAF | | 0.47 | 17 |
| 6His-P109pAF-30K | 454 | 4.5 | 190 |
| 6His-L110pAF | ND | 0 5 (n = 1) | 13 |
| 6His-L110pAF-30K | 133 ± 116 (n = 2) | 2.7 ± 0.8 (n = 2) | 167.5 + 10.6 (n = 2) |
| 6His-E113pAF | ND | 0.7 (n = 1) | 19 |
| 6His-E113pAF-30K | 262 ± 132 (n = 2) | 3.7 (n = 1) | 150 |
| 6His-L117pAF | ND | 0.2 (n = 1) | 8 |
| 6His-L117pAF-30K | 242 (n = 1) | 4.0 (n = 1) | 140 |
| 6His-R120pAF | ND | 4.0 (n = 1) | 4 |
| 6His-R120pAF-30K | >1,000 | no inhibition | 280 |
| 6HisY122S | ND | 11.2 (n = 1) | 300 |
| 6His-R125pAF | 16.0 (n = 1) | 0.5 (n = 1) | 19 |
| 6His-R125pAF-30K | 225 (n = 1) | 1.7 (n = 1) | 330 |
| 6His-K134pAF | ND | 0.25 (n = 1) | 10 |
| 6His-K134pAF-30K | 108 ± 47 (n = 2) | 2.6 (n = 1) | 270 |
| 6His-R149pAF | ND | 0.85 (n = 1) | 75 |
| 6His-R149pAF-30K | >29.4 | >70 (n = 1) | >5000 |
| 6His-E159pAF | ND | 0.2 (n = 1) | 3.5 |
| 6His-E159pAF-30K | 384 (n = 1) | 16.9 (n = 1) | 160 |

ND = not done

Table 5 shows assay results with PEGASUS® fixed as 100%.

| IFNα2A Variants | pSTAT1 % | Proliferation % |
|---|---|---|
| WHO IFNα2A | 3.34 | 2.33 |
| Sigma IFNαA | 2.95 | 2.93 |
| Infergen | ND | 1.78 |
| PEGASYS ® | 100.00 | 100.00 |
| 6His-IFNα2A | 3.68 | 2.50 |
| 6His IFNα-2a + limitin loop (pool) | 13.1 | 4.79 |
| 6HisC1G/C98 IFNα-2a + limitin loop (pool) | 6.27 | 7.99 |
| 6His IFNα-2a + limitin loop (select) | | |
| 6HisC1G/C98 IFNα-2a + limitin loop (select) | 7.27 | |
| 6His-F36S | ND | 570.92 |
| 6His-F38L | 2.72 | 1.78 |
| 6His-F38S | 3.76 | 1.78 |
| 6His-L9pAF | | 4.44 |
| 6His-L9pAF-30K | 89.83 | 106.50 |
| 6His-R12pAF | | 5.33 |
| 6His-R12pAF-30K | 137.88 | 147.84 |
| 6His-R13pAF | | 4.53 |
| 6His-R13pAF-30K | 168.59 | >289.01 |
| 6His-M16pAF | | 3.11 |
| 6His-M16pAF-30K | 42.2 | 73.70 |
| 6His-I24pAF | | 1.69 |
| 6His-I24pAF-30K | 7.31 | 19.53 |
| 6His-F27pAF | | 2.66 |
| 6His-F27pAF-30K | 66.02 | 49.72 |
| 6His-K31pAF | 10.24 | 5.33 |
| 6His-K31pAF-30K | 62.47 | 42.62 |
| 6His-H34pAF | 25.04 | 1.78 |
| 6His-H34pAF-30K | 33.64 | 7.99 |
| 6His-G37pAF | 4.55 | 2.66 |
| 6His-G37pAF-30K | 40.32 | 19.53 |
| 6His-P39pAF | | 2.66 |
| 6His-P39pAF-30K | 52.91 | 113.65 |
| 6His-E41pAF | 3.97 | 1.78 |
| 6His-E41pAF-30K | 25.17 | 23.09 |
| 6His-N45pAF | | 4.44 |
| 6His-N45pAF-30K | 18.24 | 63.04 |
| 6His-Q48pAF | | 2.1 |
| 6His-Q48pAF-30K | 24.86 | 26.6 |
| 6His-K49pAF | | 1.2 |
| 6His-K49pAF-30K | 27.99 | 28.4 |
| 6His-Q61pAF | | 13.3 |
| 6His-Q61pAF-30K | >18572 | no inhibition |
| 6His-N65pAF | 2.44 | 6.22 |
| 6His-N65pAF-30K | >532.04 | 1296.34 |
| 6His-E78pAF | | 1.15 |
| 6His-E78pAF-30K | 9.40 | 16.87 |
| 6His-Y89pAF | | 1.15 |
| 6His-Y89pAF-30K | 50.97 | 38.62 |
| 6His-E96pAF | | 4.87 |
| 6His-E96pAF-30K | 457.52 | 186.73 |
| 6His-I100pAF | | 3.55 |
| 6His-I100pAF-30K | 27.16 | 21.31 |
| 6His-G102pAF | | 12.40 |
| 6His-G102pAF-30K | 204.94 | 47.90 |
| 6His-V103pAF | | 5.30 |
| 6His-V103pAF-30K | 39.69 | 32.00 |
| 6His-T106pAF | | 0.71 |
| 6His-T106pAF-30K | 28.41 | 15.09 |
| 6His-E107pAF | 6.43 | 1.78 |
| 6His-E107pAF-30K | 22.28 | 27.52 |
| 6His-E107pAF-B2 | | 1.78 |
| 6His-E107pAF-30K-B2 | 7.27 | 26.64 |
| 6His-P109pAF | | 4.16 |
| 6His-P109pAF-30K | 94.85 | 39.82 |
| 6His-L110pAF | | 4.44 |
| 6His-L110pAF-30K | 27.82 | 23.97 |
| 6His-E113pAF | | 6.22 |
| 6His-E113pAF-30K | 54.74 | 32.85 |
| 6His-L117pAF | | 1.78 |
| 6His-L117pAF-30K | 50.56 | 35.52 |
| 6His-R120pAF | | 35.5 |
| 6His-R120pAF-30K | >208.91 | no inhibition |
| 6HisY122S | | 99.45 |
| 6His-R125pAF | 3.34 | 4.44 |
| 6His-R125pAF-30K | 47.01 | 15.09 |
| 6His-K134pAF | | 2.22 |
| 6His-K134pAF-30K | 22.52 | 23.09 |
| 6His-R149pAF | | 7.55 |
| 6His-R149pAF-30K | >6.14 | >621.5 |
| 6His-E159pAF | | 1.78 |
| 6His-E159pAF-30K | 80.22 | 150.1 |

Colony Formation Assays

Colony formation assays such as those described by Giron-Michel, J. in Leukemia 2002 16:1135-1142 may be used to evaluate proliferation of progenitor cells by hIFN polypeptides of the invention. Cord blood may be used in colony formation assays.

Evaluation of the Toxicity of hIFN Polypeptides on Human Myeloid and Erythroid Progenitors Using a methylcelluose-based in vitro colony forming assay, the hematopoietic toxicity of ten compounds (nine hIFN polypeptides and PEGASYS®) was tested.

Cells: Normal human bone marrow light density cells (Poietics Inc., Maryland) were stored at −152° C. until required for the assay. On the day of the experiment, the cells were thawed rapidly at 37° C., the contents of the vial were diluted in 10 mls of Iscove's medium containing 2% fetal bovine serum and washed by centrifugation. The supernatant was discarded, and the cell pellet resuspended in a known volume of Iscove's medium containing 2% FBS. A cell count (3% glacial acetic acid) and viability assessment by Trypan Blue exclusion was performed.

Test samples: Compounds were 40×stocks in a buffer of 20 mM NaAc, 50 mM NaCl, 5% glycerol, pH 6.0. Dilutions of each compound were prepared with the same buffer to generate stock concentrations of 144, 72, 36, 18, and 9 ug/ml. When added to methylcellulose, the buffer was at a final concentration of 2.5% and compound concentrations ranged from 3.6-0.225 ug/ml. A control containing 50 EU/ml endotoxin in a buffer of 20 mM NaAc, 50 mM NaCl, 5% glycerol, pH 6.0 was diluted with the same buffer 1:40 into methylcellulose to examine the effects of similar levels of endotoxin.

Method: Clonogenic progenitors of the erythroid (CFU-E and BFU-E), granulocyte-monocyte (CFU-GM) and multi-potential (CFU-GEMM) lineages were assessed in methyl-cellulose-based medium (MethoCult™ 4434) containing saturating concentrations of the cytokines SCF (Stem Cell Factor; 50 ng/mL), GM-CSF (Granulocyte Macrophage Colony Stimulating Factor; 10 ng/mL), IL-3 (Interleukin 3; 10 ng/mL), and EPO (Erythropoietin; 3 U/mL). CFU-E is a small erythroid colony derived from the most mature erythroid colony forming cells. It contains one to two clusters with a total number of 8-200 erythroblasts. BFU-E is a larger erythroid colony derived from a more primitive cell. It contains greater than 200 erythroblasts. CFU-GM is a colony that is derived from a colony forming cell capable of producing colonies with forty or more granulocyte-monocyte and/or macrophage cells. CFU-GEMM is a colony that contains cells from more than one lineage. It is derived from the most primitive colony forming cell and contains erythroid cells as well as twenty or more granulocytes, macrophages, and megakaryocytes. As controls, cultures were also set-up containing vehicle (20 mM NaAc, 50 mM NaCl, 5% glycerol, pH 6.0), vehicle containing endotoxin, and various concentrations of 5-Fluorouracil (a known myelosuppressive compound). Standard cultures containing no buffer or compound were also established.

Clonogenic progenitors of the erythroid (CFU-E and BFU-E), granulocyte-monocyte/myeloid (CFU-GM) and multipotential (CFU-GEMM) lineages were set up in the methylcellulose-based media described. The compounds were added to the MethoCult™ to give final concentrations of 3.6, 1.8, 0.9, 0.45, and 0.225 ug/ml. Vehicle control cultures containing no compound but equivalent concentrations of vehicle buffer, endotoxin control cultures containing no compound but equivalent concentrations of endotoxin, as well as standard controls containing no compounds or vehicle buffer were also initiated. In addition, cultures were initiated with 5-Fluorouracil (5-FU) at 5, 1, 0.5, and 0.1 ug/ml to serve as positive controls for toxicity. All cultures were set up in triplicate at $1 \times 10^4$ cells per culture. Following 14 days in culture, the colonies were assessed and scored. The colonies were divided into the following categories, based on size and morphology: CFU-E, BFU-E, CFU-GM, and CFU-GEMM.

Results and analysis: Triplicate cultures for CFU-E, BFU-E, CFU-GM, and CFU-GEMM were enumerated. In addition, the distribution of colony types as well as general colony and cellular morphology were analyzed. The variance in colony number detected in replicate cultures is representative of the coefficient of variation for colony enumeration. The results are shown in Table 6. For statistical analysis, all compounds were compared to the vehicle control. Standard t-tests were performed to assess if there was a difference in the number of colonies generated between control and treated cultures. Due to the potential subjectivity of colony enumeration, a p value of less than 0.01 is deemed significant.

TABLE 6

|  | CFU-E | BFU-E | Total Erythroid | CFU-GM | CFU-GEMM | Total CFC |
|---|---|---|---|---|---|---|
| Standard | 10 +/− 1 | 43 +/− 7 | 53 +/− 8 | 61 +/− 5 | 1 +/− 1 | 115 +/− 7 |
| Vehicle control | 10 +/− 3 | 40 +/− 8 | 50 +/− 6 | 61 +/− 9 | 1 +/− 1 | 112 +/− 15 |
| Endotoxin control | 10 +/− 4 | 41 +/− 8 | 51 +/− 11 | 57 +/− 9 | 1 +/− 1 | 109 +/− 20 |
| 5-FU |  |  |  |  |  |  |
| 5 ug/ml | ND* | ND# | ND** | ND** | ND | ND** |
| 1 ug/ml | 13 +/− 2 | 4 +/− 2* | 17 +/− 2# | 2 +/− 1** | ND | 19 +/− 3** |
| 0.5 ug/ml | 12 +/− 3 | 24 +/− 7 | 36 +/− 9 | 20 +/− 5* | ND | 56 +/− 8* |
| 0.1 ug/ml | 12 +/− 3 | 36 +/− 6 | 48 +/− 9 | 46 +/− 5 | 1 +/− 1 | 95 +/− 13 |
| PEGASYS ® |  |  |  |  |  |  |
| 3.6 ug/ml | 10 +/− 2 | 5 +/− 3* | 15 +/− 5* | 16 +/− 3* | ND | 31 +/− 8# |
| 1.8 ug/ml | 10 +/− 2 | 9 +/− 3* | 19 +/− 4* | 19 +/− 6* | ND | 38 +/− 10* |
| 0.9 ug/ml | 11 +/− 4 | 10 +/− 2* | 21 +/− 4* | 21 +/− 5* | ND | 42 +/− 1* |
| 0.45 ug/ml | 10 +/− 4 | 12 +/− 3* | 22 +/− 2* | 27 +/− 3* | ND | 49 +/− 2* |
| 0.225 ug/ml | 13 +/− 3 | 19 +/− 3$ | 32 +/− 1$ | 31 +/− 7 | ND | 63 +/− 7$ |
| 6His M16pAF-30K |  |  |  |  |  |  |
| 3.6 ug/ml | 12 +/− 2 | 8 +/− 1* | 20 +/− 1# | 14 +/− 4* | ND | 34 +/− 5# |
| 1.8 ug/ml | 12 +/− 2 | 7 +/− 2* | 19 +/− 3* | 12 +/− 3# | ND | 31 +/− 2# |
| 0.9 ug/ml | 11 +/− 3 | 11 +/− 3* | 22 +/− 6* | 19 +/− 1* | ND | 41 +/− 7* |
| 0.45 ug/ml | 11 +/− 1 | 17 +/− 10 | 28 +/− 10 | 31 +/− 4$ | ND | 59 +/− 13$ |
| 0.225 ug/ml | 12 +/− 4 | 19 +/− 3 | 31 +/− 7 | 25 +/− 8$ | ND | 56 +/− 15$ |
| 6His I24pAF-30K |  |  |  |  |  |  |
| 3.6 ug/ml | 11 +/− 2 | 1 +/− 1# | 12 +/− 3# | 7 +/− 4# | ND | 19 +/− 6# |
| 1.8 ug/ml | 10 +/− 4 | 2 +/− 3* | 12 +/− 3# | 7 +/− 2# | ND | 19 +/− 5** |

TABLE 6-continued

|  | CFU-E | BFU-E | Total Erythroid | CFU-GM | CFU-GEMM | Total CFC |
|---|---|---|---|---|---|---|
| 0.9 ug/ml | 11 +/− 3 | 2 +/− 2# | 13 +/− 4# | 9 +/− 4# | ND | 22 +/− 8# |
| 0.45 ug/ml | 10 +/− 3 | 4 +/− 1* | 14 +/− 3# | 10 +/− 3# | ND | 24 +/− 4# |
| 0.225 ug/ml | 10 +/− 2 | 11 +/− 2* | 21 +/− 3* | 12 +/− 5* | ND | 33 +/− 5# |
| 6 His F27pAF-30K | | | | | | |
|  | | | | | | |
| 3.6 ug/ml | 15 +/− 5 | 3 +/− 1# | 18 +/− 6* | 8 +/− 2# | ND | 26 +/− 4# |
| 1.8 ug/ml | 13 +/− 2 | 3 +/− 1* | 16 +/− 2# | 11 +/− 3# | ND | 27 +/− 4# |
| 0.9 ug/ml | 18 +/− 5 | 7 +/− 2* | 25 +/− 6$ | 12 +/− 3# | ND | 37 +/− 9* |
| 0.45 ug/ml | 11 +/− 4 | 11 +/− 4* | 22 +/− 6* | 16 +/− 4* | ND | 38 +/− 10* |
| 0.225 ug/ml | 14 +/− 4 | 12 +/− 2* | 26 +/− 6$ | 15 +/− 3* | ND | 41 +/− 9* |
| 6His N45pAF-30K | | | | | | |
|  | | | | | | |
| 3.6 ug/ml | 12 +/− 1 | 4 +/− 1* | 16 +/− 1# | 9 +/− 4# | ND | 25 +/− 3# |
| 1.8 ug/ml | 13 +/− 3 | 4 +/− 2* | 17 +/− 4* | 12 +/− 2# | ND | 29 +/− 6# |
| 0.9 ug/ml | 16 +/− 3 | 8 +/− 4* | 24 +/− 7$ | 18 +/− 4* | ND | 42 +/− 10* |
| 0.45 ug/ml | 12 +/− 2 | 11 +/− 4* | 23 +/− 5* | 18 +/− 3* | ND | 41 +/− 5* |
| 0.225 ug/ml | 10 +/− 3 | 15 +/− 5$ | 25 +/− 5$ | 19 +/− 4* | ND | 44 +/− 7* |
| 6His N65pAF-30K | | | | | | |
|  | | | | | | |
| 3.6 ug/ml | 13 +/− 4 | 12 +/− 7$ | 25 +/− 8$ | 20 +/− 5* | ND | 45 +/− 11* |
| 1.8 ug/ml | 17 +/− 2 | 12 +/− 3* | 29 +/− 4$ | 20 +/− 5* | ND | 49 +/− 7* |
| 0.9 ug/ml | 13 +/− 3 | 12 +/− 2* | 25 +/− 4* | 28 +/− 4$ | ND | 53 +/− 8* |
| 0.45 ug/ml | 14 +/− 3 | 12 +/− 1* | 26 +/− 3* | 29 +/− 8$ | ND | 55 +/− 11$ |
| 0.225 ug/ml | 12 +/− 3 | 22 +/− 3 | 34 +/− 5 | 27 +/− 5* | ND | 61 +/− 8$ |
| 6His E78pAF-30K | | | | | | |
|  | | | | | | |
| 3.6 ug/ml | 12 +/− 3 | 4 +/− 4* | 16 +/− 6* | 3 +/− 3# | ND | 19 +/− 8# |
| 1.8 ug/ml | 13 +/− 3 | 3 +/− 3* | 16 +/− 4* | 14 +/− 4* | ND | 30 +/− 8# |
| 0.9 ug/ml | 11 +/− 2 | 7 +/− 4* | 18 +/− 4* | 19 +/− 6* | ND | 37 +/− 9* |
| 0.45 ug/ml | 13 +/− 3 | 7 +/− 3* | 20 +/− 2* | 22 +/− 4* | ND | 42 +/− 3* |
| 0.225 ug/ml | 10 +/− 1 | 12 +/− 2* | 22 +/− 1* | 22 +/− 4* | ND | 44 +/− 3* |
| 6His E107pAF-30K | | | | | | |
|  | | | | | | |
| 3.6 ug/ml | 7 +/− 3 | 2 +/− 3* | 9 +/− 6* | 8 +/− 1# | ND | 17 +/− 6** |
| 1.8 ug/ml | 12 +/− 3 | 3 +/− 1# | 15 +/− 3# | 12 +/− 2# | ND | 27 +/− 5# |
| 0.9 ug/ml | 15 +/− 4 | 4 +/− 1* | 18 +/− 4* | 13 +/− 3* | ND | 31 +/− 6# |
| 0.45 ug/ml | 15 +/− 2 | 6 +/− 4* | 21 +/− 4* | 18 +/− 6* | ND | 39 +/− 6* |
| 0.225 ug/ml | 12 +/− 4 | 9 +/− 1* | 21 +/− 4* | 18 +/− 2* | ND | 39 +/− 2* |
| 6His R125pAF-30K | | | | | | |
|  | | | | | | |
| 3.6 ug/ml | 13 +/− 1 | 4 +/− 2* | 17 +/− 2# | 12 +/− 3# | ND | 29 +/− 4# |
| 1.8 ug/ml | 12 +/− 4 | 4 +/− 2* | 16 +/− 3# | 13 +/− 3# | ND | 29 +/− 5# |
| 0.9 ug/ml | 10 +/− 1 | 5 +/− 3* | 15 +/− 3# | 16 +/− 4* | ND | 31 +/− 6# |
| 0.45 ug/ml | 15 +/− 2 | 6 +/− 4* | 21 +/− 5* | 21 +/− 2* | ND | 42 +/− 6* |
| 0.225 ug/ml | 11 +/− 2 | 10 +/− 5* | 21 +/− 5* | 17 +/− 5* | ND | 38 +/− 9* |
| 6His K134pAF-30K | | | | | | |
|  | | | | | | |
| 3.6 ug/ml | 6 +/− 3 | 1 +/− 1# | 7 +/− 2** | 10 +/− 2# | ND | 17 +/− 4** |
| 1.8 ug/ml | 10 +/− 3 | 2 +/− 2# | 12 +/− 4# | 11 +/− 3# | ND | 23 +/− 3** |
| 0.9 ug/ml | 8 +/− 3 | 1 +/− 2# | 9 +/− 3** | 11 +/− 3# | ND | 20 +/− 6# |
| 0.45 ug/ml | 14 +/− 2 | 4 +/− 2* | 18 +/− 3* | 12 +/− 3# | ND | 30 +/− 5# |
| 0.225 ug/ml | 10 +/− 4 | 6 +/− 2* | 16 +/− 5* | 12 +/− 4* | ND | 28 +/− 6# |

ND = none detected
Total Erythroid = CFU-E + BFU-E
Total CFC = Total Erythroid + CFU-GM + CFU-GEMM
$p < 0.01
*p < 0.005
p < 0.001
**p < 0.0005

The number and distribution of colonies detected in the vehicle and endotoxin controls were no different from the standard control (containing no compound and no vehicle buffer). A dose-dependent toxic effect (inhibitory effect on erythroid and myeloid progenitor proliferation) was seen in cultures incubated with 5-fluorouracil. Complete inhibition of growth was seen at the highest concentration of 5 ug/ml. A significant decrease from control numbers was also seen at 1 ug/ml for erythoid and myeloid growth and at 0.5 ug/ml for myeloid growth only, indicating that 5-FU is more toxic to the myeloid cell lineage. Colony numbers recovered to near control levels at 0.1 ug/ml.

In the presence of each hIFN polypeptide or PEGASYS®, the morphology of the resulting erythroid and myeloid colonies was not perturbed. However, where colony numbers were affected so was the size of both colony types. All hIFN polypeptides and PEGASYS® were found to be toxic to the total number of colony forming cells (myeloid and erythroid progenitors) at all concentrations tested, showing a slight dose dependent effect. hIFN polypeptides and PEGASYS® did cause a slight gradual dose dependent effect on progenitor compounds. PEGASYS® was found not to be significantly toxic at 0.225 ug/ml, and 6HisM16pAF-30K PEG and 6HisN65pAF-30K PEG were found not to be significantly toxic to erythoid progenitors at 0.45 (6HisM16pAF-30K PEG only) and 0.225 ug/ml. However, for all compounds the total number of CFC was significantly inhibited at all concentrations tested. Colony size was also found to be smaller in the presence of all compounds and size reflected the toxicity seen. For example, colonies in the presence of 3.6 ug/ml PEGASYS® were smaller than those observed at 0.225 ug/ml.

PEG appeared to be approximately two fold less toxic having equal colony counts as PEGASYS® at 2 fold higher unit concentrations. For example, the 6HisE78pAF-30K PEG colony count of 22 at a concentration of 1600 units/ml is compared to the PEGASYS® colony count of 21 at 900 units/ml. Further studies of toxicity include but are not limited to CFU-GM toxicity studies with 12 point concentration curves run from 15000 to 1 unit/ml for each hIFN polypeptide to determine the IC50 for CFU-GM toxicity.

Table 7 shows hematopoietic toxicity data obtained with PEGASYS® and Ribavirin. PEGASYS® was in a buffer of 20 mM Na Acetate, 137 mM NaCl, 0.005% polysorbate 80, pH6.0 and had a starting concentration of 180 ug/ml. Ribavirin (Calbiochem cat #555580) in PBS was at a starting concentration of 7.63 mg/ml. Dilutions of each were tested, as shown in Table 7.

TABLE 7

|  | CFU-E | BFU-E | Total Erythroid | CFU-GM | CFU-GEMM | Total CFC |
|---|---|---|---|---|---|---|
| Standard | 13 +/− 5 | 55 +/− 6 | 68 +/− 11 | 88 +/− 5 | ND | 156 +/− 7 |
| PBS control | 16 +/− 7 | 57 +/− 4 | 73 +/− 10 | 85 +/− 6 | ND | 158 +/− 16 |
| ABX buffer control | 13 +/− 3 | 60 +/− 4 | 73 +/− 7 | 91 +/− 5 | ND | 164 +/− 11 |
| PEGASYS ® | | | | | | |
| 13.5 ug/mL | ND | ND | ND | ND | ND | ND |
| 4.5 ug/mL | 11 +/− 3 | 2 +/− 1 | 13 +/− 3 | 10 +/− 3 | ND | 23 +/− 5 |
| 1.5 ug/mL | 15 +/− 2 | 11 +/− 3 | 26 +/− 4 | 18 +/− 5 | ND | 44 +/− 9 |
| 0.5 ug/mL | 17 +/− 3 | 28 +/− 3 | 45 +/− 4 | 32 +/− 7 | ND | 77 +/− 10 |
| 0.17 ug/mL | 14 +/− 4 | 25 +/− 5 | 39 +/− 2 | 46 +/− 3 | ND | 85 +/− 2 |
| 0.056 ug/mL | 15 +/− 1 | 42 +/− 8 | 57 +/− 9 | 49 +/− 10 | ND | 106 +/− 9 |
| 0.019 ug/mL | 17 +/− 1 | 41 +/− 7 | 58 +/− 7 | 63 +/− 8 | ND | 121 +/− 2 |
| 0.006 ug/mL | 17 +/− 4 | 42 +/− 3 | 59 +/− 4 | 68 +/− 6 | ND | 127 +/− 3 |
| 0.002 ug/mL | 12 +/− 2 | 46 +/− 7 | 58 +/− 6 | 71 +/− 6 | ND | 129 +/− 6 |
| Ribavirin | | | | | | |
| 636 ug/mL | ND | ND | ND | ND | ND | ND |
| 212 ug/mL | ND | ND | ND | ND | ND | ND |
| 70.67 ug/mL | ND | ND | ND | ND | ND | ND |
| 23.56 ug/mL | ND | ND | ND | ND | ND | ND |
| 7.85 ug/mL | ND | ND | ND | ND | ND | ND |
| 2.62 ug/mL | ND | ND | ND | ND | ND | ND |
| 0.87 ug/mL | 19 +/− 1 | 31 +/− 5 | 50 +/− 5 | 42 +/− 6 | ND | 92 +/− 2 |
| 0.29 ug/mL | 16 +/− 4 | 33 +/− 3 | 49 +/− 2 | 69 +/− 5 | ND | 118 +/− 3 |
| 0.1 ug/mL | 17 +/− 4 | 39 +/− 2 | 56 +/− 6 | 73 +/− 4 | ND | 129 +/− 9 |
| 0.03 ug/mL | 16 +/− 4 | 50 +/− 8 | 66 +/− 4 | 86 +/− 4 | ND | 152 +/− 8 |
| 0.01 ug/mL | 12 +/− 2 | 51 +/− 4 | 63 +/− 4 | 84 +/− 12 | ND | 147 +/− 9 |
| 0.0036 ug/mL | 16 +/− 1 | 53 +/− 7 | 69 +/− 7 | 83 +/− 9 | ND | 152 +/− 11 |

Figure 10:
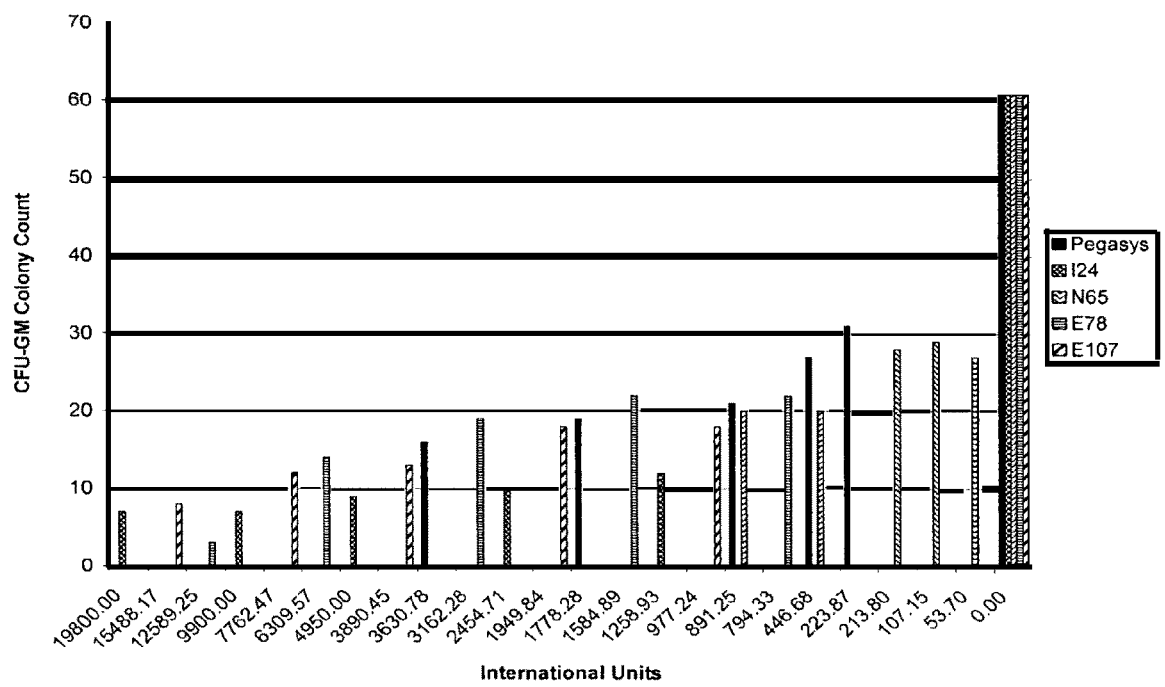
FIG. 10—A graph of CFU-GM colony count vs. International Units is shown for PEGASYS® and four hIFN polypeptides.

Further analysis of the CFU-GM colony count (Y-axis) is shown as FIG. 10, with International Units of anti-viral activity on the X-axis. The specific activity of PEGASYS® in anti-viral assays is 1 ng/unit. Mass concentrations of the PEGylated hIFN polypeptides were converted to International Units using the anti-viral IC50 values measured in the VSV replication assay. The CFU-GM colony count for the control standard is plotted on the far right of the graph. CFU-GM colony counts for the five concentrations of PEGASYS® tested in the assay are plotted. There is an increase in colony count as PEGASYS® concentration is decreased from approximately 3600 units/ml to 225 units/ml. The colony counts of the PEGylated hIFN polypeptides are also shown.

All hIFN polypeptides showed a concentration dependent effect on the CFU-GM count. On a per unit basis, hIFN polypeptides 6HisI24pAF-30K PEG and 6HisN65pAF-30K PEG appeared to be more toxic than PEGASYS® in this assay. 6HisN65pAF-30K PEG was at least 5-fold less potent than PEGASYS® in anti-viral assays, but was found to bind tightly to the IFNR2 receptor. In contrast, 6HisE78pAF-30K Graphs generated that plot BFU-E, CFU-GM, or Total CFC vs. concentration (ug/ml) for each of the compounds are shown as FIGS. 12-17.

Anti-Viral Assays

Antiviral activity of hIFN polypeptides may be measured by a variety of assays. One such assay involves studying the reduction of cytopathic effect (CPE) of cells infected with Vesicular Stomatitis Virus (VSV). VSV (ATCC) is produced by infecting the baby hamster kidney cell line BHK21 (ATCC). Briefly, cells are infected with various amounts of virus, and 24 hours post infection the supernatant containing virus is collected. Cell debris is eliminated by centrifugation of the supernatant for 5 minutes at 1,200 rpm. The stock of virus is stored in 1 ml aliquots at −80° C. The titer of virus is calculated by using plaque assays. Titration is expressed by PFU/ml (plaque-forming unit). Additional assays for testing antiviral activity of hIFN polypeptides of the invention include, but are not limited to, an assay based on the HCV replicon (Dr. Brent Korba at Department of Microbiology and Immunology, Georgetown University Medical Center). A variety of hIFN polypeptides are assayed in the stably HCV RNA-replicating cell line, AVA5; this cell line is derivative of the human hepatoblastoma Huh7. Intracellular HCV RNA levels are measured 24 hours after the last dose of hIFN polypeptide has been added. The RNA levels are measured using standard blot hybridization techniques. Two strains of HCV replicon are tested, HCV strain 1a and 1b. Another HCV assay is based upon measurement of HCV replication in specific human cells that support HCV replication (Dr. Brent E. Korba or Dr. Thomas I. Michalak, M. D., Ph.D. (Faculty of Medicine Health Science Centre Memorial University St. John's, Canada)). Another assay to assess the biological activity of hIFN polypeptides utilizes woodchuck hepatocytes. Human IFN-α up-regulates class I MHC antigen expression and 2'-5-OAS mRNA in this type of cells (Dr. Thomas I. Michalak, M. D., Ph.D). The effects of hIFN polypeptides of the invention on Class I MHC expression and/or 2'-5'-OAS levels are measured in the hepatocytes.

To evaluate hIFN polypeptide activity, $3\times10^4$ human WISH cells (ATCC) were seeded in a 96 well/plate and were subsequently infected with 10,000 PFU of VSV per well. At the time of infection, different amounts of hIFN polypeptide were added. 48 hours post-infection the CPE was evaluated; 42-48 hours was the minimum time required to obtain 100% CPE. CPE was identified by staining the cells with 0.1 ml of 1 mg/ml 3-(4,5-dimethylthiazol-2-yl) 2,5-diphenyltetrazolium bromide (MTT) followed by spectrophotometric reading at 570 nm with 690 nm as the reference wavelength. MTT measures metabolic reduction in mitochondria.

Figure 9:
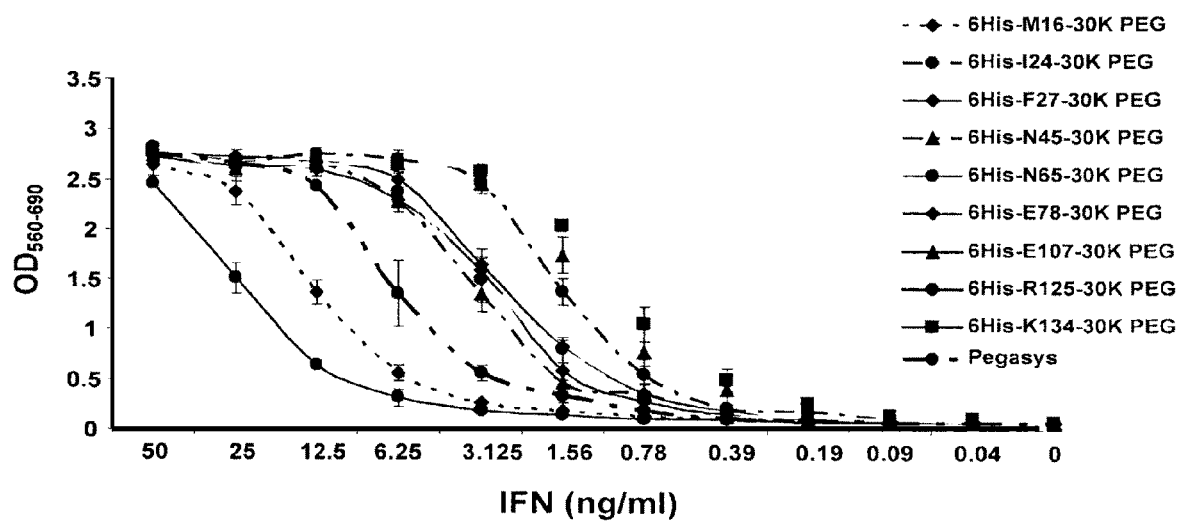
FIG. 9—A diagram of CPE results obtained with nine PEGylated hIFN polypeptides and PEGASYS® is shown.

Table 8 summarizes the IC50 values obtained with PEGASYS® and thirty-three hIFN polypeptides that have a substitution at the site indicated and were PEGylated. UnPEGylated hIFN polypeptides with a para-acetylphenylalanine substitution were also tested with this assay. FIG. 9 shows dose response curves obtained with nine PEGylated hIFN polypeptides and PEGASYS®.

TABLE 8

| hIFN | $IC_{50}$ (ng/ml) | hIFN | $IC_{50}$ (ng/ml) |
|---|---|---|---|
| 6His-L9-30K PEG | 11.7 | 6His-E96-30K PEG | 5.8 |
| 6His-R12-30K PEG | 17.7 | 6His-I100-30K PEG | 2.4 |
| 6His-R13-30K PEG | 27.9 | 6His-G102-30K PEG | 5.7 |
| 6His-M16-30K PEG | 3.8 | 6His-V103-30K PEG | 3.1 |
| 6His-I24-30K PEG | 1.1 | 6His-T106-30K PEG | 3.1 |
| 6His-F27-30K PEG | 3.5 | 6His-E107-30K PEG | 1.9 |
| 6His-K31-30K PEG | 3.8 | 6His-P109-30K PEG | 2.2 |
| 6His-G37-30K PEG | 1.8 | 6His-L110-30K PEG | 2.5 |
| 6His-P39-30K PEG | 10.3 | 6His-E113-30K PEG | 2.7 |
| 6His-E41-30K PEG | 3.5 | 6His-L117-30K PEG | 3.8 |
| 6His-N45-30K PEG | 1.9 | 6His-R120-30K PEG | 50 |
| 6His-Q48-30K PEG | 2.9 | 6His-R125-30K PEG | 5.4 |
| 6His-K49-30K PEG | 4.3 | 6His-K134-30K PEG | 2.1 |
| 6His-Q61-30K PEG | 50 | 6His-R149-30K PEG | 13.5 |
| 6His-N65-30K PEG | 50 | 6His-E159-30K PEG | 16.6 |
| 6His-E78-30K PEG | 1.7 | 6His-K164-30K PEG | 9.2 |
| 6His-Y89-30K PEG | 7.05 | PEGASYS ® | 7.6 |

Figure 11:
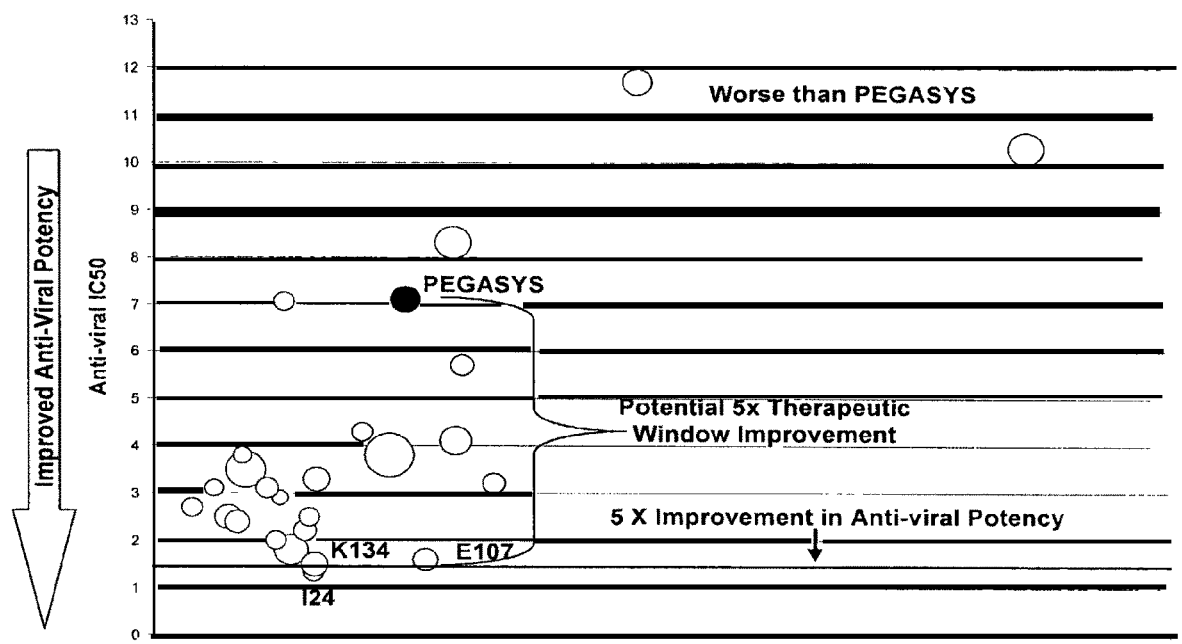
FIG. 11—An analysis of anti-viral IC50 and $K_D$ for IFNR2 is shown.
Figure 12:
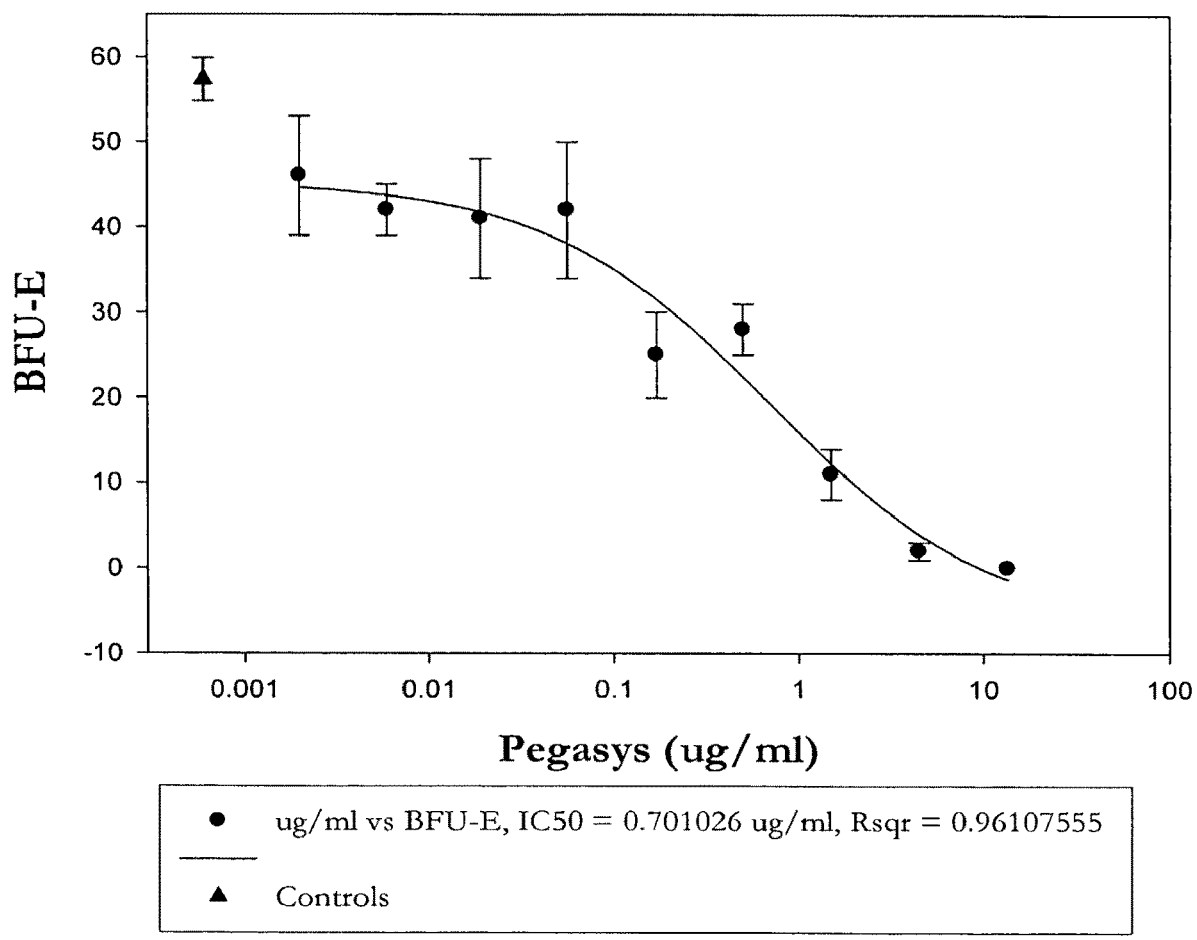
FIG. 12—Results from a hematopoietic toxicity assay are shown.
Figure 13:
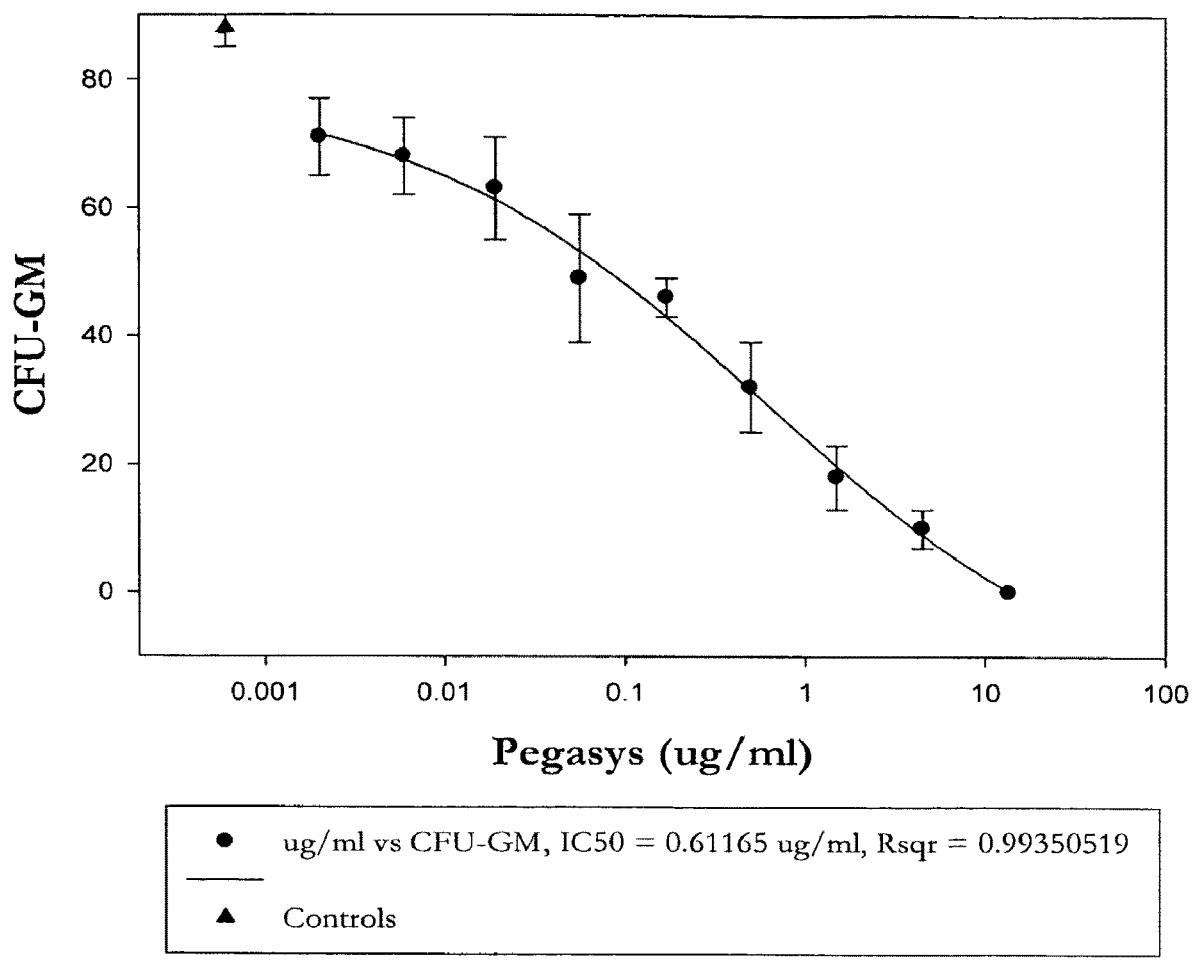
FIG. 13—Results from a hematopoietic toxicity assay are shown.
Figure 14:
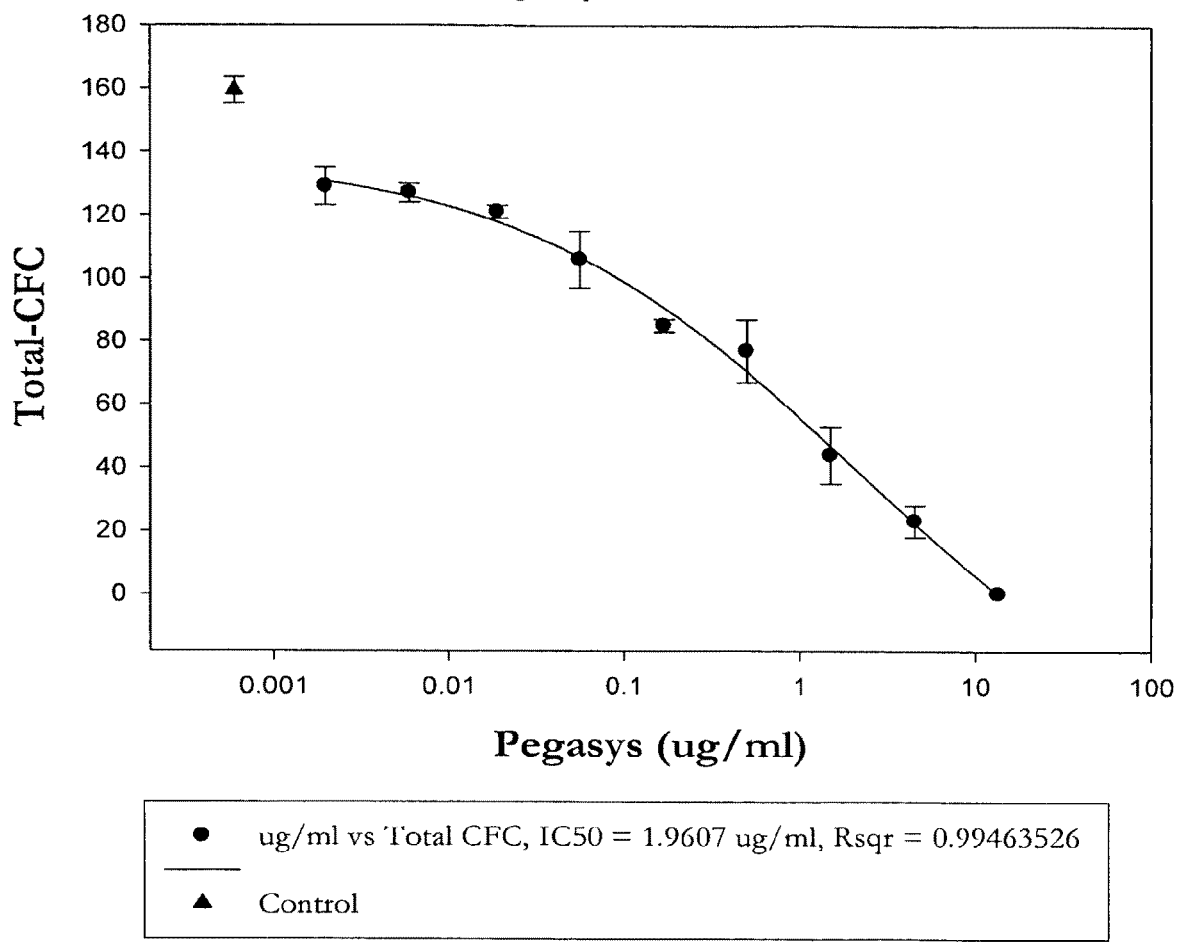
FIG. 14—Results from a hematopoietic toxicity assay are shown.
Figure 15:
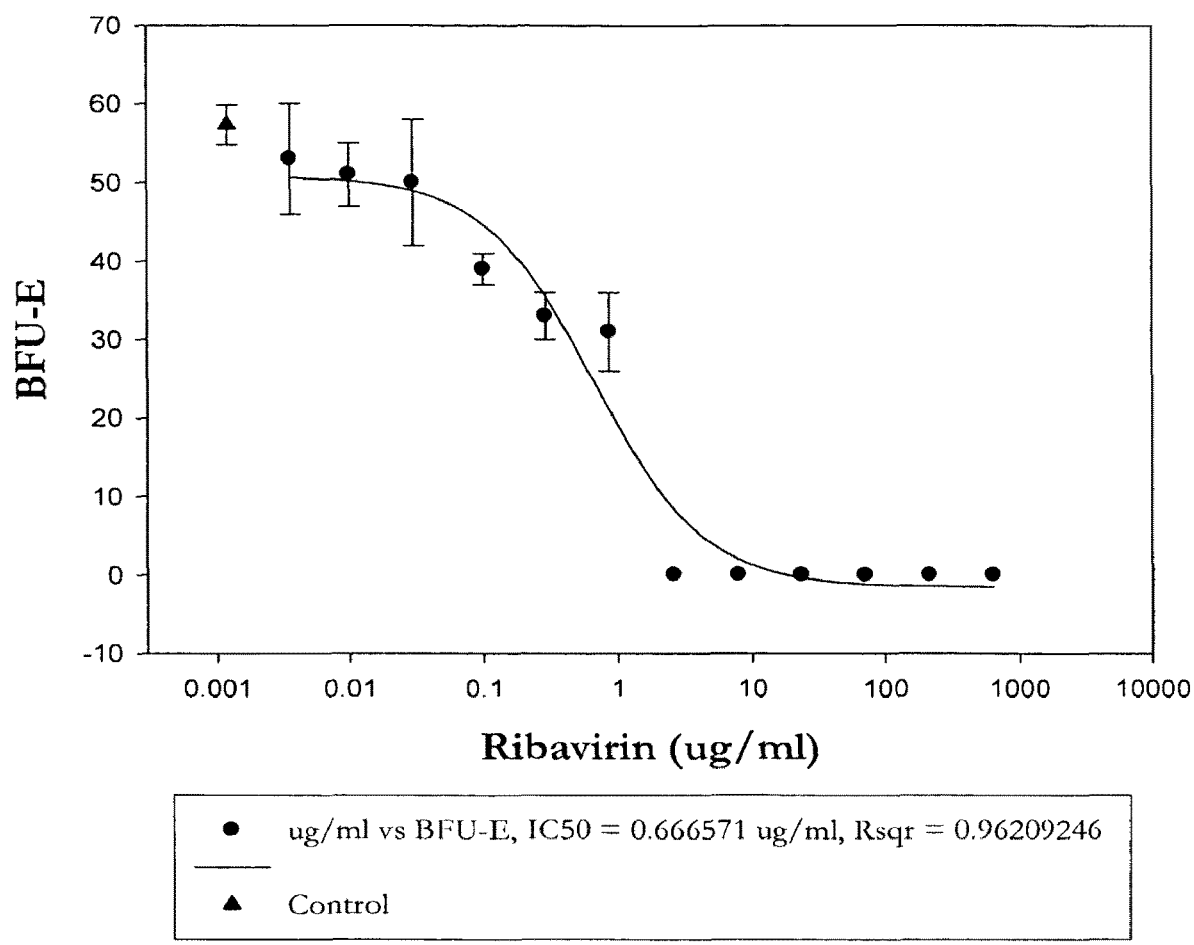
FIG. 15—Results from a hematopoietic toxicity assay are shown.
Figure 16:
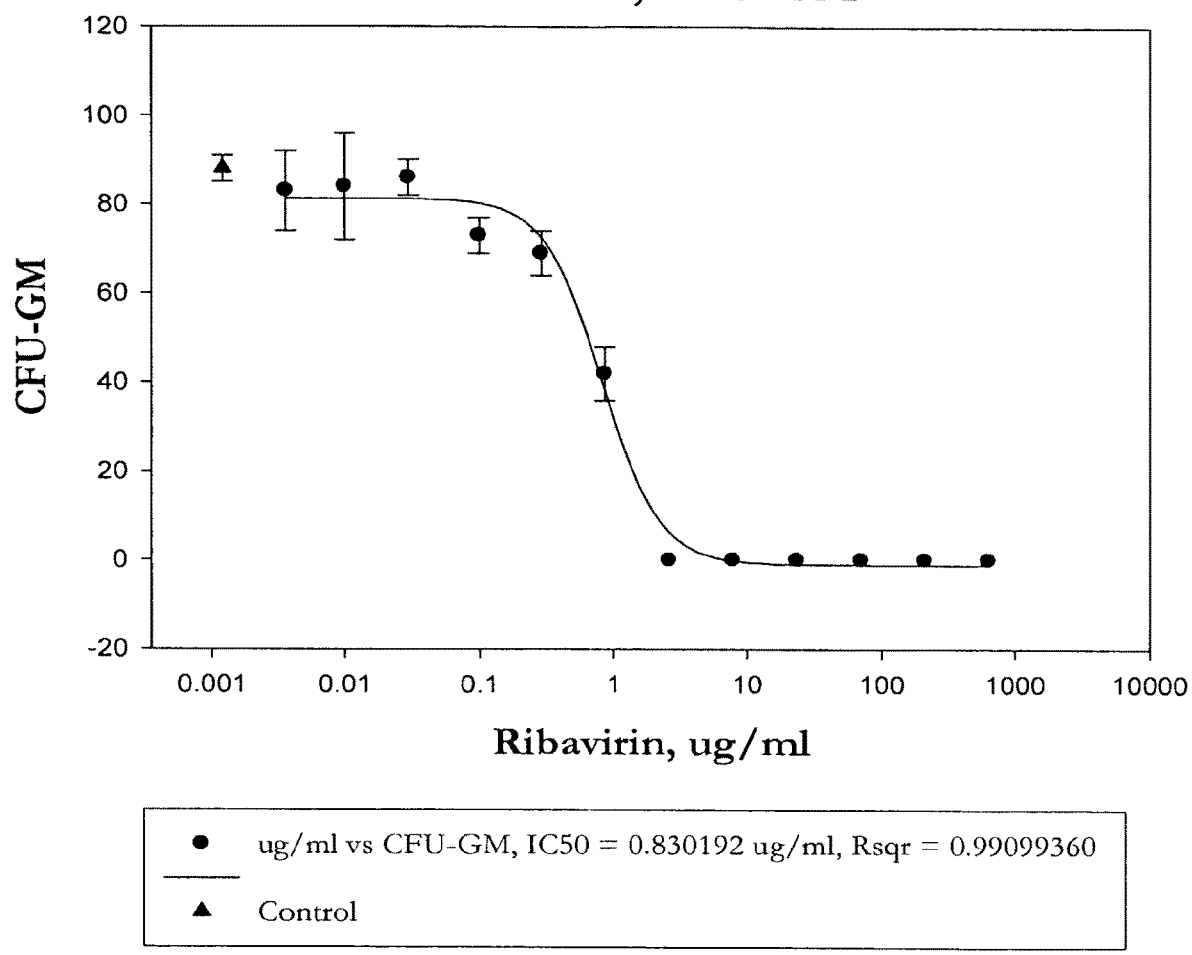
FIG. 16—Results from a hematopoietic toxicity assay are shown.
Figure 17:
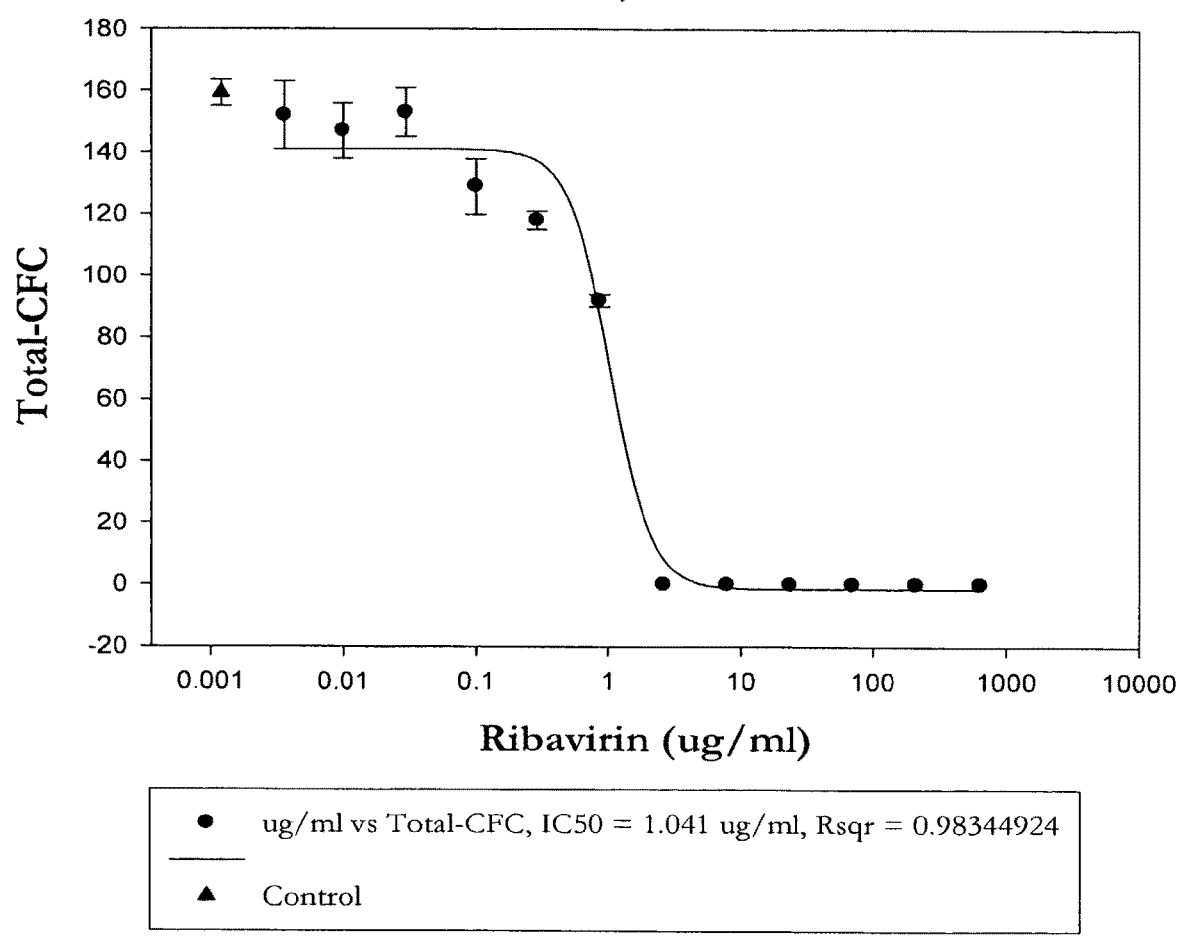
FIG. 17—Results from a hematopoietic toxicity assay are shown.

Site specific PEGylation was found to alter the activity of IFN and may separate various biochemical properties of the protein. This effect of site specific PEGylation was found as a result of an analysis of the anti-viral IC50 data with the $K_D$ of each hIFN polypeptide for the high affinity IFN receptor IFNR2, as shown in FIG. 11. The size of the bubbles represents the measured $K_D$ of each hIFN polypeptide for IFNR2. Two hIFN polypeptides, 6HisI24pAF-30K PEG and 6HisE107pAF-30K PEG, were approximately five fold more potent in the cell based anti-viral assay than PEGASYS®. Also, there was a lack of correlation between IFNR2 receptor $K_D$ and anti-viral activity. Thus, there is evidence that site specific PEGylation can differentially alter the biochemical activity of IFN. Thus, hIFN polypeptides have been produced that have improved anti-viral potency that also differ in various other measured biochemical properties.

Example 26

Other Assays

Measurement of HLA-A, B, C Expression

Figure 7:
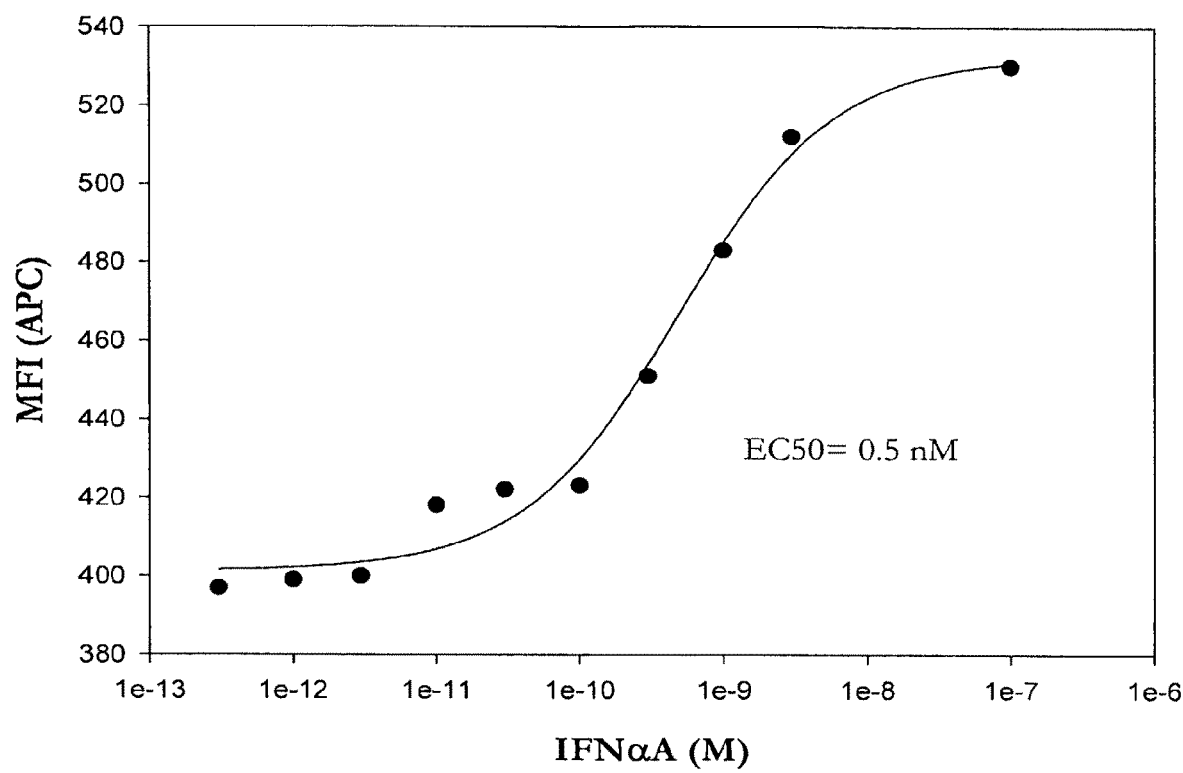
FIG. 7—A diagram of results obtained from an assay measuring induction of HLA expression is shown.

An assay measuring the increase in cell surface MHC class I expression in THP-1 cells may also be used to test activity of hIFN polypeptides. The human monocyte line THP-1 was cultured as indicated above. THP-1 cells, at a cell concentration of $5\times10^5$ cell/ml, were first differentiated in the presence of 5 nM phorbol 12-myristate 13-acetate (Sigma, St Louis, Mo.). Differentiated THP-1 cells were then stimulated with increasing concentrations of IFNα2A for 24 hours at 37° C. IFNα2A activated cells were then harvested; washed and stained for surface HLA expression. Immunofluorescent staining with APC-conjugated anti-HLA-A,B,C antibody in the presence of propidium iodide (BD Biosciences, San Diego, Calif.) enabled sample analysis on the FACS Array with acquired data analysis on the Flowjo software. $EC_{50}$ values were estimated from dose response curves plotted with mean fluorescent intensity against protein concentration utilizing SigmaPlot. See FIG. 7.

PGE2 and cAMP Assays

Examples of in vitro assays that are used to evaluate hIFN polypeptides include, but are not limited to, assays that detect an increase in prostaglandin E2 (PGE2) or decrease in cAMP as described for example, in Wang et al, J. of Neuroimmunology 2004 156:107-112 and Jiang et al, Neurochemistry 2000 36:193-196, which are incorporated herein by reference. Additional citations describing PGE2 secretion assays include but are not limited to, Mazzucco et al. J. Leukoc Biol 1996; 60 (2):271-7; Hoozemans et al. Exp. Gerontol. 2001 March; 36 (3):559-70; Fiebich et al. J. Neurochem. 2000 November; 75 (5):2020-8; Schwende et al. J Leukoc Biol 1996; 59 (4):555-61; and Hoozemans et al. Acta Neuropathol (Berl.) 2001 January; 101 (1):2-8, which are incorporated herein by reference. Modifications to these methods are known to one of ordinary skill in the art.

Cell based assays are performed, for example, comparing hIFN polypeptides of the invention with controls that modulate PGE2 or cAMP levels or current IFN therapeutics. Such assays measuring PGE2 secretion involve cell lines such as human THP-1 leukemia cells and human neuroblastoma cells (SK-N-SH). Differentiated THP-1 cells challenged with lipopolysaccharide (LPS) showed an increase in secretion of PGE2. In SK-N-SH cells, IL-1β increased PGE2 secretion. Such assays may be used to investigate the correlation of fever induction and/or the analgesic effect found with current IFN therapies with modulated secretion of prostaglandin E2 (PGE2) or cAMP levels.

cAMP levels are detected as follows. $5\times10^4$ SK-N-SH neuroblastoma cells (ATCC) are allowed to adhere overnight onto a 96-well assay plate (Applied Biosystems, Foster City, Calif.). Cells are then stimulated at 37° C. for 15 minutes with (a) 10 uM forskolin alone; (b) 10 uM forskolin plus hIFN polypeptides (60 pM for non-PEG version and 600 pM for PEG form) and (c) 10 uM forskolin plus hIFN polypeptides plus 20 uM naloxone (an opioid receptor antagonist). Cells are then lysed, and the lysates are incubated with a cAMP-alkaline phosphatase conjugate and an anti-cAMP antibody for 1 hour at room temperature. A chemiluminescent substrate is then added and the level of light emission measured on a Topcount luminescent reader. The amount of cAMP present in the lysates is quantitated from a cAMP standard curve.

Gene Expression Profiling

Transcriptional activity of monoPEGylated interferon-α-2a isomers is described in Foser et al. Pharmacogenomics Journal 2003; 3:312-319 using oligonucleotide array transcript analysis. Cell lines that may be used in expression studies include but are not limited to melanoma cell lines such as ME15. Alternate assays to DNA arrays may be performed with hIFN polypeptides of the invention to provide mRNA profiling or differential gene expression information.

Additional Assays

Assays to support preliminary formulation studies include assays for protein de-amidation, aggregation, oxidation, acetylation, and other stability indicating assays. Other assays include, but are not limited to, assays that investigate other potential degradation products, including but not limited to, disulfide rearrangements and proteolytic degradation products.

Example 27

This example describes an alternate system for cloning, expression and purification of hIFN polypeptides of the invention. Possible advantages of this alternate system include, but are not limited to, the deletion of one or more steps that involve refolding of hIFN polypeptides. NusA fusion proteins and TEV are discussed in Davis et al. Biotechnol Bioeng (1999); 65:382-388; Shih et al. Protein Science 2005; 14:936-941; and U.S. Pat. Nos. 5,162,601, 5,532,142; 5,766,885; and 5,989,868, all of which are incorporated by reference herein.

Cloning and Constructs for Nus-hIFN Polypeptide Fusions

To generate NusA-hIFN fusions, hIFN nucleotide sequences were cloned downstream of NusA between SpeI and KpnI restriction sites, separated by the sequence GSGENLYFQ (which includes a GSG linker and the recognition sequence for TEV). All initial cloning steps were completed using Novagen's pET44 vector, and then the whole Nus-IFN fusion cassette was transferred into another vector that allows for expression of hIFN controlled by the T71ac promoter and induction of protein expression with 1 mM IPTG. The transformation of E. coli (Origami 2) with constructs containing the modified hIFN polynucleotide sequence and the orthogonal aminoacyl tRNA synthetase/tRNA pair (specific for the desired non-naturally encoded amino acid) allows the site-specific incorporation of non-naturally encoded amino acid into the hIFN polypeptide.

Purification and Cleavage of Nus-hIFN Fusions

A 5 ml LB culture was grown from a single colony of E. coli transformed with a construct encoding the NusA-hIFN fusion. 0.5 liters of LB with ampicillin was inoculated, and the non-naturally encoded amino acid p-acetyl-phenylalanine was added to the culture. The culture was grown overnight at 28° C.-32° C. When the OD of the culture was greater than 0.8-1, the culture was transferred to 30° C., and induction was performed with 1 mM IPTG. The culture continued to grow for 4 hours at 30° C., and a sample was collected for SDS-PAGE analysis. The cells were collected by centrifugation and frozen at −80° C.

The cells were lysed in 25-30 ml of 50 mM Tris, pH 8, 200 mM NaCl, 5% glycerol. The samples were sonicated in a glass beaker for 25 sec 5-6 times, while keeping the samples on ice. The cells were incubated with 10 uL DNAse for 30 minutes at room temperature. The samples were then spun down and the supernatant removed. 5 mM imidazole was added to the supernatant.

The supernatant was then loaded onto a 5 ml HisTrap column at 3 ml/min. Prior to loading the supernatant, the HisTrap column is equilibrated with 20 mM Tris pH 8, 300 mM NaCl, 0.005% Tween80, 10 mM imidazole (Buffer A). After washing the column with Buffer A, elution was performed with the following step gradient: 4 column volumes of 8% Buffer B (20 mM Tris pH 8, 300 mM NaCl, 0.005% Tween80, 0.5M imidazole); 5 column volumes of 30% Buffer B; and 100% Buffer B wash. The NusA-hIFN fusion eluted during the 30% Buffer B step. The column was washed with 1M NaOH/1M NaCl and was stripped and recharged (or replaced) after five runs.

Samples from the step gradient were analyzed by SDS-PAGE, and the fractions with the fusion (ca 75 kDa) were pooled and dialyzed against 20 mM Tris, pH 8, 20 mM NaCl, 5% glycerol overnight at 4° C. The sample was diluted to 30 uM protein with dialysis buffer. The following was added to the sample: cysteamine to 0.2 mM, EDTA to 1 mM, and TEV to 0.8 uM. The samples were then incubated for 24-48 hours at 4° C., or overnight at room temperature.

After the incubation, the samples were diluted 1:3 with ddH$_2$O and loaded onto a 5 ml Q HP column. Elution was performed with a 0-40% gradient of 10 mM Tris, pH 8 (Buffer A') into Buffer B' (10 mM Tris, pH 8, 1M NaCl) over eighteen column volumes. hIFN polypeptides eluted at approximately 100 mM NaCl; TEV at 250 mM NaCl, and NusA at 400 mM NaCl. The column was washed with 2.5 mM NaCl, followed by 1M NaCl/1M NaOH.

Eluted fractions were analyzed by SDS-PAGE. hIFN polypeptide fractions were pooled, and the pH of the pool was adjusted by adding 1/20 volume of 1M NaAc, pH 4.5, and the hIFN pool was then dialyzed against 20 mM NaAc, pH 4, 20 mM NaCl, 5% glycerol overnight. The sample was then concentrated to greater than 1 mg/ml, keeping the volume greater than 300 mcl. The extinction coefficient at 280 nm is 22,500 $M^{-1}$ or 1.17 $mg/ml^{-1}$.

PEGylation

Oxyamino-derivatized 30K PEG was added to hIFN polypeptide at a 1:12 molar ratio (30 mg/mg IFN/ml), and the mixture was incubated at 28° C. for 16-48 hours. FIG. 19 shows the 30K PEG used in the conjugation. The sample was diluted ten times with SP buffer A (50 mM Na acetate, pH 5). To purify the PEGylated hIFN polypeptides, a 5 ml SP HP AKTA column was used with a gradient of 0-50% SP buffer B (50 mM Na acetate, pH 5, 0.5 M NaCl, 10% ethylene glycol) over ten column volumes. PEGylated IFN eluted around 100 mM salt, followed by non-PEGylated monomer (baseline separation). The fractions of PEGylated hIFN were pooled, dialyzed against the following storage buffer: 20 mM NaAcetate, pH 6, 0.005% Tween, 125 mM NaCl. The samples were then concentrated to >8 microM and stored at 4° C.

Purification of TEV

Purified TEV was generated with the following protocol. 0.5-2 liter cultures of BL21(DE3)RIL cells (Stratagene) were transformed with pRK793-TEV(S219V) plasmid (from NCI) at 30° C. Induction was performed when the OD600 was 0.8-1.2, and growth was continued for 4-5 hours at 30° C. The cells were resuspended in 20-30 ml of NTA buffer (50 mM Tris, pH 7, 300 mM NaCl). The samples were then sonicated five times for thirty seconds on ice, incubated at room temperature for thirty minutes, and centrifuged for twenty minutes at 12,000 rpm. The supernatant was removed, and imidazole was added to 15 mM.

The supernatant was loaded onto a 5 mL HisTrap column equilibrated in NTA buffer supplemented with 15 mM imidazole. Elution was performed with a gradient of 0-100% B (NTA buffer with 0.5M imidazole) over eighteen column volumes. TEV eluted as a broad peak starting 200 mM imidazole. The eluted fractions were analyzed by SDS-PAGE, and the fractions containing clean TEV were pooled. The pooled fractions were dialyzed overnight against the following buffer (30 mM Tris, pH 7.2, 200 mM NaCl, 0.5 mM EDTA, 1 mM DTT). The dialyzed sample was centrifuged to remove any precipitate.

The spun material was then dialyzed four-fold with ddH$_2$O and loaded onto 5 ml SP FF AKTA column equilibrated with Buffer A (10 mM Tris pH 7, 50 mM NaCl). The column was eluted with a linear gradient 0-100% B (10 mM Tris, pH 7, 0.5M NaCl) over eighteen column volumes. The eluted TEV fractions were pooled, and the following was added to the pool: 1 mM DTT, 1 mM EDTA, 20% glycerol. The sample was concentrated to >20 uM (ext. coeff. 32,500, pI is 9.6), aliquoted at 500 mcl/tube, and stored at −20° C.

Anti-Viral Activity

Figure 18:
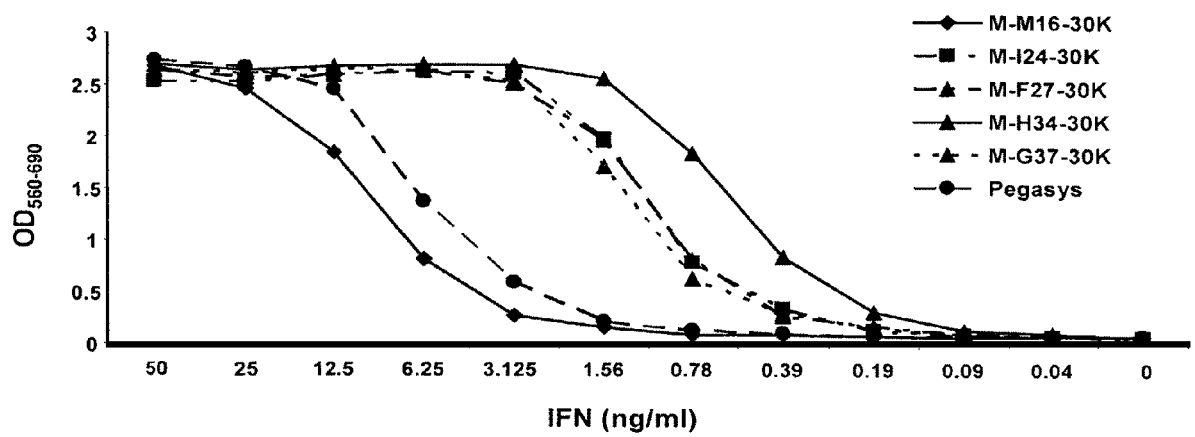
FIG. 18—A diagram of CPE results obtained with five PEGylated hIFN polypeptides and PEGASYS®.

To evaluate the activity of hIFN polypeptides generated via the methods described in this Example, $3 \times 10^4$ human WISH cells (ATCC) were seeded in a 96 well/plate and were subsequently infected with 10,000 PFU of VSV per well. At the time of infection, different amounts of hIFN polypeptide were added. 48 hours post-infection the CPE was evaluated; 42-48 hours was the minimum time required to obtain 100% CPE. CPE was identified by staining the cells with 0.1 ml of 1 mg/ml 3-(4,5-dimethylthiazol-2-yl) 2,5-diphenyltetrazolium bromide (MTT) followed by spectrophotometric reading at 570 nm with 690 nm as the reference wavelength. MTT measures metabolic reduction in mitochondria. The antiviral activity of five PEGylated hIFN polypeptides and PEGASYS® is shown in FIG. 18. Methionyl hIFN polypeptides comprising a non-naturally encoded amino acid are designated with an "M-" hIFN polypeptides without a methionine as the first amino acid are also generated using methods involving NusA.

Example 28

This example describes methods to measure in vitro and in vivo activity of hIFN polypeptides of the invention.

Cell Binding Assays.

Cells ($3 \times 10^6$) are incubated in duplicate in PBS/1% BSA (100 μl) in the absence or presence of various concentrations (volume: 10 μl) of unlabeled IFN, hIFN or GM-CSF and in the presence of $^{125}$I-IFN (approx 100,000 cpm or 1 ng) at 0° C. for 90 minutes (total volume: 120 μl). Cells are then resuspended and layered over 200 μl ice cold FCS in a 350 μl plastic centrifuge tube and centrifuged (1000 g; 1 minute). The pellet is collected by cutting off the end of the tube and pellet and supernatant counted separately in a gamma counter (Packard).

Specific binding (cpm) is determined as total binding in the absence of a competitor (mean of duplicates) minus binding (cpm) in the presence of 100-fold excess of unlabeled IFN (non-specific binding). The non-specific binding is measured for each of the cell types used. Experiments are run on separate days using the same preparation of $^{125}$I-IFN and should display internal consistency. $^{125}$I-IFN demonstrates binding to the Daudi cells. The binding is inhibited in a dose dependent manner by unlabeled natural IFN or hIFN, but not by GM-CSF or other negative control. The ability of hIFN to compete for the binding of natural $^{125}$I-IFN, similar to natural IFN, suggests that the receptors recognize both forms equally well.

In Vivo Studies from PEGylated IFN

PEG-hIFN, unmodified hIFN and buffer solution are administered to mice or rats. The results will show superior activity and prolonged half life of the PEGylated hIFN of the present invention compared to unmodified hIFN which is indicated by significantly increased inhibition of viral replication using the same dose per mouse or rat.

Measurement of the In Vivo Half-Life of Conjugated and Non-Conjugated hIFN and Variants Thereof.

Male Sprague Dawley rats (about 7 weeks old) are used. On the day of administration, the weight of each animal is measured. 100 μg per kg body weight of the non-conjugated and conjugated hIFN samples are each injected intravenously into the tail vein of three rats. At 1 minute, 30 minutes, 1, 2, 4, 6, and 24 hours after the injection, 500 μl of blood is withdrawn from each rat while under CO$_2$-anesthesia. The serum is isolated from the blood samples by centrifugation (4° C., 18000×g for 5 minutes). The serum samples are stored at −80°C. until the day of analysis. The amount of active IFN in the serum samples is quantified by the IFN in vitro activity assay after thawing the samples on ice.

Antiviral Activity

There are many assays known to those skilled in the art that measure the degree of resistance of cells to viruses (McNeill T A, J Immunol Methods. (1981) 46 (2):121-7). These assays generally can be categorized into three types: inhibition of cytopathic effect; virus plaque formation; and reduction of virus yield. Viral cytopathic effect assays measure the degree of protection induced in cell cultures pretreated with IFN and subsequently infected with viruses. Vesicular stomatitis virus, for instance, is an appropriate virus for use in such an assay. This type of assay is convenient for screening numerous different IFNs, as it can be performed in 96-well plates. An example of a cytopathic effect reduction assay is detailed in Wang et al. NeuroReport (2001) 12 (4):857-859. Plaque-reduction assays measure the resistance of IFN-treated cell cultures to a plaque-forming virus (for instance, measles virus). One benefit to this assay is that it allows precise measurement of a 50% reduction in plaque formation. Finally, virus yield assays measure the amount of virus released from cells during, for instance, a single growth cycle. Such assays are useful for testing the antiviral activity of IFNs against viruses that do not cause cytopathic effects, or that do not build plaques in target-cell cultures. The multiplicity of infection (moi) is an important factor to consider when using either plaque-reduction or virus-yield assays.

Other clinically important interferon characteristics are also easily assayed in the laboratory setting. One such characteristic is the ability of an interferon polypeptide to bind to specific cell-surface receptors. For instance, some IFNα-2as exhibit different cell-surface properties compared to IFNα-2b, the IFN most widely used in clinical trials. While IFNα-2b is an effective antiviral agent, it causes significant adverse side effects. Interferons that exhibit distinct binding properties from IFNα-2b may not cause the same adverse effects. Therefore, interferons that compete poorly with IFNα-2b for binding sites on cells are of clinical interest. Competitive interferon binding assays are well known in the art (Hu et al., J Biol. Chem. (1993) Jun. 15; 268 (17):12591-5; Di Marco et al., (1994) Biochem. Biophys. Res. Comm. 202:1445-1451, which are incorporated by reference herein). In general, such assays involve incubation of cell culture cells with a mixture of $^{125}$I-labeled IFNα-2b and an unlabeled interferon of interest. Unbound interferon is then removed, and the amount of bound label (and by extension, bound $^{125}$I-labeled IFNα-2b) is measured. By comparing the amount of label that binds to cells in the presence or absence of competing interferons, relative binding affinities can be calculated.

Another prominent effect of IFNα's is their ability to inhibit cell growth, which is of major importance in determining anti-tumor action. Growth inhibition assays are well established, and usually depend on cell counts or uptake of tritiated thymidine ([$^3$H] thymidine) or another radiolabel. The human lymphoblastoid Daudi cell line has proven to be extremely sensitive to IFNα's, and it has been used to measure antiproliferative activity in many IFNα's and derived hybrid polypeptides (Meister et al., J Gen Virol. (1986) August; 67 (Pt 8):1633-43). Use of this cell line has been facilitated by its ability to be grown in suspension cultures (Evinger and Pestka, (1981) Methods Enzymol. 79:362-368). IFNα's also exhibit many immunomodulatory activities (Zoon et al., (1986) In, The Biology of the Interferon System. Cantell and Schellenkens, Eds., Martinus Nyhoff Publishers, Amsterdam).

Although IFNs were first discovered by virologists, their first clinical use (in 1979) was as therapeutic agents for myeloma (Joshua et al., (1997) Blood Rev. 11 (4):191-200). IFNα's have since been shown to be efficacious against a myriad of diseases of viral, malignant, angiogenic, allergic, inflammatory, and fibrotic origin (Tilg, (1997) Gastroenterology. 112 (3):1017-1021). It has also proven efficacious in the treatment of metastatic renal carcinoma and chronic myeloid leukemia (Williams and Linch, (1997) Br. J. Hosp. Med. 57 (9):436-439). Clinical uses of IFNs are reviewed in Gresser (1997) J. Leukoc. Biol. 61 (5):567-574 and Pfeffer (1997) Semin. Oncol. 24 (3 Suppl. 9):S9-S63S969.

Analgesia Assays

Pain threshold studies may be performed with hIFN polypeptides to investigate the analgesic effect of these compounds. One such analgesia assay is described in Wang et al. NeuroReport (2001) 12 (4):857-859, which is incorporated by reference herein.

Example 29

This example describes methods to measure in vivo activity and toxicity of hIFN polypeptides of the invention.

Animal models used to study antiviral activity of hIFN polypeptides include, but are not limited to, the chimpanzee HCV (Purcell R H, FEMS Microbiol Rev. 1994 July; 14 (3):181-91), the HCV-Trimera mouse (Ilan E et al. J Infect Dis. 2002 Jan. 15; 185 (2):153-61), and the Alb-uPA transgenic mouse models (Mercer D F et al. Nat. Med. 2001 August; 7 (8):927-33; Kneteman, N et al (2003) 10th HCV Meeting Kyoto Japan, P-187), all of which are incorporated by reference herein. Woodchuck hepatitis virus (WHV) infection in woodchucks is a useful model to study the pathogenesis, prevention, and treatment of HBV infection (Berraondo, P. et al, J. Med. Virology 2002; 68, 424-432). The condition of woodchucks exposed prenatally to WHV is similar to HBV infection. Compounds, either PEGylated human interferon polypeptides, PEGylated woodchuck interferon compound analogs, or PEGylated human interferon polypeptides modified in some way so as to increase their species cross-reactivity towards woodchuck sufficiently for antiviral efficacy evaluation, are evaluated in the woodchuck hepatitis model.

Cynomolgus monkeys are also used to study in vivo activity and bone marrow toxicity. Activity is assayed by measuring the induction of downstream markers including but not limited to 2',5'-OAS by hIFN polypeptides of the invention compared to current IFN therapeutics such as PEGASYS®. Circulating blood cells, including but not limited to neutrophils, RBCs, and platelets are evaluated in bone marrow toxicity studies after administration of hIFN polypeptides compared to current IFN therapeutics such as PEGASYS®. 2',5'-OAS is an enzyme induced by interferon and is directly related to the anti-viral activity of interferon. This enzyme produces a mixture of oligonucleotides (2-5A) which are thought to activate the inactive RNAse present in cells and hinder the protein synthesis of cells or viruses through the breakdown of mRNA. Detection of 2',5'-OAS activity may be performed by a variety of assays known to those of ordinary skill in the art, including but not limited to, radioimmunoassay (RIA; EIKEN) which measures levels of 2-5A. Cynomolgus serum, for example, may be used to measure 2',5'-OAS activity levels. Neopterin is a non-species specific immune marker that is produced by macrophages upon exposure to interferon. Detection of neopterin may be performed by a variety of assays known to those of ordinary skill in the art, including but not limited to, EIA (IBL). Levels of other molecules may be measured in such studies, including but not limited to cortisol levels. Cortisol, an element of the HPA axis, has been implicated in depression, stress, and weight gain. Detection of cortisol may be performed by a variety of assays known to those of ordinary skill in the art, including but not limited to, EIA (RnD). Cytokine panels may be performed throughout the study after administration of hIFN polypeptides of the invention and levels of various cytokines compared to basal levels to evaluate toxicity of the hIFN polypeptides. A variety of assays known to those of ordinary skill in the art may be used, including but not limited to, ELISA, bead arrays (BD Biosciences) and other assay formats (Luminex) and may involve different types of readouts, including but not limited to, fluorescent readouts. Measurement of compound levels in serum or plasma may be detected using a variety of assays known to those of ordinary skill in the art, including but not limited to, ELISA (PBL). Antibodies used for detection by ELISA or other methods may be anti-IFN alpha antibodies or anti-PEG antibodies for hIFN polypeptides that are PEGylated. Various assay formats known to those of ordinary skill in the art may be used for detection including those involving fluorescence.

Evaluation of hIFN polypeptides of the invention is performed with the following pre-clinical plan. In Study 1, a dose-range finding pharmacokinetics (PK), pharmacodynamics (PD), and safety study is initiated in female cynomolgus monkeys and involves placebo and four doses of PEGASYS® (0, 1.5, 15, 50, and 150 ug/kg). The monkeys are acclimated for two weeks. 15, 50 and 150 ug/kg of PEGASYS® is administered on Day 1 and Day 5. 1.5 ug/kg of PEGASYS® is administered on Day 1 only. There are three female monkeys in each of the five groups. The duration of in-life is 14 days with an option to proceed for at least an additional week in the event that data so warrant. The endpoints are compound levels in the plasma measured by integrating the AUC through Day 8 and Day 15; and 2',5'-OAS and neopterin levels through Day 15. In this study, hematology studies are performed investigating the effect of the administered hIFN polypeptides on neutrophils and platelets on Day 3, Day 8 and Day 15. A prebleed is also done on the animals for comparison. Cytokine panels are also performed through Day 15, measuring levels of various cytokines including but not limited to, IL-2, IL-4, IL-5, IL-6, TNF, and IFN-γ. Cortisol is measured as well through Day 15. Rectal body temperature of the monkeys is also be measured, since fever is also a known side effect of current IFN therapeutics.

After one or two doses have been selected from the first study, Study 2 involves comparing hIFN polypeptides of the invention with PEGASYS® at the one or two doses. If a single dose is suitable for a comparison of PK, efficacy, and toxicity, then the particular dose of PEGASYS® is tested in cynomolgus monkeys and compared to one or more hIFN polypeptides at the same dose, and placebo. Three female monkeys are in each group; the acclimation period is two weeks. As in Study 1, 2',5'-OAS levels, hematology, body temperature, cortisol, and cytokine panels are studied. If two doses are required i.e. a low dose is required for PK and efficacy and another dose is needed for toxicity comparison, then PEGASYS® is compared to one or more hIFN polypeptides at both doses and placebo. As in Study 1, 2',5'-OAS levels, hematology, body temperature, cortisol, and cytokine panels are studied. The end of study in-life is Day 15, with an option to proceed for at least an additional week in the event that data so warrant.

Bone marrow is collected and evaluated from animals exposed to hIFN polypeptides of the invention. For example, bone marrow aspirates and/or core biopsies from treated animals (e.g. from primates) are examined histologically, and the ratio of myeloid to nucleated erythroid cells (M:E ratio) is estimated. A low M:E ratio, in conjunction with neutropenia, may be indicative of granulocytic hypoplasia with decreased production of neutrophils. Isolated bone marrow cells from treated animals are assayed for hematopoietic progenitors. That is, cell isolates are subjected to CFU-GM or BFU-E colony assay. The results (i.e. number of hematopoietic progenitor cells) would show the effect, if any, of treatment on myeloid and/or erythroid progenitor cells.

Such bone marrow toxicity studies may involve hIFN polypeptides administered via different routes, including but not limited to, subcutaneously and intravenously. Intravenous administration may allow for longer dosing regimens and better evaluation of bone marrow toxicity than subcutaneous administration. Such improvements may result from a modulation of immunogenicity or an antibody response to the compound administered. Toxicity studies include evaluation of neutrophil and platelet number/mL of plasma or serum.

Other animal models include but are not limited to, depression models. One mouse model involves the Tail-Suspension Test. Assays measuring the levels of cortisol and ACTH in mice after administration of hIFN polypeptide are also performed. Both cortisol and ACTH are components of the HPA axis and have been implicated in playing a role in interferon-treatment induced depression in patients.

Example 30

This example details the isolation of hIFN polypeptides and the measurement of hIFN activity and affinity of these hIFN polypeptides for the hIFN receptor.
Purification by Copper Column
500 ml LB Shake Flask Expression:

For each hIFN polypeptide, E. coli transformed with a construct encoding an orthogonal tRNA (J17 described in U.S. Patent Publication No. 20030108885) and an orthogonal aminoacyl tRNA synthetase (E9 described in U.S. patent application Ser. No. 11/292,903 entitled "Compositions of Aminoacyl-tRNA Synthetase and Uses Thereof") with a mutated hIFN polynucleotide were streaked onto a plate to obtain colonies. 2 mL LB containing antibiotic was inoculated with a single colony from the freshly transformed plate. The culture was incubated under constant agitation (250 rpm) at 37° C. until the culture reached an OD600 of approximately 0.05-0.3 (approximately 5-6 hours). 500 mL LB (containing antibiotic and 4 mM pAF) was inoculated with all or part of the 2 mL culture, normalizing the inoculation to synchronize cultures. The culture was incubated under constant agitation (250 rpm) at 37° C. until culture reached an OD600 of approximately 1.0 (approximately 4-5 hours). The culture was then induced with 1 mM IPTG, and the culture was incubated overnight at 37° C. The cells were harvested by centrifugation at 8000 rpm/12000 g; 15 minutes; 4° C. The cell paste was scraped out and stored in 40 mL Oak Ridge tubes. The cell pellets were then frozen at −80° C. until the inclusion body preparation was initiated.
Inclusion Body Preparation from 500 mL Shake Flask:

Buffer 1 was 50 mM NaAc pH 6.0; 100 mM NaCl; 1 mM EDTA; 1.0% Triton X-100. Buffer 2 was 50 mM NaAc pH 6.0; 100 mM NaCl; 1 mM EDTA. Table 9 shows the procedure used for inclusion body preparation.

TABLE 9

| # | Step | Technique | Buffer | Volume (mL) | Centrifugation (g, minutes) |
|---|---|---|---|---|---|
| 1 | Lysis | Avestin C3, 2 passes | 1 | 23 | 20000, 15 |
| 2 | Wash 1 | Sonication, 30 seconds | 1 | 25 | 20000, 15 |
| 3 | Wash 2 | Sonication, 30 seconds | 1 | 25 | 20000, 15 |
| 4 | Rinse 1 | Sonication, 30 seconds | 2 | 25 | 20000, 15 |
| 5 | Rinse 2 | Sonication, 30 seconds | 2 | 25 | 20000, 15 |

For the Lysis step, cells were resuspended in 23 mL chilled Buffer 1 by shaking for 1 hour at 4° C. The Avestin C3 was cleaned and rinsed with 100 mL water and then with 30 mL Buffer 1. The cells were then homogenized with 2 passes in Avestin at 15,000-20,000 psi with cooling at 4° C. in the following manner: 1) The sample was added. 2) The sample was processed once until Avestin reservoir was nearly empty; the sample was collected in the original tube (also done for subsequent steps). 3) The collected sample was added back to the Avestin reservoir and re-homogenized. 4) The sample was washed out by homogenizing 12 mL Buffer 1; this was added to the sample. 5) The sample was transferred to 40 mL Oak Ridge Centrifuge tube. 6) The sample was stored and 100 mL water was run through the Avestin, adding it slowly while running to flush the system. 7) 30 mL Buffer 1 was then added to the reservoir and homogenized to prepare for next sample. 8) The steps were then repeated to process the next sample.

For the Wash and Rinse steps, a spatula was used to loosen the pellet off the tube after pouring off supernatant from the last wash and pouring in fresh buffer. Sonication was performed at 75% power with a normal tip, not a microtip. The tip was rinsed with water and wiped with a Kimwipe between samples.

During the first 4 steps, the samples were spun in 40 mL Oak Ridge tubes used to store cell pellets. Rinse 2 was spun by splitting each sample to 2 15 mL conical tubes.
Solubilization and Refolding:

Solubilization was performed with 8M GndHCl pH between 5.5-8.5 using 50 mM NaAc or Tris. The inclusion bodies were solubilized to a final concentration between 5-10 mg/mL. The material was refolded or stored at −80° C. for long term storage.

Refolding was performed by diluting solubilized material to a final total protein concentration of 0.5 mg/mL in 4° C.

Refold Buffer (100 mM NaAc, pH 6.0 or 50 mM Tris, pH 8.0; 0.1% Tween 20). The refolding mixture was stored at 4° C. for 24 to 72 hours.

Cu Purification:

The refolded sample was allowed to warm to room temperature. A final concentration of 50 µM CuCl was added to the refolded sample, and the sample was incubated at room temperature for 10-30 minutes. The sample was filtered with a 0.22 µm PES filter and loaded onto a Chelating Sepharose HP column (GE Healthcare) charged with Cu and equilibrated with Cu Buffer A (50 mM NaAc, pH 5.0; 150 mM NaCl; 0.1% Tween 20). A linear gradient was run to 100% Cu Buffer B (100 mM NaAc, pH 3.5; 150 mM NaCl; 0.1% Tween 20) over 18 column volumes, and samples were collected in tubes containing 1 mM EDTA.

SP HP Purification of Cu Pool:

The hIFN polypeptide peak was collected from the Cu column and loaded straight onto a SP HP column (GE Healthcare) equilibrated in SP Buffer A (50 mM NaAc, pH 5.0; 1 mM EDTA). A linear gradient was run to 50% SP Buffer B (50 mM NaAc, pH 5.0; 0.5M NaCl; 10% ethylene glycol; 1 mM EDTA) over 15 column volumes.

Figure 20:
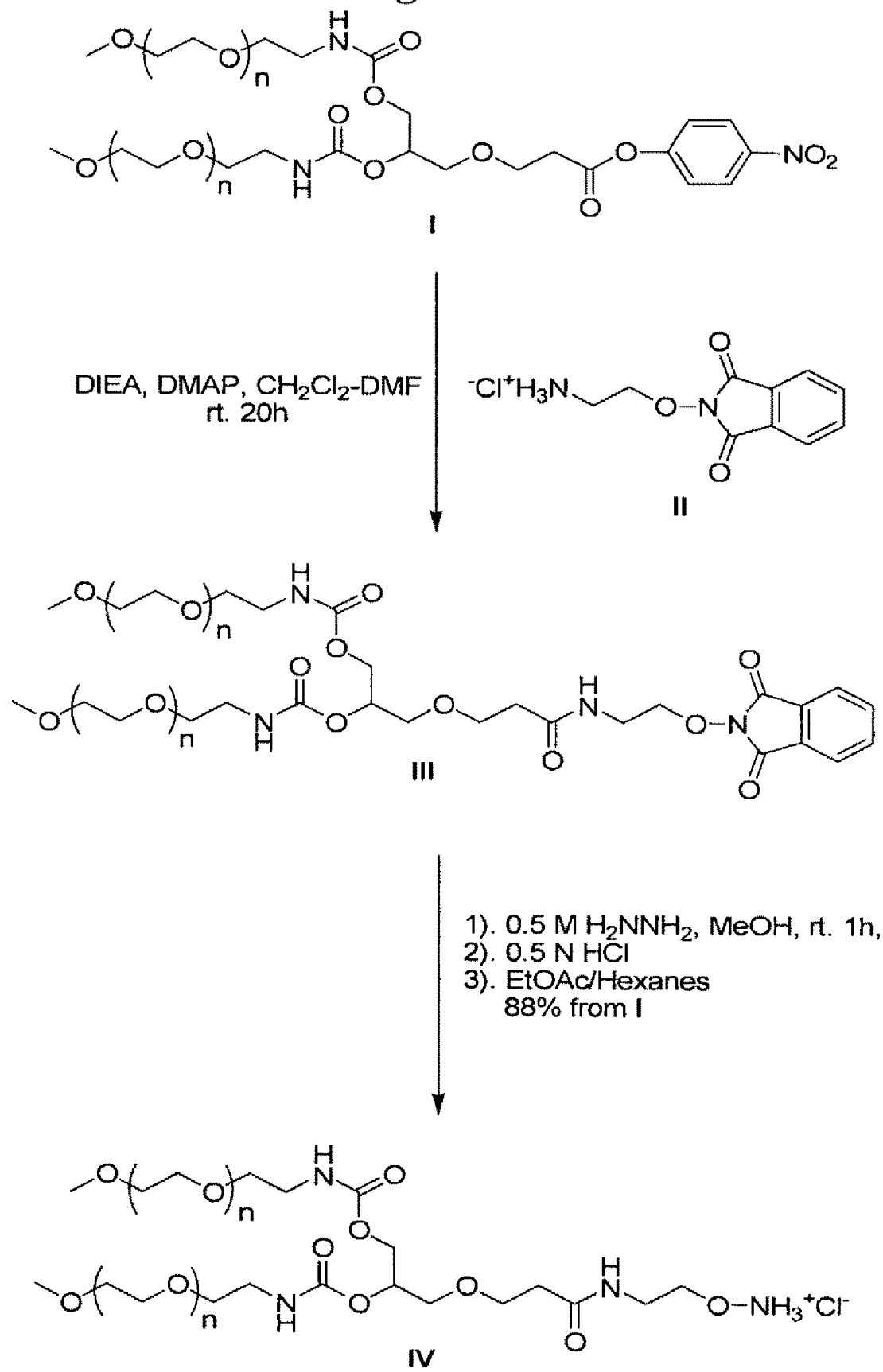
FIG. 20—A diagram is shown of the synthesis of mPEG (40K) aminoethoxyamine hydrochloride from mPEG (40K) p-nitrophenolcarbonate.

PEGylation and Purification:

The hIFN polypeptide samples were pooled from the SP HP column and concentrated to 1.0-2.0 mg/mL. 10% Acetic Acid was added to the sample to drop the pH down to 4.0. Oxyamino-derivatized 30K PEG was added to hIFN polypeptide at a 1:12 molar ratio (30 mg/mg IFN/ml), and the mixture was incubated at 28° C. for 48-72 hours. FIG. 19 shows the 30K PEG used in the conjugation. One hIFN polypeptide comprising the non-natural amino acid para-acetylphenylalanine at position 107 was conjugated to a branched 40K PEG. This PEG is shown in FIG. 20 as compound IV (mPEG (40K) aminoethoxyamine hydrochloride), and the figure shows the synthesis scheme from mPEG (40K) p-nitrophenolcarbonate. The molar ratio and conjugation conditions as well as the purification method used for the 40K PEGylated product was the same as the 30K PEGylated products. The sample was diluted ten-fold with SP Buffer A (50 mM Na acetate, pH 5; 1 mM EDTA). To purify the PEGylated hIFN, a SP HP column (GE Healthcare) was used with a gradient of 0-50% SP buffer B (50 mM Na acetate, pH 5, 0.5 M NaCl, 10% ethylene glycol; 1 mM EDTA) over 15 column volumes. PEGylated IFN eluted around 100 mM salt, followed by non-PEGylated monomer (baseline separation). The fractions of PEGylated hIFN were pooled, dialyzed against the following storage buffer: 20 mM NaAcetate, pH 6, 0.005% Tween, 125 mM NaCl. Samples were concentrated to 1.0-2.0 mg/mL and stored at −80° C.

The method used to functionalize the glycerol-based branched 40K PEG shown was as follows (FIG. 20). To a mixture of mPEG(40K) p-nitrophenolcarbonate I (20 g, 0.5 mmol) and N-aminoethoxyphthalimide hydrochloride II (0.6 g, 2.5 mmol) in N,N-dimethylformamide-methylene chloride (1:2, 150 mL) were added diisopropylethylamine (DIEA, 0.27 mL, 1.5 mmol) and 4-dimethylaminopyridine (DMAP, cat.). The resultant mixture was stirred at room temperature for 20 h. Ethyl acetate-hexanes (1:1, 1 L) was added. The precipitate was filtered, washed with ethylacetate-hexanes (1 L) and dried in vacuo to afford product III as a white powder.

mPEG(40K) N-aminoethoxyphthalimide III from the previous step was dissolved in a 0.5 M solution of hydrazine in methylene chloride-methanol (1:1, 100 mL). The resultant mixture was stirred at room temperature for 1.0 h and then washed with aqueous HCl solution (0.5 N, 300 mL). The organic layer was dried over anhydrous $Na_2SO_4$, filtered and concentrated. The residue was dissolved in $CH_2Cl_2$ (100 mL).

Ethyl acetate-hexanes (1:1, 1 L) was added to precipitate the mPEG(40K) aminoethoxyamine hydrochloride product IV (17.6 g, 88% from I) as a white powder.

Biacore Studies (Receptor Binding Affinity)

The sequence for the IFNAR2 extracellular domain (consisting of 206 amino acids ending with sequence LLPPGQ) was amplified from clone MHS1101-61064 (OpenBiosystems, Huntsville, Ala.). This insert was cloned into the pET20 expression vector (Novagen) downstream of the T7 promoter. Protein expression was induced with 0.4 mM IPTG in BL21 (DE3) cells (Novagen).

Since the expressed protein was insoluble, the inclusion bodies were purified from lysed cells and solubilized in 6M GndCl. A 5 ml aliquot (50 mg amount) was reduced with 10 mM DTT for 45 minutes at 37° C. Then the mixture was injected into 200 ml of refolding buffer which consisted of 50 mM Tris pH 8, 20 mM NaCl, 0.5 M Arginine, 10% glycerol at 4° C. and incubated overnight with gentle stirring.

The refolding reaction was then concentrated to 25 ml using an Amicon stirring cell, and dialyzed overnight against 20 mM Tris, pH 8, 20 mM NaCl, 10% glycerol. Monomeric refolded IFNAR ECD was purified on HP Q Sepharose using the AKTA FPLC system (Amersham). Purified IFNAR2 ECD was immobilized on CM5 Biacore chip using a lysine-specific coupling procedure recommended by the manufacturer. About 200 RUs of functional protein were immobilized. Various concentrations of IFN variants in HBS-EP buffer (Biacore) were injected at a flow rate of 50 mcl/minute over the flowcell containing immobilized IFNAR2, and a control flowcell containing immobilized bovine serum albumin. Sensograms generated were fit to the 1:1 interaction model to calculate $k_{on}$, $k_{off}$ and $K_d$ values using BiaEvaluation software (Biacore). The receptor binding affinity of hIFN polypeptides PEGylated at the non-naturally encoded amino acid (para-acetylphenylalanine; pAF) were observed. Additional mutants were tested that were PEGylated at pAF and had a naturally encoded amino acid substitution at position 149. Methionyl wild-type interferon (M-WT) was included as a control sample. Table 10 shows the $k_{on}$, $k_{off}$ and $K_d$ obtained. hIFN polypeptides shown do not have a 6-His tag and were refolded as described in this Example.

TABLE 10

Binding parameters for IFNα2A:IFNAR2 interaction, as determined by SPR

| hIFN polypeptide | $k_{on}$, × 10$^{-4}$ 1/M * s | $k_{off}$, 1/s | $K_d$, nM |
|---|---|---|---|
| M-WT | 640 | 0.025 | 4 |
| T6 pAF-30K PEG | 8.3 | 0.045 | 540 |
| M16 pAF-30K PEG | 6.6 | 0.043 | 650 |
| T108 pAF-30K PEG | 13 | 0.035 | 280 |
| M111 pAF-30K PEG | 10.5 | 0.046 | 430 |
| D114 pAF-30K PEG | 10.4 | 0.040 | 380 |
| E107 pAF-40K PEG | 7.7 | 0.035 | 460 |
| E107 pAF-30K PEG | 17 | 0.031 | 180 |
| N45 pAF-30K PEG | 8 | 0.048 | 600 |
| Q46 pAF-30K PEG | 8.1 | 0.038 | 460 |
| F64 pAF-30K PEG | 15 | 0.036 | 240 |
| E78 pAF-30K PEG | 9.7 | 0.033 | 335 |
| E87 pAF-30K PEG | 5.9 | 0.026 | 440 |
| Y85 pAF-30K PEG | 11 | 0.054 | 490 |
| Q101 pAF-30K PEG | 9 | 0.038 | 425 |
| E96 pAF-30K PEG | 13 | 0.038 | 300 |
| A118 pAF-30K PEG | 11 | 0.037 | 350 |
| N156 pAF-30K PEG | 9.9 | 0.038 | 380 |
| R149 pAF-30K PEG | | | >10 uM |
| R149Y/E107 pAF-30K PEG | | | >10 uM |
| R149S/E107 pAF-30K PEG | | | >10 uM |

TABLE 10-continued

Binding parameters for IFNα2A:IFNAR2 interaction, as determined by SPR

| hIFN polypeptide | $k_{on}$, × $10^{-4}$ 1/M * s | $k_{off}$, 1/s | $K_d$, nM |
|---|---|---|---|
| R149E/E107 pAF-30K PEG | | | >10 uM |
| A145 pAF-30K PEG | | no binding observed | |

Anti-Viral Assays

To evaluate hIFN polypeptide anti-viral activity, $3\times10^4$ human WISH cells (ATCC) were seeded in a 96 well/plate and were subsequently infected with 10,000 PFU of VSV per well. At the time of infection, different amounts of hIFN polypeptide were added. 48 hours post-infection the CPE was evaluated; 42-48 hours was the minimum time required to obtain 100% CPE. CPE was identified by staining the cells with 0.1 ml of 1 mg/ml 3-(4,5-dimethylthiazol-2-yl) 2,5-diphenyltetrazolium bromide (MTT) followed by spectrophotometric reading at 570 nm with 690 nm as the reference wavelength. MTT measures metabolic reduction in mitochondria.

Table 11 and 12 shows the % relative anti-viral activity based on the $IC_{50}$ values obtained with hIFN polypeptides that have a non-natural amino substitution (para-acetylphenylalanine, pAF) at the site indicated and were PEGylated at that site. A few of the hIFN polypeptides had a natural amino acid substitution at position 149 as well. A couple of mutants were made using the NusA system described in Example 27 and contain a methionine at the N-terminus (designated with "M-"). PEGASYS® was used as a control.

TABLE 11

| hIFN polypeptide | % Relative Activity |
|---|---|
| T6 pAF-30K PEG | 25 |
| M16 pAF-30K PEG | 41 |
| M-H34 pAF-30K PEG | 1220 |
| M-G37 pAF-30K PEG | 455 |
| N45 pAF-30K PEG | 67 |
| Q46 pAF-30K PEG | 100 |
| F64 pAF-30K PEG | No activity observed |
| E78 pAF-30K PEG | 111 |
| Y85 pAF-30K PEG | No activity observed |
| E87 pAF-30K PEG | 32 |
| E96 pAF-30K PEG | 20 |
| Q101 pAF-30K PEG | 80 |
| T108 pAF-30K PEG | 571 |
| M111 pAF-30K PEG | 89 |
| D114 pAF-30K PEG | 114 |
| A118 pAF-30K PEG | 72 |
| Q124 pAF-30K PEG | 385 |
| A145 pAF-30K PEG | No activity observed |
| R149 pAF-30K PEG | No activity observed |
| N156 pAF-30K PEG | 49 |
| R149Y/E107 pAF-30K PEG | No activity observed |
| R149S/E107 pAF-30K PEG | No activity observed |
| R149E/E107 pAF-30K PEG | No activity observed |
| PEGASYS ® | 100 |

TABLE 12

| hIFN polypeptide | % Relative Activity |
|---|---|
| E107 pAF-30K PEG | 640 |
| E107 pAF-40K PEG | 62 |
| PEGASYS ® | 100 |

Example 31

This example details the measurement of hIFN activity and affinity of hIFN polypeptides for the hIFN receptor. The hIFN polypeptides described in this Example were generated using the NusA system in Example 27. Natural amino acid substitutions were made to the IFNα2a polypeptide sequence (SEQ ID NO: 2) based on a sequence comparison between limitin and IFNα2a. The "M-" indicates that methionine was the first amino acid in the polypeptide. The M-IFN "HV" or "HV" mutant was generated with the following substitutions in hIFNα-2a (SEQ ID NO: 2): D77-D94 is replaced with the mouse limitin sequence HERALDQLLSSLWRELQV. The M-IFN "CD" or "CD" mutant was generated with the following substitutions in hIFNα-2a (SEQ ID NO: 2): V105-D114 with GQSAPLP.

Biacore Studies (Receptor Binding Affinity)

The sequence for the IFNAR2 extracellular domain (consisting of 206 amino acids ending with sequence LLPPGQ) was amplified from clone MHS1011-61064 (OpenBiosystems, Huntsville, Ala.). This insert was cloned into the pET20 expression vector (Novagen) downstream of the T7 promoter. Protein expression was induced with 0.4 mM IPTG in BL21 (DE3) cells (Novagen).

Since the expressed protein was insoluble, the inclusion bodies were purified from lysed cells and solubilized in 6M GndCl. A 5 ml aliquot (50 mg amount) was reduced with 10 mM DTT for 45 minutes at 37° C. Then the mixture was injected into 200 ml of refolding buffer which consisted of 50 mM Tris pH 8, 20 mM NaCl, 0.5 M Arginine, 10% glycerol at 4° C. and incubated overnight with gentle stirring.

The refolding reaction was then concentrated to 25 ml using an Amicon stirring cell, and dialyzed overnight against 20 mM Tris, pH 8, 20 mM NaCl, 10% glycerol. Monomeric refolded IFNAR ECD was purified on HP Q Sepharose using the AKTA FPLC system (Amersham). Purified IFNAR2 ECD was immobilized on CM5 Biacore chip using a lysine-specific coupling procedure recommended by the manufacturer. About 200 RUs of functional protein were immobilized. Various concentrations of IFN variants in HBS-EP buffer (Biacore) were injected at a flow rate of 50 mcl/minute over the flowcell containing immobilized IFNAR2, and a control flowcell containing immobilized bovine serum albumin. Sensograms generated were fit to the 1:1 interaction model to calculate $k_{on}$, $k_{off}$ and $K_d$ values using BiaEvaluation software (Biacore). Methionyl wild-type interferon (M-WT) was included as a control sample.

Table 13 shows the $k_{on}$, $k_{off}$ and $K_d$ obtained with hIFN polypeptides comprising one or more natural amino acid substitution. These mutants were made using the NusA system described in Example 27 and contain a methionine at the N-terminus (designated with an "M-"). The sequences for the mutants were generated based on amino acid differences found between IFNα2a and limitin.

Table 14 shows the $k_{on}$, $k_{off}$, and $K_d$ obtained with hIFN polypeptides comprising a non-natural amino acid substitution (para-acetylphenylalanine) that was PEGylated with the linear 30K PEG shown in FIG. 19. These mutants were made using the NusA system described above and contain a methionine at the N-terminus (designated with an "M-").

TABLE 13

Binding parameters for IFNα2A:IFNAR2 interaction, as determined by SPR

| IFNα2A | $k_{on}$, × $10^{-4}$ 1/M * s | $k_{off}$, 1/s | $K_d$, nM |
|---|---|---|---|
| M-WT | 6.4 | 0.025 | 4 |
| M-G10E | 6 | 0.03 | 5 |
| M-M16R | 11 | 0.012 | 1.1 |
| M-T79R | 9.2 | 0.026 | 2.8 |
| M-K83Q | 5.1 | 0.027 | 5.4 |
| M-K83S | 3.7 | 0.029 | 7.7 |
| M-Y85L | 7.3 | 0.051 | 7 |
| M-T86S | 6.6 | 0.024 | 3.6 |
| M-E87S | 8 | 0.066 | 9 |
| M-Q90R | 9.9 | 0.021 | 2.1 |
| M-Q91E | 5.5 | 0.041 | 7.5 |
| M-D94V | 7 | 0.017 | 2.4 |
| M-E96K | 7.5 | 0.025 | 3.3 |
| M-R120K | 5.5 | 0.026 | 4.6 |
| M-K121T | 6 | 0.027 | 4.5 |
| M-Q124R/R125G | 6.5 | 0.023 | 3.5 |
| M-L128R | 8.3 | 0.026 | 3.1 |
| M-IFN "HV" | 7.5 | 0.056 | 7.5 |
| M-N93Q | 4.9 | 0.027 | 5.5 |
| M-IFN "CD" | 6.5 | 0.022 | 3.3 |
| M-M16R/Q90R/D94V | 52 | 0.03 | 0.58 |
| M-M16R/Q20R | 21 | 0.022 | 1 |
| M-R149E | | | >10 uM |

TABLE 14

Binding parameters for IFNα2A:IFNAR2 interaction, as determined by SPR

| IFNα2A | $k_{on}$, × $10^{-6}$ 1/M * s | $k_{off}$, 1/s | $K_d$, nM |
|---|---|---|---|
| M-M16 pAF-30K PEG | 0.084 | 0.038 | 460 |
| M-I24 pAF-30K PEG | 0.112 | 0.016 | 145 |
| M-F27 pAF-30K PEG | 0.09 | 0.0086 | 96 |
| M-H34 pAF-30K PEG | 0.18 | 0.019 | 105 |
| M-G37pAF-30K PEG | 0.197 | 0.047 | 240 |

Anti-Viral Assays

To evaluate hIFN polypeptide anti-viral activity, $3 \times 10^4$ human WISH cells (ATCC) were seeded in a 96 well/plate and were subsequently infected with 10,000 PFU of VSV per well. At the time of infection, different amounts of hIFN polypeptide were added. 48 hours post-infection the CPE was evaluated; 42-48 hours was the minimum time required to obtain 100% CPE. CPE was identified by staining the cells with 0.1 ml of 1 mg/ml 3-(4,5-dimethylthiazol-2-yl) 2,5-diphenyltetrazolium bromide (MTT) followed by spectrophotometric reading at 570 nm with 690 nm as the reference wavelength. MTT measures metabolic reduction in mitochondria.

Table 15 shows the % relative anti-viral activity based on the $IC_{50}$ values obtained with hIFN polypeptides that comprise one or more natural amino substitutions.

TABLE 15

| hIFN polypeptide | % Relative Activity |
|---|---|
| M-G10E | 80 |
| M-M16R | 177 |
| M-T79R | 91 |
| M-K83Q | 72 |
| M-K83S | 106 |
| M-Y85L | 53 |
| M-T86S | 114 |
| M-E87S | 90 |
| M-Q90R | 800 |

TABLE 15-continued

| hIFN polypeptide | % Relative Activity |
|---|---|
| M-Q91E | 38 |
| M-N93Q | 90 |
| M-D94V | 200 |
| M-E96K | 50 |
| M-R120K | 105 |
| M-K121T | 52 |
| M-L128R | 70 |
| M-R149E | No activity observed |
| M-Q124R/R125G | 166 |
| M-M16R/Q20R | 500 |
| M-M16R/Q90R/D94V | 0800 |
| M-IFN "HV" | 142 |
| M-IFN "CD" | 70 |
| M-WT | 142 |
| ROFERON ® | 100 |

Example 32

This example details the measurement of hIFN activity and affinity of hIFN polypeptides for the hIFN receptor. The hIFN polypeptides described in this Example were generated using the following method.

Purification by HIC Column 500 ml LB Shake Flask Expression:

For each hIFN polypeptide, *E. coli* transformed with a construct encoding an orthogonal tRNA (J17 described in U.S. Patent Publication No. 20030108885) and an orthogonal aminoacyl tRNA synthetase (E9 described in U.S. patent application Ser. No. 11/292,903 entitled "Compositions of Aminoacyl-tRNA Synthetase and Uses Thereof") with a mutated hIFN polynucleotide were streaked onto a plate to obtain colonies. 2 mL LB containing antibiotic was inoculated with a single colony from the freshly transformed plate. The culture was incubated under constant agitation (250 rpm) at 37° C. until the culture reached an OD600 of approximately 0.05-0.3 (approximately 5-6 hours). 500 mL LB (containing antibiotic and 4 mM pAF) was inoculated with all or part of the 2 mL culture, normalizing the inoculation to synchronize cultures. The culture was incubated under constant agitation (250 rpm) at 37° C. until culture reached an OD600 of approximately 1.0 (approximately 4-5 hours). The culture was then induced with 1 mM IPTG, and the culture was incubated overnight at 37° C. The cells were harvested by centrifugation at 8000 rpm/12000 g; 15 minutes; 4° C. The cell paste was scraped out and stored in 40 mL Oak Ridge tubes. The cell pellets were then frozen at −80° C. until the inclusion body preparation was initiated.

Inclusion Body Preparation from 500 mL Shake Flask:

Buffer 1 was 50 mM NaAc pH 6.0; 100 mM NaCl; 1 mM EDTA; 1.0% Triton X-100. Buffer 2 was 50 mM NaAc pH 6.0; 100 mM NaCl; 1 mM EDTA. Table 16 shows the procedure used for inclusion body preparation.

TABLE 16

| # | Step | Technique | Buffer | Volume (mL) | Centrifugation (g, minutes) |
|---|---|---|---|---|---|
| 1 | Lysis | Avestin C3, 2 passes | 1 | 23 | 20000, 15 |
| 2 | Wash 1 | Sonication, 30 seconds | 1 | 25 | 20000, 15 |
| 3 | Wash 2 | Sonication, 30 seconds | 1 | 25 | 20000, 15 |
| 4 | Rinse 1 | Sonication, 30 seconds | 2 | 25 | 20000, 15 |

TABLE 16-continued

| # | Step | Technique | Buffer | Volume (mL) | Centrifugation (g, minutes) |
|---|------|-----------|--------|-------------|------------------------------|
| 5 | Rinse 2 | Sonication, 30 seconds | 2 | 25 | 20000, 15 |

For the Lysis step, cells were resuspended in 23 mL chilled Buffer 1 by shaking for 1 hour at 4° C. The Avestin C3 was cleaned and rinsed with 100 mL water and then with 30 mL Buffer 1. The cells were then homogenized with 2 passes in Avestin at 15,000-20,000 psi with cooling at 4° C. in the following manner: 1) The sample was added. 2) The sample was processed once until Avestin reservoir was nearly empty; the sample was collected in the original tube (also done for subsequent steps). 3) The collected sample was added back to the Avestin reservoir and re-homogenized. 4) The sample was washed out by homogenizing 12 mL Buffer 1; this was added to the sample. 5) The sample was transferred to 40 mL Oak Ridge Centrifuge tube. 6) The sample was stored and 100 mL water was run through the Avestin, adding it slowly while running to flush the system. 7) 30 mL Buffer 1 was then added to the reservoir and homogenized to prepare for next sample. 8) The steps were then repeated to process the next sample.

For the Wash and Rinse steps, a spatula was used to loosen the pellet off the tube after pouring off supernatant from the last wash and pouring in fresh buffer. Sonication was performed at 75% power with a normal tip, not a microtip. The tip was rinsed with water and wiped with a Kimwipe between samples.

During the first 4 steps, the samples were spun in 40 mL Oak Ridge tubes used to store cell pellets. Rinse 2 was spun by splitting each sample to 2 15 mL conical tubes.

Solubilization and Refolding:

Solubilization was done with 8M GndHCl pH between 5.5-8.5 using 50 mM NaAc or Tris. The inclusion bodies were solublized to a final concentration between 5-10 mg/mL. A final concentration of 10 mM β-Mercaptoethanol was added, and the sample was incubated at room temperature for 30-60 minutes. The material was refolded or stored at –80° C. for long term storage.

The refolding was performed by diluting the solubilized material to a final total protein concentration of 0.5 mg/mL in 4° C. Refold Buffer (50 mM Tris, pH 8.3; 0.5M Arginine). The refolding mixture was stored at 4° C. for 2-4 days.

HIC Purification:

hIFN polypeptide refold samples were allowed to warm to room temperature. A final concentration of 1.5M NaCl was added to the sample, and the sample was incubated at room temperature for 30-60 minutes. Samples were filtered with a 0.22 μM PES filter and loaded onto a Butyl 650M column (Tosoh) equilibrated in HIC Buffer A (20 mM sodium phosphate, pH 7.0; 1.5M NaCl; 2M Urea). A linear gradient to 100% HIC Buffer B (20 mM sodium phosphate, pH 7.0; 2M Urea) was run over 20 column volumes.

SP HP Purification of HIC Pool:

The IFN polypeptide peak was collected from the Butyl column and diluted to less than 30 m/S with water. The pH of samples were adjusted to 3.0 with HCl and were loaded onto a SP HP column (GE Healthcare) equilibrated in SP Buffer A1 (50 mM NaAc, pH 3.0; 1 mM EDTA). After the sample was loaded, the column was washed with 2 column volumes of SP Buffer A followed by 4 column volumes of SP Buffer A2 (50 mM NaAc, pH 5.0; 1 mM EDTA). A linear gradient was run from 100% SP Buffer A2 to 50% SP B Buffer (50 mM NaAc, pH 5.0; 0.5M NaCl; 10% ethylene glycol; 1 mM EDTA) over 15 column volumes.

PEGylation and Purification:

The hIFN polypeptide samples were pooled from the SP HP column and concentrated to 1.0-2.0 mg/mL. 10% Acetic Acid was added to the sample to drop the pH down to 4.0. Oxyamino-derivatized 30K PEG was added to hIFN polypeptide at a 1:12 molar ratio (30 mg/mg IFN/ml), and the mixture was incubated at 28° C. for 48-72 hours. FIG. 19 shows the 30K PEG used in the conjugation. The sample was diluted ten fold with SP Buffer A (50 mM Na acetate, pH 5; 1 mM EDTA). To purify the PEGylated hIFN, a SP HP column (GE Healthcare) was used with a gradient of 0-50% SP buffer B (50 mM Na acetate, pH 5, 0.5 M NaCl, 10% ethylene glycol; 1 mM EDTA) over 15 column volumes. PEGylated IFN eluted around 100 mM salt, followed by non-PEGylated monomer (baseline separation). The fractions of PEGylated hIFN were pooled, dialyzed against the following storage buffer: 20 mM NaAcetate, pH 6, 0.005% Tween, 125 mM NaCl. Samples were concentrated to 1.0-2.0 mg/mL and stored at –80° C.

Biacore Studies (Receptor Binding Affinity)

The sequence for the IFNAR2 extracellular domain (consisting of 206 amino acids ending with sequence LLPPGQ) was amplified from clone MHS1011-61064 (OpenBiosystems, Huntsville, Ala.). This insert was cloned into the pET20 expression vector (Novagen) downstream of the T7 promoter. Protein expression was induced with 0.4 mM IPTG in BL21 (DE3) cells (Novagen).

Since the expressed protein was insoluble, the inclusion bodies were purified from lysed cells and solubilized in 6M GndCl. A 5 ml aliquot (50 mg amount) was reduced with 10 mM DTT for 45 minutes at 37° C. Then the mixture was injected into 200 ml of refolding buffer which consisted of 50 mM Tris pH 8, 20 mM NaCl, 0.5 M Arginine, 10% glycerol at 4° C. and incubated overnight with gentle stirring.

The refolding reaction was then concentrated to 25 ml using an Amicon stirring cell, and dialyzed overnight against 20 mM Tris, pH 8, 20 mM NaCl, 10% glycerol. Monomeric refolded IFNAR ECD was purified on HP Q Sepharose using the AKTA FPLC system (Amersham). Purified IFNAR2 ECD was immobilized on CM5 Biacore chip using a lysine-specific coupling procedure recommended by the manufacturer. About 200 RUs of functional protein were immobilized. Various concentrations of IFN variants in HBS-EP buffer (Biacore) were injected at a flow rate of 50 mcl/minute over the flowcell containing immobilized IFNAR2, and a control flowcell containing immobilized bovine serum albumin. Sensograms generated were fit to the 1:1 interaction model to calculate $k_{on}$, $k_{off}$ and $K_d$ values using BiaEvaluation software (Biacore). Methionyl wild-type interferon (M-WT) and PEGASYS® were included as control samples.

Table 17 shows the $k_{on}$, $k_{off}$, and $K_d$ obtained with hIFN polypeptides comprising the non-naturally encoded amino acid pAF and were PEGylated at the non-naturally encoded amino acid with the linear 30K PEG as shown in FIG. 19. In addition, some of the hIFN polypeptides tested have a natural amino acid substitution. For example, T79R/N45 pAcF-30K PEG was generated by substituting the non-natural amino acid pAF at position 45 of SEQ ID NO: 2 and the threonine amino acid at position 79 was substituted with the naturally encoded amino acid arginine.

TABLE 17

Binding parameters for IFNα2A:IFNAR2 interaction, as determined by SPR

| IFNα2A | $k_{on}, \times 10^{-4}$ 1/M * s | $k_{off}$, 1/s | $K_d$, nM |
|---|---|---|---|
| M-WT | 640 | 0.025 | 4 |
| PEGASYS ® | 6.9 | 0.027 | 390 |
| N45 pAF-30K PEG | 11 | 0.035 | 330 |
| T79R/N45 pAF-30K PEG | 17 | 0.042 | 240 |
| Y85L/N45 pAF-30K PEG | 16 | 0.077 | 480 |
| E87S/N45 pAF-30K PEG | 15 | 0.117 | 800 |
| Q46 pAF-30K PEG | 11 | 0.03 | 270 |
| T79R/Q46 pAF-30K PEG | 15 | 0.032 | 210 |
| Y85L/Q46 pAF-30K PEG | 16.5 | 0.07 | 420 |
| E87S/Q46 pAF-30K PEG | 15 | 0.093 | 630 |
| E107 pAF-30K PEG | 14.5 | 0.029 | 200 |
| T79R/E107 pAF-30K PEG | 17 | 0.03 | 170 |
| Y85L/E107 pAF-30K PEG | 20 | 0.065 | 330 |
| Y85S/E107 pAF-30K PEG | 19 | 0.057 | 300 |
| E87S/E107 pAF-30K PEG | 18 | 0.09 | 500 |
| L80 pAF-30K PEG | 6.7 | 0.034 | 500 |
| Y89 pAF-30K PEG | 14 | 0.029 | 200 |

Anti-Viral Assays

To evaluate hIFN polypeptide anti-viral activity, $3 \times 10^4$ human WISH cells (ATCC) were seeded in a 96 well/plate and were subsequently infected with 10,000 PFU of VSV per well. At the time of infection, different amounts of hIFN polypeptide were added. 48 hours post-infection the CPE was evaluated; 42-48 hours was the minimum time required to obtain 100% CPE. CPE was identified by staining the cells with 0.1 ml of 1 mg/ml 3-(4,5-dimethylthiazol-2-yl) 2,5-diphenyltetrazolium bromide (MTT) followed by spectrophotometric reading at 570 nm with 690 nm as the reference wavelength. MTT measures metabolic reduction in mitochondria.

Table 18 shows the % relative anti-viral activity based on the $IC_{50}$ values obtained with hIFN polypeptides that have a non-natural amino substitution at the site indicated and were PEGylated at that site. hIFN polypeptides with a lower $IC_{50}$ value show higher % relative activity. Some of the PEGylated hIFN polypeptides in addition had a naturally encoded amino acid substitution (T79R; Y85L; E87S; Y85S).

TABLE 18

| hIFN polypeptide | % Relative Activity |
|---|---|
| PEGASYS ® | 100 |
| N45pAF-30K PEG | 300 |
| T79R/N45pAF-30K PEG | 529 |
| Y85L/N45pAF-30K PEG | 150 |
| E87S/N45pAF-30K PEG | 139 |
| Q46pAF-30K PEG | 395 |
| T79R/Q46pAF-30K PEG | 441 |
| Y85L/Q46pAF-30K PEG | 188 |
| E87S/Q46pAF-30K PEG | 197 |
| E107pAF-30K PEG | 740 |
| T79R/E107pAF-30K PEG | 728 |
| Y85L/E107pAF-30K PEG | 336 |
| Y85S/E107pAF-30K PEG | 176 |
| E87S/E107pAF-30K PEG | 268 |
| L80pAF-30K PEG | 145 |
| Y89pAF-30K PEG | 176 |

Example 33

Measurement of Anti-Proliferative Activity hIFN polypeptides described in the previous examples (Examples 30-32) were also assayed for anti-proliferative activity. A prominent effect of IFNα's is their ability to inhibit cell growth, which is of major importance in determining anti-tumor action. The human lymphoblastoid Daudi cell line has proven to be extremely sensitive to IFNα's, and it has been used to measure antiproliferative activity in many IFNα's and derived hybrid polypeptides (Meister et al., J Gen Virol. (1986) August; 67 (Pt 8):1633-43). Use of this cell line has been facilitated by its ability to be grown in suspension cultures (Evinger and Pestka, (1981) Methods Enzymol. 79:362-368).

The human Daudi B cell line was purchased from ATCC (Manassas, Va.) and grown in RPMI 1640 supplemented with 10% heat inactivated fetal bovine serum (Hyclone, Logan, Utah). The cell culture was maintained at 37° C. in a humidified atmosphere of 5% $CO_2$.

The Daudi cells were plated at a density of $1 \times 10^4$ cells/well in a flat-bottom, 96-well plate. The cells were treated with increasing concentration of IFNα2A in triplicates per dose concentration in a final volume of 200 ul. Following a 4-day incubation period at 37° C. with 5% $CO_2$, 20 ul of WST-1 solution Reagent (Roche cat#1644807) was added to each well, and the culture was allowed to incubate for an additional 6 hours. Absorbance was read at 440 nm using a Spectromax. $IC_{50}$s were obtained from dose response curves plotted with OD 440 nm (average of triplicates) against protein concentration with SigmaPlot.

Table 19 shows the results obtained with different hIFN molecules that are nonPEGylated and PEGylated. "Cu" indicates polypeptides that were made using the copper column as described in Example 30. "HIC" indicates polypeptides that were made using the HIC method as described in Example 32.

TABLE 19

| PEG | hIFN polypeptide | $IC_{50}$ | % PEGASYS ® |
|---|---|---|---|
| 30K PEG | PEGASYS ® | 0.41 | 100% |
| 40K PEG | E107 pAF | 0.84 | 206% |
| 30K PEG | E107 pAF Cu | 0.04 | 10% |
| 30K PEG | T108 pAF | 0.09 | 22% |
| 30K PEG | D114 pAF | 0.27 | 66% |
| 30K PEG | A118 pAF | 0.40 | 98% |
| 30K PEG | M111 pAF | 0.26 | 64% |
| 30K PEG | Q101 pAF | 0.28 | 69% |
| 30K PEG | N156 pAF | 0.56 | 137% |
| 30K PEG | E96 pAF | 1.27 | 311% |
| 30K PEG | Q46 pAF | 0.14 | 34% |
| 30K PEG | E78 pAF | 0.22 | 54% |
| 30K PEG | E87 pAF | 0.86 | 211% |
| 30K PEG | N45 pAF | 0.34 | 83% |
| 30K PEG | M16 pAF | 0.52 | 127% |
| 30K PEG | T6 pAF | 0.79 | 193% |
| 30K PEG | R149Y/E107 pAF | 3.84 | 940% |
| No PEG | M-Q90R | 0.01 | 3% |
| No PEG | M-D94V | 0.01 | 3% |
| No PEG | M-IFN "HV" | 0.02 | 5% |
| No PEG | M-Q124R/R125G | 0.01 | 3% |
| No PEG | M-K83S | 0.02 | 5% |
| No PEG | M-WT | 0.02 | 4% |
| No PEG | M-N93Q | 0.01 | 3% |
| No PEG | M-T86S | 0.01 | 3% |
| No PEG | M-K121T | 0.02 | 5% |
| No PEG | M-R120K | 0.01 | 3% |
| No PEG | M-K83Q | 0.03 | 7% |
| No PEG | M-M16R | 0.01 | 2% |
| No PEG | M-E87S | 0.02 | 4% |
| No PEG | ROFERON ® | 0.01 | 3% |
| No PEG | M-IFN "CD" | 0.01 | 3% |
| No PEG | M-G10E | 0.01 | 3% |
| No PEG | M-T79R | 0.01 | 4% |
| No PEG | M-Y85L | 0.03 | 7% |
| No PEG | M-E96K | 0.13 | 32% |
| No PEG | M-R149E* | dead | dead |

TABLE 19-continued

| PEG | hIFN polypeptide | IC$_{50}$ | % PEGASYS ® |
|---|---|---|---|
| No PEG | Sigma WT IFN | 0.01 | 2% |
| 30K PEG | N45 pAF Cu | 0.22 | 55% |
| 30K PEG | N45 pAF HIC | 0.07 | 17% |
| 30K PEG | Q46 pAF Cu | 0.12 | 30% |
| 30K PEG | Q46 pAF HIC | 0.12 | 28% |
| 30K PEG | L80 pAF | 0.08 | 19% |
| 30K PEG | Y89 pAF | 0.11 | 27% |
| 30K PEG | E107pAF HIC | 0.03 | 7% |
| 30K PEG | T79R/N45 pAF | 0.04 | 10% |
| 30K PEG | Y85L/E107 pAF | 0.06 | 14% |
| 30K PEG | Y85S/E107 pAF | 0.12 | 30% |

Example 34

Colony Formation Assays

Colony formation assays such as those described by Giron-Michel, J. in Leukemia 2002 16:1135-1142 may be used to evaluate proliferation of progenitor cells by hIFN polypeptides of the invention, Cord blood may be used in colony formation assays.

Evaluation of the Toxicity of hIFN Polypeptides on Human Myeloid and Erythroid Progenitors Using a methylcelluose-based in vitro colony forming assay, the hematopoietic toxicity of twenty one nonPEGylated compounds (twenty hIFN polypeptides with ROFERON® as control) and eighteen PEGylated compounds (seventeen polypeptides PEGylated with a 30K PEG with PEGASYS® as a control) were tested. The nonPEGylated hIFN polypeptides were made by the NusA method shown in Example 27 and were characterized as shown in Example 31. PEGylated hIFN polypeptides were generated and characterized as shown in Examples 30 and 31.

Cells: Normal human bone marrow light density cells (Poietics Inc., Maryland) were stored at −152° C. until required for the assay. On the day of the experiment, the cells were thawed rapidly at 37° C., and the contents of the vial were diluted in 10 mls of Iscove's medium containing 2% fetal bovine serum and washed by centrifugation. The supernatant was discarded, and the cell pellet resuspended in a known volume of Iscove's medium containing 2% FBS. A cell count (3% glacial acetic acid) and viability assessment by Trypan Blue exclusion was performed.

Test samples: Compounds were in a buffer of 20 mM NaAc, 125 mM NaCl, 0.005% Tween 80, pH 6.0. Each compound was tested in ten test concentrations in a series of five fold dilutions. Triplicates were performed at each dose concentration. Dilutions of each compound were prepared with the same buffer to generate the required dilutions. When added to methylcellulose, the buffer was at a final concentration of 6.7% and compound concentrations ranged from 5-0.00000256 ug/ml for nonPEGylated hIFN test polypeptides and 26-0.0000133 ug/ml for 30K PEGylated hIFN test polypeptides. In instances where the initial 30K PEGylated hIFN test polypeptides concentrations are low, a concentration range of 14-0.000007168 ug/ml was adopted instead.

Method: Clonogenic progenitors of the erythroid (CFU-E and BFU-E), granulocyte-monocyte (CFU-GM) and multi-potential (CFU-GEMM) lineages were assessed in methylcellulose-based medium (MethoCult™ 4434) containing saturating concentrations of the cytokines SCF (Stem Cell Factor; 50 ng/mL), GM-CSF (Granulocyte Macrophage Colony Stimulating Factor; 10 ng/mL), IL-3 (Interleukin 3; 10 ng/mL), and EPO (Erythropoietin; 3 U/mL). CFU-E is a small erythroid colony derived from the most mature erythroid colony forming cells. It contains one to two clusters with a total number of 8-200 erythroblasts. BFU-E is a larger erythroid colony derived from a more primitive cell. It contains greater than 200 erythroblasts. CFU-GM is a colony that is derived from a colony forming cell capable of producing colonies with forty or more granulocyte-monocyte and/or macrophage cells. CFU-GEMM is a colony that contains cells from more than one lineage. It is derived from the most primitive colony forming cell and contains erythroid cells as well as twenty or more granulocytes, macrophages, and megakaryocytes. At each assay set up, a standard control containing MethoCult™ 4434, cells and media and a buffer control containing MethoCult™4434, cells and equivalent amount of buffer but no compound were included to establish a condition in which no toxicity should be observed.

Clonogenic progenitors of the erythroid (CFU-E and BFU-E), granulocyte-monocyte/myeloid (CFU-GM) and multipotential (CFU-GEMM) lineages were set up in the methylcellulose-based media described. The compounds were added to the MethoCult™ to give final concentrations as described above. Vehicle control cultures containing no compound but equivalent concentrations of vehicle buffer as well as standard controls containing no compounds or vehicle buffer but media alone were also initiated. All cultures were set up in triplicate at $1 \times 10^4$ cells per culture. Following 14 days in culture, the colonies were assessed and scored. The colonies were divided into the following categories, based on size and morphology: CFU-E, BFU-E, CFU-GM, and CFU-GEMM.

Results and analysis: Triplicate cultures for CFU-E, BFU-E, CFU-GM, and CFU-GEMM were enumerated. In addition, the distribution of colony types as well as general colony and cellular morphology were analyzed. In all test sets, no difference between the numbers of colonies generated in standard cultures compared to the buffer controls were observed. However, in the presence of each nonPEGylated or PEGylated hIFN polypeptides, colony numbers as well as colony size of both the myeloid and erythroid lineage were perturbed when compared to standard and buffer assay controls. The morphology of the resulting erythroid and myeloid colonies was however not affected. A dose dependent toxic effect on both myeloid and erythroid progenitors were seen for all nonPEGylated and PEGylated hIFN tested including compound controls ROFERON® and PEGASYS®.

Further analysis of test compounds were performed to normalize for differences in anti-viral activity observed between compounds. Mass concentrations of hIFN polypeptides used in the colony formation assay were divided by the anti-viral IC$_{50}$ values measured in the VSV replication assay. The myeloid and erythroid colony counts were then plotted on Y-axis against the normalized protein concentration on a log x-axis. Relative toxicity of each test polypeptides compared to the appropriate compound control was determined by the factor rho where rho represents the shift in x-axis between two curves. When rho>1, test compound is more potent and hence more toxic than control. When rho>1, the fold improvement was represented as a negative number that has the value of rho (−rho) (See Tables 22 and 23). When rho<1, test compound is less toxic than compound control. When rho<1, the fold improvement was represented as a positive number that has the value of 1/rho (1/rho) (See Tables 20 and 21). For nonPEGylated hIFN polypeptides, ROFERON® was used as the compound control. For PEGylated hIFN polypeptides, PEGASYS® was used as the compound control.

TABLE 20

| nonPEG Candidates | Fold improvement in toxicity |
|---|---|
| M-G10E | −1.69 |
| M-M16R | −1.97 |
| M-T79R | 2.33 |
| M-K83Q | −2.13 |
| M-K83S | 1.71 |
| M-Y85L | 6.63 |
| M-T86S | 2.74 |
| M-E87S | 4.50 |
| M-Q90R | −5.03 |
| M-Q91E | 1.81 |
| M-N93Q | −4.31 |
| M-D94V | −36.79 |
| M-E96K | −1.76 |
| M-R120K | −14.11 |
| M-K121T | −2.13 |
| M-Q124R/R125G | −25.33 |
| M-L128R | −1.79 |
| M-IFN "CD" | −2.60 |
| M-IFN "HV" | −101.85 |

TABLE 21

| PEG Candidates | Fold improvement in toxicity |
|---|---|
| T6pAF-30K PEG | 1.56 |
| M16pAF-30K PEG | 3.13 |
| M-H34pAF 30K PEG | −3.19 |
| M-G37pAF 30K PEG | 2.78 |
| N45pAF 30K PEG | 5.26 |
| Q46pAF 30K PEG | 4.76 |
| E78pAF 30K PEG | 1.64 |
| E87pAF 30K PEG | 1.92 |
| E96pAF 30k PEG | −11.06 |
| Q101pAF 30K PEG | −2.76 |
| E107pAF 30K PEG | 2.50 |
| E107pAF 40K PEG | 1.67 |
| T108pAF 30K PEG | 2.38 |
| M111pAF 30K PEG | −1.24 |
| D114pAF 30K PEG | −1.83 |
| A118pAF 30K PEG | −2.89 |
| N156pAF 30K PEG | −2.77 |

Example 34

Comparison of hIFN Polypeptides

For the VSV assay, more active molecules have a lower $IC_{50}$ value. If the VSV $IC_{50}$ of the test compound was less than the VSV $IC_{50}$ of M-WT (wild-type interferon with a methionine at the N-terminus), then the fold improvement was expressed as VSV $IC_{50}$ M-WT/VSV $IC_{50}$ test compound. If the VSV $IC_{50}$ of the test compound was greater than the VSV $IC_{50}$ of M-WT, then the fold improvement was expressed as −(VSV $IC_{50}$ test compound/VSV $IC_{50}$ M-WT). Table 22 shows the fold improvement data for a set of hIFN polypeptides described also in Example 33.

TABLE 22

| nonPEG Candidates | Fold improvement in VSV anti-viral activity |
|---|---|
| M-G10E | −1.79 |
| M-M16R | 1.24 |
| M-T79R | −1.55 |
| M-K83Q | −1.96 |
| M-K83S | −1.34 |
| M-Y85L | −2.68 |
| M-T86S | −1.25 |
| M-E87S | −1.61 |
| M-Q90R | 5.60 |
| M-Q91E | −3.75 |
| M-N93Q | −1.61 |
| M-D94V | 1.40 |
| M-E96K | −3.00 |
| M-R120K | −1.36 |
| M-K121T | −2.71 |
| M-Q124R/R125G | 1.17 |
| M-L128R | −2.00 |
| M-IFN "CD" | −2.14 |
| M-IFN "HV" | 1.00 |

For the VSV assay, more active molecules have a lower $IC_{50}$ value. If the VSV $IC_{50}$ of the test compound was less than the VSV $IC_{50}$ of PEGASYS®, then the fold improvement was expressed as VSV $IC_{50}$ PEGASYS®/VSV $IC_{50}$ test compound. If the VSV $IC_{50}$ of the test compound was greater than the VSV $IC_{50}$ of PEGASYS®, then the fold improvement was expressed as −(VSV $IC_{50}$ test compound/VSV $IC_{50}$ PEGASYS®). Table 23 shows the fold improvement data for one set of PEGylated hIFN polypeptides described also in Example 33.

TABLE 23

| PEG Candidates | Fold improvement in VSV anti-viral activity |
|---|---|
| T6pAF-30K PEG | −4.00 |
| M16pAF-30K PEG | −2.43 |
| M-H34pAF 30K PEG | 12.20 |
| M-G37pAF 30K PEG | 4.55 |
| N45pAF 30K PEG | −1.50 |
| Q46pAF 30K PEG | 1.00 |
| E78pAF 30K PEG | 1.11 |
| E87pAF 30K PEG | −3.13 |
| E96pAF 30K PEG | −5.00 |
| Q101pAF 30K PEG | −1.25 |
| E107pAF 30K PEG | 4.95 |
| E107pAF 40K PEG | −1.73 |
| T108pAF 30K PEG | 5.71 |
| M111pAF 30K PEG | −1.13 |
| D114pAF 30K PEG | 1.14 |
| A118pAF 30K PEG | −1.38 |
| N156pAF 30K PEG | −2.04 |

Table 24 shows a list of candidates with improved toxicity and their associated fold improvement in anti-viral activity.

TABLE 24

| hIFN polypeptide | Fold improvement anti-viral activity | Fold improvement in Toxicity |
|---|---|---|
| M-T79R | −1.55 | 2.33 |
| M-K83S | −1.34 | 1.71 |
| M-Y85L | −2.68 | 6.63 |
| M-T86S | −1.25 | 2.74 |
| M-E87S | −1.61 | 4.50 |
| M-Q91E | −3.75 | 1.81 |
| T6pAF 30K PEG | −4.00 | 1.56 |
| M16pAF 30K PEG | −2.43 | 3.13 |
| M-G37pAF 30K PEG | 4.55 | 2.78 |
| N45pAF 30K PEG | −1.50 | 5.26 |
| Q46pAF 30K PEG | 1.00 | 4.76 |
| E78pAF 30K PEG | 1.11 | 1.64 |
| E87pAF 30K PEG | −3.13 | 1.92 |
| E107pAF 30K PEG | 4.95 | 2.50 |
| T108pAF 30K PEG | 5.71 | 2.38 |

Example 35

Human Clinical Trial of the Safety and/or Efficacy of PEGylated hIFN Comprising a Non-Naturally Encoded Amino Acid A Phase 0 study is performed to investigate microdosing of hIFN polypeptides of the invention. This study involves a small number of subjects. These studies involve measuring changes in molecular markers with administration of a fraction of the therapeutic dose. These same markers correlate with a therapeutic response when the drug is administered to an affected individual. The drug-response information obtained is useful for Phase I and Phase II trial design.

Objective To compare the safety and pharmacokinetics of subcutaneously administered PEGylated recombinant human hIFN comprising a non-naturally encoded amino acid with the commercially available hIFN products ROFERON A® or INTRON A®.

Patients Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to hIFN within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design This will be a Phase I, single-center, open-label, randomized, two-period crossover study in healthy male volunteers. Eighteen subjects are randomly assigned to one of two treatment sequence groups (nine subjects/group). IFN is administered over two separate dosing periods as a bolus s.c. injection in the upper thigh using equivalent doses of the PEGylated hIFN comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated hIFN as well. Multiple formulations of IFN that are approved for human use may be used in this study. ROFERON A® and/or INTRON A® are commercially available IFN products approved for human use. The experimental formulation of hIFN is the PEGylated hIFN comprising a non-naturally encoded amino acid.

Blood Sampling Serial blood is drawn by direct vein puncture before and after administration of hIFN. Venous blood samples (5 mL) for determination of serum IFN concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods An ELISA kit procedure (BioSource International (Camarillo, Calif.)), is used for the determination of serum IFN concentrations.

Safety Determinations Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis Post-dose serum concentration values are corrected for pre-dose baseline IFN concentrations by subtracting from each of the post-dose values the mean baseline IFN concentration determined from averaging the IFN levels from the three samples collected at 30, 20, and 10 minutes before dosing. Pre-dose serum IFN concentrations are not included in the calculation of the mean value if they are below the quantification level of the assay. Pharmacokinetic parameters are determined from serum concentration data corrected for baseline IFN concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results Mean serum IFN concentration-time profiles (uncorrected for baseline IFN levels) in all 18 subjects after receiving a single dose of commercially available hIFN (e.g. ROFERON A® or INTRON A®) are compared to the PEGylated hIFN comprising a non-naturally encoded amino acid at each time point measured. All subjects should have pre-dose baseline IFN concentrations within the normal physiologic range. Pharmacokinetic parameters are determined from serum data corrected for pre-dose mean baseline IFN concentrations and the $C_{max}$ and $t_{max}$ are determined. The mean $t_{max}$ for hIFN (e.g. ROFERON®) is significantly shorter than the $t_{max}$ for the PEGylated hIFN comprising the non-naturally encoded amino acid. Terminal half-life values are significantly shorter for hIFN (e.g. INTRON A®) compared with the terminal half-life for the PEGylated hIFN comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery. Alternatively, the Phase I study is performed in HCV subjects to evaluate PEGylated hIFN polypeptide.

In conclusion, subcutaneously administered single doses of PEGylated hIFN comprising non-naturally encoded amino acid will be safe and well tolerated by healthy male subjects or HCV subjects. Based on a comparative incidence of adverse events, clinical laboratory values, vital signs, and physical examination results, the safety profiles of hIFN (e.g. ROFERON A®) and PEGylated hIFN comprising non-naturally encoded amino acid will be equivalent. The PEGylated hIFN comprising non-naturally encoded amino acid potentially provides large clinical utility to patients and health care providers.

Example 36

This example details methods used to generate hIFN polypeptides comprising a non-naturally encoded amino acid. Purified refolded hIFN polypeptides were conjugated to poly(ethylene glycol) according to the methods described below. Modifications to the methods described below and alternate methods to refold polypeptides such as hIFN polypeptides are known to those of ordinary skill in the art. Modifications to the methods described include, but are not limited to, the addition, substitution, or subtraction of one or more steps mentioned below. Potential methods that may be used or one or more modifications to the methods described include, but are not limited to, washing inclusion bodies with reagents that reduce the amount of contaminant proteins that potentially interact with the hIFN polypeptide such reagents include but are not limited to urea and deoxycholic acid; adding a reagent to the refolding reaction such reagents include but are not limited to a denaturant, guanidine HCl, urea, cysteine, and catalytic amounts of a reducing agent. Columns other than those described may be used in to isolate or purify hIFN polypeptides comprising a non-naturally encoded amino acid. Such columns include but are not limited to a hydrophobic interaction chromatography (HIC) column such as a butyl, octyl, or phenyl HIC column. Alternate conditions and solutions may be used for isolation or purification of hIFN polypeptides, including but not limited to the use of alternate salts such as ammonium sulfate, sodium citrate, and other salts; the adjustment of buffer components including but not limited to, the adjustment of salt concentrations to facilitate binding to a column used in purification/isolation; alterations in pH; the replacement of one or more reagents; and the inclusion of one or more reagents, including but not limited to, arginine.

Alternate methods include but are not limited to, solubilization of cell pellets with guanidine and other methods known to those of ordinary skill in the art. Different strains of bacteria may also be used in the expression of hIFN polypeptides.

Purification of IFN Inclusion Bodies

For each hIFN polypeptide, *E. coli* strains BL21(A1), BL21(DE3) or W3110(B2) transformed with a construct encoding an orthogonal tRNA (J17 described in U.S. Patent Publication No. 20030108885) and an orthogonal aminoacyl tRNA synthetase (E9 described in U.S. patent application Ser. No. 11/292,903 entitled "Compositions of Aminoacyl-tRNA Synthetase and Uses Thereof") with a mutated hIFN polynucleotide. The bacteria were plated onto LB Agar with ampicillin plates and incubated overnight at 37° C. Colonies were selected and grown in culture to make glycerol stocks.

5 ul aliquots of glycerol stock were used to make a 5 ml starter culture in the morning. The starter culture was added to LB media containing para-acetylphenylalanine (pAF) in the morning (1×LB; 4 mM pAF; 1×AMP), and the cells were induced in the evening or when the culture had an OD of greater than 1.0. The culture was grown/induced at 37° C. degrees with shaking at 250 rpm overnight.

The next morning the OD was measured of the cultures, and the cells were pelleted. The OD measurements of the cultures were between about 3 and about 8. The cell pellet was either frozen at −80° C. or the inclusion bodies were prepared from the pellet immediately. An aliquot was analyzed by SDS-PAGE with a Coomassie stain to check expression and the length of product produced. The bacterial pellet was resuspended in 35 ml of IB1 buffer (50 mM NaAc, pH 6.0; 100 mM NaCl; 1 mM EDTA; 0.1% Triton X). Then the sample was sonicated six times to resuspend and lyse the cells. 30 second bursts of sonication were followed by 1 minute incubations on ice. The bacterial lysate was centrifuged in a 50 ml Oakridge tube at 13,000 rpm for 20 minutes at 4° C., and the supernatant was discarded. The pellet was washed four times with IB1 buffer using sonication to resuspend. The inclusion bodies were spun down, and the supernatant was discarded. The pellet was washed two times with IB2 buffer (50 mM NaAc, pH 6.0; 100 mM NaCl; 1 mM EDTA), and the supernatant was discarded. The pellet was resuspended in 5-15 ml of 8M Guanidine HCl (8 M GnHCl; 50 mM NaAc pH 6.0) and were resuspended using a douncer. The concentration of the sample was determined using a 100× dilution, and the OD was measured at 280 nm. The IFN extinction coefficient is 22800 or 1.17. Sample concentrations were normalized to 5.0 mg/ml protein. The purity of the inclusion bodies was determined by SDS PAGE gel with a Coomasie stain. Twenty-seven hIFN polypeptides with a para-acetylphenylalanine substitution were suppressed, and inclusion bodies for twenty-seven mutants were isolated. Each of the twenty-seven mutants generated had one non-naturally encoded amino acid substitution in which para-acetylphenylalanine replaced a naturally encoded amino acid in hIFN (SEQ ID NO: 2). The 27 hIFN polypeptides generated had a substitution at one of the following positions: 23, 24, 25, 26, 27, 28, 30, 31, 32, 33, 128, 129, 131, 132, 133, 134, 135, 136, 137, 158, 159, 160, 161, 162, 163, 164, and 165.

Refolding hIFN Using Purified Inclusion Bodies 100 mg of 5.0 mg/ml hIFN was added to 400 ml Refolding Buffer (50 mM NaAc pH 6.0; 0.1% Tween 20) while spinning slowly at 4° C. Refolding was performed for 24 to 48 hours. The refolding mixture was then brought to room temperature. Then 50 uM CuCl was added, and the sample was mixed. The sample was incubated for 15 minutes at room temperature.

Protein Purification and PEGylation

Any precipitate that formed during refolding was spun down or filtered, and the correctly folded hIFN polypeptide was purified using a copper chelate column. Copper Column Buffer A was 50 mM NaAc, pH 5.0; 0.15 M NaCl; 0.1% Tween 20. Copper Column Buffer B was 100 mM NaAc. pH 3.5; 0.15 M NaCl; 0.1% Tween 20.

An aliquot was checked at this point by SDS-PAGE with a Commassie stain. Pooled fractions from the copper column were loaded onto a 5 ml SP HP cation exchange column. The 5 ml SP HP Buffer A was 50 mM NaAc pH 6.0; 1 mM EDTA. The 5 ml SP HP buffer B was 50 mM NaAc pH 6.0; 1 mM EDTA; 500 mM NaCl; 10% Ethylene glycol. The amount of total protein was measured at this point using by measuring the OD at 280 nm, and SDS-PAGE with a Commassie stain was also performed.

Fractions from the copper chelate column were pooled and were concentrated to greater than 1.0 mg/ml and 10% acetic acid was added to each sample to bring the pH to 4.0. The linear 30K PEG shown in FIG. 19 was added at a 12:1 molar ratio. The sample was incubated at 28° C. for 24 to 48 hours. The sample was then diluted 10-fold with Milli-Q water, and the PEGylated hIFN polypeptide was purified over a 5 ml SP HP column. SDS-PAGE was performed with a Commassie stain to analyze the sample and determine the level of higher molecular weight species and unPEGylated contaminants. Fractions from the SP column were collected, and then the pool was dialyzed against Storage Buffer (25 mM NaAc, pH 6.0; 120 mM NaCl; 0.005% Tween 80). An aliquot of the final product was then analyzed by SDS-PAGE. The final product was concentrated to 180 ug/ml, and aliquots were stored at −80° C.

Example 37

VSV Anti-Viral Assay

Antiviral activity of hIFN polypeptides may be measured by a variety of assays. The antiviral activity of PEGylated hIFN polypeptides was determined using the Vesicular Stomatitis Virus (VSV). The culture media for this assay was DMEM, 10% FBS, 1% Penicillin/Streptomycin, 5 ml HEPES. Additional reagents included RPMI without FBS and Phenol Red. The concentration of MTT stock used was 5 mg/mL in PBS. This stock solution was stored for only two weeks at 4° C.

Human WISH cells were seeded at 30,000 cells/well in 50 µL of culture media. The following day, 2× serial dilutions were performed of the hIFN polypeptides in culture media. PEGASYS® was used as a control in these experiments. In triplicate, 100 µL of the diluted hIFN polypeptides was added to the WISH cells for a final well volume of 150 µL. The cells and hIFN polypeptides were incubated for 6 hours at 37° C. in a $CO_2$ incubator. After this six hour incubation, 10,000 PFU of VSV was added per well, in a volume of 50 µL of media; 20 µL of VSV was diluted in 5 ml of media per 96 well/plate. The media was removed by aspiration forty-five hours post-infection. The plates were gently tapped on paper towels to remove residual media.

50 µL of 1 mg/mL MTT (3-(4,5-dimethylthiazol-2-yl) 2,5-diphenyltetrazolium bromide) prepared in RPMI without Phenol Red and FBS was added from a 5 mg/mL MTT stock solution. 1 mg/mL MTT was usually prepared fresh for every assay. Next, the plates were incubated for three hours at 37° C. in the $CO_2$ incubator. The MTT was carefully removed by aspiration. 50 µL of isopropanol was added per well. The plates were placed on a plate-shaker for 30 to 40 seconds to complete the formation of MTT. The plates were read at 560 nm with 690 nm as a reference wavelength. The data was plotted and the $IC_{50}$ calculated using the Sigma-Plot program.

Table 25 summarizes the anti-viral activity of 20 hIFN polypeptides that were conjugated to 30K PEG via a para-acetylphenylalanine substitution in the polypeptide. The second column lists the averaged $IC_{50}$ values for each compound across multiple anti-viral activity experiments. The third column is the % Efficacy relative to the averaged $IC_{50}$ values found in the second column.

The fourth column is the Average % Efficacies. For this data, the % Efficacy was established by comparing $IC_{50}$s to the $IC_{50}$ of PEGASYS® in individual experiments. Then the % Efficacies from all experiments were averaged.

TABLE 25

| hIFN polypeptide | AVE IC50 | % Efficacy | AVE % Efficacy (individual expts.) |
| --- | --- | --- | --- |
| PEGASYS ® | 7.26 | 100% | 100% |
| K23 pAF-30K PEG | 7.18 | 101% | 95% |
| I24 pAF-30K PEG | 2.78 | 261% | 261% |
| S25 pAF-30K PEG | 27.51 | 26% | 22% |
| L26 pAF-30K PEG | No Activity observed to 50 ng/mL | No Activity observed to 50 ng/mL | No Activity observed to 50 ng/mL |
| F27 pAF-30K PEG | 2.44 | 298% | 277% |
| S28 pAF-30K PEG | not tested | not tested | not tested |
| L30 pAF-30K PEG | No Activity observed to 50 ng/mL | No Activity observed to 50 ng/mL | No Activity observed to 50 ng/mL |
| K31 pAF-30K PEG | 4.58 | 159% | 170% |
| D32 pAF-30K PEG | not tested | not tested | not tested |
| R33 pAF-30K PEG | No Activity observed to 50 ng/mL | No Activity observed to 50 ng/mL | No Activity observed to 50 ng/mL |
| L128 pAF-30K PEG | 3.45 | 211% | 200% |
| Y129 pAF-30K PEG | not tested | not tested | not tested |
| K131 pAF-30K PEG | 1.49 | 487% | 536% |
| E132 pAF-30K PEG | not tested | not tested | not tested |
| K133 pAF-30K PEG | not tested | not tested | not tested |
| K134 pAF-30K PEG | 1.46 | 496% | 560% |
| Y135 pAF-30K PEG | 10.25 | 71% | 76% |
| S136 pAF-30K PEG | not tested | not tested | not tested |
| P137 pAF-30K PEG | not tested | not tested | not tested |
| Q158 pAF-30K PEG | 7.02 | 103% | 107% |

TABLE 25-continued

| hIFN polypeptide | AVE IC50 | % Efficacy | AVE % Efficacy (individual expts.) |
|---|---|---|---|
| E159 pAF-30K PEG | 15.69 | 46% | 39% |
| S160 pAF-30K PEG | 17.95 | 40% | 35% |
| L161 pAF-30K PEG | 13.99 | 52% | 45% |
| R162 pAF-30K PEG | 22.09 | 33% | 27% |
| S163 pAF-30K PEG | 11.73 | 62% | 55% |
| K164 pAF-30K PEG | 9.96 | 73% | 69% |
| E165 pAF-30K PEG | 7.93 | 92% | 81% |

Example 38

This example details the measurement of hIFN activity and affinity of hIFN polypeptides for the hIFN receptor.
Biacore Studies (Receptor Binding Affinity)

The sequence for the IFNAR2 extracellular domain (consisting of 206 amino acids ending with sequence LLPPGQ) was amplified from clone MHS1011-61064 (OpenBiosystems, Huntsville, Ala.). This insert was cloned into the pET20 expression vector (Novagen) downstream of the T7 promoter. Protein expression was induced with 0.4 mM IPTG in BL21 (DE3) cells (Novagen).

Since the expressed protein was insoluble, the inclusion bodies were purified from lysed cells and solubilized in 6M GndCl. A 5 ml aliquot (50 mg amount) was reduced with 10 mM DTT for 45 minutes at 37° C. Then the mixture was injected into 200 ml of refolding buffer which consisted of 50 mM Tris pH 8, 20 mM NaCl, 0.5 M Arginine, 10% glycerol at 4° C. and incubated overnight with gentle stirring.

The refolding reaction was then concentrated to 25 ml using an Amicon stirring cell, and dialyzed overnight against 20 mM Tris, pH 8, 20 mM NaCl, 10% glycerol. Monomeric refolded IFNAR ECD was purified on HP Q Sepharose using the AKTA FPLC system (Amersham). Purified IFNAR2 ECD was immobilized on CM5 Biacore chip using a lysine-specific coupling procedure recommended by the manufacturer. About 200 RUs of functional protein were immobilized. Various concentrations of IFN variants in HBS-EP buffer (Biacore) were injected at a flow rate of 50 mcl/minute over the flowcell containing immobilized IFNAR2, and a control flowcell containing immobilized bovine serum albumin. Sensograms generated were fit to the 1:1 interaction model to calculate $k_{on}$, $k_{off}$ and $K_d$ values using BiaEvaluation software (Biacore). PEGASYS® was included as a control sample. Table 26 shows the average $k_{on}$, $k_{off}$ and $K_d$ obtained with the hIFN polypeptides characterized in Example 37. The standard deviations (SD) calculated for each value are also shown.

TABLE 26

| hIFN polypeptide | $k_{on}$ Average | $k_{on}$ SD | $k_{off}$ Average | $k_{off}$ SD | $K_d$ Average | $K_d$ SD |
|---|---|---|---|---|---|---|
| K31 pAF-30K PEG | 7.6 | 0.424264069 | 0.07 | 0.00 | 870 | 70.71067812 |
| S163 pAF-30K PEG | 3.85 | 0.353553391 | 0.04 | 0.00 | 1050 | 70.71067812 |
| K164 pAF-30K PEG | 5.35 | 0.353553391 | 0.04 | 0.00 | 660 | 56.56854249 |
| L26 pAF-30K PEG | No Binding observed | No Binding observed | No Binding observed | No Binding observed | No Binding observed | No Binding observed |
| R33 pAF-30K PEG | No Binding observed | No Binding observed | No Binding observed | No Binding observed | No Binding observed | No Binding observed |
| Q158 pAF-30K PEG | 6 | 0.141421356 | 0.03 | 0.00 | 440 | 21.21320344 |
| E159 pAF-30K PEG | 2.9 | 0.141421356 | 0.03 | 0.00 | 1085 | 162.6345597 |
| Y135 pAF-30K PEG | 5.95 | 0.494974747 | 0.04 | 0.00 | 712.5 | 10.60660172 |
| L30 pAF-30K PEG | No Binding observed | No Binding observed | No Binding observed | No Binding observed | No Binding observed | No Binding observed |
| K134 pAF-30K PEG | 7.4 | 0.424264069 | 0.04 | 0.00 | 495 | 35.35533906 |
| L161 pAF-30K PEG | 4.95 | 0.212132034 | 0.05 | 0.00 | 990 | 14.14213562 |
| K131 pAF-30K PEG | 9.9 | 0.141421356 | 0.03 | 0.00 | 330 | 14.14213562 |
| I24 pAF-30K PEG | 4.95 | 0.070710678 | 0.02 | 0.00 | 390 | 14.14213562 |
| S160 pAF-30K PEG | 4.825 | 0.106066017 | 0.05 | 0.00 | 1100 | 0 |
| E165 pAF-30K PEG | 5.35 | 0.070710678 | 0.03 | 0.00 | 577.5 | 3.535533906 |

TABLE 26-continued

| hIFN polypeptide | $k_{on}$ Average | $k_{on}$ SD | $k_{off}$ Average | $k_{off}$ SD | $K_d$ Average | $K_d$ SD |
|---|---|---|---|---|---|---|
| R162 pAF-30K PEG | 4.65 | 0.777817459 | 0.06 | 0.00 | 1375 | 176.7766953 |
| PEGASYS ® | 7.491666667 | 0.537044381 | 0.03 | 0.00 | 368.3333333 | 31.88521078 |
| K23 pAF-30K PEG | 5.45 | 5.727564928 | 0.13 | 0.00 | 1180 | 311.1269837 |
| S25 pAF-30K PEG | 7.95 | 2.899137803 | 0.13 | 0.02 | 1700 | 848.5281374 |
| F27 pAF-30K PEG | 4.175 | 0.247487373 | 0.01 | 0.00 | 220 | 14.14213562 |
| L128 pAF-30K PEG | 8.65 | 1.060660172 | 0.03 | 0.00 | 395 | 49.49747468 |

Example 39 hIFN polypeptides of the invention may be evaluated with a number of different assays. Potential assays include, but are not limited to, mRNA gene expression profiling, CFU assays including but not limited to CFU-GM and CFU-MK assays, assays measuring CrkL/STAT phosphorylation, MHC Class I expression assays, and mRNA profiling, as well as animal studies such as pharmacokinetics studies in rats, studies using a NOD/SCID reconstitution model, and pharmacokinetics/pharmacodynamics in monkeys. Colony formation assays such as those described by Giron-Michel, J. in Leukemia 2002 16:1135-1142 or described herein may be used to evaluate proliferation of progenitor cells by hIFN polypeptides of the invention. Bone marrow or cord blood may be used in colony formation assays.

To assess the biological activity of modified hIFN polypeptides of the invention, an assay measuring phosphorylation of STAT3, a signal transducer and activator of transcription family member, is performed using the human adenocarcinoma HeLa cell line. The human cell line HeLa is purchased from ATCC (Manassas, Va.) and is routinely passaged in DMEM plus 10% heat-inactivated fetal bovine serum. The cells are maintained at 37° C. in a humidified atmosphere of 5% $CO_2$. The HeLa cells are starved overnight in assay media without fetal bovine serum before stimulation with increasing concentrations of hIFN polypeptides for 10 minutes at 37° C. Phosphorylation of STAT3 may be measured with PathScan Phospho-STAT3 (Tyr705) ELISA Kit (Cell Signaling Technology). With this kit, the assay is performed in 96 well plates and has a calorimetric readout measurable by a spectrophotometric plate reader.

The hIFN polypeptides of the invention may be evaluated using a NOD/SCID reconstitution model. PK/PD studies in monkeys may be performed as described previously. Cynomolgus monkeys are also used to study in vivo activity and bone marrow toxicity. Activity is assayed by measuring the induction of downstream markers including but not limited to 2',5'-OAS by hIFN polypeptides of the invention. Circulating blood cells, including but not limited to neutrophils, RBCs, and platelets are evaluated in bone marrow toxicity studies after administration of hIFN polypeptides. Bone marrow is collected and evaluated from animals exposed to hIFN polypeptides of the invention. For example, bone marrow aspirates and/or core biopsies from treated animals (e.g. from primates) are examined histologically, and the ratio of myeloid to nucleated erythroid cells (M:E ratio) is estimated. A low M:E ratio, in conjunction with neutropenia, may be indicative of granulocytic hypoplasia with decreased production of neutrophils. Isolated bone marrow cells from treated animals are assayed for hematopoietic progenitors. That is, cell isolates are subjected to CFU-GM or BFU-E colony assay. The results (i.e. number of hematopoietic progenitor cells) would show the effect, if any, of treatment on myeloid and/or erythroid progenitor cells. Such bone marrow toxicity studies may involve hIFN polypeptides administered via different routes, including but not limited to, subcutaneously and intravenously. Intravenous administration may allow for longer dosing regimens and better evaluation of bone marrow toxicity than subcutaneous administration. Such improvements may result from a modulation of immunogenicity or an antibody response to the compound administered. Toxicity studies include evaluation of neutrophil and platelet number/mL of plasma or serum.

Assays to support preliminary formulation studies may be performed which include but are not limited to, assays for protein de-amidation, aggregation, oxidation, acetylation, and other stability indicating assays. Other assays may be used that investigate other potential degradation products including, but not limited to, disulfide rearrangements and proteolytic degradation products.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference herein in their entirety for all purposes.

TABLE 27 hIFN Sequences Cited.

| SEQ ID # | Sequence Name |
|---|---|
| 1 | Full-length amino acid sequence of hIFN |
| 2 | The mature amino acid sequence of hIFN |
| 3 | The mature amino acid sequence of consensus hIFN |
| 21 | Nucleotide Sequence of full length hIFN |
| 22 | Nucleotide sequence of mature hIFN cDNA |
| 23 | Amino acid sequence of limitin |

What is claimed is:

1. A human interferon alpha (hIFN) polypeptide comprising a non-naturally encoded amino acid at amino acid position 134 of the hIFNα polypeptide in SEQ ID NO: 2 or the corresponding amino acid position in SEQ ID NO: 1, 3 or other known IFN polypeptide sequence, wherein the non-naturally encoded amino acid has the structure:

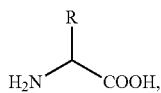

wherein the R group is any substituent other than one used in the twenty natural amino acids, wherein the non-naturally encoded amino acid is linked to a water soluble branched polymer, and wherein the resulting hIFNα polypeptide has a serum half-life that is at least twice as long as the wild type hIFNα polypeptide.

2. The hIFN polypeptide of claim 1, wherein the branched polymer is greater than 30 kDa.

3. The hIFN polypeptide of claim 1, wherein the branched polymer is between about 40 kDa and 50 kDa.

4. A method of making the hIFN polypeptide of claim 1, the method comprising contacting an isolated hIFN polypeptide comprising a non-naturally encoded amino acid with a water soluble branched polymer that reacts with the non-naturally encoded amino acid.

5. The hIFN polypeptide of claim 1 wherein the polypeptide comprises SEQ ID NO: 2.

* * * * *